US008383839B2

(12) United States Patent
Uchida et al.

(10) Patent No.: US 8,383,839 B2
(45) Date of Patent: Feb. 26, 2013

(54) HETEROCYCLIDENE ACETAMIDE DERIVATIVE

(75) Inventors: Hideharu Uchida, Shinjuku-ku (JP); Naoto Kosuga, Shinjuku-ku (JP); Tsutomu Satoh, Shinjuku-ku (JP); Daido Hotta, Shinjuku-ku (JP); Tomoyuki Kamino, Shinjuku-ku (JP); Yoshitaka Maeda, Shinjuku-ku (JP); Ken-ichi Amano, Shinjuku-ku (JP); Yasushige Akada, Shinjuku-ku (JP)

(73) Assignee: Mochida Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 13/008,456

(22) Filed: Jan. 18, 2011

(65) Prior Publication Data

US 2011/0112071 A1 May 12, 2011

Related U.S. Application Data

(62) Division of application No. 11/988,659, filed as application No. PCT/IB2006/002016 on Jul. 24, 2006, now Pat. No. 7,910,751.

(30) Foreign Application Priority Data

Jul. 22, 2005 (JP) ................................ 2005-213534
Nov. 15, 2005 (JP) ................................ 2005-330890
Feb. 22, 2006 (JP) ................................ 2006-045985

(51) Int. Cl.
*C07D 313/00* (2006.01)
*C07D 309/00* (2006.01)

(52) U.S. Cl. ........................................ 549/355; 549/356

(58) Field of Classification Search .................. 549/355, 549/356

See application file for complete search history.

(56) References Cited

U.S. PATENT DOCUMENTS

| | | | |
|---|---|---|---|
| 4,977,166 | A | 12/1990 | Hardy et al. |
| 5,710,150 | A | 1/1998 | Taniguchi et al. |
| 6,120,964 | A | 9/2000 | Wilson et al. |
| 6,340,678 | B1 | 1/2002 | Matsuhisa et al. |
| 2004/0038969 | A1 | 2/2004 | Doherty et al. |
| 2004/0204477 | A1 | 10/2004 | Moll et al. |
| 2005/0004103 | A1 | 1/2005 | Koshio et al. |
| 2006/0035882 | A1 | 2/2006 | Koga et al. |
| 2007/0167444 | A1 | 7/2007 | Kuramochi et al. |
| 2010/0016285 | A1 | 1/2010 | Uchida et al. |

FOREIGN PATENT DOCUMENTS

| | | | |
|---|---|---|---|
| EP | 0 411 751 | A1 | 2/1991 |
| EP | 1 109 071 | A1 | 6/2001 |
| EP | 1 619 185 | A1 | 1/2006 |
| EP | 1 829 864 | A1 | 9/2007 |
| JP | A-4-178381 | | 6/1992 |
| JP | 05-339223 | A | 12/1993 |
| JP | A-9-221475 | | 8/1997 |
| JP | A-2001-213870 | | 8/2001 |
| JP | A-2005-187449 | | 7/2005 |
| WO | WO 94/26692 | | 11/1994 |
| WO | WO 95/06035 | | 3/1995 |
| WO | WO 97/12870 | A1 | 4/1997 |
| WO | WO 98/07704 | A1 | 2/1998 |
| WO | WO 98/39325 | | 9/1998 |
| WO | WO 98/42673 | A1 | 10/1998 |
| WO | WO 03/042181 | A1 | 5/2003 |
| WO | WO 03/049702 | A2 | 6/2003 |
| WO | WO 2004/052846 | A1 | 6/2004 |
| WO | WO 2004/056774 | A2 | 7/2004 |
| WO | WO 2004/069792 | A2 | 8/2004 |
| WO | WO 2004/100865 | A2 | 11/2004 |
| WO | WO 2004/110986 | A1 | 12/2004 |
| WO | WO 2005/016922 | A1 | 2/2005 |
| WO | WO 2005/030766 | A1 | 4/2005 |
| WO | WO 2005/040100 | A1 | 5/2005 |
| WO | WO 2005/040119 | A1 | 5/2005 |
| WO | WO 2005/040121 | A2 | 5/2005 |

(Continued)

OTHER PUBLICATIONS

Di Fabio et al., "Benzoazepine derivative as potent antagonists of the glycine binding site associated to the NMDA receptor," *Il Farmaco*, vol. 58, No. 9, 2003, pp. 723-738.

(Continued)

*Primary Examiner* — Nizal Chandrakumar
(74) *Attorney, Agent, or Firm* — Oliff & Berridge, PLC

(57) ABSTRACT

A compound represented by formula (I'):

[Ch. 1]

(I')

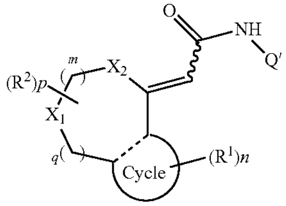

(wherein m, n, and p each represent 0 to 2; q represents 0 or 1; $R^1$ represents halogen, a hydrocarbon group, a heterocyclic group, an alkoxy group, an alkoxycarbonyl group, a sulfamoyl group, a CN group, an $NO_2$ group, or the like; $R^2$ represents halogen, amino, a hydrocarbon group, an aromatic heterocyclic group, or an oxo group; $X_1$ represents O, —$NR^3$—, or —S(O)r-; $X_2$ represents a methylene group, O, —$NR^3$—, or —S(O)r-; Q' represents a heteroaryl group, a heteroarylalkyl group, a substituted aryl group, or an aralkyl group; Cycle moiety represents an aryl ring or a heteroaryl ring; and the wavy line represents an E-isomer or a Z-isomer), a salt of the compound, or a solvate of the compound or the salt. A pharmaceutical composition and a transient receptor potential type I (TRPV1) receptor antagonist each contain, as an active ingredient, at least one of the compound, a salt of the compound, and a solvate of the compound or the salt.

13 Claims, No Drawings

FOREIGN PATENT DOCUMENTS

| | | | |
|---|---|---|---|
| WO | WO 2005/046683 | A1 | 5/2005 |
| WO | WO 2005/070885 | A1 | 8/2005 |
| WO | WO 2005/095329 | A1 | 10/2005 |
| WO | WO 2006/006741 | A1 | 1/2006 |
| WO | WO 2006/038871 | A1 | 4/2006 |
| WO | WO 2006/058338 | A2 | 6/2006 |
| WO | WO 2006/064075 | A1 | 6/2006 |
| WO | WO 2008/091021 | A1 | 7/2008 |
| WO | WO 2010/010933 | A1 | 1/2010 |
| WO | WO 2010/010934 | A1 | 1/2010 |
| WO | WO 2010/010935 | A1 | 1/2010 |
| WO | WO 2010/038803 | A1 | 4/2010 |

OTHER PUBLICATIONS

Messeri et al., "Efficient synthesis of novel benzo[*e*]-[1,4]-diazepine derivatives," *Tetrahedron Letters*, vol. 42, No. 18, 2001, pp. 3227-3230.

Matsuhisa et al., "Nonpeptide Arginine Vasopressin Antagonists for Both $V_{1A}$ and $V_2$ Receptors: Synthesis and Pharmacological Properties of 4'-[5-(Substituted Methylidene)-2,3,4,5-tetrahydro-1*H*-1-benzoazepine-1-carbonyl]benzanilide and 4'-[5-(Substituted Methyl)-2,3-dihydro-1*H*-1benzoazepine-1-carbonyl]benzanilide Derivatives," *Chemical Pharmaceutical Bulletin*, vol. 47, No. 3, 1999, pp. 329-339.

Tacconi, "Reazione di Schmidt su ossindolil e ossindolidenchetoni," *Gazzetta Chimica Italiana*, vol. 98, No. 3, 1968, pp. 344-357 (with abstract).

Barberan et al., "Synthesis of *E*- and *Z*-substituted methylene-3,4-dihydro-2*H*-1-benzopyrans by region- and stereocontrolled palladium-catalyzed intramolecular cyclization," *Tetrahedron Letters*, vol. 42, No. 14, 2001.

Canoira et al., "Synthesis of Oxindole Derivatives from *N*-Alkenyl-*o*-Chloroanilides with Zero-Valent Nickel Complex," *Journal of Heterocyclic Chemistry*, vol. 22, No. 6, 1985, pp. 1511-1518.

R. Di Fabio, "Enantiomerically Pure Tetrahydroquinoline Derivatives as In Vivo Potent Antagonists of the Glycine Binding Site Associated to the NMDA Receptor", *Bioorganic & Medicinal Chemistry Letters*, vol. 13, No. 21, pp. 3863-3866, Nov. 2003.

Supplementary European Search Report dated Sep. 10, 2009.

Dorwald F. A., "Side Reactions in Organic Synthesis", 2005, Wiley: VCH, Weinheim p. IX of Preface p. 1-15.

West, Solid State Chemistry and its applications, John Wiley & Sons, 1984, p. 358.

Bannon et al., "Involvement of TRPV1 in the Regulation of Body Temperature in Rats and Mice", Society for Neuroscience Abstract 30:890.24, pp. 1-2, 2004.

Gavva et al., "The Vanilloid Receptor TRPV1 is Tonically Activated In Vitro and Involved in Body Temperature Regulation", The Journal of Neuroscience, vol. 27, No. 13, pp. 3366-3374, Mar. 28, 2007.

Gavva, "Body-Temperature Maintenance as the Predominant Function of The Vanilloid Receptor TRPV1", Trends in Pharmacological Science, vol. 29, No. 11, pp. 550-557, Sep. 19, 2008.

Swanson et al., "Identification and Biological Evaluation of 4-(3-Trifluoromethylpyridin-2-yl)peperazine-1-carboxylic Acid (5-Trifluoromethylpyridin-2-yl)amide, a High Affinity TRPV1 (VR1) Vanilloid Receptor Antagonist", J. Med. Chem., vol. 48, pp. 1857-1872, 2005.

HETEROCYCLIDENE ACETAMIDE DERIVATIVE

CROSS-REFERENCE TO RELATED APPLICATIONS

This is a Division of application Ser. No. 11/988,659 filed Mar. 7, 2008, which in turn is a National Phase of Application No. PCT/IB2006/002016 filed Jul. 24, 2006, which claims the benefit of Japanese Application No. 2005-213534, filed Jul. 22, 2005, Japanese Application No. 2005-330890, filed Nov. 15, 2005 and Japanese Application No. 2006-045985, filed Feb. 22, 2006. The disclosures of the prior applications are hereby incorporated by reference herein in their entirety.

TECHNICAL FIELD

The present invention relates to a medicine, in particular, a compound having a transient receptor potential type I receptor (hereinafter referred to as "TRPV1 receptor") antagonism, in particular, to an acetamide derivative having a heterocyclidene skeleton, a TRPV1 receptor antagonist comprising the derivative as an active ingredient, and an agent for preventing or treating diseases which cause pain and in which the TRPV1 receptor is involved, the preventive or treatable agent comprising the derivative as an active ingredient.

BACKGROUND ART

In a study related to the pain-producing mechanism, a receptor of capsaicin (8-methyl-N-vanillyl-6-nonenamide), which is a main pungent taste component of chili pepper, (TRPV1 receptor) was cloned in 1997 (Caterina M J, Schumacher M A, Tominaga M, Rosen T A, Levine J D, and Julius D., Nature, Vol. 389, pp. 816-824, 1997). The TRPV1 receptor, which is a receptor that recognizes capsaicin, frequently expressed in primary sensory neurons involved in the sense of pain, and sensory afferent fibers containing C-fiber nerve endings. Thereafter, many TRP family receptors were cloned.

The structures of the TRP family receptors are similar to each other. The TRP family receptors each have a six transmembrane domain, and the N-terminal and the C-terminal of the molecule are disposed in a cell. In response to capsaicin stimulation, an acid (pH 6.0 or less), or heat (43° C. or higher), the TRPV1 receptor allows cations such as a calcium ion and a sodium ion to flow into a cell. Accordingly, considering the expression sites of the TRPV1 receptor and the action of capsaicine, a marked contribution of the TRPV1 receptor to the excitement of nerve was assumed. Furthermore, contributions of the TRPV1 receptor to living organisms have been elucidated from information disclosed in many previous reports. In particular, in a mouse in which the TRPV1 receptor has been deleted (TRPV1 knockout mouse), enhancement of heat sensitivity due to neuropathic pain is not observed, development of edema is suppressed in a Complete Freund's Adjuvant (CFA)-induced inflammatory pain model (Szabo A, Helyes Z, Sandor K, Bite A, Pinter E, Nemeth J, Banvolgyi A, Bolcskei K, Elekes K, and Szolcsanyi J, Journal of Pharmacology And Experimental Therapeutics, Vol. 314, pp. 111-119, 2005), and desensitization action by a TRPV1 receptor agonist disclosed in a previous report exhibits an analgetic effect in a neuropathic pain model and an inflammatory pain model, and thus, an involvement of the TRPV1 receptor in pain has been suggested (Rashid M H, Inoue M, Kondo S, Kawashima T, Bakoshi S, and Ueda H, Journal of Pharmacology And Experimental Therapeutics, Vol. 304, pp. 940-948, 2003).

Application of capsaicin causes a temporary acute pain, but then induces desensitization to cause an analgetic effect. On the basis of this characteristic, many TRPV1 receptor agonists, such as a capsaicin cream, have been under development as analgetic drugs (Saper J R, Klapper J, Mathew N T, Rapoport A, Phillips S B, and Bernstein J E, Archives of Neurology, Vol. 59, pp. 990-994, 2002).

Recently, it has been reported that, in dorsal root ganglion cells of a diabetic pain model rat induced by administering streptozotocin, depolarization due to capsaicin stimulation is accelerated, that is, the sensitivity of the TRPV1 receptor is enhanced. Thus, an involvement of the TRPV1 receptor in diabetic pain has been suggested (Hong S and Wiley J W, The Journal of Biological Chemistry, Vol. 280, pp. 618-627, 2005). In addition, it has been reported that the desensitization action of capsaicin, which is a TRPV1 receptor agonist, is effective for improving the bladder function, and thus, a contribution to urination has also been suggested (Masayuki Takeda and Isao Araki, Nippon Yakurigaku zasshi (Folia Pharmacologica Japonica), Vol. 121, pp. 325-330, 2003). Furthermore, contraction of bronchia caused by capsaicin stimulation, an inhibition effect of a TRPV1 receptor antagonist for this action, and the like have also been reported, and thus, an involvement in respiratory organs has also been suggested. It has been elucidated that the TRPV1 receptor is involved in various diseases. From the information described above, TRPV1 receptor regulators that modulate the function of the TRPV1 receptor have been expected to be useful.

Among such TRPV1 regulators, agonists that stimulate the TRPV1 receptor to induce desensitization and antagonists are expected to be useful in treating various diseases. Among these agonists and antagonists, since the agonists cause pain involving temporary acute stimulation and so forth, TRPV1 receptor antagonists that do not induce such excitation due to stimulation have attracted attention. Currently, compounds having a TRPV1 receptor antagonism are expected to be widely useful for, for example, analgetic drugs, therapeutic drugs for urinary incontinence, and therapeutic drugs for respiratory diseases.

Pain is defined as "an unpleasant, sensory and emotional experience that is caused by a substantial or latent lesion of a tissue, and a sensory and emotional experience that is described using such an expression". Pain can be roughly divided into three categories: 1. nociceptive pain, 2. neuropathic pain, and 3. psychogenic pain.

The nociceptive pain is physiological pain caused by mechanical stimuli, thermal stimuli, or chemical stimuli. In general, the nociceptive pain acute pain and serves as a biosensor based on unpleasant sensory experiences to protect the body from danger. It has been thought that pain such as rheumatism is surely acute pain. However, a prolonged period from the onset thereof and the chronicity of inflammation bring about chronic pain.

Hyperalgesia to thermal to thermal stimuli or mechanical stimuli arises after tissue damage or during inflammation. The sensitization of receptors to a pain-inducing material and pain-inducing stimuli is reported in explanation of the hyperalgesia to thermal stimuli or mechanical stimuli. Examples thereof include sensitization of pain receptors due to inflammatory mediators occurring in local inflammation and a decrease in the pH therein, an increase in reactivity to bradykinin and histamine due to an increase in the temperature of local inflammation, and sensitization due to nerve growth factor (NGF) (reference: Kazuo Hanaoka, Itami-Kiso, Shindan, Chiryo- (Pain-Base, Diagnosis, and Therapy-), Asakura Shoten, 2004). Specific examples thereof include chronic rheumatism and knee osteoarthritis, which are typical examples. Non-steroidal anti-inflammatory drugs (NSAIDs) have been used for treatment of inflammatory pain due to pain chronic rheumatism and knee osteoarthritis for a long period of time. However, the use thereof is restricted because of side effects due to a disorder of apparatus digestorius and renal disorder. Furthermore, although cyclooxygenase-2-selective inhibitors (COX2 inhibitors) have been developed for reducing the side effects of NSAIDs, there is concern abut side effect that can lead to cardiac insufficiency which has become a social problem. Accordingly, an inflammatory pain therapeutic agent having higher efficacy in oral administration and having fewer side effects is required.

Postoperative pain is basically inflammatory pain which tissue damage accompanies, and includes factors of neurogenic pain factor derived from nerve injury. Postoperative pain is broadly divided into somatic pain and visceral pain. Somatic pain is further divided into superficial pain and deep pain. Among these, when severe postoperative pain is left untreated, nerve sensitization occurs; hence, pain is also evoked by innocuous stimuli, such as a touch and a press (allodynia). When such pain occurs, there are many intractable cases that cannot be controlled by nerve block therapy and the administration of drugs, such as NSAIDs, antiepileptic drugs, and opioid agonists. Furthermore, these drugs used have side effects. For example, the NSAIDs have side effects due to disorder of apparatus digestorius organs and renal disorder. In the antiepileptic drugs, carbamazepine and Phenyloin have side effects, such as tibutation, eruption, digestive symptoms, and cardiotoxicity; and Gabapentin has side effects such as somnolence and vertigo. The opioid agonists have side effects such as constipation. Accordingly, a postoperative pain therapeutic agent having higher efficacy and having fewer side effects is required.

Neuropathic pain is pain caused by primary damage of a certain portion in a neurotransmission system ranging from a periphery to center or caused by a malfunction thereof (Kenjiro Dan, Zusetsu Saishin Masuikagaku sirizu 4, Itami no rinsho (Textbook of anesthesiology 4, Fully illustrated) Chapter 1, 1998, Medical View Co., Ltd.).

Nerve injuries that cause neuropathic pain are typically external injuries or lesions on a peripheral nerve, a nerve plexus, or perineural soft-tissue. However, neuropathic pain is also caused by lesions on central somatosensory pathways (for example, ascending somatosensory pathways in spinal cord, brainstem, the thalamic or cortex level, and the like). For example, neuropathic pain is possibly caused by any of neurodegenerating diseases, osteolytic disease, metabolic disorder, cancer, infection, inflammation, after surgical operation, external injuries, radiotherapy, treatment using anticancer agents, and the like. However, the pathophysiological mechanism, or in particular, the molecular mechanism of the onset, has not yet been completely elucidated.

Allodynia is known as an example of an abnormal skin reaction characterizing neuropathic pain is allodynia. Allodynia is a state in which a person feels pain even with stimulation that would not result in normal person feeling pain. In allodynia, pain is evoked by tactile stimulus. That is, fundamental characteristics of allodynia are qualitative change in sensory responses and a low pain threshold. In postherpetic neuralgia, which is representative of neuropathic pain, it is confirmed that 87% of patients have allodynia. It is alleged that the strength of pain in postherpetic neuralgia is proportional to the degree of allodynia. Allodynia, which is a symptom that markedly constrains patients' freedom, draws attention as a therapeutic target of postherpetic neuralgia.

Herpes is a disease in which an infected herpes virus is neurons to cause onset, and 70% of herpes patients feel severe pain. This pain disappears as the disease is treated. However, about 10% of the patients suffers from so-called postherpetic neuralgia in which the pain remains for many years even after the disease is cured. On pathogenetic mechanism, it is said that the herpes virus proliferates again from a nerve ganglion, and nerve lesions generated during this proliferation accelerate reorganization of synapses, thus causing allodynia, which is neuropathic pain. In clinical settings, elderly people are more likely to develop the postherpetic neuralgia, and 70% or more of the cases of postherpetic neuralgia occur in patients 60 years old or older. Examples of a therapeutic agent used include anticonvulsant agents, non-steroidal anti-inflammatory agents, steroids, and the like, but there is no complete therapy (reference: Kazuo Hanaoka, Itami-Kiso, Shindan, Chiryo- (Pain-Base, Diagnosis, and Therapy-), Asakura Shoten, 2004).

Diabetic pain is broadly categorized into acute pain that occurs when hyperglycemia is rapidly remedied and chronic pain that occurs due to factors such as demyelination or nerve regeneration. Among these types of diabetic pain, the chronic pain is neuropathic pain due to inflammation of the dorsal root ganglion caused by a decrease in the bloodstream due to diabetes, and spontaneous firing of neurons and excitability caused by the subsequent regeneration of nerve fibers. Non-steroidal anti-inflammatory agents, antidepressant agents, capsaicin creams and the like are used for therapy. However, there is no perfect therapeutic agent for treatment of diabetic pain that can cure all the types of diabetic pain using a single agent (Reference: Iyaku no ayumi (Progress in Medicine) (Journal of Clinical and Experimental Medicine), Vol. 211, No. 5, 2004, Special feature "Itami shigunaru no seigyo kiko to saishin chiryo ebidensu" ("Control mechanisms of Pain Signal and Latest Evidence-based Therapy")).

In neuropathic pain, analgesic treatment for patients who complain of a chronic pain symptom that interferes with their daily life directly improves the quality of life. However, it is believed that central analgetic agents represented by morphine, non-steroidal anti-inflammatory analgesic agents, and steroids are not effective against neuropathic pain. In practical pharmacotherapy, antidepressant agents such as amitriptyline; antiepileptic drugs such as Gabapentin, Pregabalin, carbamazepine, and phenyloin; and antiarrhythmic agents such as mexiletine are also used and prescribed for the treatment of neuropathic pain. However, it is known that these drugs have the following side effects: Amitriptyline causes side effects such as dry mouth, drowsiness, sedation, constipation, and dysuria. Carbamazepine and phenyloin cause side effects such as light-headedness, eruption, digestive apparatus symptoms, and cardiotoxicity. Gabapentin causes side effects such as somnolence and vertigo. Mexiletine causes side effects such as vertigo and digestive apparatus symptoms. These drugs, which are not specific neuropathic pain therapeutic agents, have poor dissociation between drug efficacy and side effect, thus, resulting in low treatment of satisfaction. Accordingly, a neuropathic pain therapeutic agent that exhibits a higher efficacy in oral administration and that have fewer side effects is required.

Recently, compounds having a TRPV1 receptor antagonism have been studied. Known heterocyclic compounds each having an amide bond are disclosed in, for example, PCT Publication No. 03/049702 pamphlet (Patent Document 1), PCT Publication No. 04/056774 pamphlet (Patent Document 2), PCT Publication No. 04/069792 pamphlet (Patent Document 3), PCT Publication No. 04/100865 pamphlet (Patent Document 4), PCT Publication No. 04/110986 pamphlet (Patent Document 5), PCT Publication No. 05/016922 pamphlet (Patent Document 6), PCT Publication No. 05/030766 pamphlet (Patent Document 7), PCT Publication No. 05/040121 pamphlet (Patent Document 8), PCT Publication No. 05/046683 pamphlet (Patent Document 9), PCT Publication No. 05/070885 pamphlet (Patent Document 10), PCT Publication No. 05/095329 pamphlet (Patent Document 11), PCT Publication No. 06/006741 pamphlet (Patent Document 12), PCT Publication No. 06/038871 pamphlet (Patent Document 13), and PCT Publication No. 06/058338 pamphlet (Patent Document 14). However, these patent documents do not disclose heterocyclidene acetamide derivatives.

Examples of the related art that disclose a compound having a heterocyclidene skeleton include that are PCT Publication No. 94/26692 pamphlet (Patent Document 15), PCT Publication No. 95/06035 pamphlet (Patent Document 16), PCT Publication No. 98/39325 pamphlet (Patent Document 17), PCT Publication No. 03/042181 pamphlet (Patent Document 18), Japanese Patent Application Laid-open No. 2001-213870 (Patent Document 19), PCT Publication No. 06/064075 pamphlet (Patent Document 20), Journal of Heterocyclic Chemistry, Vol. 22, No. 6, pp. 1511-18, 1985 (Non-Patent Document 1), Tetrahedron Letters, Vol. 42, No. 18, pp. 3227-3230, 2001 (Non-Patent Document 2), and Chemical Pharmaceutical Bulletin, Vol. 47, No. 3, pp. 329-339, 1999 (Non-Patent Document 3).

Patent Document 15 discloses, as a muscle relaxant, a compound with a structure which has a 2H-1-benzopyran-4-ylidene skeleton or a 1,2,3,4-tetrahydro-4-quinolidene skeleton and in which a hydrogen atom, an alkyl group, or a cycloalkyl group is bonded to the N atom of the acetamide structure. However, a compound in which a substituted aryl group, heteroaryl group, or the like is bonded to the N atom is not disclosed. Patent Documents 16 to 18 disclose, as an arginine vasopressin antagonist or an oxytocin antagonist, a compound with a specific structure which has a 4,4-difluoro-2,3,4,5-tetrahydro-1H-1-benzodiazepine skeleton and in which an aryl carbonyl group substituted an aryl is bonded to the N atom of the 1-position of the skeleton.

Patent Document 19 discloses, as a 2-(1,2-benzisothiazol-3(2H)-ylidene 1,1-dioxide) acetamide derivative used as a novel charge-control agent for a toner for electrostatography, a specific compound in which the N atom of the acetamide has a substituted phenyl group.

Patent Document 20 discloses, as an amide derivative of a 2,3-dihydro-1-oxo-1H-isoquinolin-4-ylidene used as a calpain inhibitor, a compound with a specific structure which has a sec-butyl group at the 3-position.

In a report related to the synthesis of an oxyindole derivative, Non-Patent Document 1 discloses 2-(1,2-dihydro-2-oxo-3H-indol-3-ylidene)-N,N-dimethyl-acetamide. However, a substituted aryl group or heteroaryl group, or the like is not bonded to the N atom.

Non-Patent Document 2 discloses, as a (1,2,3,4-tetrahydro-2-oxo-5H-1,4,-benzodiazepin-5-ylidene)acetamide derivative used for an N-methyl-D-aspartate (NMDA) antagonist, a compound with a specific structure in which a phenyl group is bonded to the N atom of the acetamide.

Non-Patent Document 3 discloses, as a (2,3,4,5-tetrahydro-1H-1-benzodiazepin-5-ylidene)acetamide derivative used as a nonpeptide arginine vasopressin antagonist, a compound with a specific structure in which a 2-pyridylmethyl group is bonded to the N atom of the acetamide, and the benzodiazepine skeleton does not have a substituent.

Patent Documents 15 to 20 and Non-Patent Documents 1 to 3 disclose compounds each having a heterocyclidene skeleton, but the antagonism of the TRPV1 receptor is not disclosed or suggested.

In the development of pharmaceuticals, it is required to satisfy strict criteria for not only target pharmacological activity but also absorption, distribution, metabolism, excretion, and the like. With respect to drug interactions, desensitization or tolerance, digestive absorption in oral administration, the rate of transfer to a small intestine, the rate of absorption and first-pass effect, an organ barrier, protein binding, induction of a drug-metabolizing enzyme, an excretion pathway and body clearance, a method of administration (an application site, a method, and purpose), and the like, various agenda are required. However, a drug that satisfies these requirements is seldom discovered.

These comprehensive problems in drug development also exist for TRPV1 receptor antagonists, and TRPV1 receptor antagonists have not yet been released onto the market. More specifically, compounds having a TRPV1 receptor antagonism also include problems in terms of usefulness and safety. For example, these compounds have low metabolic stability and oral administration of these compounds is difficult; these compounds exhibit inhibitory activity of the human ether-a-go-go related gene (hERG) channel, which may cause arrhythmia, and pharmacokinetics of these compounds are not satisfactory. Accordingly, a compound in which these problems are solved and which has high activity has been desired.

In addition, a compound that causes fewer of the above-mentioned side effects than known drugs that are currently used in the treatment of pain including the above-described types of neuropathic pain has been desired.

DISCLOSURE OF INVENTION

Problems to be Solved by the Invention

Under the above-described circumstances, a TRPV1 receptor antagonist that can be orally administered, that has high safety, and that has excellent effectiveness, an agent for preventing or treating diseases in which the TRPV1 receptor is involved, and in particular, an agent for preventing or treating pain have been desired. In the related art, amitriptyline causes side effects such as dry mouth, drowsiness, sedation, constipation, and dysuria; carbamazepine and phenyloin cause side effects such as eruption, digestive apparatus symptoms, and cardiotoxicity; gabapentin causes side effects such as somnolence and vertigo; mexiletine causes side effects such as vertigo and digestive apparatus symptoms; non-steroidal anti-inflammatory drugs cause side effects such as gastrointestinal damage; and COX2 inhibitors cause a side effect of heart failure. Accordingly, in particular, an agent for preventing or treating pain which can orally administered to mammals including humans, in particular, which can be clinically easily used, and in which at least one of the above-described problems of the related art is overcome, for example, one which causes fewer of the above-mentioned side effects than known drugs, one which does not have an inhibitory action of an hERG current, one which has satisfactory metabolic stability, one which can be orally administered, or one which has satisfactory pharmacokinetics has been strongly desired.

Means for Solving the Problems

The present invention provides a compound having a TRPV1 receptor antagonism, in particular, a heterocyclidene acetamide derivative represented by formula (I), a pharmaceutically acceptable salt thereof, and a solvate thereof; a TRPV1 receptor antagonist, and an agent for preventing or treating pain, in particular, an agent for preventing or treating neuropathic pain, and an agent for preventing or treating inflammatory pain that contain the derivative as an active ingredient.

Advantages of the Invention

In order to solve the above problems and to obtain a compound having a TRPV1 receptor antagonism having high safety and excellent effectiveness, the present inventors have conducted intensive studies and found that acetamide derivatives having a heterocyclidene skeleton and represented by formula (I), pharmaceutically acceptable salts thereof, and solvates thereof have an excellent TRPV1 receptor antagonism. The group of these compounds does not have an inhibitory action of an hERG channel and has high safety, high metabolic stability, and excellent oral absorbability. Accordingly, a pharmaceutical composition comprising one of the compounds as an active ingredient is promising as an agent for preventing or treating pain that can be orally administered, in particular, as an agent for preventing or treating neuropathic pain, or an agent for preventing or treating inflammatory pain.

BEST MODE FOR CARRYING OUT THE INVENTION

The present invention provides a TRPV1 receptor antagonist, and an agent for preventing or treating pain that comprise a compound represented by formula (I) described in embodiments below, a pharmaceutically acceptable salt thereof, or a solvate thereof as an active ingredient; a heterocyclidene acetamide derivative represented by formula (I'), a salt thereof, a pharmaceutical composition comprising the derivative or a salt thereof; and pharmaceutical use of the derivative or a salt thereof.

Embodiments of the present invention will now be described. In the description related to the compounds of the present invention, for example, the expression "$C_{1-6}$" means, unless otherwise stated, "a linear or branched chain having 1 to 6 carbon atoms" for a linear group, and "the number of carbon atoms constituting a ring" for a cyclic group.

The molecular weight of a compound represented by formula (I) of the present invention is not particularly limited. However, the molecular weight is preferably 1000 or less, and more preferably 700 or less. When the structure of a compound is specified in recent drug design, in addition to the basic skeleton having a pharmacological feature, a limitation such as that of the molecular weight is normally used as another significant limiting factor. In particular, when the oral absorbability of the drug is considered, the molecular weight is preferably 700 or less.

[Embodiments of the Present Invention]

[First Embodiment of the Present Invention]

A first embodiment of the present invention provides a TRPV1 receptor antagonist comprising at least one of compounds represented by formula (I):

[Ch. 1]

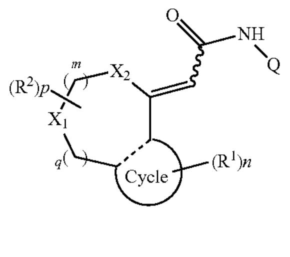

(wherein m, n, and p each independently represent an integer of 0 to 2; q represents an integer of 0 or 1; $R^1$ represents a group selected from a halogen atom, a substituted or unsubstituted hydrocarbon group, a substituted or unsubstituted heterocyclic group, a substituted or unsubstituted $C_{1-6}$ alkoxy group, a substituted or unsubstituted $C_{1-6}$ alkoxycarbonyl group, an amino group which may be mono- or di-substituted with a substituted or unsubstituted $C_{1-6}$ alkyl group, a protected or unprotected hydroxyl group, a protected or unprotected carboxyl group, a carbamoyl group which may be mono- or di-substituted with a substituted or unsubstituted $C_{1-6}$ alkyl group, a $C_{1-6}$ alkanoyl group, a $C_{1-6}$ alkylthio group, a $C_{1-6}$ alkylsulfinyl group, a $C_{1-6}$ alkylsulfonyl group, a sulfamoyl group which may be mono- or di-substituted with a substituted or unsubstituted $C_{1-6}$ alkyl group, a cyano group, and a nitro group; $R^2$ represents a group selected from a halogen atom, a substituted or unsubstituted amino group, a substituted or unsubstituted hydrocarbon group, a substituted or unsubstituted aromatic heterocyclic group, and an oxo group, or two geminal or vicinal $R^2$'s may bind to each other to form a $C_{2-6}$ alkylene group, and form a cyclo ring group together with the carbon atom to which the two $R^2$'s are bonded; $X_1$ represents an oxygen atom, —$NR^3$— (wherein $R^3$ is a hydrogen atom, a substituted or unsubstituted hydrocarbon group, a substituted or unsubstituted heterocyclic group, or a substituted or unsubstituted acyl group), or —S(O)r- (wherein r is an integer of 0 to 2); $X_2$ represents a methylene group, an oxygen atom, —$NR^3$— (wherein $R^3$ is a hydrogen atom, a substituted or unsubstituted hydrocarbon group, a substituted or unsubstituted heterocyclic group, or a substituted or unsubstituted acyl group) or —S(O)r- (wherein r is an integer of 0 to 2); Q represents a substituted or unsubstituted heteroaryl group, a substituted or unsubstituted heteroarylalkyl group, a substituted or unsubstituted aryl group, or a substituted or unsubstituted aralkyl group; Cycle moiety represents a five- or six-membered aryl ring or heteroaryl ring; the broken line represents a condensation of two rings; and the wavy line represents an E-isomer or a Z-isomer), pharmaceutically acceptable salts thereof, and solvates thereof as an active ingredient.

Each of the groups in formula (I) used in the pharmaceutical composition of embodiment [1] above will now be described specifically. In the following description, the expression "$C_{1-6}$" means that the number of carbon atoms is in the range of 1 to 6. For example, a $C_{1-6}$ alkyl group represents an alkyl group having 1 to 6 carbon atoms.

[1-1] In the compounds represented by formula (I), $R^1$ is a halogen atom, a substituted or unsubstituted hydrocarbon group, a substituted or unsubstituted heterocyclic group, a substituted or unsubstituted $C_{1-6}$ alkoxy group, a substituted or unsubstituted $C_{1-6}$ alkoxycarbonyl group, an amino group which may be mono- or di-substituted with a substituted or unsubstituted $C_{1-6}$ alkyl group, a protected or unprotected hydroxyl group, a protected or unprotected carboxyl group, a carbamoyl group which may be mono- or di-substituted with a substituted or unsubstituted $C_{1-6}$ alkyl group, a $C_{1-6}$ alkanoyl group, a $C_{1-6}$ alkylthio group, a $C_{1-6}$ alkylsulfinyl group, a $C_{1-6}$ alkylsulfonyl group, a sulfamoyl group which may be mono- or di-substituted with a substituted or unsubstituted $C_{1-6}$ alkyl group, a cyano group, or a nitro group. Among these, a substituted or unsubstituted hydrocarbon group is preferred.

Examples of the "halogen atom" include a fluorine atom, a chlorine atom, a bromine atom, and an iodine atom.

The "hydrocarbon groups" of the "substituted or unsubstituted hydrocarbon groups" include aliphatic hydrocarbon groups, alicyclic hydrocarbon groups, and aryl groups. Among these, aliphatic hydrocarbon groups are preferred.

Examples of the "aliphatic hydrocarbon groups" in the "substituted or unsubstituted aliphatic hydrocarbon groups" include liner or branched hydrocarbon groups such as alkyl groups, alkenyl groups, and alkynyl groups.

Examples of the "alkyl groups" include $C_{1-10}$ (more preferably $C_{1-6}$) alkyl groups such as methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-hexyl, 1-methyl-heptyl, and n-nonyl.

Examples of the "alkenyl groups" include $C_{2-6}$ alkenyl groups such as vinyl, allyl, isopropenyl, 2-methylallyl, butenyl, pentenyl, and hexenyl.

Examples of the "alkynyl groups" include $C_{2-6}$ alkynyl groups such as ethynyl, 1-propynyl, 2-propynyl, butynyl, pentynyl, and hexynyl.

Examples of the "alicyclic hydrocarbon groups" include saturated and unsaturated alicyclic hydrocarbon groups such as cycloalkyl groups, cycloalkenyl groups, and cycloalkanedienyl groups.

Examples of the "cycloalkyl groups" include $C_{3-9}$ cycloalkyl groups such as cyclopropyl, cyclobutyl, cyclopentyl, cyclohexyl, cycloheptyl, cyclooctyl, and cyclononyl.

Examples of the "cycloalkenyl groups" include $C_{3-6}$ cycloalkenyl groups such as 1-cyclopropen-1-yl, 1-cyclobuten-1-yl, 1-cyclopenten-1-yl, 2-cyclopenten-1-yl, 3-cyclopenten-1-yl, and 1-cyclohexen-1-yl.

Examples of the "cycloalkanedienyl groups" include $C_{4-6}$ cycloalkanedienyl groups such as 2,4-cyclopentadien-1-yl and 2,5-cyclohexadien-1-yl.

Examples of the "aryl groups" include $C_{6-14}$ aryl groups such as phenyl, naphthyl, biphenylyl, 2-anthryl, phenanthryl, acenaphthyl, and 5,6,7,8-tetrahydronaphthalenyl; and partially hydrogenated fused aryl such as indanyl and tetrahydronaphthyl.

Examples of the heterocyclic groups of the "substituted or unsubstituted heterocyclic groups" in $R^1$ include aromatic heterocyclic groups and saturated or unsaturated non-aromatic heterocyclic groups. Examples of the rings include five- to fourteen-membered rings, preferably five- to twelve-membered rings, containing at least one heteroatom (preferably, 1 to 4 heteroatoms) selected from N, O, and S in addition to the carbon atoms.

The "aromatic heterocyclic groups" include monocyclic aromatic heterocyclic groups and fused aromatic heterocyclic groups. Preferably, the monocyclic aromatic heterocyclic groups each have a five- or six-membered ring. Examples thereof include pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,2,5-triazinyl, 1,3,5-triazinyl, and thiadiazinyl.

Preferably, the fused aromatic heterocyclic groups each have an eight- to twelve-membered ring. These groups include, for example, monovalent groups obtained by removing any hydrogen atom from a ring formed by condensing the above-mentioned five- or six-membered aromatic ring with one or a plurality of (preferably 1 to 2) aromatic rings (such as benzene rings).

Specific examples thereof include indolyl, isoindolyl, 1H-indazolyl, benzofuranyl(-2-yl), isobenzofuranyl, benzothienyl(-2-yl), isobenzothienyl, benzindazolyl, benzoxazolyl(-2-yl), 1,2-benzisoxazolyl, benzothiazolyl(-2-yl), 1,2-benzisothiazolyl, 2H-benzopyranyl (-3-yl), (1H—) benzimidazolyl(-2-yl), 1H-benzotriazolyl, 4H-1,4-benzoxazinyl, 4H-1,4-benzothiazinyl, quinolyl, isoquinolyl, cinnolinyl, quinazolinyl, quinoxalinyl, phthalazinyl, naphthylizinyl, purinyl, pteridinyl, carbazolyl, carbolinyl, acridinyl, phenoxazinyl, phenothiazinyl, phenazinyl, phenoxathinyl, thianthrenyl, phenanthridinyl, phenanthrolinyl, indolizinyl, (4,5,6,7-)tetrahydrothiazolo[5,4-c]pyridyl(-2-yl), (4,5,6,7-) tetrahydrothieno[3,2-c]pyridyl, (1,2,3,4-) tetrahydroisoquinolyl(-6-yl), thiazolo[5,4-c]pyridyl(-2-yl), pyrrolo[1,2-b] pyridazinyl, pyrazo[1,5-a]pyridyl, imidazo[1,2-a]pyridyl, imidazo[1,5-a]pyridyl, imidazo[1,2-b]pyridazinyl, imidazo [1,5-a]pyrimidinyl, [1,2,4]triazolo[4,3-a]pyridyl, 1,2,4-triazolo[4,3-b]pyridazinyl, chromenyl (2H-chromenyl), 1H-pyrazolo[3,4-b]pyridyl, and [1,2,4]triazolo[1,5a]pyrimidinyl (Preferred embodiments are indicated in the parenthesis "( )").

Examples thereof also include partially hydrogenated fused aromatic heterocyclic groups and the like, such as tetrahydroquinolinyl, tetrahydroisoquinolinyl, tetrahydrobenzoxazepinyl, tetrahydrobenzoazepinyl, tetrahydronaphthpyridinyl, tetrahydroquinoxalinyl, chromanyl, dihydrobenzoxazinyl, 3,4-dihydro-2H-1,4-benzothiazinyl, dihydrobenzothiazolyl, 3,4-dihydro-2H-1,4-benzoxazinyl, isochromanyl, indolinyl, pteridinyl, 2,3-dihydrobenzo[b][1,4]dioxinyl, 1,2,3,4-tetrahydro-1-methylquinolinyl, 1,3-dihydro-1-oxoisobenzofuranyl, and 6,7,8,9-tetrahydro-5H-cyclohepta[b]pyridyl.

Examples of the "non-aromatic heterocyclic groups" include three- to eight-membered saturated and unsaturated non-aromatic heterocyclic groups such as azetidinyl, oxiranyl, oxetanyl, thietanyl, pyrrolidinyl, tetrahydrofuryl, thiolanyl, pyrazolinyl, pyrazolidinyl, piperidyl, tetrahydropyranyl, piperadinyl, morpholinyl, oxazolinyl, thiazolinyl, thiomorpholinyl, and quinuclidinyl.

In the "substituted or unsubstituted $C_{1-6}$ alkoxy group", examples of the $C_{1-6}$ alkoxy groups include a methoxy group, ethoxy group, propoxy group, isopropoxy group, butoxy group, isobutoxy group, sec-butoxy group, tert-butoxy group, pentyloxy group, isopentyloxy group, 3-pentyloxy group, tert-pentyloxy group, neopentyloxy group, 2-methylbutoxy group, 1,2-dimethylpropoxy group, 1-ethylpropoxy group, hexyloxy group, cyclopropyloxy group, cyclobutyloxy group, cyclopentyloxy group, cyclohexyloxy group, cyclopropylmethyloxy group, 1-cyclopropylethyloxy group, 2-cyclopropylethyloxy group, cyclobutylmethyloxy group, 2-cyclobutylethyloxy group, and cyclopentylmethyloxy group.

In the "substituted or unsubstituted $C_{1-6}$ alkoxycarbonyl group", examples of the $C_{1-6}$ alkoxycarbonyl groups include a methoxycarbonyl group, ethoxycarbonyl group, propoxycarbonyl group, isopropoxycarbonyl group, butoxycarbonyl group, isobutoxycarbonyl group, sec-butoxycarbonyl group, tert-butoxycarbonyl group, pentyloxycarbonyl group, isopentyloxycarbonyl group, neopentyloxycarbonyl group, tert-pentyloxycarbonyl group, hexyloxycarbonyl group, cyclopropyloxycarbonyl group, cyclobutyloxycarbonyl group, cyclopentyloxycarbonyl group, cyclohexyloxycarbonyl group, cyclopropylmethyloxycarbonyl group, 1-cyclopropylethyloxycarbonyl group, 2-cyclopropylethyloxycarbonyl group, cyclobutylmethyloxycarbonyl group, 2-cyclobutylethyloxycarbonyl group and cyclopentylmethyloxycarbonyl group.

In the "amino group which is optionally mono- or di-substituted with a substituted or unsubstituted $C_{1-6}$ alkyl group", the amino group which may be mono- or di-substituted with a $C_{1-6}$ alkyl group means an amino group in which one or two hydrogen atoms of the amino group may be substituted with the above-mentioned "$C_{1-6}$ alkyl group". Specific examples thereof include an amino group, methylamino group, ethylamino group, propylamino group, isopropylamino group, butylamino group, isobutylamino group, pentylamino group, isopentylamino group, hexylamino group, isohexylamino group, dimethylamino group, diethylamino group, dipropylamino group, diisopropylamino group, dibutylamino group, dipentylamino group, ethylmethylamino group, methylpropylamino group, ethylpropylamino group, butylmethylamino group, butylethylamino group, and butylpropylamino group.

Examples of the protective group for the "protected or unprotected hydroxyl group" include alkyl protective groups such as a methyl group, tert-butyl group, benzyl group, trityl group, and methoxymethyl group; silyl protective groups such as a trimethylsilyl group and tert-butyldimethylsilyl group; acyl protective groups such as a formyl group, acetyl group, and benzoyl group; and carbonate protective groups such as a methoxycarbonyl group and benzyloxycarbonyl group.

Examples of the protective group for the "protected or unprotected carboxyl group" include alkylester protective groups such as a methyl group, ethyl group, tert-butyl group, benzyl group, diphenylmethyl group, and trityl group; and silyl ester protective groups such as a trimethylsilyl group and tert-butyldimethylsilyl group.

In the "carbamoyl group which is optionally mono- or di-substituted with a substituted or unsubstituted $C_{1-6}$ alkyl group", the carbamoyl group which may be mono- or di-substituted with a $C_{1-6}$ alkyl group means a carbamoyl group in which one or two hydrogen atoms bonded to the nitrogen atom of the carbamoyl group may be substituted with the above-mentioned "$C_{1-6}$ alkyl group". Specific examples thereof include a carbamoyl group, methylcarbamoyl group, ethylcarbamoyl group, propylcarbamoyl group, isopropylcarbamoyl group, cyclopropylcarbamoyl group, butylcarbamoyl group, isobutylcarbamoyl group, pentylcarbamoyl group, isopentylcarbamoyl group, hexylcarbamoyl group, isohexylcarbamoyl group, dimethylcarbamoyl group, diethylcarbamoyl group, dipropylcarbamoyl group, diisopropylcarbamoyl group, dibutylcarbamoyl group, dipentylcarbamoyl group, ethylmethylcarbamoyl group, methylpropylcarbamoyl group, ethylpropylcarbamoyl group, butylmethylcarbamoyl group, butylethylcarbamoyl group, and butylpropylcarbamoyl group.

Examples of the "$C_{1-6}$ alkanoyl group" include a formyl group, acetyl group, propionyl group, butyryl group, isobutyryl group, valeryl group, isovaleryl group, pivaloyl group, and hexanoyl group.

Examples of the "$C_{1-6}$ alkylthio group" include a methylthio group, ethylthio group, propylthio group, isopropylthio group, butylthio group, isobutylthio group, sec-butylthio group, tert-butylthio group, pentylthio group, isopentylthio group, tert-pentylthio group, neopentylthio group, 2-methylbutylthio group, 1,2-dimethylpropylthio group, 1-ethylpropylthio group, hexylthio group, cyclopropylthio group, cyclobutylthio group, cyclopentylthio group, cyclohexylthio group, cyclopropylmethylthio group, 1-cyclopropylethylthio group, 2-cyclopropylethylthio group, cyclobutylmethylthio group, 2-cyclobutylethylthio group, and cyclopentylmethylthio group.

Examples of the "$C_{1-6}$ alkylsulfinyl group" include a methylsulfinyl group, ethylsulfinyl group, propylsulfinyl group, isopropylsulfinyl group, butylsulfinyl group, isobutylsulfinyl group, sec-butylsulfinyl group, tert-butylsulfinyl group, pentylsulfinyl group, isopentylsulfinyl group, tert-pentylsulfinyl group, neopentylsulfinyl group, 2-methylbutylsulfinyl group, 1,2-dimethylpropylsulfinyl group, 1-ethylpropylsulfinyl group, hexylsulfinyl group, cyclopropylsulfinyl group, cyclobutylsulfinyl group, cyclopentylsulfinyl group, cyclohexylsulfinyl group, cyclopropylmethylsulfinyl group, 1-cyclopropylethylsulfinyl group, 2-cyclopropylethylsulfinyl group, cyclobutylmethylsulfinyl group, 2-cyclobutylethylsulfinyl group, and cyclopentylmethylsulfinyl group.

Examples of the "$C_{1-6}$ alkylsulfonyl group" include a methylsulfonyl group, ethylsulfonyl group, propylsulfonyl group, isopropylsulfonyl group, butylsulfonyl group, isobutylsulfonyl group, sec-butylsulfonyl group, tert-butylsulfonyl group, pentylsulfonyl group, isopentylsulfonyl group, tert-pentylsulfonyl group, neopentylsulfonyl group, 2-methylbutylsulfonyl group, 1,2-dimethylpropylsulfonyl group, 1-ethylpropylsulfonyl group, hexylsulfonyl group, cyclopropylsulfonyl group, cyclobutylsulfonyl group, cyclopentylsulfonyl group, cyclohexylsulfonyl group, cyclopropylmethylsulfonyl group, 1-cyclopropylethylsulfonyl group, 2-cyclopropylethylsulfonyl group, cyclobutylmethylsulfonyl group, 2-cyclobutylethylsulfonyl group, and cyclopentylmethylsulfonyl group.

In the "sulfamoyl group which may be mono- or di-substituted with a substituted or unsubstituted $C_{1-6}$ alkyl group", the sulfamoyl group which may be mono- or di-substituted with a $C_{1-6}$ alkyl group means a sulfamoyl group in which one or two hydrogen atoms bonded to the nitrogen atom of the sulfamoyl group may be substituted with the above-mentioned "$C_{1-6}$ alkyl group". Specific examples thereof include a sulfamoyl group, methylsulfamoyl group, ethylsulfamoyl group, propylsulfamoyl group, isopropylsulfamoyl group, cyclopropylsulfamoyl group, butylsulfamoyl group, isobutylsulfamoyl group, pentylsulfamoyl group, isopentylsulfamoyl group, hexylsulfamoyl group, isohexylsulfamoyl group, dimethylsulfamoyl group, diethylsulfamoyl group, dipropylsulfamoyl group, diisopropylsulfamoyl group, dibutylsulfamoyl group, dipentylsulfamoyl group, ethylmethylsulfamoyl group, methylpropylsulfamoyl group, ethylpropylsulfamoyl group, butylmethylsulfamoyl group, butylethylsulfamoyl group, and butylpropylsulfamoyl group.

Examples of the "substituents" of the "substituted or unsubstituted hydrocarbon group", the "substituted or unsubstituted heterocyclic group", the "substituted or unsubstituted $C_{1-6}$ alkoxy group", the "substituted or unsubstituted $C_{1-6}$ alkoxycarbonyl group", the "amino group which may be mono- or di-substituted with a substituted or unsubstituted $C_{1-6}$ alkyl group", the "carbamoyl group which may be mono- or di-substituted with a substituted or unsubstituted $C_{1-6}$ alkyl group", or the "sulfamoyl group which may be mono- or di-substituted with a substituted or unsubstituted $C_{1-6}$ alkyl group" in $R^1$ include (a) alkyl, alkenyl, alkynyl, aryl, cycloalkyl, and cycloalkenyl; (b) heterocyclic groups; (c) amino; (d) imidoyl, amidino, hydroxyl, thiol, and oxo; (e) halogen atoms such as fluorine, chlorine, bromine, and iodine, cyano, and nitro; (f) carboxyl; and (g) carbamoyl, thiocarbamoyl, sulfonyl, sulfinyl, sulfide, and acyl. Among (a) to (g) mentioned above, the groups except for (e) may further have a substituent. The above groups in $R^1$ may be optionally substituted with 1 to 5 such substituents. Examples of the substituents (a) to (g) will now be described specifically.

(a) The alkyl, alkenyl, alkynyl, aryl, cycloalkyl, and cycloalkenyl groups may be any of the "alkyl groups", "alkenyl groups", "alkynyl groups", "aryl groups", "cycloalkyl groups" and "cycloalkenyl groups" mentioned as examples of the "hydrocarbon group" for $R^1$. The preferred groups are $C_{1-6}$ alkyl groups, $C_{2-6}$ alkenyl groups, $C_{2-6}$ alkynyl groups, $C_{6-14}$ aryl groups, $C_{3-7}$ cycloalkyl groups, and $C_{3-6}$ cycloalkenyl groups.

These groups may further include an optional substituent RI (wherein RI represents a group selected from $C_{1-6}$ alkoxy, $C_{1-6}$ alkoxycarbonyl, carboxyl, carbamoyl which may be mono- or di-substituted with $C_{1-6}$ alkyl, halogen, $C_{1-6}$ alkyl, halogenated $C_{1-6}$ alkyl, amino which may be mono- or di-substituted with $C_{1-6}$ alkyl, $C_{2-6}$ alkenoylamino, nitro, hydroxyl, phenyl, phenoxy, benzyl, pyridyl, oxo, cyano, and amidino).

(b) The heterocyclic group may be any of the "aromatic heterocyclic groups" and "non-aromatic heterocyclic groups" mentioned as examples of the "heterocyclic group" for $R^1$. More preferably, the heterocyclic groups include (i) "five- or six-membered, monocyclic aromatic heterocyclic groups", (ii) "eight- to twelve-membered, fused, aromatic heterocyclic groups", and (iii) "three- to eight-membered, saturated or unsaturated, non-aromatic heterocyclic groups" which contain 1 to 4 heteroatoms selected from a nitrogen atom, an oxygen atom, and a sulfur atom in addition to carbon atoms.

These groups may further include 1 to 3 optional substituents $R^{11}$ (wherein $R^{11}$ represents a halogen atom such as fluorine, chlorine, bromine, or iodine; a $C_{1-6}$ alkyl group, a $C_{1-6}$ alkanoyl group, or a benzoyl group).

(c) The "substituted or unsubstituted amino group" may be, for example, an amino group which may be mono- or di-substituted with a substituent RIII (wherein RIII represents a group selected from $C_{1-6}$ alkyl, $C_{1-6}$ alkanoyl, $C_{2-6}$ alkenoyl, benzoyl, benzyl, phenyl, pyridyl which may be substituted with a group selected from $C_{1-6}$ alkyl, halogen, and trifluoromethyl, and $C_{1-6}$ alkoxycarbonyl which may be substituted with 1 to 5 halogen atoms), or three- to eight-membered monocyclic amino group which may be substituted with a group selected from $C_{1-6}$ alkyl, $C_{7-10}$ aralkyl, and $C_{6-10}$ aryl.

(d) Examples of the substituents in "the substituted or unsubstituted imidoyl group, the substituted or unsubstituted amidino group, the substituted or unsubstituted hydroxyl group, and the substituted or unsubstituted thiol group" include RIII (wherein RIII represents a group selected from $C_{1-6}$ alkyl, $C_{1-6}$ alkanoyl, $C_{2-6}$ alkenoyl, benzoyl, benzyl, phenyl, pyridyl which is optionally substituted with a group selected from $C_{1-6}$ alkyl, halogen, and trifluoromethyl, and $C_{1-6}$ alkoxycarbonyl which may be substituted with 1 to 5 halogen atoms) described in (c) described above.

Accordingly, examples of (d) include $C_{1-6}$ alkylimidoyl groups, a formimidoyl group, an amidino group, $C_{1-6}$ alkoxy groups, a benzyloxy group, $C_{1-6}$ alkanoyloxy groups, a phenoxy group, pyridyloxy groups which may be substituted with a group selected from $C_{1-6}$ alkyl, halogen, and trifluoromethyl, and an oxo group.

Examples of (e) include halogen atoms such as fluorine, chlorine, bromine, and iodine; a cyano group; and a nitro group.

(f) The "substituted or unsubstituted carboxyl groups" include a carboxyl group, $C_{1-6}$ alkoxycarbonyl groups, $C_{7-12}$ aryloxycarbonyl groups, and $C_{6-10}$ aryl-$C_{1-4}$ alkoxycarbonyl groups. The aryl group in such (f) may be further substituted with a substituent RIV. RIV represents an amino group which may be mono- or di-substituted with a substituent RII' (wherein RII' represents a $C_{1-6}$ alkyl group, a $C_{1-6}$ alkanoyl group, or a benzoyl group); a halogen atom; a hydroxyl group; a nitro group; a cyano group; a $C_{1-6}$ alkyl group which may be substituted with 1 to 5 halogen atoms; or an alkoxy group which may be substituted with 1 to 5 halogen atoms.

(g) Examples of "the substituted or unsubstituted carbamoyl group, the substituted or unsubstituted thiocarbamoyl group, the substituted or unsubstituted sulfonyl group, the substituted or unsubstituted sulfinyl group, the substituted or unsubstituted sulfide group, and the substituted or unsubstituted acyl group" include groups represented by —CONRgRg', —CSNRgRg', —$SO_y$-Rg, or —CO-Rg, wherein Rg represents a hydrogen atom or a substituent RV (wherein RV represents $C_{1-6}$ alkyl, $C_{3-6}$ cycloalkyl, $C_{6-10}$ aryl, $C_{7-10}$ aralkyl, or a heterocyclic group; the heterocyclic group is any one of (i) five- or six-membered monocyclic aromatic heterocyclic groups, (ii) eight- to twelve-membered fused aromatic heterocyclic groups, and (iii) three- to eight-membered saturated or unsaturated non-aromatic heterocyclic groups which contain 1 to 4 heteroatoms selected from an oxygen atom, a sulfur atom, and a nitrogen atom in addition to the carbon atoms; and the alkyl, the cycloalkyl, the aryl, the aralkyl, or the heterocyclic group may be further substituted with 1 to 5 substituents RIV of (f) described above); Rg' is a hydrogen atom or a group selected from $C_{1-6}$ alkyl groups, $C_{3-6}$ cycloalkyl groups, and $C_{7-10}$ aralkyl groups; and y is 0, 1, or 2.

[1-1-a]

In the compounds represented by formula (I) which is used for the pharmaceutical composition of embodiment [1], examples of $R^1$ preferably include halogen atoms, substituted or unsubstituted hydrocarbon groups, substituted or unsubstituted heterocyclic groups, and substituted or unsubstituted $C_{1-6}$ alkoxy groups. Examples of the "substituted or unsubstituted hydrocarbon group" and the "substituted or unsubstituted heterocyclic group" include (1) $C_{1-10}$ alkyl groups; (2) $C_{2-6}$ alkenyl groups; (3) $C_{2-6}$ alkynyl groups; (4) $C_{3-9}$ cycloalkyl groups; (5) $C_{3-6}$ cycloalkenyl groups; (6) $C_{4-6}$ cycloalkanedienyl groups; (7) $C_{6-14}$ aryl groups; (8) heterocyclic groups each containing 1 to 4 hetero-atoms selected from an oxygen atom, a sulfur atom, and a nitrogen atom in addition to the carbon atoms, the heterocyclic groups being selected from (i) five- or six-membered, monocyclic aromatic heterocyclic groups, (ii) eight- to twelve-membered, fused aromatic heterocyclic groups, and (iii) "three- to eight-membered, saturated or unsaturated, non-aromatic heterocyclic groups; and (9) substituted or unsubstituted $C_{1-6}$ alkoxy groups. Each of the groups in (1) to (9) may be either unsubstituted or substituted with 1 to 5 substituents in a class selected from (a-1) to (g-1) as described below.

The classes are as follows.

(a-1): Substituents include $C_{1-6}$ alkyl groups, $C_{2-6}$ alkenyl groups, $C_{2-6}$ alkynyl groups, $C_{6-14}$ aryl groups, $C_{3-7}$ cycloalkyl groups, and $C_{3-6}$ cycloalkenyl groups. These substituents may be further substituted with a substituent RI (wherein RI represents a group selected from $C_{1-6}$ alkoxy, $C_{1-6}$ alkoxycarbonyl, carboxyl, carbamoyl which is optionally mono- or di-substituted with $C_{1-6}$ alkyl, halogen, $C_{1-6}$ alkyl, halogenated $C_{1-6}$ alkyl, amino which is optionally mono- or di-substituted with $C_{1-6}$ alkyl, $C_{2-6}$ alkenoylamino, nitro, hydroxyl, pyridyl, oxo, cyano, and amidino).

(b-1): Substituents are any one of heterocyclic groups of (i) five- or six-membered, monocyclic aromatic heterocyclic groups, (ii) eight- to twelve-membered, fused aromatic heterocyclic groups, and (iii) "three- to eight-membered, saturated or unsaturated, non-aromatic heterocyclic groups which contain 1 to 4 heteroatoms selected from an oxygen atom, a sulfur atom, and a nitrogen atom in addition to the carbon atoms. These heterocyclic groups may be further substituted with a substituent RII (wherein RII represents a group selected from halogen atoms such as fluorine, chlorine, bromine, and iodine; $C_{1-6}$ alkyl, $C_{1-6}$ alkanoyl, and benzoyl).

(c-1): Substituents in (c-1) include an amino group which may be substituted with a substituent RIII (wherein RIII represents a group selected from $C_{1-6}$ alkyl, $C_{1-6}$ alkanoyl, $C_{2-6}$ alkenoyl, benzoyl, benzyl, phenyl, pyridyl which may be substituted with a group selected from $C_{1-6}$ alkyl, halogen, and trifluoromethyl, and $C_{1-6}$ alkoxycarbonyl which may be substituted with 1 to 5 halogen atoms), or a three- to eight-membered monocyclic amino group which may be substituted with a group selected from $C_{1-6}$ alkyl, $C_{7-10}$ aralkyl, and $C_{6-10}$ aryl.

(d-1): Substituents in (d-1) include an imidoyl group, an amidino group, a hydroxyl group, a thiol group, and an oxo group. These substituents may be substituted with groups selected from the substituents RIII described in (c-1) described above.

(e-1): Substituents in (e-1) include halogen atoms such as fluorine, chlorine, bromine, and iodine, a cyano group, and a nitro group.

(f-1): Substituents in (f-1) include a carboxyl group, $C_{1-6}$ alkoxycarbonyl groups, $C_{7-12}$ aryloxycarbonyl groups, and $C_{6-10}$ aryl-$C_{1-4}$ alkoxycarbonyl groups. The aryl groups in (f-1) may be further substituted with a substituent RIV' (wherein RIV' represents amino which may be mono- or di-substituted with groups selected from RIII described in (c-1) described above; $C_{1-6}$ alkyl or $C_{1-6}$ alkoxy which may be substituted with 1 to 5 halogen atoms; halogen atoms; hydroxyl; nitro; and cyano).

(g-1): Substituents in (g-1) include groups represented by —CONRgRg', —CSNRgRg', —CO-Rg, and —$SO_y$-Rg wherein Rg represents a hydrogen atom or a substituent RV (wherein RV represents $C_{1-6}$ alkyl, $C_{3-6}$ cycloalkyl, $C_{6-10}$ aryl, $C_{7-10}$ aralkyl, or a heterocyclic group; the heterocyclic group is any one of (i) five- or six-membered monocyclic aromatic heterocyclic groups, (ii) eight- to twelve-membered fused aromatic heterocyclic groups, and (iii) three- to eight-membered saturated or unsaturated non-aromatic heterocyclic groups which contain 1 to 4 heteroatoms selected from an oxygen atom, a sulfur atom, and a nitrogen atom in addition to the carbon atoms; and the alkyl, the cycloalkyl, the aryl, the aralkyl, or the heterocyclic group may be further substituted with 1 to 5 substituents RIV of (f) described above); Rg' is a hydrogen atom or a group selected from $C_{1-6}$ alkyl groups, $C_{3-6}$ cycloalkyl groups, and $C_{7-10}$ aralkyl groups; and y is 0, 1, or 2.

In the groups listed in (a-1) to (g-1) described above, "particularly preferable groups" include substituents such as $C_{1-6}$ alkyl, $C_{2-6}$ alkenyl, $C_{2-6}$ alkynyl, halogen atoms, halogenated $C_{1-6}$ alkyl, cyano, amino, hydroxyl, carbamoyl, $C_{1-6}$ alkoxy, $C_{2-6}$ alkenyloxy, $C_{2-6}$ alkynyloxy, $C_{1-6}$ alkylthio, $C_{1-6}$ alkylsulfinyl, $C_{1-6}$ alkylsulfonyl, mono/di $C_{1-6}$ alkylamino, $C_{1-6}$ alkoxycarbonyl, $C_{2-6}$ alkanoyl, $C_{2-6}$ alkanoylamino, hydroxy-$C_{1-6}$ alkyl, $C_{1-6}$ alkoxy-$C_{1-6}$ alkyl, carboxy-$C_{1-6}$ alkyl, $C_{1-6}$ alkoxycarbonyl-$C_{1-6}$ alkyl, carbamoyl-$C_{1-6}$ alkyl, N—$C_{1-6}$ alkylcarbamoyl-$C_{1-6}$ alkyl, N,N-di $C_{1-6}$ alkylcarbamoyl-$C_{1-6}$ alkyl, phenyl, phenoxy, phenylthio, phenylsulfinyl, phenylsulfonyl, benzyl, benzoyl, morpholino, oxo, morpholinylcarbonyl, morpholinylsulfonyl, 5-trifluoromethylpyridin-2-yloxy, quinoxalin-2-yl, (pyridin-4-yl)methyl, 1,2,3-thiadiazolo-4-yl, 1H-pyrazolo-1-yl, and 4-chlorophenyl. The aromatic rings in these substituents may be further substituted with 1 to 5 substituents selected from halogen atoms, trifluoromethyl, cyano, hydroxyl, amino, nitro, carboxyl, carbamoyl, $C_{1-6}$ alkyl, $C_{1-6}$ alkoxy, mono/di $C_{1-6}$ alkylamino, di-$C_{1-6}$ alkylcarbamoyl, $C_{1-6}$ alkoxycarbonyl, N—$C_{1-6}$ alkylcarbamoyl, N,N-di $C_{1-6}$ alkylcarbamoyl, and $C_{2-6}$ alkenoylamino.

[1-1-b] Preferably, $R^1$ is a halogen atom, and (1) a $C_{1-6}$ alkyl group, (2) a $C_{2-6}$ alkenyl group, (7) a $C_{6-14}$ aryl group, and (9) a $C_{1-6}$ alkoxy group. Each group in (1), (2), (7), and (9) is optionally substituted with 1 to 5 substituents in a class selected from (a-1) to (g-1) in [1-1] described above (in particular, the substituents listed as "particularly preferable groups").

[1-1-c] More preferably, $R^1$ is a halogen atom (a fluorine atom, a chlorine atom, a bromine atom, or an iodine atom), and a $C_{1-6}$ alkyl group (in particular, $C_{1-4}$ alkyl group) or $C_{1-6}$ alkoxy group (in particular, $C_{1-4}$ alkoxy group) which may be substituted with 1 to 5 halogen atoms.

[1-1-d] Further preferably, $R^1$ is a halogen atom (particularly preferably, a fluorine atom or a chlorine atom), and a $C_{1-4}$ alkyl group or $C_{1-4}$ alkoxy group which is optionally substituted with 1 to 5 halogen atoms. More specifically, examples thereof include a fluorine atom, a chlorine atom, methyl, ethyl, propyl, isopropyl, butyl, isobutyl, sec-butyl, tert-butyl, trifluoromethyl, methoxy, ethoxy, propoxy, isopropoxy, butoxy, sec-butoxy, tert-butoxy, trifluoromethoxy, and tetrafluoroethoxy.

[1-1-e] Particularly preferably, $R^1$ is a fluorine atom, a chlorine atom, isobutyl, tert-butyl, trifluoromethyl, or tetrafluoroethoxy. Still more preferably, $R^1$ is trifluoromethyl.

[1-2] In the compounds represented by formula (I) which is used for the pharmaceutical composition of embodiment [1], n is an integer of 0 to 2. Preferably, n is 1 or 2, and more preferably, n is 1.

The substitution position of $R^1$ may be any position except for the condensation position of the five- or six-membered aryl ring or heteroaryl ring represented by "Cycle" in formula (I).

[1-2-1]

More preferably, when the "Cycle" is a six-membered ring, at least one of $R^1$'s is preferably bonded to the 4th position ($A_2$) in the clockwise direction from the condensation position close to the carbon atom of the cyclidene in the partial structural formula (wherein each of $A_1$ to $A_4$ is either CH or N) below.

[Ch. 1a]

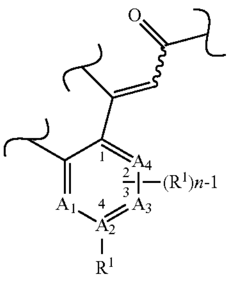

[1-2-1a]

For example, this position corresponds to the 7th position of a chroman ring, a pyridochroman ring, a 2,3-dihydroquinoline ring, or the like, which belongs to a skeleton in which m=1 and q=0, or an isochroman ring or the like, which belongs to a skeleton in which m=0 and q=1.

[1-2-1b]

This position corresponds to the 8th position of a 3,4-dihydrobenzo[b]oxepine ring or a 1,2,3,4-tetrahydrobenzo[b]azepine ring, which belongs to a skeleton in which m=2 and q=0, or a 3,4-dihydrobenzo[b]isooxepine ring or the like, which belongs to a skeleton in which m=1 and q=1.

[1-2-2]

When the "Cycle" is a five-membered ring, at least one of $R^1$'s is preferably bonded to the 3rd position ($B_2$) in the clockwise direction from the condensation position close to the carbon atom of the cyclidene in the partial structural formula (wherein each of $B_1$ to $B_3$ is any one of CH, N, O, and S) below.

[Ch. 1b]

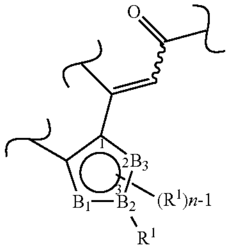

[1-2-2a]

For example, this position corresponds to the 6th position of a 2,3-dihydro-4H-pyrano[2,3b]pyrrole ring or a 2,3-dihydro-thieno[2,3-b]pyran ring, which belongs to a skeleton in which m=1 and q=0. This position corresponds to the 2nd position of a 5,6-dihydro-furo[2,3-b]pyran ring, which belongs to a skeleton in which m=1 and q=0.

In the all embodiments [1-2] to [1-2-2b], at least one of $R^1$'s is preferably a fluorine atom, a chlorine atom, isobutyl, tert-butyl, trifluoromethyl, or tetrafluoroethoxy. More preferably, at least $R^1$ bonded to $A_2$ or $B_2$ is a fluorine atom, a chlorine atom, isobutyl, tert-butyl, trifluoromethyl, or tetrafluoroethoxy, and particularly preferably, trifluoromethyl.

[1-3] In the compounds represented by formula (I) which is used for the pharmaceutical composition of embodiment [1], $R^2$ is a halogen atom, a substituted or unsubstituted amino group, a substituted or unsubstituted hydrocarbon group, a substituted or unsubstituted aromatic heterocyclic group, or an oxo group.

Examples of the "halogen atom" include a fluorine atom, a chlorine atom, a bromine atom, and an iodine atom.

Examples of the "substituted or unsubstituted amino group" include amino groups which may be mono- or di-substituted with a substituent RIII (wherein RIII represents a group selected from $C_{1-6}$ alkyl, $C_{1-6}$ alkanoyl, $C_{2-6}$ alkenoyl, benzoyl, and $C_{1-6}$ alkoxycarbonyl which is optionally substituted with 1 to 5 halogen atoms), or three- to eight-membered monocyclic amino group which may be substituted with a group selected from $C_{1-6}$ alkyl, $C_{7-10}$ aralkyl, and $C_{6-10}$ aryl.

Aromatic rings of these substituents may further include 1 to 3 optional substituents selected from halogen atoms, trifluoromethyl, cyano, hydroxyl, amino, nitro, carboxyl, carbamoyl, $C_{1-6}$ alkyl, $C_{1-6}$ alkoxy, mono/di $C_{1-6}$ alkylamino, di-$C_{1-6}$ alkylcarbamoyl, $C_{1-6}$ alkoxycarbonyl, N—$C_{1-6}$ alkylcarbamoyl, N,N-di $C_{1-6}$ alkylcarbamoyl, and $C_{2-6}$ alkenoylamino.

The "substituted or unsubstituted hydrocarbon group" represents the same meaning as described in $R^1$ of embodiment [1-1] described above. Examples of the "hydrocarbon group" include alkyl groups (for example, $C_{1-10}$ (more preferably $C_{1-6}$) alkyl groups), alkenyl groups (for example, $C_{2-6}$ alkenyl groups), cycloalkyl groups (for example, $C_{3-9}$ cycloalkyl groups), cycloalkenyl groups (for example, $C_{3-6}$ cycloalkenyl groups), and aryl groups.

The "aromatic heterocyclic group" of the "substituted or unsubstituted aromatic heterocyclic group" represents the same meaning as described in $R^1$ described above.

Substituents of these groups are the same groups as those listed as "particularly preferable groups" in the groups described in (a-1) to (g-1) in $R^1$ described above.

[1-3-a] In the compounds represented by formula (I) which is used for the pharmaceutical composition of embodiment [1], $R^2$ is preferably a fluorine atom, a chlorine atom, an amino group which is optionally mono-substituted with a substituent RIII, a $C_{1-6}$ alkyl group, or a phenyl group. More preferably, $R^2$ is a $C_{1-6}$ alkyl group (in particular, a $C_{1-4}$ alkyl group such as methyl, ethyl, propyl, isopropyl, butyl, isobutyl, sec-butyl, or tert-butyl). Further preferably, $R^2$ is methyl.

[1-4] In the compounds represented by formula (I) which is used for the pharmaceutical composition of embodiment [1], p is an integer of 0 to 2. Preferably, p is 0 or 2.

[1-4-a] However, in the compounds represented by formula (I), when $R^2$ is a $C_{1-6}$ alkyl group (in particular, a $C_{1-4}$ alkyl group such as methyl, ethyl, propyl, isopropyl, butyl, isobutyl, sec-butyl, or tert-butyl), p is preferably 1 or 2, and more preferably 2. Alternatively, two geminal or vicinal $R^2$'s may bind to each other to form a $C_{2-6}$ alkylene group, and form a cyclo ring group together with the carbon atom to which the two $R^2$'s are bonded. For example, a cyclopropane ring, a cyclobutane ring, a cyclopentane ring, or a cyclohexane ring can be formed. An example of the case where a carbon atom of a chroman ring forms such a cyclo ring is a 2,2-cyclobutyl chroman ring.

[1-4-b] However, in the compounds represented by formula (I), when $R^2$ is a fluorine atom, p is preferably 1 or 2, and more preferably 2.

[1-4-c] In the compounds represented by formula (I), when $R^2$ is an amino group which may be mono-substituted with a substituent RIII or an oxo group, p is preferably 1 or 2, and more preferably 1.

[1-5] In the compounds represented by formula (I) which is used for the pharmaceutical composition of embodiment [1], m is 0 to 2, and preferably 1 or 2. In either case, the carbon atom or atoms located at the position corresponding to m may be substituted with $R^2$.

[1-6] In the compounds represented by formula (I) which is used for the pharmaceutical composition of embodiment [1], $X_1$ represents an oxygen atom, —$NR^3$— (wherein $R^3$ is a hydrogen atom, a substituted or unsubstituted hydrocarbon group, a substituted or unsubstituted heterocyclic group, or a substituted or unsubstituted acyl group), or —S(O)r- (wherein r is an integer of 0 to 2).

When $R^3$ is a substituted or unsubstituted hydrocarbon group or a substituted or unsubstituted heterocyclic group, examples of the hydrocarbon group or the heterocyclic group include those listed in the "substituted or unsubstituted hydrocarbon groups" or the "substituted or unsubstituted heterocyclic groups", respectively, in [1-1] mentioned above. These groups may be substituted with 1 to 3 "substituents" listed in (a) to (g).

When $R^3$ is a "substituted or unsubstituted acyl group", $R^3$ is a group represented by —CO—$R^9$ (wherein $R^9$ is the same as the above) in (g) of [1-1] described above.

[1-6-a] In the compounds represented by formula (I) which is used for the pharmaceutical composition of embodiment [1], preferably, $X_1$ is an oxygen atom or —$NR^{3'}$— (wherein $R^{3'}$ is a substituted or unsubstituted hydrocarbon group, a substituted or unsubstituted heterocyclic group, or a substituted or unsubstituted acyl group all of which is defined in $R^3$). More preferably, $X_1$ is an oxygen atom.

[1-6-b] When $X_1$ is —$NR^{3'}$—, examples of the "substituted or unsubstituted hydrocarbon group" or the "substituted or unsubstituted heterocyclic group" of $R^{3'}$ preferably include (1) $C_{1-10}$ alkyl groups; (2) $C_{2-6}$ alkenyl groups; (3) $C_{2-6}$ alkynyl groups; (4) $C_{3-9}$ cycloalkyl groups; (5) $C_{3-6}$ cycloalkenyl groups; (6) $C_{4-6}$ cycloalkanedienyl groups; (7) $C_{6-14}$ aryl groups; and (8) heterocyclic groups each containing 1 to 4 hetero-atoms selected from an oxygen atom, a sulfur atom, and a nitrogen atom in addition to the carbon atoms, the heterocyclic groups being selected from (i) five- or six-membered, monocyclic aromatic heterocyclic groups, (ii) eight- to twelve-membered, fused aromatic heterocyclic groups, and (iii) "three- to eight-membered, saturated or unsaturated, non-aromatic heterocyclic groups, and each of the groups in (1) to (8) may be either unsubstituted or optionally substituted with 1 to 5 substituents in a class selected from (a-1) to (g-1) described in [1-1-a] above.

When $X_1$ is —$NR^{3'}$—, examples of the "substituted or unsubstituted acyl group" of $R^{3'}$ preferably include groups represented by —CO—Rg" (wherein Rg" represents a substituent RV (wherein RV represents $C_{1-6}$ alkyl, $C_{3-6}$ cycloalkyl, $C_{6-10}$ aryl, $C_{7-10}$ aralkyl, or a heterocyclic group; the heterocyclic group is any one of (i) five- or six-membered monocyclic aromatic heterocyclic groups, (ii) eight- to twelve-membered fused aromatic heterocyclic groups, and (iii) three- to eight-membered saturated or unsaturated non-aromatic heterocyclic groups which contain 1 to 4 heteroatoms selected from an oxygen atom, a sulfur atom, and a nitrogen atom in addition to the carbon atoms; and the alkyl, the cycloalkyl, the aryl, the aralkyl, or the heterocyclic group may be further substituted with 1 to 5 substituents RIV of (f) described above).

[1-6-c] More preferably, when $X_1$ is —$NR^{3'}$—, examples of the "substituted or unsubstituted hydrocarbon group" or the "substituted or unsubstituted heterocyclic group" of $R^{3'}$ include (1') $C_{1-6}$ alkyl groups; (2') $C_{2-6}$ alkenyl groups; (4') $C_{3-6}$ cycloalkyl groups; (7') $C_{6-14}$ aryl groups; and (8') heterocyclic groups each containing 1 heteroatom or 2 heteroatoms selected from an oxygen atom, a sulfur atom, and a nitrogen atom in addition to the carbon atoms, the heterocyclic groups being selected from (i) five- or six-membered, monocyclic aromatic heterocyclic groups, (ii) eight- to twelve-membered, fused aromatic heterocyclic groups, and (iii) "three- to eight-membered, saturated or unsaturated, non-aromatic heterocyclic groups, and each of the groups in (1'), (2'), (4'), (7'), and (8') may be mono-substituted with a substituent in a class selected from the substituents (a-1) to (g-1) (in particular, the substituents listed as "particularly preferable groups" in (a-1) to (g-1)).

More preferably, when $X_1$ is —$NR^{3'}$—, examples of the "substituted or unsubstituted acyl group" of $R^{3'}$ include groups represented by —CO-Rg''' (wherein Rg''' represents a substituent RV' (wherein RV' represents $C_{1-6}$ alkyl, $C_{3-6}$ cycloalkyl, $C_{6-10}$ aryl, or a heterocyclic group; the heterocyclic group is any one of (i) five- or six-membered monocyclic aromatic heterocyclic groups, (ii) eight- to twelve-membered fused aromatic heterocyclic groups, and (iii) three- to eight-membered saturated or unsaturated non-aromatic heterocyclic groups which contain 1 heteroatom or 2 heteroatoms selected from an oxygen atom, a sulfur atom, and a nitrogen atom in addition to the carbon atoms; and the alkyl, the cycloalkyl, the aryl, or the heterocyclic group may be further substituted with 1 to 5 substituents RIV of (f) described above).

[1-6-d] Further preferably, when $X_1$ is —$NR^{3'}$—, examples of the "substituted or unsubstituted hydrocarbon group" or the "substituted or unsubstituted heterocyclic group" of $R^{3'}$ include (1") $C_{1-6}$ alkyl groups; (4") $C_{3-6}$ cycloalkyl groups; (7") $C_{6-14}$ aryl groups; and (8") heterocyclic groups each containing a heteroatom selected from an oxygen atom, a sulfur atom, and a nitrogen atom in addition to the carbon atoms, the heterocyclic groups being selected from (i) five- or six-membered, monocyclic aromatic heterocyclic groups, (ii) eight- to twelve-membered, fused aromatic heterocyclic groups, and (iii) "three- to eight-membered, saturated or unsaturated, non-aromatic heterocyclic groups, and each of the groups in (1"), (4"), (7"), and (8") may be mono-substituted with a substituent in a class selected from the substituents (a-1) to (g-1) (in particular, the substituents listed as "particularly preferable groups" in (a-1) to (g-1)).

Further preferably, when $X_1$ is —$NR^{3'}$—, examples of the "substituted or unsubstituted acyl group" of $R^{3'}$ include groups represented by —CO—Rg"" (wherein Rg"" represents a substituent RV" (wherein RV" represents $C_{1-6}$ alkyl, $C_{3-6}$ cycloalkyl, $C_{6-10}$ aryl, or a heterocyclic group; the heterocyclic group is any one of (i) five- or six-membered monocyclic aromatic heterocyclic groups, (ii) eight- to twelve-membered fused aromatic heterocyclic groups, and (iii) three- to eight-membered saturated or unsaturated non-aromatic heterocyclic groups which contain a heteroatom selected from an oxygen atom, a sulfur atom, and a nitrogen atom in addition to the carbon atoms; and the alkyl, the cycloalkyl, the aryl, or the heterocyclic group may be further substituted with 1 to 3 substituents RIV of (f) described above).

[1-6-e] Particularly preferably, when $X_1$ is —$NR^{3'}$—, examples of the "substituted or unsubstituted hydrocarbon group" or the "substituted or unsubstituted heterocyclic group" of $R^{3'}$ include (1''') methyl and (1''') ethyl, (4''') cyclohexyl, (7''') phenyl and (7''') naphthyl (e.g., naphthalen-1-yl and naphthalen-2-yl), and (8''') pyridyl (e.g., pyridin-2-yl, pyridin-3-yl, and pyridin-4-yl) which may be substituted with a halogen atom. More specifically, examples thereof include methyl, trifluoromethyl, ethyl, cyclohexyl, 2-chlorophenyl, 3-chlorophenyl, 4-chlorophenyl, naphthalen-1-yl, naphthalen-2-yl, and 3-chloro-pyridin-2-yl.

Particularly preferably, when $X_1$ is —$NR^{3'}$—, examples of the "substituted or unsubstituted acyl group" of $R^{3'}$ include groups represented by —CO—Rg""' (wherein Rg""' represents a substituent RV''' (wherein RV''' represents methyl; ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethylpropyl, 1-ethyl-1-methylpropyl, 1-ethyl-2-methylpropyl, n-hexyl, cyclopropyl, cyclobutyl, cyclopentyl, cyclohexyl, phenyl, naphthyl, tetrahydropyran-4-yl, pyridyl (e.g., pyridin-2-yl, pyridin-3-yl, and pyridin-4-yl), 2,2-dimethylpropyl, 2-methylpropyl, 3-methylbutyl, 2-methylbutyl, 1-methylbutyl, 1,1-dimethylbutyl, 4,4-difluorocyclohexyl, 3-fluorocyclopentyl, 1-methylcyclopropyl, 1-methylcyclobutyl, 3,3,3-trifluoropropyl, 2,2,2-trifluoroethyl, 4,4,4-trifluorobutyl, phenylmethyl, 1,1-difluoropropyl, and 1-fluoro-1-methylethyl; and the alkyl, the cycloalkyl, the aryl, or the heterocyclic group may be further substituted with a substituent RIV of (f) described above).

More specifically, examples of the groups represented by —CO-Rg'''' include acyl groups which may be halogenated, such as acetyl, pentanoyl, 2-ethylbutanoyl, cyclohexanecarbonyl, 4-pyranoyl, benzoyl, nicotinoyl, cyclopentanecarbonyl, pentanoyl, cyclobutanecarbonyl, 3,3-dimethylbutanoyl, 3-methylbutanoyl, 4-methylpentanoyl, 3-methylpentanoyl, 2-methylpentanoyl, 2,2-dimethylpentanoyl, 4,4-difluorocyclohexanecarbonyl, 3-cyclopentanecarbonyl, 1-methylcyclopropanecarbonyl, 1-methylcyclobutanecarbonyl, 4,4,4-trifluorobutanoyl, 3,3,3-trifluoropropanoyl, 5,5,5-trifluoropentanoyl, 1-phenylacetyl, 2,2-difluorobutanoyl, and 2-fluoro-2-methylpropanoyl.

[1-7] $X_2$ represents a methylene group, an oxygen atom, —$NR^4$— (wherein $R^4$ is a hydrogen atom, a $C_{1-6}$ alkyl group (in particular, a $C_{1-4}$ alkyl group such as methyl, ethyl, propyl, isopropyl, butyl, isobutyl, sec-butyl, or tert-butyl), or —S(O) r- (wherein r is an integer of 0 to 2).

[1-7-a] In the compounds represented by formula (I) which is used for the pharmaceutical composition of embodiment [1], $X_2$ is preferably a methylene group or an —NH— group. More preferably, $X_2$ is a methylene group.

[1-8] In the compounds represented by formula (I) which is used for the pharmaceutical composition of embodiment [1], Q is a substituted or unsubstituted heteroaryl group, a substituted or unsubstituted heteroarylalkyl group (aromatic heterocyclic-$C_{1-6}$ alkyl group), a substituted or unsubstituted aryl group, or a substituted or unsubstituted aralkyl group (aryl-$C_{1-6}$ alkyl group). As described in a method of producing a compound of the present invention below, this Q moiety is produced by allowing Q-$NH_2$ (formula (IX) described below, for example, a known amine) to react with an acyl moiety (for example, a compound represented by formula (VIII) described below) and forms a partial structure in the molecule of the compounds represented by formula (I).

Examples of the aromatic heterocyclic groups of the "substituted or unsubstituted heteroaryl group" include the heterocyclic groups listed in the "substituted or unsubstituted heterocyclic groups" in $R^1$ of [1-1] described above. Examples of the rings include five- to fourteen-membered rings, preferably five- to twelve-membered rings, containing at least one heteroatom (preferably, 1 to 4 hetero-atoms) selected from N, O, and S in addition to carbon atoms.

The "heteroaryl groups" in Q include monocyclic heteroaryl groups and fused heteroaryl groups. Preferably, the monocyclic heteroaryl groups each have a five- or six-membered ring. Examples thereof include pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,2,5-triazinyl, 1,3,5-triazinyl, and thiadiazinyl.

Preferably, the fused heteroaryl groups each have an eight- to twelve-membered ring. These groups include, for example, monovalent groups obtained by removing optional hydrogen atom from a ring formed by condensing the above-mentioned five- or six-membered aromatic ring with one or a plurality of (preferably 1 or 2) aromatic rings (such as benzene rings).

Specific examples thereof include indolyl, isoindolyl, 1H-indazolyl, benzofuranyl(-2-yl), isobenzofuranyl, benzothienyl(-2-yl), isobenzothienyl, benzindazolyl, benzoxazolyl(-2-yl), 1,2-benzisoxazolyl, benzothiazolyl(-2-yl), 1,2-benzisothiazolyl, 2H-benzopyranyl (-3-yl), (1H-) benzimidazolyl(-2-yl), 1H-benzotriazolyl, 4H-1,4-benzoxazinyl, 4H-1,4-benzothiazinyl, quinolyl, isoquinolyl, cinnolinyl, quinazolinyl, quinoxalinyl, phthalazinyl, naphthylizinyl, purinyl, pteridinyl, carbazolyl, carbolinyl, acridinyl, phenoxazinyl, phenothiazinyl, phenazinyl, phenoxathinyl, thianthrenyl, phenanthridinyl, phenanthrolinyl, indolizinyl, (4,5,6,7-)tetrahydrothiazolo[5,4-c]pyridyl(-2-yl), (4,5,6,7-) tetrahydrothieno[3,2-c]pyridyl, (1,2,3,4-) tetrahydroisoquinolyl(-6-yl), thiazolo[5,4-c]pyridyl(-2-yl), pyrrolo[1,2-b] pyridazinyl, pyrazo[1,5-a]pyridyl, imidazo[1,2-a]pyridyl, imidazo[1,5-a]pyridyl, imidazo[1,2-b]pyridazinyl, imidazo [1,5-a]pyrimidinyl, [1,2,4]triazolo[4,3-a]pyridyl, 1,2,4-triazolo[4,3-b]pyridazinyl, chromenyl (2H-chromenyl), 1H-pyrazolo[3,4-b]pyridyl, and [1,2,4]triazolo[1,5-a]pyrimidinyl (Preferred embodiments are indicated in the parenthesis "( )").

Examples thereof also include partially hydrogenated fused heteroaryl groups and the like, e.g., tetrahydroquinolinyl, tetrahydroisoquinolinyl, tetrahydro benzoxazepinyl, tetrahydrobenzoazepinyl, tetrahydronaphthpyridinyl, tetrahydroquinoxalinyl, chromanyl, dihydrobenzoxazinyl, 3,4-dihydro-2H-1,4-benzothiazinyl, dihydrobenzothiazolyl, 3,4-dihydro-2H-1,4-benzoxazinyl, isochromanyl, indolinyl, pteridinyl, 2,3-dihydrobenzo[b][1,4]dioxinyl, 1,2,3,4-tetrahydro-1-methylquinolinyl, 1,3-dihydro-1-oxoisobenzofuranyl, and 6,7,8,9-tetrahydro-5H-cyclohepta[b]pyridyl. Here, the partially hydrogenated fused heteroaryl groups and the like are preferably groups each having the above-mentioned eight- to twelve-membered ring. These groups mean monovalent groups obtained by removing optional hydrogen atom from such a ring produced by partially hydrogenating a ring formed by condensing a five- or six-membered aromatic ring with one or a plurality of (preferably 1 or 2) aromatic rings (such as benzene rings). Either the hydrogen atom of the aromatic moiety or the hydrogen atom of the hydrogenated moiety may be removed. For example, in the case of tetrahydroquinolinyl groups, a 5,6,7,8-tetrahydroquinolyl group, a 1,2,3,4-tetrahydroquinolyl group, and the like are included. For example, in the case of a 5,6,7,8-tetrahydroquinolyl group, examples of the monovalent group include a 5,6,7,8-tetrahydroquinolin-7-yl group and a 5,6,7,8-tetrahydroquinolin-3-yl group in accordance with the position where a hydrogen atom is removed. Similarly, in the case of a 1,2,3,4-tetrahydroquinolyl group, examples of the monovalent group include a 1,2,3,4-tetrahydroquinolin-7-yl group and a 1,2,3,4-tetrahydroquinolin-3-yl group.

Examples of the aromatic heterocyclic-$C_{1-6}$ alkyl group in the "substituted or unsubstituted heteroarylalkyl group (aromatic heterocyclic-$C_{1-6}$ alkyl group)" include groups in which the above-mentioned "heteroaryl group" is bonded to a $C_{1-6}$ alkyl group bonded to the NH of —CONH—. Examples of the $C_{1-6}$ alkyl group include the alkyl groups listed in [1-1] described above.

Examples of the aryl group of the "substituted or unsubstituted aryl group" include $C_{6-14}$ aryl groups such as phenyl, naphthyl, biphenylyl, 2-anthryl, phenanthryl, acenaphthyl, and 5,6,7,8-tetrahydronaphthalenyl; and partially hydrogenated fused aryl such as indanyl and tetrahydronaphthyl. Herein, the partially hydrogenated aryl groups mean monovalent groups obtained by removing optional hydrogen atom from a partially hydrogenated ring. Either the hydrogen atom of the aromatic moiety or the hydrogen atom of the hydrogenated moiety may be removed. For example, in the case of tetrahydronaphthyl groups, 5,6,7,8-tetrahydronaphthalen(-1-yl, -2-yl, -3-yl, and -4-yl) groups, 1,2,3,4-tetrahydronaphthalen(-1-yl, -2-yl, -3-yl, and -4-yl) groups, and the like are included. More specifically, examples of such monovalent groups include a 7-oxo-5,6,7,8-tetrahydronaphthalen-1-yl group, a 7-hydroxy-5,6,7,8-tetrahydronaphthalen-1-yl group, and a 7-hydroxy-1,2,3,4-tetrahydronaphthalen-1-yl group.

Examples of the aryl-$C_{1-6}$ alkyl in the "substituted or unsubstituted aralkyl group (aryl-$C_{1-6}$ alkyl group)" include groups in which the above-mentioned "aryl group" is bonded to a $C_{1-6}$ alkyl group bonded to the NH of —CONH—. Examples of the $C_{1-6}$ alkyl group include the alkyl groups listed in [1-1] described above.

In Q, examples of the "substituents" of the "substituted or unsubstituted heteroaryl group", the "substituted or unsubstituted heteroarylalkyl group (aromatic heterocyclic-$C_{1-6}$ alkyl group)", the "substituted or unsubstituted aryl group", or the "substituted or unsubstituted aralkyl group (aryl-$C_{1-6}$ alkyl group)" include (a) to (g) in [1-1] described above. The groups except for (e) may further have a substituent. The above groups in Q may be substituted with 1 to 5 such substituents.

[1-8-a] In the compounds represented by formula (I), examples of the "substituted or unsubstituted heteroaryl group" in Q preferably include pyrrolyl, furyl, thienyl, oxazolyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,2,5-triazinyl, 1,3,5-triazinyl, and thiadiazinyl; indolyl, isoindolyl, 1H-indazolyl, benzofuranyl (-2-yl), isobenzofuranyl, benzothienyl(-2-yl), isobenzothienyl, benzindazolyl, benzoxazolyl(-2-yl), 1,2-benzisoxazolyl, benzothiazolyl(-2-yl), 1,2-benzisothiazolyl, 2H-benzopyranyl(-3-yl), (1H-)benzimidazolyl(-2-yl), 1H-benzotriazolyl, 4H-1,4-benzoxazinyl, 4H-1,4-benzothiazinyl, quinolyl, isoquinolyl, cinnolinyl, quinazolinyl, quinoxalinyl, phthalazinyl, naphthylizinyl, purinyl, pteridinyl, carbazolyl, carbolinyl, acridinyl, phenoxazinyl, phenothiazinyl, phenazinyl, phenoxathinyl, thianthrenyl, phenanthridinyl, phenanthrolinyl, indolizinyl, (4,5,6,7-)tetrahydrothiazolo[5,4-c]pyridyl(-2-yl), (4,5,6,7-)tetrahydrothieno[3,2-c]pyridyl, (1,2,3,4-) tetrahydroisoquinolyl(-6-yl), thiazolo[5,4-c]pyridyl(-2-yl), pyrrolo[1,2-b]pyridazinyl, pyrazo[1,5-a]pyridyl, imidazo[1,2-a]pyridyl, imidazo[1,5-a]pyridyl, imidazo[1,2-b]pyridazinyl, imidazo[1,5-a]pyrimidinyl, 1,2,4-triazolo[4,3-a]pyridyl, 1,2,4-triazolo[4,3-b]pyridazinyl, chromenyl (2H-chromenyl), 1H-pyrazolo[3,4-b]pyridyl, and 1,2,4-triazolo[1,5-a] pyrimidinyl (Preferred embodiments are indicated in the parenthesis "( )"). Examples thereof also include partially hydrogenated fused heteroaryl groups and the like, e.g., tetrahydroquinolinyl, tetrahydroisoquinolinyl, tetrahydrobenzoxazepinyl, tetrahydrobenzoazepinyl, tetrahydronaphthpyridinyl, tetrahydroquinoxalinyl, chromanyl, dihydrobenzoxazinyl, 3,4-dihydro-2H-1,4-benzothiazinyl, dihydrobenzothiazolyl, 3,4-dihydro-2H-1,4-benzoxazinyl, isochromanyl, indolinyl, pteridinyl, 2,3-dihydrobenzo[b][1,4]dioxinyl, 1,2,3,4-tetrahydro-1-methylquinolinyl, 1,3-dihydro-1-oxoisobenzofuranyl, and 6,7,8,9-tetrahydro-5H-cyclohepta[b]pyridyl. Furthermore, examples of the "substituted or unsubstituted heteroaryl group" in Q include 1H-indolyl, 1,1-dioxobenzo[b]thienyl, cinnolinyl, imidazo[1,2-a]pyridinyl, 2-dihydro-2-oxo-quinolyl, 1,2-dihydro-1-methyl-2-oxo-quinolyl, 1,2-dihydro-3H-3-oxo-indazolyl, 2,3-dihydro-1H-indenyl, 2,3-dihydro-3-hydroxy-1H-indenyl, 2,3-dihydro-2-oxo-benzoxazolyl, 2,3-dihydro-3-oxo-1H-indenyl, 2,3-dihydro-1-oxo-1H-indenyl, 3-dihydro-1-methyl-1H-indolyl, 2,3-dihydro-2-oxo-1H-indolyl, 2,3-dihydro-1-methyl-2-oxo-1H-indolyl, 2,3-dihydro-1,3,3-trimethyl-2-oxo-1H-indolyl, 2,3-dihydro-3-methyl-2-oxo-benzothiazolyl, 2,3-dihydro-2-oxo-4-(trifluoromethyl)-1H-indolyl, 3,4-dihydro-4-methyl-3-oxo-2H-1,4-benzoxazinyl, 3,4-dihydro-3-oxo-2H-benzoxazinyl, 3,4-dihydro-3-oxo-2H-1,4-benzothiazinyl, 3,4-dihydro-4-methyl-3-oxo-2H-1,4-benzothiazinyl, 3,4-dihydro-2-methyl-3-oxo-2H-1,4-benzoxazinyl, 3,4-dihydro-2,2-dimethyl-3-oxo-2H-1,4-benzoxazinyl, 1,2,3,4-tetrahydro-2-oxo-quinolinyl, 1,2,3,4-tetrahydro-1-methyl-2-oxo-quinolinyl, 1,2,3,4-tetrahydro-1-methyl-quinolinyl, 1,2,3,4-tetrahydro-1-methyl-2-oxo-quinolinyl, 1,2,3,4-tetrahydro-3-hydroxy-1-methyl-quinolinyl, 1-methyl-3,4-dihydro-1H-quinolin-2-on-7-yl, 1-methyl-2-quinolon-7-yl, 4-methyl-2-quinolon-7-yl, 1-methyl-2-quinolon-5-yl, 3,4-dihydro-2H-1,4-ethanoquinolin-7-yl, 3,3-dimethylindolinyl, 1-methyl-3,3-dimethylindolinyl, 3,3-dimethyl-1-(2-hydroxyethyl) indolinyl, 3,3-dimethyl-1-(2-(N,N-dimethylamino)ethyl) indolinyl, 3,3-dimethyl-1-(2-(4-morpholino)ethyl)indolin-6-yl, 1,1-dioxo-2,3-dihydro-4H-benzo[1,4]thiazinyl, 1,1-dioxo-4-methyl-2,3-dihydro-4H-benzo[1,4]thiazinyl, 1,1-dioxo-4-(2-hydroxyethyl)-2,3-dihydro-4H-benzo[1,4] thiazinyl, 1,1-dioxo-4-(2-(N,N-dimethylamino)ethyl)-2,3-dihydro-4H-benzo[1,4]thiazinyl, 1,1-dioxo-4-(2-(4-morpholino)ethyl)-2,3-dihydro-4H-benzo[1,4]thiazinyl, 1-acetyl-1,2,3,4-tetrahydroquinolinyl, 1,2,3,4-tetrahydroquinolinyl, 1-(2-hydroxyethyl)-1,2,3,4-tetrahydroquinolinyl, 1-(2-(N,N-dimethylamino)ethyl)-1,2,3,4-tetrahydroquinolinyl, 1-(2-(4-morpholino)ethyl)-1,2,3,4-tetrahydroquinolinyl, 4,4-dimethyl-1,2,3,4-tetrahydroquinolinyl, 1-methyl-4,4-dimethyl-1,2,3,4-tetrahydroquinolinyl, 1-(2-hydroxyethyl)-4,4-dimethyl-1,2,3,4-tetrahydroquinolinyl, 1-(2-(N,N-dimethylamino)ethyl)-4,4-dimethyl-1,2,3,4-tetrahydroquinolinyl, 1-(2-(4-morpholino)ethyl)-4,4-dimethyl-1,2,3,4-tetrahydroquinolinyl, 2,3-dihydro-4H-benzo[1,4]oxazinyl, 4-methyl-2,3-dihydro-4H-benzo[1,4]oxazinyl, 4-(2-hydroxyethyl)-2,3-dihydro-4H-benzo[1,4]oxazinyl, 4-(2-(N,N-dimethylamino)ethyl)-2,3-dihydro-4H-benzo[1,4]oxazinyl, 4-(2-(4-morpholino)ethyl)-2,3-dihydro-4H-benzo[1,4] oxazinyl, 4,4-dimethyl-1,2,3,4-tetrahydroisoquinolinyl, 2,4,4-trimethyl-1,2,3,4-tetrahydroisoquinolinyl, 2-(2-hydroxyethyl)-4,4-dimethyl-1,2,3,4-tetrahydroisoquinolinyl, 2-(2-(N,N-dimethylamino)ethyl)-4,4-dimethyl-1,2,3,4-tetrahydroisoquinolinyl, 2-(2-(4-morpholino)ethyl)-4,4-dimethyl-1,2,3,4-tetrahydroisoquinolinyl, 6-hydroxyquinolin-4-yl, 6-hydroxyisoquinolin-4-yl, 7-hydroxyisoquinolin-1-yl, 6-hydroxyquinazolin-4-yl, 1,2,3,4-tetrahydro-3-hydroxy-quinolinyl, 1,2,3,4-tetrahydro-1-methyl-3-hydroxy-quinolinyl, 1,2,3,4-tetrahydro-1-(2-hydroxyethyl)-3-hydroxy-quinolinyl, 1,2,3,4-tetrahydro-1-(2-(N,N-dimethylamino) ethyl)-3-hydroxy-quinolinyl, 1,2,3,4-tetrahydro-1-(2-(4-morpholino)ethyl)-quinolinyl, 3-hydroxy-3,4-dihydro-2 (1H)-quinolinon-5-yl, 1-methylisoquinolinyl, 3-methylisoquinolinyl, 1,3-dimethylisoquinolinyl, 2-methylquinolinyl, indol-4-yl, 1-methylindol-4-yl, 1-(2-hydroxyethyl)indol-4-yl, 1-(2-(N,N-dimethylamino)ethyl)indol-4-yl, 1-(2-(4-morpholino)ethyl)indol-4-yl, indol-6-yl, 1-methylindol-6-yl, 1-(2-hydroxyethyl)indol-6-yl, 1-(2-(N,N-dimethylamino)ethyl)indol-6-yl, 1-(2-(4-morpholino) ethyl)indol-6-yl, indolin-6-yl, 1-methyl-indolin-6-yl, 1-(2-hydroxyethyl)indolin-6-yl, 1-(2-(N,N-dimethylamino)ethyl) indolin-6-yl, 1-(2-(4-morpholino)ethyl) indolin-6-yl, 5-trifluoromethyl-pyridinyl, 1,3,4,5-tetrahydrobenzo[b] azepin-2-on-8-yl, 1-methyl-1,3,4,5-tetrahydrobenzo[b] azepin-2-on-8-yl, 2H-benzo[1,4]oxazin-3(4H)-on-6-yl, 2-methyl-(2H)1,4-benzoxazin-3(4H)-on-6-yl, 3,3-difluoro-1-methyl-2-oxoindolin-5-yl, 2-(N,N-dimethylamino)-3-fluoropyridin-5-yl, 3-acetylpyridin-5-yl, 2-(cyclohexanecarbonyl)pyridin-4-yl, 5-oxo-5,6,7,8-tetrahydroquinolin-3-yl, 2,2'-bipyridin-3-yl, 2,2'-bipyridin-4-yl, 2-hydroxymethyl-1,3-benzothiazol-5-yl, 1,3-benzodioxol-5-yl, 2,2-difluoro-1,3-benzodioxol-5-yl, 3,4-dihydro-2H-1,5-benzo[b]dioxepin-7-yl, and 2-chloropyridin-4-yl.

Examples of the "substituted or unsubstituted heteroarylalkyl group (aromatic heterocyclic-$C_{1-6}$ alkyl group)" in Q preferably include groups in which the above-mentioned "heteroaryl group" is bonded to a $C_{1-4}$ alkyl group bonded to the NH of —CONH—.

Examples of the "substituted or unsubstituted aryl group" in Q preferably include $C_{6-14}$ aryl groups such as phenyl, naphthyl, biphenylyl, 2-anthryl, phenanthryl, acenaphthyl, and 5,6,7,8-tetrahydronaphthalenyl; and partially hydrogenated fused aryl such as indanyl and tetrahydronaphthyl. Furthermore, examples of the aryl group include 3-fluoro-4-methanesulfonylaminobenzyl, 5-hydroxy-1,2,3,4-tetrahydronaphthyl, 5-tert-butyl-2,3-dihydro-1H-indenyl, 5-hydroxy-naphthyl, 7-hydroxy-naphthyl, 2,4-dibromo-7-hydroxy-naphthyl, 2,4-dichloro-7-hydroxy-naphthyl, 4-chloro-3-(trifluoromethyl)phenyl, 7-hydroxynaphthalen-2-yl, 6-hydroxynaphthalen-1-yl, 5,6,7,8-tetrahydro-7-naphthol-2-yl, indan-2-ol-5-yl, 5,6,7,8-tetrahydro-7-naphthol-1-yl, 5,6,7,8-tetrahydronaphthalene-6,7-diol-1-yl, 5,6,7,8-tetrahydronaphthalen-8-ol-2-yl, 3-acetylphenyl, 3-acetyl-4-methylphenyl, 3-(4-morpholinylcarbonyl)phenyl, 3-n-butynylphenyl, 3-cyclohexynylphenyl, 3-(picolinyl)phenyl, 8-methoxy-5,6,7,8-tetrahydronaphthalen-2-yl, 8-(N,N-dimethylamino)-5,6,7,8-tetrahydronaphthalen-2-yl, 3-methoxy-5-trifluoromethylphenyl, 4-chloro-3-trifluoromethylphenyl, 4-methanesulfonylphenyl, 3-trifluoromethylphenyl, 3-methanesulfonylphenyl, 4-trifluoromethoxyphenyl, 4-isopropylphenyl, 2-(hydroxyethyl)phenyl, 3-(N,N-dimethylamino)phenyl, and 4-(N,N-diethylamino)phenyl.

Examples of the "substituted or unsubstituted aralkyl group (aryl-$C_{1-6}$ alkyl group)" in Q preferably include groups in which the above-mentioned "aryl group" is bonded to a $C_{1-4}$ alkyl group bonded to the NH of —CONH—.

Preferably, each of the groups in Q may be either unsubstituted or substituted with 1 to 3 substituents in a class selected from (a-1) to (g-1) described in [1-1-a] above. In the groups listed in (a-1) to (g-1) above, "particularly preferable groups" include substituents such as $C_{1-6}$ alkyl, $C_{2-6}$ alkenyl, $C_{2-6}$ alkynyl, halogen atoms, halogenated $C_{1-6}$ alkyl, cyano, amino, hydroxyl, carbamoyl, $C_{1-6}$ alkoxy, $C_{2-6}$ alkenyloxy, $C_{2-6}$ alkynyloxy, $C_{1-6}$ alkylthio, $C_{1-6}$ alkylsulfinyl, $C_{1-6}$ alkylsulfonyl, mono/di $C_{1-6}$ alkylamino, $C_{1-6}$ alkoxycarbonyl, $C_{2-6}$ alkanoyl, $C_{2-6}$ alkanoylamino, hydroxy-$C_{1-6}$ alkyl, $C_{1-6}$ alkoxy-$C_{1-6}$ alkyl, carboxy-$C_{1-6}$ alkyl, $C_{1-6}$ alkoxycarbonyl-$C_{1-6}$ alkyl, carbamoyl-$C_{1-6}$ alkyl, N—$C_{1-6}$ alkylcarbamoyl-$C_{1-6}$ alkyl, N,N-di $C_{1-6}$ alkylcarbamoyl-$C_{1-6}$ alkyl, phenyl, phenoxy, phenylthio, phenylsulfinyl, phenylsulfonyl, benzyl, benzoyl, morpholino, oxo, morpholinylcarbonyl, morpholinylsulfonyl, 5-trifluoromethylpyridin-2-yloxy, quinoxalin-2-yl, (pyridin-4-yl)methyl, 1,2,3-thiadiazolo-4-yl, 1H-pyrazolo-1-yl, and 4-chlorophenyl. The aromatic rings in these substituents may be further substituted with 1 to 3 substituents selected from halogen atoms, trifluoromethyl, cyano, hydroxyl, amino, nitro, carboxyl, carbamoyl, $C_{1-6}$ alkyl, $C_{1-6}$ alkoxy, mono/di $C_{1-6}$ alkylamino, di-$C_{1-6}$ alkylcarbamoyl, $C_{1-6}$ alkoxycarbonyl, N—$C_{1-6}$ alkylcarbamoyl, N,N-di $C_{1-6}$ alkylcarbamoyl, and $C_{2-6}$ alkenoylamino.

[1-8-b] More preferably, examples of Q include thiazolyl, pyrazolyl, pyridyl, 1H-indazolyl, benzothiazolyl (-2-yl), (1H-)benzimidazolyl(-2-yl), quinolyl, isoquinolyl, quinoxalinyl, [1,2,4]triazolo[4,3-a]pyridyl, chromenyl (2H-chromenyl), 1H-pyrazolo[3,4-b]pyridyl, [1,2,4]triazolo[1,5-a]pyrimidinyl, tetrahydroquinolinyl, 2,3-dihydrobenzo[b][1,4]dioxinyl, 1,2,3,4-tetrahydro-1-methylquinolinyl, 1,3-dihydro-1-oxoisobenzofuranyl, and 6,7,8,9-tetrahydro-5H-cyclohepta[b]pyridyl. Examples of Q further include 1H-indol-4-yl, 1H-indol-6-yl, 1H-indazol-4-yl, 1H-indazol-5-yl, 5-benzothiazolyl, 1,1-dioxobenzo[b]thien-6-yl, 4-hydroxy-2-quinolinyl, 3-quinolinyl, 2-methylquinolin-6-yl, 3-methylisoquinolin-5-yl, 1-methylisoquinolin-5-yl, 2-methylbenzothiazol-5-yl, 3-methyl-cinnolinyl-5-yl, imidazo[1,2-a]pyridin-7-yl, 1,2-dihydro-2-oxo-5-quinolinyl, 1,2-dihydro-2-oxo-7-quinolinyl, 1,2-dihydro-1-methyl-2-oxo-7-quinolinyl, 1,2-dihydro-3H-3-oxo-indazol-6-yl, 2,3-dihydro-1H-inden-5-yl, 2,3-dihydro-3-hydroxy-1H-inden-5-yl, 2,3-dihydro-2-oxo-5-benzoxazolyl, 2,3-dihydro-2-oxo-6-benzoxazolyl, 2,3-dihydro-3-oxo-1H-inden-5-yl, 2,3-dihydro-1-oxo-1H-inden-4-yl, 2,3-dihydro-1-methyl-1H-indol-6-yl, 2,3-dihydro-2-oxo-1H-indol-6-yl, 2,3-dihydro-1-methyl-2-oxo-1H-indol-6-yl, 2,3-dihydro-1,3,3-trimethyl-2-oxo-1H-indole-6-yl, 2,3-dihydro-3-methyl-2-oxo-5-benzothiazolyl, 2,3-dihydro-2-oxo-4-(trifluoromethyl)-1H-indol-6-yl, 3,4-dihydro-4-methyl-3-oxo-2H-1,4-benzoxazin-6-yl, 3,4-dihydro-3-oxo-2H-benzoxazin-6-yl, 3,4-dihydro-3-oxo-2H-1,4-benzothiazin-6-yl, 3,4-dihydro-4-methyl-3-oxo-2H-1,4-benzothiazin-6-yl, 3,4-dihydro-2-methyl-3-oxo-2H-1,4-benzoxazin-6-yl, 3,4-dihydro-2,2-dimethyl-3-oxo-2H-1,4-benzoxazin-6-yl, 1,2,3,4-tetrahydro-2-oxo-7-quinolinyl, 1,2,3,4-tetrahydro-1-methyl-2-oxo-7-quinolinyl, 1,2,3,4-tetrahydro-1-methyl-7-quinolinyl, 1,2,3,4-tetrahydro-1-methyl-2-oxo-7-quinolinyl, 1,2,3,4-tetrahydro-3-hydroxy-1-methyl-quinolin-5-yl; 1-methyl-3,4-dihydro-1H-quinolin-2-on-7-yl, 1-methyl-2-quinolon-7-yl, 4-methyl-2-quinolon-7-yl, 1-methyl-2-quinolon-5-yl, 3,4-dihydro-2H-1,4-ethanoquinolin-7-yl, 3,3-dimethylindolin-6-yl, 1-methyl-3,3-dimethylindolin-6-yl, 3,3-dimethyl-1-(2-hydroxyethyl)indolin-6-yl, 3,3-dimethyl-1-(2-(N,N-dimethylamino)ethyl)indolin-6-yl, 3,3-dimethyl-1-(2-(4-morpholino)ethyl)indolin-6-yl, 1,1-dioxo-2,3-dihydro-4H-benzo[1,4]thiazin-6-yl, 1,1-dioxo-4-methyl-2,3-dihydro-4H-benzo[1,4]thiazin-6-yl, 1,1-dioxo-4-(2-hydroxyethyl)-2,3-dihydro-4H-benzo[1,4]thiazin-6-yl, 1,1-dioxo-4-(2-(N,N-dimethylamino)ethyl)-2,3-dihydro-4H-benzo[1,4]thiazin-6-yl, 1,1-dioxo-4-(2-(4-morpholino)ethyl)-2,3-dihydro-4H-benzo[1,4]thiazin-6-yl, 1-acetyl-1,2,3,4-tetrahydroquinolin-7-yl, 1,2,3,4-tetrahydroquinolin-7-yl, 1-(2-hydroxyethyl)-1,2,3,4-tetrahydroquinolin-7-yl, 1-(2-(N,N-dimethylamino)ethyl)-1,2,3,4-tetrahydroquinolin-7-yl, 1-(2-(4-morpholino)ethyl)-1,2,3,4-tetrahydroquinolin-7-yl, 4,4-dimethyl-1,2,3,4-tetrahydroquinolin-7-yl, 1-methyl-4,4-dimethyl-1,2,3,4-tetrahydroquinolin-7-yl, 1-(2-hydroxyethyl)-4,4-dimethyl-1,2,3,4-tetrahydroquinolin-7-yl, 1-(2-(N,N-dimethylamino)ethyl)-4,4-dimethyl-1,2,3,4-tetrahydroquinolin-7-yl, 1-(2-(4-morpholino)ethyl)-4,4-dimethyl-1,2,3,4-tetrahydroquinolin-7-yl, 2,3-dihydro-4H-benzo[1,4]oxazin-6-yl, 4-methyl-2,3-dihydro-4H-benzo[1,4]oxazin-6-yl, 4-(2-hydroxyethyl)-2,3-dihydro-4H-benzo[1,4]oxazin-6-yl, 4-(2-(N,N-dimethylamino)ethyl)-2,3-dihydro-4H-benzo[1,4]oxazin-6-yl, 4-(2-(4-morpholino)ethyl)-2,3-dihydro-4H-benzo[1,4]oxazin-6-yl, 4,4-dimethyl-1,2,3,4-tetrahydroisoquinolin-7-yl, 2-methyl-4,4-dimethyl-1,2,3,4-tetrahydroisoquinolin-7-yl, 2-(2-hydroxyethyl)-4,4-dimethyl-1,2,3,4-tetrahydroisoquinolin-7-yl, 2-(2-(N,N-dimethylamino)ethyl)-4,4-dimethyl-1,2,3,4-tetrahydroisoquinolin-7-yl, 2-(2-(4-morpholino)ethyl)-4,4-dimethyl-1,2,3,4-tetrahydroisoquinolin-7-yl, 6-hydroxyquinolin-4-yl, 6-hydroxyisoquinolin-4-yl, 7-hydroxyisoquinolin-1-yl, 6-hydroxyquinazolin-4-yl, 1,2,3,4-tetrahydroquinolin-3-ol-5-yl, 1-methyl-1,2,3,4-tetrahydroquinolin-3-ol-5-yl, 1-(2-hydroxyethyl)-1,2,3,4-tetrahydroquinolin-3-ol-5-yl, 1-(2-(N,N-dimethylamino)ethyl)-1,2,3,4-tetrahydroquinolin-3-ol-5-yl, 1-(2-(4-morpholino)ethyl)-1,2,3,4-tetrahydroquinolin-3-ol-5-yl, 3-hydroxy-3,4-dihydro-2(1H)-quinolinon-5-yl, 1-methylisoquinolin-5-yl, 3-methylisoquinolin-5-yl, 1,3-dimethylisoquinolin-5-yl, 2-methylquinolin-7-yl, indol-4-yl, 1-methylindol-4-yl, 1-(2-hydroxyethyl)indol-4-yl, 1-(2-(N,N-dimethylamino)ethyl)indol-4-yl, 1-(2-(4-morpholino)ethyl)indol-4-yl, indol-6-yl, 1-methylindol-6-yl, 1-(2-hydroxyethyl)indol-6-yl, 1-(2-(N,N-dimethylamino)ethyl)indol-6-yl, 1-(2-(4-morpholino)ethyl)indol-6-yl, indolin-6-yl, 1-methyl-indolin-6-yl, 1-(2-hydroxyethyl)indolin-6-yl, 1-(2-(N,N-dimethylamino)ethyl)indolin-6-yl, 1-(2-(4-morpholino)ethyl)indolin-6-yl, 5-trifluoromethyl-pyridin-2-yl, 1,3,4,5-tetrahydrobenzo[b]azepin-2-on-8-yl, 1-methyl-1,3,4,5-tetrahydrobenzo[b]azepin-2-on-8-yl, 2H-benzo[1,4]oxazin-3(4H)-on-6-yl, 2-methyl-(2H)1,4-benzoxazin-3(4H)-on-6-yl, 3,3-difluoro-1-methyl-2-oxoindolin-5-yl, 2-(N,N-dimethylamino)-3-fluoropyridin-5-yl, 3-acetylpyridin-5-yl, 2-(cyclohexanecarbonyl)pyridin-4-yl, 5-oxo-5,6,7,8-tetrahydroquinolin-3-yl, 2,2'-bipyridin-3-yl, 2,2'-bipyridin-4-yl, 2-hydroxymethyl-1,3-benzothiazol-5-yl, 1,3-benzodioxol-5-yl, 2,2-difluoro-1,3-benzodioxol-5-yl, 3,4-dihydro-2H-1,5-benzo[b]dioxepin-7-yl, 2-chloropyridin-4-yl, indan-5-yl, 3-fluoro-4-methanesulfonylaminobenzyl, 5-hydroxy-1,2,3,4-tetrahydronaphthalen-1-yl, 5-tert-butyl-2,3-dihydro-1H-inden-1-yl, 5-hydroxy-2-naphthalenyl, 7-hydroxy-1-naphthyl, 2,4-dibromo-7-hydroxy-1-naphthyl, 2,4-dichloro-7-hydroxy-1-naphthyl, 4-chloro-3-(trifluoromethyl)phenyl; 7-hydroxynaphthalen-2-yl, 6-hydroxynaphthalen-1-yl, 5,6,7,8-tetrahydro-7-naphthol-2-yl, indan-2-hydroxy-5-yl, 5,6,7,8-tetrahydro-7-naphthol-1-yl, 5,6,7,8-tetrahydronaphthalene-6,7-diol-1-yl, 5,6,7,8-tetrahydronaphthalen-8-ol-2-yl, 3-acetylphenyl, 3-acetyl-4-methylphenyl, 3-(4-morpholinylcarbonyl)phenyl, 3-n-butynylphenyl, 3-cyclohexynylphenyl, 3-(picolinyl)phenyl, 8-methoxy-5,6,7,8-tetrahydronaphthalen-2-yl, 8-(N,N-dimethylamino)-5,6,7,8-tetrahydronaphthalen-2-yl, 3-methoxy-5-trifluoromethylphenyl, 4-chloro-3-trifluoromethylphenyl, 4-methanesulfonylphenyl, 3-trifluoromethylphenyl, 3-methanesulfonylphenyl, 4-trifluoromethoxyphenyl, 4-isopropylphenyl, 2-(hydroxyethyl)phenyl, 3-(N,N-dimethylamino)phenyl, 4-(N,N-diethylamino)phenyl; and 2-(2-chlorophenyl)ethyl.

[1-8-c] More specifically, further preferable examples of Q are as follows. Specific examples of the "substituted or unsubstituted heteroaryl group" include a 2,3-dihydrobenzo[b][1,4]dioxin-6-yl group, isoquinolin-5-yl group, 5,6,7,8-tetrahydroquinolin-7-yl group, quinolin-7-yl group, quinoxalin-6-yl group, 1,2,3,4-tetrahydro-1-methylquinolin-7-yl group, 2-methyl-1,3-benzothiazolo-5-yl group, 2-morpholinopyridin-3-yl group, 4-methyl-2-oxo-2H-chromen-7-yl group, 6-phenoxypyridin-2-yl group, 1,3-dihydro-1-oxoisobenzofuran-6-yl group, 1-methyl-1H-pyrazolo[3,4-b]pyridin-3-yl group, 1H-indazol-3-yl group, 1-ethyl-1H-benzo[d]imidazolo-2-yl group, [1,2,4]triazolo[1,5-a]pyrimidin-7-yl group, 6,7,8,9-tetrahydro-5H-cyclohepta[b]pyridin-8-yl group, 1-tert-butyl-3-methyl-1H-pyrazolo-5-yl group, 4-phenylthiazolo-2-yl group, 2-hydroxymethyl-1,3-benzothiazol-5-yl group, 3-hydroxy-2-oxo-1,2,3,4-tetrahydroquinolin-5-yl group, 3-hydroxy-1,2,3,4-tetrahydroquinolin-5-yl group, 1-methyl-3-hydroxy-1,2,3,4-tetrahydroquinolin-5-yl group, 1-(2-hydroxyethyl)-1,2,3,4-tetrahydroquinolin-7-yl group, 1-(2-(4-morpholino)ethyl)-1,2,3,4-tetrahydroquinolin-7-yl group, 1-(2-(N,N-dimethylamino)ethyl)-1,2,3,4-tetrahydroquinolin-7-yl group, 3,4-dihydro-1H-quinolin-2-on-7-yl group, 2-quinolon-7-yl group, 5-trifluoromethyl-pyridin-2-yl group, 3,4-dihydro-2H-1,5-benzo[b]dioxepin-7-yl group, 2,2-difluoro-1,3-benzodioxol-5-yl group, 1-methylindol-5-yl group, 1-(2-hydroxyethyl)indol-6-yl group, 1-(1-oxopentyl)-1,2,3,4-tetrahydroquinolin-7-yl group, 1-((1-oxo-2-acetoxy)ethyl)-1,2,3,4-tetrahydroquinolin-7-yl group, 1-trifluoroacetyl-1,2,3,4-tetrahydroquinolin-7-yl group, 3-hydroxymethylindol-4-yl group, 1-(2-hydroxyethyl)indol-5-yl group, 3-hydroxymethyl-2,3-dihydro-1,4-benzodioxin-6-yl group, 2,3-dihydro-isoindol-1-on-6-yl group, 1,2,3,4-tetrahydroquinolin-7-yl group, (1-(2-hydroxy-1-oxo)ethyl)-1,2,3,4-tetrahydroquinolin-7-yl group, 1a,2,7,7a-tetrahydronaphtho[2,3-b]oxirene-3-yl group, 2-quinolon-8-yl group, 1-methylindol-6-yl group, 1-methyl-2-oxo-1,2,3,4-tetrahydroquinolin-7-yl group, 1,2,3,4-tetrahydroisoquinolin-8-yl group, 2-hydroxyethyl-1,2,3,4-tetrahydroisoquinolin-8-yl group, 3,4-dihydro-2H-isoquinolin-1-on-7-yl group, 2-hydroxyethyl-2,3-dihydro-isoindol-1-on-6-yl group, 3-hydroxy-2,3-dihydro-(1H)-4-benzopyran-5-yl group, 6-hydroxy-2,3-dihydro-(1H)-4-benzopyran-4-yl group, 6-hydroxy-1,2,3,4-tetrahydroquinolin-4-yl group, 2-oxo-1,2,3,4-tetrahydroquinolin-8-yl group, 3-hydroxyquinolin-5-yl group, 6-hydroxyquinolin-4-yl group, 2-acetyl-1,2,3,4-tetrahydroisoquinolin-8-yl group, 4-(2-hydroxyacetyl)-3,4-dihydro-2H-benzo[b][1,4]oxazin-6-yl group, 4-(2-hydroxypropynoyl)-3,4-dihydro-2H-benzo[b][1,4]oxazin-6-yl group, 4-(2-hydroxyethyl)-3,4-dihydro-2H-benzo[b][1,4]oxazin-6-yl group, 2-methylthieno[2,3-c]pyridin-3-yl group, 5-(2-hydroxymethylphenyl)-3-pyridyl group, 2-hydroxymethyl-1,3-benzothiazolo-5-yl group, 3-chloro-5-hydroxymethyl-2-pyridyl group, 6-hydroxychroman-4-yl group, 1H-indazol-4-yl group, 1H-indazol-7-yl group, and 3-amino-1H-pyrrolo[2,3-c]pyridin-3-yl group.

Specific examples of the "substituted or unsubstituted heteroarylalkyl group (aromatic heterocyclic-$C_{1-6}$ alkyl group)" include a 1-(pyridin-2-yl)ethyl group, phenyl(pyridin-2-yl)methyl group, (2,3-dihydrobenzo[b][1,4]dioxin-6-yl)methyl group, 1-(2,3-dihydrobenzo[b][1,4]dioxin-6-yl)ethyl group, (2,3-dihydrobenzo[b][1,4]dioxin-3-yl)methyl group, (2,3-dihydrobenzofuran-6-yl)methyl group, (2-(4-chlorophenyl)-4-methylthiazol-5-yl)methyl group, and (1,2,4-triazolo[4,3-a]pyridin-3-yl)methyl group.

Specific examples of the "substituted or unsubstituted aryl group" include a 4-tert-butylphenyl group, 4-(trifluoromethyl)phenyl group, 3-methoxyphenyl group, 7-hydroxynaphthalen-1-yl group, 1,2,3,4-tetrahydro-1-oxonaphthalen-7-yl group, 4-(4-morpholinylcarbonyl)phenyl group, 4-(4-morpholinylsulfonyl)phenyl group, 4-((5-trifluoromethyl)pyridin-2-yloxy)phenyl group, 3-(quinoxalin-2-yl)phenyl group, 3-((pyridin-4-yl)methyl)phenyl group, 2-(hydroxyethyl)phenyl group, 7-oxo-5,6,7,8-tetrahydronaphthalen-1-yl group, 7-hydroxy-5,6,7,8-tetrahydronaphthalen-1-yl group, 5,6,7,8-tetrahydro-trans-6,7-dihydroxynaphthalen-1-yl group, 5,6,7,8-tetrahydro-cis-6,7-dihydroxynaphthalen-1-yl group, 6-hydroxynaphthalen-1-yl group, 7-hydroxynaphthalen-2-yl group, 7-methoxynaphthalen-1-yl group, 3-methoxy-5-trifluoromethylphenyl group, 4-chloro-3-trifluoromethylphenyl group, 5-hydroxynaphthalen-1-yl group, indan-1-on-6-yl group, indan-2-acetoxy-4-yl group, indan-2-ol-4-yl group, 7-dimethylamino-naphthalen-1-yl group, 8-hydroxymethyl-5,6,7,8-tetrahydronaphthalen-2-yl group, 7-hydroxy-7-methyl-5,6,7,8-tetrahydronaphthalen-1-yl group, 7-hydroxy-1,2,3,4-tetrahydronaphthalen-1-yl group, (Z)-7-hydroxyimino-5,6,7,8-tetrahydronaphthalen-1-yl group, (E)-7-hydroxyimino-5,6,7,8-tetrahydronaphthalen-1-yl group, 1-hydroxy-1,2,3,4-tetrahydronaphthalen-8-yl group, indan-1-ol-6-yl group, 3-hydroxy-2-carboxymethylphenyl group, 3-hydroxy-2-carbamoylmethylphenyl group, 6,7,8-tetrahydronaphthalen-1-yl group, 3-((3-hydroxymethyl)-2-pyridyl)phenyl group, 2-(3-hydroxy-2-pyridyl)phenyl group, 2-hydroxy-1,1'-biphenyl-2'-yl group, 2-(3-hydroxypyrrolidin-1-yl)phenyl group, and 3-(2-hydroxymethylpyrrolidin-1-yl)phenyl group.

Specific examples of the "substituted or unsubstituted aralkyl group (aryl-$C_{1-6}$ alkyl group)" include a 2-morpholinophenylmethyl group, 4-(1,2,3-thiadiazolo-4-yl)phenylmethyl group, 4-(1H-pyrazolo-1-yl)phenylmethyl group, 2-(7-hydroxy-5,6,7,8-tetrahydronaphthalen-1-yl)ethyl group, 2-(7-hydroxy-5,6,7,8-tetrahydronaphthalen-1-yl)propyl group, and 2-(2-chlorophenyl)ethyl group.

[1-8-d] In the substituted or unsubstituted heteroaryl group, the substituted or unsubstituted heteroarylalkyl group, the substituted aryl group, or the substituted or unsubstituted aralkyl group listed in [1-8-c] above, more preferable Q is a bicyclic group or a group having a bicyclic group and a $C_{1-6}$ alkylene group located between the bicyclic group and the NH (for example, a bicyclic heteroarylalkyl group (aromatic $_{heterocyclic\text{-}C1\text{-}6}$ alkyl group) or a bicyclic aralkyl group (aryl-$C_{1-6}$ alkyl group). Preferable examples of the substituted or unsubstituted bicyclic heteroaryl group described in [1-8] include fused heteroaryl groups. (As regards the fused heteroaryl groups, eight- to twelve membered fused heteroaryl groups are preferred. Examples thereof include monovalent groups obtained by removing optional hydrogen atom from a ring formed by condensing the above-mentioned five- or six-membered aromatic ring with an aromatic ring (such as a benzene ring, a pyridine ring, a thiophene ring, or a furan ring).) Examples of the substituted or unsubstituted bicyclic heteroaryl groups also include partially hydrogenated fused heteroaryl groups. In each of the monovalent groups, either the hydrogen atom of the aromatic moiety or the hydrogen atom of the hydrogenated moiety may be removed. Examples of the aryl groups in the "substituted bicyclic aryl group" include $C_{10-12}$ aryl groups such as naphthyl and 5,6,7,8-tetrahydronaphthalenyl, and partially hydrogenated fused aryl such as indanyl and tetrahydronaphthyl. Herein, the partially hydrogenated aryl groups mean monovalent groups obtained by removing optional hydrogen atom from a partially hydrogenated ring. Either the hydrogen atom of the aromatic moiety or the hydrogen atom of the hydrogenated moiety may be removed. For example, in the case of tetrahydronaphthyl groups, 5,6,7,8-tetrahydronaphthalen(-1-yl, -2-yl, -3-yl, and -4-yl) groups, 1,2,3,4-tetrahydronaphthalen(-1-yl, -2-yl, -3-yl, and -4-yl) groups, and the like are included. More specifically, examples of such monovalent groups include 7-oxo-5,6,7,8-tetrahydronaphthalen-1-yl group, and a 7-hydroxy-1,2,3,4-tetrahydronaphthalen-1-yl group. The heteroaryl group or aryl group serving as Q may be bonded to a $C_{1-6}$ alkyl group bonded to the NH of —CONH—. Examples of the $C_{1-6}$ alkyl group include the alkyl groups listed in [1-1] above.

The bicyclic group serving as Q is represented by formula (A):

[Ch. 2]

(A)

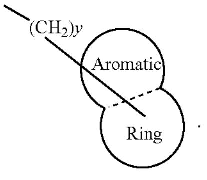

(wherein Aromatic represents a monocyclic aromatic heteroaryl ring or a benzene ring, Ring represents an alicyclic hydrocarbon ring, or a monocyclic heterocycle which is optionally hydrogenated, Aromatic moiety and Ring moiety are condensed, and y represents an integer of 0 to 6), and $(CH_2)_y$ may be bonded to either the Aromatic moiety or the Ring moiety. Formula (A) can be replaced with Q in formula (I). Specific examples thereof are described in embodiment [1-8-c].

More preferably, the bicyclic group serving as Q is represented by formula (B):

[Ch. 3]

(B)

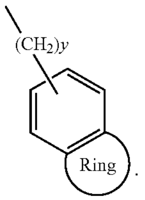

(wherein Ring and y represent the same as the above.) Preferably, y is in the range of 0 to 4, and more preferably, y is 0, 1, 2, or 3.

Specific examples of formula (B) include a 2,3-dihydrobenzo[b][1,4]dioxin-6-yl group, isoquinolin-5-yl group, quinolin-7-yl group, quinoxalin-6-yl group, 1,2,3,4-tetrahydro-1-methylquinolin-7-yl group, 2-methyl-1,3-benzothiazolo-5-yl group, 4-methyl-2-oxo-2H-chromen-7-yl group, 1,3-dihydro-1-oxoisobenzofuran-6-yl group, 2-hydroxymethyl-1,3-benzothiazol-5-yl group, 3-hydroxy-2-oxo-1,2,3,4-tetrahydroquinolin-5-yl group, 3-hydroxy-1,2,3,4-tetrahydroquinolin-5-yl group, 1-methyl-3-hydroxy-1,2,3,4-tetrahydroquinolin-5-yl group, 1-(2-hydroxyethyl)-1,2,3,4-tetrahydroquinolin-7-yl group, 1-(2-(4-morpholino)ethyl)-1,2,3,4-tetrahydroquinolin-7-yl group, 1-(2-(N,N-dimethylamino)ethyl)-1,2,3,4-tetrahydroquinolin-7-yl group, 3,4-dihydro-1H-quinolin-2-on-7-yl group, 2-quinolon-7-yl group, 3,4-dihydro-2H-1,5-benzo[b]dioxepin-7-yl group, 2,2-difluoro-1,3-benzodioxol-5-yl group, 1-methylindol-5-yl group, 1-(2-hydroxyethyl)indol-6-yl group, 1-(1-oxopentyl)-1,2,3,4-tetrahydroquinolin-7-yl group, 1-((1-oxo-2-acetoxy)ethyl)-1,2,3,4-tetrahydroquinolin-7-yl group, 1-trifluoroacetyl-1,2,3,4-tetrahydroquinolin-7-yl group, 3-hydroxymethylindol-4-yl group, 1-(2-hydroxyethyl)indol-5-yl group, 3-hydroxymethyl-2,3-dihydro-1,4-benzodioxin-6-yl group, 2,3-dihydro-isoindol-1-on-6-yl group, 1,2,3,4-tetrahydroquinolin-7-yl group, (1-(2-hydroxy-1-oxo)ethyl)-1,2,3,4-tetrahydroquinolin-7-yl group, 1a,2,7,7a-tetrahydronaphtho[2,3-b]oxirene-3-yl group, 2-quinolon-8-yl group, 1-methylindol-6-yl group, 1-methyl-2-oxo-1,2,3,4-tetrahydroquinolin-7-yl group, 1,2,3,4-tetrahydroisoquinolin-8-yl group, 2-hydroxyethyl-1,2,3,4-tetrahydroisoquinolin-8-yl group, 3,4-dihydro-2H-isoquinolin-1-on-7-yl group, 2-hydroxyethyl-2,3-dihydro-isoindol-1-on-6-yl group, 3-hydroxy-2,3-dihydro-(1H)-4-benzopyran-5-yl group, 6-hydroxy-2,3-dihydro-(1H)-4-benzopyran-4-yl group, 6-hydroxy-1,2,3,4-tetrahydroquinolin-4-yl group, 2-oxo-1,2,3,4-tetrahydroquinolin-8-yl group, 3-hydroxyquinolin-5-yl group, 2-acetyl-1,2,3,4-tetrahydroisoquinolin-8-yl group, 4-(2-hydroxyacetyl)-3,4-dihydro-2H-benzo[b][1,4]oxazin-6-yl group, 4-(2-hydroxypropanoyl)-3,4-dihydro-2H-benzo[b][1,4]oxazin-6-yl group, 4-(2-hydroxyethyl)-3,4-dihydro-2H-benzo[b][1,4]oxazin-6-yl group, 2-hydroxymethyl-1,3-benzothiazolo-5-yl group, 1H-indazol-4-yl group, 1H-indazol-7-yl group; (2,3-dihydrobenzo[b][1,4]dioxin-6-yl)methyl group, 1-(2,3-dihydrobenzo[b][1,4]dioxin-6-yl)ethyl group, (2,3-dihydrobenzo[b][1,4]dioxin-3-yl)methyl group, (2,3-dihydrobenzofuran-6-yl)methyl group, (2-(4-chlorophenyl)-4-methylthiazol-5-yl)methyl group, (1,2,4-triazolo[4,3-a]pyridin-3-yl)methyl group; 7-hydroxynaphthalen-1-yl group, 1,2,3,4-tetrahydro-1-oxonaphthalen-7-yl group, 7-oxo-5,6,7,8-tetrahydronaphthalen-1-yl group, 7-hydroxy-5,6,7,8-tetrahydronaphthalen-1-yl group, 5,6,7,8-tetrahydro-trans-6,7-dihydroxynaphthalen-1-yl group, 5,6,7,8-tetrahydro-cis-6,7-dihydroxynaphthalen-1-yl group, 6-hydroxynaphthalen-1-yl group, 7-hydroxynaphthalen-2-yl group, 7-methoxynaphthalen-1-yl group, 5-hydroxynaphthalen-1-yl group, indan-1-on-6-yl group, indan-2-acetoxy-4-yl group, indan-2-ol-4-yl group, 7-dimethylamino-naphthalen-1-yl group, 8-hydroxymethyl-5,6,7,8-tetrahydronaphthalen-2-yl group, 7-hydroxy-7-methyl-5,6,7,8-tetrahydronaphthalen-1-yl group, (Z)-7-hydroxyimino-5,6,7,8-tetrahydronaphthalen-1-yl group, (E)-7-hydroxyimino-5,6,7,8-tetrahydronaphthalen-1-yl group, 1-hydroxy-1,2,3,4-tetrahydronaphthalen-8-yl group, indan-1-ol-6-yl group, 5,6,7,8-tetrahydronaphthalen-1-yl group, 2-(7-hydroxy-5,6,7,8-tetrahydronaphthalen-1-yl)ethyl group, 2-(7-hydroxy-5,6,7,8-tetrahydronaphthalen-1-yl)propyl group, and 2-(2-chlorophenyl)ethyl group. More preferably, examples thereof include a 2-hydroxymethyl-1,3-benzothiazol-5-yl group, 7-hydroxy-5,6,7,8-tetrahydronaphthalen-1-yl group, 3-hydroxy-2-oxo-1,2,3,4-tetrahydroquinolin-5-yl group, and 3-hydroxy-1,2,3,4-tetrahydroquinolin-5-yl group.

[1-8-e]

Each of the groups of the specific examples of Q described in embodiments [1-8-c] and [1-8-d] may not have further substituents, or may be further substituted with 1 to 3 substituents in a class selected from (a-1) to (g-1) described in [1-1-a], or may be exchanged for any substituents in the specific examples. In the groups listed in (a-1) to (g-1) described above, "particularly preferable groups" include substituents such as $C_{1-6}$ alkyl, $C_{2-6}$ alkenyl, $C_{2-6}$ alkynyl, halogen atoms, halogenated $C_{1-6}$ alkyl, cyano, amino, hydroxyl, carbamoyl, $C_{1-6}$ alkoxy, $C_{2-6}$ alkenyloxy, $C_{2-6}$ alkynyloxy, $C_{1-6}$ alkylthio, $C_{1-6}$ alkylsulfinyl, $C_{1-6}$ alkylsulfonyl, mono/di $C_{1-6}$ alkylamino, $C_{1-6}$ alkoxycarbonyl, $C_{2-6}$ alkanoyl, $C_{2-6}$ alkanoylamino, hydroxy-$C_{1-6}$ alkyl, $C_{1-6}$ alkoxy-$C_{1-6}$ alkyl, carboxy-$C_{1-6}$ alkyl, $C_{1-6}$ alkoxycarbonyl-$C_{1-6}$ alkyl, carbamoyl-$C_{1-6}$ alkyl, N—$C_{1-6}$ alkylcarbamoyl-$C_{1-6}$ alkyl, N,N-di $C_{1-6}$ alkylcarbamoyl-$C_{1-6}$ alkyl, phenyl, phenoxy, phenylthio, phenylsulfinyl, phenylsulfonyl, benzyl, benzoyl, morpholino, oxo, morpholinylcarbonyl, morpholinylsulfonyl, 5-trifluoromethylpyridin-2-yloxy, quinoxalin-2-yl, (pyridin-4-yl)methyl, 1,2,3-thiadiazolo-4-yl, 1H-pyrazolo-1-yl, and 4-chlorophenyl. The aromatic rings in these substituents may be further substituted with 1 to 3 substituents selected from halogen atoms, trifluoromethyl, cyano, hydroxyl, amino, nitro, carboxyl, carbamoyl, $C_{1-6}$ alkyl, $C_{1-6}$ alkoxy, mono/di $C_{1-6}$ alkylamino, di-$C_{1-6}$ alkylcarbamoyl, $C_{1-6}$ alkoxycarbonyl, N—$C_{1-6}$ alkylcarbamoyl, N,N-di $C_{1-6}$ alkylcarbamoyl, and $C_{2-6}$ alkenoylamino.

[1-9] In the compounds represented by formula (I) which is used for the pharmaceutical composition of embodiment [1], r is an integer of 0 or 1. Preferably, r is 0.

[1-10] In the compounds represented by formula (I) which is used for the pharmaceutical composition of embodiment [1], examples of the Cycle moiety include the rings described as "aryl groups" in $R^1$ and the five- to fourteen-membered rings, preferably five- to twelve-membered rings, containing at least one heteroatom (preferably, 1 to 4 heteroatoms) selected from N, O, and S in addition to the carbon atoms, which are described as "aromatic heterocyclic groups".

[1-10-a] More preferably, examples of the Cycle moiety include monocyclic, five- or six-membered rings. A benzene ring and some of the groups described as examples of the monocyclic aromatic heterocyclic groups in $R^1$ of embodiment [1-1] above correspond to such rings. Specific examples thereof include a benzene ring, a pyridine ring, a pyrimidine ring, a pyridazine ring, a pyrrole ring, a thiophene ring, a furan ring, an imidazole ring, a thiazole ring, and an isothiazole ring.

Regarding the condensation form of the monocyclic aromatic heterocyclic groups, at least one heteroatom is preferably located at positions selected from $A_1$, $A_2$, and $A_3$, or $B_1$, $B_2$, and $B_3$ in the following formulae. More preferably, at least one heteroatom is located at the position of $A_1$ or $B_1$.

[Ch. 3a]

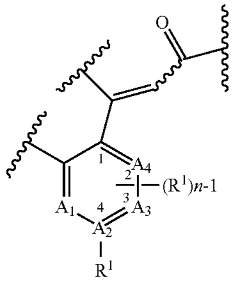

or

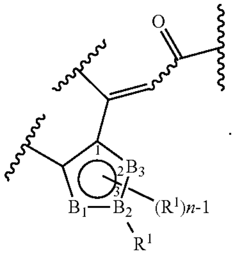

[1-10-b] Zero to two $R^1$'s described above can be bonded to the Cycle moiety. More specifically, n represents an integer of 0 to 2. Preferably, n is an integer of 1 or 2, and more preferably, n is 1.

[1-10-c]

When n is 1, the substitution position of $R^1$ corresponds to the 7th position of a chroman ring, a pyridochroman ring, a 2,3-dihydroquinoline ring, or the like, which belongs to a skeleton in which m=1 and q=0, or an isochroman ring or the like, which belongs to a skeleton in which m=0 and q=1. This position also corresponds to the 8th position of a 3,4-dihydrobenzo[b]oxepine ring or a 1,2,3,4-tetrahydrobenzo[b]azepine ring, which belongs to a skeleton in which m=2 and q=0, or a 3,4-dihydrobenzo[b]isooxepine ring or the like, which belongs to a skeleton in which m=1 and q=1. In the substitution positions of $R^1$'s, at least one of $R^1$'s is preferably a fluorine atom, a chlorine atom, isobutyl, tert-butyl, trifluoromethyl, or tetrafluoroethoxy. More preferably, at least $R^1$ bonded to $A_2$ or $B_2$ is a fluorine atom, a chlorine atom, isobutyl, tert-butyl, trifluoromethyl, or tetrafluoroethoxy, and particularly preferably, trifluoromethyl.

In the compounds represented by formula (I), preferable compounds can be determined by optional combinations of [1-1] to [1-10] described above. Examples of the compounds having specific combinations are described in [1-11].

[1-11] In formula (I),

[Ch. 4]

(I)

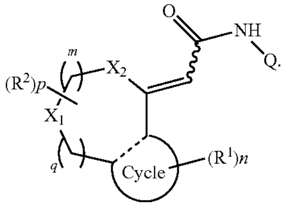

$R^1$ is a halogen atom, (1) a $C_{1-6}$ alkyl group, (2) a $C_{2-6}$ alkenyl group, (7) a $C_{6-14}$ aryl group, or (9) a $C_{1-6}$ alkoxy group, wherein each group in (1), (2), (7), and (9) is optionally substituted with 1 to 3 substituents in a class selected from (a-1) to (g-1) in [1-1] above (in particular, the substituents listed as "particularly preferable groups" in (a-1) to (g-1)).

More preferably, $R^1$ is a halogen atom (a fluorine atom, a chlorine atom, a bromine atom, or an iodine atom), a $C_{1-6}$ alkyl group (in particular, $C_{1-4}$ alkyl group) and $C_{1-6}$ alkoxy group (in particular, $C_{1-4}$ alkoxy group) which may be substituted with 1 to 3 halogen atoms.

Further preferably, $R^1$ is a halogen atom (particularly preferably, a fluorine atom or a chlorine atom), a $C_{1-4}$ alkyl group and $C_{1-4}$ alkoxy group which may be substituted with 1 to 3 halogen atoms. More specifically, examples thereof include a fluorine atom, a chlorine atom, methyl, ethyl, propyl, isopropyl, butyl, isobutyl, sec-butyl, tert-butyl, trifluoromethyl, methoxy, ethoxy, propoxy, isopropoxy, butoxy, sec-butoxy, tert-butoxy, trifluoromethoxy, and tetrafluoroethoxy.

Particularly preferably, $R^1$ is a fluorine atom, a chlorine atom, isobutyl, tert-butyl, trifluoromethyl, or tetrafluoroethoxy. Still more preferably, $R^1$ is trifluoromethyl.

In formula (I), n is an integer of 0 to 2, preferably, n is an integer of 1 or 2, and more preferably n is 1.

$R^2$ is a halogen atom, a substituted or unsubstituted amino group, a substituted or unsubstituted hydrocarbon group, a substituted or unsubstituted aromatic heterocyclic group, or an oxo group.

Preferably, $R^2$ is a fluorine atom, a chlorine atom, an amino group which may be mono-substituted with a substituent RIII, a $C_{1-6}$ alkyl group, or a phenyl group, more preferably $R^2$ is a $C_{1-6}$ alkyl group (in particular, a $C_{1-4}$ alkyl group such as methyl, ethyl, propyl, isopropyl, butyl, isobutyl, sec-butyl, or tert-butyl), and further preferably, $R^2$ is methyl.

In formula (I), p is an integer of 0 to 2, preferably, p is 0 or 2.

However, in the compounds represented by formula (I), when $R^2$ is a $C_{1-6}$ alkyl group (in particular, a $C_{1-4}$ alkyl group such as methyl, ethyl, propyl, isopropyl, butyl, isobutyl, sec-butyl, or tert-butyl), p is preferably 1 or 2, and more preferably 2. Alternatively, when p is 2, two geminal or vicinal $R^2$'s may bind to each other to may form a $C_{2-6}$ alkylene group, and form a cyclo ring group together with the carbon atom or atoms to which the two $R^2$'s are bonded. For example, a cyclopropane ring, a cyclobutane ring, a cyclopentane ring, or a cyclohexane ring can be formed. An example of the case where a carbon atom of a chroman ring forms such a cyclo ring is a 2,2-cyclobutyl chroman ring.

When $R^2$ is a fluorine atom, p is preferably 1 or 2, and more preferably 2. When $R^2$ is an amino group which is optionally mono-substituted with a substituent RIII or an oxo group, p is preferably 1 or 2, and more preferably 1.

In formula (I), m is 0 to 2, and preferably 1 or 2.

$X_1$ is an oxygen atom or —$NR^{3'}$— (wherein $R^{3'}$ is a substituted or unsubstituted hydrocarbon group, a substituted or unsubstituted heterocyclic group, or a substituted or unsubstituted acyl group all of which is defined in $R^3$), and more preferably, $X_1$ is an oxygen atom.

When $X_1$ is —$NR^{3'}$—, more preferably, examples of the "substituted or unsubstituted hydrocarbon group" or the "substituted or unsubstituted heterocyclic group" of $R^{3'}$ include (1') $C_{1-6}$ alkyl groups; (2') $C_{2-6}$ alkenyl groups; (4') $C_{3-6}$ cycloalkyl groups; (7') $C_{6-14}$ aryl groups; and (8') heterocyclic groups each containing 1 heteroatom or 2 hetero-atoms selected from an oxygen atom, a sulfur atom, and a nitrogen atom in addition to the carbon atoms, the heterocyclic groups being selected from (i) five- or six-membered, monocyclic aromatic heterocyclic groups, (ii) eight- to twelve-membered, fused aromatic heterocyclic groups, and (iii) "three- to eight-membered, saturated or unsaturated, non-aromatic heterocyclic groups, and each of the groups in (1'), (2'), (4'), (7'), and (8') may be mono-substituted with a substituent in a class selected from the substituents (a-1) to (g-1) (in particular, the substituents listed as "particularly preferable groups" in (a-1) to (g-1)).

Examples of the "substituted or unsubstituted acyl group" of $R^{3'}$ include groups represented by —CO-Rg''' (wherein Rg''' represents a substituent RV' (wherein RV' represents $C_{1-6}$ alkyl, $C_{3-6}$ cycloalkyl, $C_{6-10}$ aryl, or a heterocyclic group; the heterocyclic group is any one of (i) five- or six-membered monocyclic aromatic heterocyclic groups, (ii) eight- to twelve-membered fused aromatic heterocyclic groups, and (iii) three- to eight-membered saturated or unsaturated non-aromatic heterocyclic groups which contain 1 hetero-atom or 2 heteroatoms selected from an oxygen atom, a sulfur atom, and a nitrogen atom in addition to the carbon atoms; and the alkyl, the aryl, or the heterocyclic group is optionally further substituted with 1 to 5 substituents RIV of (f) described above).

When $X_1$ is —$NR^{3'}$—, further preferably, examples of the "substituted or unsubstituted hydrocarbon group" or the "substituted or unsubstituted heterocyclic group" of $R^{3'}$ include (7'') $C_{6-14}$ aryl groups and (8'') heterocyclic groups each containing a hetero-atom selected from an oxygen atom, a sulfur atom, and a nitrogen atom in addition to the carbon atoms, the heterocyclic groups being selected from (i) five- or six-membered, monocyclic aromatic heterocyclic groups, (ii) eight- to twelve-membered, fused aromatic heterocyclic groups, and (iii) "three- to eight-membered, saturated or unsaturated, non-aromatic heterocyclic groups, and each of the groups in (7'') and (8'') may be mono-substituted with a substituent in a class selected from the substituents (a-1) to (g-1) (in particular, the substituents listed as "particularly preferable groups" in (a-1) to (g-1)).

Examples of the "substituted or unsubstituted acyl group" of $R^{3'}$ include groups represented by —CO-Rg'''' (wherein Rg'''' represents a substituent RV'' (wherein RV'' represents $C_{1-6}$ alkyl, $C_{3-6}$ cycloalkyl, $C_{6-10}$ aryl, or a heterocyclic group; the heterocyclic group is any one of (i) five- or six-membered monocyclic aromatic heterocyclic groups, (ii) eight- to twelve-membered fused aromatic heterocyclic groups, and (iii) three- to eight-membered saturated or unsaturated non-aromatic heterocyclic groups which contain a heteroatom selected from an oxygen atom, a sulfur atom, and a nitrogen atom in addition to the carbon atoms; and the alkyl, the cycloalkyl, the aryl, or the heterocyclic group may be further substituted with 1 to 3 substituents RIV of (f) above).

When $X_1$ is —$NR^{3'}$—, particularly preferably, examples of the "substituted or unsubstituted hydrocarbon group" or the "substituted or unsubstituted heterocyclic group" of $R^{3'}$ include (7''') phenyl and naphthyl (e.g., naphthalen-1-yl and naphthalen-2-yl) and (8''') pyridyl (e.g., pyridin-2-yl, pyridin-3-yl, and pyridin-4-yl) which may be mono-substituted with a halogen atom, more specifically, examples thereof include methyl, trifluoromethyl, ethyl, cyclohexyl, 2-chlorophenyl, 3-chlorophenyl, 4-chlorophenyl, naphthalen-1-yl, naphthalen-2-yl, and 3-chloro-pyridin-2-yl.

Examples of the "substituted or unsubstituted acyl group" of $R^{3'}$ include groups represented by —CO-Rg''''' (wherein Rg''''' represents a substituent RV''' (wherein RV''' represents methyl, ethyl, propyl, isopropyl, butyl, isobutyl, sec-butyl, tert-butyl, pentyl, isopentyl, neopentyl, tert-pentyl, 1-methylbutyl, 2-methylbutyl, 1,2-dimethylpropyl, hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-hexyl, cyclopropyl, cyclobutyl, cyclopentyl, cyclohexyl, phenyl, naphthyl, pyridyl (e.g., pyridin-2-yl, pyridin-3-yl, and pyridin-4-yl), 2,2-dimethylpropyl, 2-methylpropyl, 3-methylbutyl, 2-methylbutyl, 1-methylbutyl, 1,1- dimethylbutyl, 4,4-difluorocyclohexyl, 3-fluorocyclopentyl, 1-methylcyclopropyl, 1-methylcyclobutyl, 3,3,3-trifluoropropyl, 2,2,2-trifluoroethyl, 4,4,4-trifluorobutyl, phenylmethyl, 1,1-difluoropropyl, and 1-fluoro-1-methylethyl; and the alkyl, the cycloalkyl, the aryl, or the heterocyclic group may be further substituted with a substituent RIV of (f) above).

Specific examples of the groups represented by —CO-Rg'''' include acyl groups which are optionally halogenated, such as acetyl, pentanoyl, 2-ethylbutanoyl, cyclohexanecarbonyl, 4-pyranoyl, benzoyl, nicotinoyl, cyclopentanecarbonyl, pentanoyl, cyclobutanecarbonyl, 3,3-dimethylbutanoyl, 3-methylbutanoyl, 4-methylpentanoyl, 3-methylpentanoyl, 2-methylpentanoyl, 2,2-dimethylpentanoyl, 4,4-difluorocyclohexanecarbonyl, 3-fluorocyclopentanecarbonyl, 1-methylcyclopropanecarbonyl, 1-methylcyclobutanecarbonyl, 4,4,4-trifluorobutanoyl, 3,3,3-trifluoropropanoyl, 5,5,5-trifluoropentanoyl, 1-phenylacetyl, 2,2-difluorobutanoyl, and 2-fluoro-2-methylpropanoyl.

$X_2$ is a methylene group or an —NH— group, and more preferably, $X_2$ is a methylene group.

Q is a substituted or unsubstituted heteroaryl group, a substituted or unsubstituted heteroarylalkyl group (aromatic heterocyclic-$C_{1-6}$ alkyl group), a substituted or unsubstituted aryl group, or a substituted or unsubstituted aralkyl group (aryl-$C_{1-6}$ alkyl group).

Examples of the "substituted or unsubstituted heteroaryl group" in Q preferably include pyrrolyl, furyl, thienyl, oxazolyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, tetrazolyl, pyridyl, pyridazinyl, pyrimidinyl, pyrazinyl, 1,2,3-triazinyl, 1,2,4-triazinyl, 1,2,5-triazinyl, 1,3,5-triazinyl, and thiadiazinyl, indolyl, isoindolyl, 1H-indazolyl, benzofuranyl (-2-yl), isobenzofuranyl, benzothienyl(-2-yl), isobenzothienyl, benzindazolyl, benzoxazolyl(-2-yl), 1,2-benzisoxazolyl, benzothiazolyl(-2-yl), 1,2-benzisothiazolyl, 2H-benzopyranyl(-3-yl), (1H-)benzimidazolyl(-2-yl), 1H-benzotriazolyl, 4H-1,4-benzoxazinyl, 4H-1,4-benzothiazinyl, quinolyl, isoquinolyl, cinnolinyl, quinazolinyl, quinoxalinyl, phthalazinyl, naphthylizinyl, purinyl, pteridinyl, carbazolyl, carbolinyl, acridinyl, phenoxazinyl, phenothiazinyl, phenazinyl, phenoxathinyl, thianthrenyl, phenanthridinyl, phenanthrolinyl, indolizinyl, (4,5,6,7-)tetrahydrothiazolo[5,4-c]pyridyl(-2-yl), (4,5,6,7-)tetrahydrothieno[3,2-c]pyridyl, (1,2,3,4-)tetrahydroisoquinolyl(-6-yl), thiazolo[5,4-c]pyridyl(-2-yl), pyrrolo[1,2-b]pyridazinyl, pyrazo[1,5-a]pyridyl, imidazo[1,2-a]pyridyl, imidazo[1,5-a]pyridyl, imidazo[1,2-b]pyridazinyl, imidazo[1,5-a]pyrimidinyl, [1,2,4]triazolo[4,3-a]pyridyl, and [1,2,4]-triazolo[4,3-b]pyridazinyl (Preferred embodiments are indicated in the parenthesis "( )".

Examples thereof also include partially hydrogenated fused heteroaryl groups and the like, e.g., tetrahydroquinolinyl, tetrahydroisoquinolinyl, tetrahydrobenzoxazepinyl, tetrahydrobenzoazepinyl, tetrahydronaphthpyridinyl, tetrahydroquinoxalinyl, chromanyl, dihydrobenzoxazinyl, 3,4-dihydro-2H-1,4-benzothiazinyl, dihydrobenzothiazolyl, 3,4-dihydro-2H-1,4-benzoxazinyl, isochromanyl, indolinyl, and pteridinyl. Furthermore, examples of the "substituted or unsubstituted heteroaryl group" include 1H-indolyl, 1,1-dioxobenzo[b]thienyl, cinnolinyl, imidazo[1,2-a]pyridinyl, 2-dihydro-2-oxo-quinolyl, 1,2-dihydro-1-methyl-2-oxo-quinolyl, 1,2-dihydro-3H-3-oxo-indazolyl, 2,3-dihydro-1H-indenyl, 2,3-dihydro-3-hydroxy-1H-indenyl, 2,3-dihydro-2-oxo-benzoxazolyl, 2,3-dihydro-3-oxo-1H-indenyl, 2,3-dihydro-1-oxo-1H-indenyl, 3-dihydro-1-methyl-1H-indolyl, 2,3-dihydro-2-oxo-1H-indolyl, 2,3-dihydro-1-methyl-2-oxo-1H-indolyl, 2,3-dihydro-1,3,3-trimethyl-2-oxo-1H-indolyl, 2,3-dihydro-3-methyl-2-oxo-benzothiazolyl, 2,3-dihydro-2-oxo-4-(trifluoromethyl)-1H-indolyl, 3,4-dihydro-4-methyl-3-oxo-2H-1,4-benzoxazinyl, 3,4-dihydro-3-oxo-2H-benzoxazinyl, 3,4-dihydro-3-oxo-2H-1,4-benzothiazinyl, 3,4-dihydro-4-methyl-3-oxo-2H-1,4-benzothiazinyl, 3,4-dihydro-2-methyl-3-oxo-2H-1,4-benzoxazinyl, 3,4-dihydro-2,2-dimethyl-3-oxo-2H-1,4-benzoxazinyl, 1,2,3,4-tetrahydro-2-oxo-quinolinyl, 1,2,3,4-tetrahydro-1-methyl-2-oxo-quinolinyl, 1,2,3,4-tetrahydro-1-methyl-quinolinyl, 1,2,3,4-tetrahydro-1-methyl-2-oxo-quinolinyl, 1,2,3,4-tetrahydro-3-hydroxy-1-methyl-quinolinyl, 1-methyl-3,4-dihydro-1H-quinolin-2-on-7-yl, 1-methyl-2-quinolon-7-yl, 4-methyl-2-quinolon-7-yl, 1-methyl-2-quinolon-5-yl, 3,4-dihydro-2H-1,4-ethanoquinolin-7-yl, 3,3-dimethylindolinyl, 1-methyl-3,3-dimethylindolinyl, 3,3-dimethyl-1-(2-hydroxyethyl)indolinyl, 3,3-dimethyl-1-(2-(N,N-dimethylamino)ethyl)indolinyl, 3,3-dimethyl-1-(2-(4-morpholino)ethyl)indolin-6-yl, 1,1-dioxo-2,3-dihydro-4H-benzo[1,4]thiazinyl, 1,1-dioxo-4-methyl-2,3-dihydro-4H-benzo[1,4]thiazinyl, 1,1-dioxo-4-(2-hydroxyethyl)-2,3-dihydro-4H-benzo[1,4]thiazinyl, 1,1-dioxo-4-(2-(N,N-dimethylamino)ethyl)-2,3-dihydro-4H-benzo[1,4]thiazinyl, 1,1-dioxo-4-(2-(4-morpholino)ethyl)-2,3-dihydro-4H-benzo[1,4]thiazinyl, 1-acetyl-1,2,3,4-tetrahydroquinolinyl, 1,2,3,4-tetrahydroquinolinyl, 1-(2-hydroxyethyl)-1,2,3,4-tetrahydroquinolinyl, 1-(2-(N,N-dimethylamino)ethyl)-1,2,3,4-tetrahydroquinolinyl, 1-(2-(4-morpholino)ethyl)-1,2,3,4-tetrahydroquinolinyl, 4,4-dimethyl-1,2,3,4-tetrahydroquinolinyl, 1-methyl-4,4-dimethyl-1,2,3,4-tetrahydroquinolinyl, 1-(2-hydroxyethyl)-4,4-dimethyl-1,2,3,4-tetrahydroquinolinyl, 1-(2-(N,N-dimethylamino)ethyl)-4,4-dimethyl-1,2,3,4-tetrahydroquinolinyl, 1-(2-(4-morpholino)ethyl)-4,4-dimethyl-1,2,3,4-tetrahydroquinolinyl, 2,3-dihydro-4H-benzo[1,4]oxazinyl, 4-methyl-2,3-dihydro-4H-benzo[1,4]oxazinyl, 4-(2-hydroxyethyl)-2,3-dihydro-4H-benzo[1,4]oxazinyl, 4-(2-(N,N-dimethylamino)ethyl)-2,3-dihydro-4H-benzo[1,4]oxazinyl, 4-(2-(4-morpholino)ethyl)-2,3-dihydro-4H-benzo[1,4]oxazinyl, 4,4-dimethyl-1,2,3,4-tetrahydroisoquinolinyl, 2,4,4-trimethyl-1,2,3,4-tetrahydroisoquinolinyl, 2-(2-hydroxyethyl)-4,4-dimethyl-1,2,3,4-tetrahydroisoquinolinyl, 2-(2-(N,N-dimethylamino)ethyl)-4,4-dimethyl-1,2,3,4-tetrahydroisoquinolinyl, 2-(2-(4-morpholino)ethyl)-4,4-dimethyl-1,2,3,4-tetrahydroisoquinolinyl, 6-hydroxyquinolin-4-yl, 6-hydroxyisoquinolin-4-yl, 7-hydroxyisoquinolin-1-yl, 6-hydroxyquinazolin-4-yl, 1,2,3,4-tetrahydro-3-hydroxy-quinolinyl, 1,2,3,4-tetrahydro-1-methyl-3-hydroxy-quinolinyl, 1,2,3,4-tetrahydro-1-(2-hydroxyethyl)-3-hydroxy-quinolinyl, 1,2,3,4-tetrahydro-1-(2-(N,N-dimethylamino)ethyl)-3-hydroxy-quinolinyl, 1,2,3,4-tetrahydro-1-(2-(4-morpholino)ethyl)-quinolinyl, 3-hydroxy-3,4-dihydro-2(1H)-quinolinon-5-yl, 1-methylisoquinolinyl, 3-methylisoquinolinyl, 1,3-dimethylisoquinolinyl, 2-methylquinolinyl, indol-4-yl, 1-methylindol-4-yl, 1-(2-hydroxyethyl)indol-4-yl, 1-(2-(N,N-dimethylamino)ethyl)indol-4-yl, 1-(2-(4-morpholino)ethyl)indol-4-yl, indol-6-yl, 1-methylindol-6-yl, 1-(2-hydroxyethyl)indol-6-yl, 1-(2-(N,N-dimethylamino)ethyl)indol-6-yl, 1-(2-(4-morpholino)ethyl)indol-6-yl, indolin-6-yl, 1-methyl-indolin-6-yl, 1-(2-hydroxyethyl)indolin-6-yl, 1-(2-(N,N-dimethylamino)ethyl)indolin-6-yl, 1-(2-(4-morpholino)ethyl) indolin-6-yl, 5-trifluoromethyl-pyridinyl, 1,3,4,5-tetrahydrobenzo[b]azepin-2-on-8-yl, 1-methyl-1,3,4,5-tetrahydrobenzo[b]azepin-2-on-8-yl, 2H-benzo[1,4]oxazin-3(4H)-on-6-yl, 2-methyl-(2H)1,4-benzoxazin-3(4H)-on-6-yl, 3,3-difluoro-1-methyl-2-oxoindolin-5-yl, 2-(N,N-dimethylamino)-3-fluoropyridin-5-yl, 3-acetylpyridin-5-yl, 2-(cyclohexanecarbonyl)pyridin-4-yl, 5-oxo-5,6,7,8-tetrahydroquinolin-3-yl, 2,2'-bipyridin-3-yl, 2,2'-bipyridin-4-yl, 2-hydroxymethyl-1,3-benzothiazol-5-yl, 1,3-benzodioxol-5-yl, 2,2-difluoro-1,3-benzodioxol-5-yl, 3,4-dihydro-2H-1,5-benzo[b]dioxepin-7-yl, and 2-chloropyridin-4-yl.

Examples of the "substituted or unsubstituted heteroarylalkyl group (aromatic heterocyclic-$C_{1-6}$ alkyl group)" include groups in which the above-mentioned "heteroaryl group" is bonded to a $C_{1-4}$ alkyl group bonded to the NH of —CONH—.

Examples of the "substituted or unsubstituted aryl group" include $C_{6-14}$ aryl groups such as phenyl, naphthyl, biphenylyl, 2-anthryl, phenanthryl, acenaphthyl, and 5,6,7,8-tetrahydronaphthalenyl; and partially hydrogenated fused aryl such as indanyl and tetrahydronaphthyl. Furthermore, examples of the aryl group include 3-fluoro-4-methanesulfonylaminobenzyl, 5-hydroxy-1,2,3,4-tetrahydronaphthyl, 5-tert-butyl-2,3-dihydro-1H-indenyl, 5-hydroxy-naphthyl, 7-hydroxy-naphthyl, 2,4-dibromo-7-hydroxy-naphthyl, 2,4-dichloro-7-hydroxy-naphthyl, 4-chloro-3-(trifluoromethyl)phenyl, 7-hydroxynaphthalen-2-yl, 6-hydroxynaphthalen-1-yl, 5,6,7,8-tetrahydro-7-naphthol-2-yl, indan-2-ol-5-yl, 5,6,7,8-tetrahydro-7-naphthol-1-yl, 5,6,7,8-tetrahydronaphthalen-6,7-diol-1-yl, 5,6,7,8-tetrahydronaphthalen-8-ol-2-yl, 3-acetylphenyl, 3-acetyl-4-methylphenyl, 3-(4-morpholinylcarbonyl)phenyl, 3-n-butynylphenyl, 3-cyclohexynylphenyl, 3-(picolinyl)phenyl, 8-methoxy-5,6,7,8-tetrahydronaphthalen-2-yl, 8-(N,N-dimethylamino)-5,6,7,8-tetrahydronaphthalen-2-yl, 3-methoxy-5-trifluoromethylphenyl, 4-chloro-3-trifluoromethylphenyl, 4-methanesulfonylphenyl, 3-trifluoromethylphenyl, 3-methanesulfonylphenyl, 4-trifluoromethoxyphenyl, 4-isopropylphenyl, 2-(hydroxyethyl)phenyl, 3-(N,N-dimethylamino)phenyl, and 4-(N,N-diethylamino)phenyl.

Examples of the "substituted or unsubstituted aralkyl group (aryl-$C_{1-6}$ alkyl group)" include groups in which the above-mentioned "aryl group" is bonded to a $C_{1-4}$ alkyl group bonded to the NH of —CONH—.

Preferably, each of the groups in Q may be either unsubstituted or substituted with 1 to 3 substituents in a class selected from (a-1) to (g-1) described in [1-1-a] above.

Particularly preferable substituents include $C_{1-6}$ alkyl, $C_{2-6}$ alkenyl, $C_{2-6}$ alkynyl, halogen atoms, halogenated $C_{1-6}$ alkyl, cyano, amino, hydroxyl, carbamoyl, $C_{1-6}$ alkoxy, $C_{2-6}$ alkenyloxy, $C_{2-6}$ alkynyloxy, $C_{1-6}$ alkylthio, $C_{1-6}$ alkylsulfinyl, $C_{1-6}$ alkylsulfonyl, mono/di $C_{1-6}$ alkylamino, $C_{1-6}$ alkoxycarbonyl, $C_{2-6}$ alkanoyl, $C_{2-6}$ alkanoylamino, hydroxy-$C_{1-6}$ alkyl, $C_{1-6}$ alkoxy-$C_{1-6}$ alkyl, carboxy-$C_{1-6}$ alkyl, $C_{1-6}$ alkoxycarbonyl-$C_{1-6}$ alkyl, carbamoyl-$C_{1-6}$ alkyl, N—$C_{1-6}$ alkylcarbamoyl-$C_{1-6}$ alkyl, N,N-di $C_{1-6}$ alkylcarbamoyl-$C_{1-6}$ alkyl, phenyl, phenoxy, phenylthio, phenylsulfinyl, phenylsulfonyl, benzyl, benzoyl, morpholino, oxo, morpholinylcarbonyl, morpholinylsulfonyl, 5-trifluoromethylpyridin-2-yloxy, quinoxalin-2-yl, (pyridin-4-yl)methyl, 1,2,3-thiadiazolo-4-yl, 1H-pyrazolo-1-yl, and 4-chlorophenyl. The aromatic rings in these substituents may be substituted with a halogen atom, trifluoromethyl, cyano, hydroxyl, amino, nitro, carboxyl, carbamoyl, $C_{1-6}$ alkyl, $C_{1-6}$ alkoxy, mono/di $C_{1-6}$ alkylamino, di-$C_{1-6}$ alkylcarbamoyl, $C_{1-6}$ alkoxycarbonyl, N—$C_{1-6}$ alkylcarbamoyl, N,N-di $C_{1-6}$ alkylcarbamoyl, or $C_{2-6}$ alkenoylamino.

More preferably, examples of Q include thiazolyl, pyrazolyl, pyridyl, 1H-indazolyl, benzothiazolyl (-2-yl), (1H-)benzimidazolyl(-2-yl), quinolyl, isoquinolyl, quinoxalinyl, [1,2,4]triazolo[4,3-a]pyridyl, chromenyl (2H-chromenyl), 1H-pyrazolo[3,4-b]pyridyl, [1,2,4]triazolo[1,5-a]pyrimidinyl, tetrahydroquinolinyl, 2,3-dihydrobenzo[b][1,4]dioxinyl, 1,2,3,4-tetrahydro-1-methylquinolinyl, 1,3-dihydro-1-oxoisobenzofuranyl, and 6,7,8,9-tetrahydro-5H-cyclohepta[b]pyridyl. Examples of Q further include 1H-indol-4-yl, 1H-indol-6-yl, 1H-indazol-4-yl, 1H-indazol-5-yl, 5-benzothiazolyl, 1,1-dioxobenzo[b]thien-6-yl, 4-hydroxy-2-quinolinyl, 3-quinolinyl, 2-methylquinolin-6-yl, 3-methylisoquinolin-5-yl, 1-methylisoquinolin-5-yl, 2-methylbenzothiazol-5-yl, 3-methyl-cinnolinyl-5-yl, imidazo[1,2-a]pyridin-7-yl, 1,2-dihydro-2-oxo-5-quinolinyl, 1,2-dihydro-2-oxo-7-quinolinyl, 1,2-dihydro-1-methyl-2-oxo-7-quinolinyl, 1,2-dihydro-3H-3-oxo-indazol-6-yl, 2,3-dihydro-1H-inden-5-yl, 2,3-dihydro-3-hydroxy-1H-inden-5-yl, 2,3-dihydro-2-oxo-5-benzoxazolyl, 2,3-dihydro-2-oxo-6-benzoxazolyl, 2,3-dihydro-3-oxo-1H-inden-5-yl, 2,3-dihydro-1-oxo-1H-inden-4-yl, 2,3-dihydro-1-methyl-1H-indol-6-yl, 2,3-dihydro-2-oxo-1H-indol-6-yl, 2,3-dihydro-1-methyl-2-oxo-1H-indol-6-yl, 2,3-dihydro-1,3,3-trimethyl-2-oxo-1H-indole-6-yl, 2,3-dihydro-3-methyl-2-oxo-5-benzothiazolyl, 2,3-dihydro-2-oxo-4-(trifluoromethyl)-1H-indol-6-yl, 3,4-dihydro-4-methyl-3-oxo-2H-1,4-benzoxazin-6-yl, 3,4-dihydro-3-oxo-2H-benzoxazin-6-yl, 3,4-dihydro-3-oxo-2H-1,4-benzothiazin-6-yl, 3,4-dihydro-4-methyl-3-oxo-2H-1,4-benzothiazin-6-yl, 3,4-dihydro-2-methyl-3-oxo-2H-1,4-benzoxazin-6-yl, 3,4-dihydro-2,2-dimethyl-3-oxo-2H-1,4-benzoxazin-6-yl, 1,2,3,4-tetrahydro-2-oxo-7-quinolinyl, 1,2,3,4-tetrahydro-1-methyl-2-oxo-7-quinolinyl, 1,2,3,4-tetrahydro-1-methyl-7-quinolinyl, 1,2,3,4-tetrahydro-1-methyl-2-oxo-7-quinolinyl, 1,2,3,4-tetrahydro-3-hydroxy-1-methyl-quinolin-5-yl; 1-methyl-3,4-dihydro-1H-quinolin-2-on-7-yl, 1-methyl-2-quinolon-7-yl, 4-methyl-2-quinolon-7-yl, 1-methyl-2-quinolon-5-yl, 3,4-dihydro-2H-1,4-ethanoquinolin-7-yl, 3,3-dimethylindolin-6-yl, 1-methyl-3,3-dimethylindolin-6-yl, 3,3-dimethyl-1-(2-hydroxyethyl)indolin-6-yl, 3,3-dimethyl-1-(2-(N,N-dimethylamino)ethyl)indolin-6-yl, 3,3-dimethyl-1-(2-(4-morpholino)ethyl)indolin-6-yl, 1,1-dioxo-2,3-dihydro-4H-benzo[1,4]thiazin-6-yl, 1,1-dioxo-4-methyl-2,3-dihydro-4H-benzo[1,4]thiazin-6-yl, 1,1-dioxo-4-(2-hydroxyethyl)-2,3-dihydro-4H-benzo[1,4]thiazin-6-yl, 1,1-dioxo-4-(2-(N,N-dimethylamino)ethyl)-2,3-dihydro-4H-benzo[1,4]thiazin-6-yl, 1,1-dioxo-4-(2-(4-morpholino)ethyl)-2,3-dihydro-4H-benzo[1,4]thiazin-6-yl, 1-acetyl-1,2,3,4-tetrahydroquinolin-7-yl, 1,2,3,4-tetrahydroquinolin-7-yl, 1-(2-hydroxyethyl)-1,2,3,4-tetrahydroquinolin-7-yl, 1-(2-(N,N-dimethylamino)ethyl)-1,2,3,4-tetrahydroquinolin-7-yl, 1-(2-(4-morpholino)ethyl)-1,2,3,4-tetrahydroquinolin-7-yl, 4,4-dimethyl-1,2,3,4-tetrahydroquinolin-7-yl, 1-methyl-4,4-dimethyl-1,2,3,4-tetrahydroquinolin-7-yl, 1-(2-hydroxyethyl)-4,4-dimethyl-1,2,3,4-tetrahydroquinolin-7-yl, 1-(2-(N,N-dimethylamino)ethyl)-4,4-dimethyl-1,2,3,4-tetrahydroquinolin-7-yl, 1-(2-(4-morpholino)ethyl)-4,4-dimethyl-1,2,3,4-tetrahydroquinolin-7-yl, 2,3-dihydro-4H-benzo[1,4]oxazin-6-yl, 4-methyl-2,3-dihydro-4H-benzo[1,4]oxazin-6-yl, 4-(2-hydroxyethyl)-2,3-dihydro-4H-benzo[1,4]oxazin-6-yl, 4-(2-(N,N-dimethylamino)ethyl)-2,3-dihydro-4H-benzo[1,4]oxazin-6-yl, 4-(2-(4-morpholino)ethyl)-2,3-dihydro-4H-benzo[1,4]oxazin-6-yl, 4,4-dimethyl-1,2,3,4-tetrahydroisoquinolin-7-yl, 2-methyl-4,4-dimethyl-1,2,3,4-tetrahydroisoquinolin-7-yl, 2-(2-hydroxyethyl)-4,4-dimethyl-1,2,3,4-tetrahydroisoquinolin-7-yl, 2-(2-(N,N-dimethylamino)ethyl)-4,4-dimethyl-1,2,3,4-tetrahydroisoquinolin-7-yl, 2-(2-(4-morpholino)ethyl)-4,4-dimethyl-1,2,3,4-tetrahydroisoquinolin-7-yl, 6-hydroxyquinolin-4-yl, 6-hydroxyisoquinolin-4-yl, 7-hydroxyisoquinolin-1-yl, 6-hydroxyquinazolin-4-yl, 1,2,3,4-tetrahydroquinolin-3-ol-5-yl, 1-methyl-1,2,3,4-tetrahydro-quinolin-3-ol-5-yl, 1-(2-hydroxyethyl)-1,2,3,4-tetrahydroquinolin-3-ol-5-yl, 1-(2-(N,N-dimethylamino) ethyl)-1,2,3,4-tetrahydroquinolin-3-ol-5-yl, 1-(2-(4-morpholino)ethyl)-1,2,3,4-tetrahydroquinolin-3-ol-5-yl, 3-hydroxy-3,4-dihydro-2(1H)-quinolinon-5-yl, 1-methyl-isoquinolin-5-yl, 3-methylisoquinolin-5-yl, 1,3-dimethyliso-quinolin-5-yl, 2-methylquinolin-7-yl, indol-4-yl, 1-methylindol-4-yl, 1-(2-hydroxyethyl)indol-4-yl, 1-(2-(N,N-dimethylamino)ethyl)indol-4-yl, 1-(2-(4-morpholino)ethyl) indol-4-yl, indol-6-yl, 1-methylindol-6-yl, 1-(2-hydroxyethyl)indol-6-yl, 1-(2-(N,N-dimethylamino)ethyl) indol-6-yl, 1-(2-(4-morpholino)ethyl)indol-6-yl, indolin-6-yl, 1-methyl-indolin-6-yl, 1-(2-hydroxyethyl)indolin-6-yl, 1-(2-(N,N-dimethylamino)ethyl)indolin-6-yl, 1-(2-(4-morpholino)ethyl)indolin-6-yl, 5-trifluoromethyl-pyridin-2-yl, 1,3,4,5-tetrahydrobenzo[b]azepin-2-on-8-yl, 1-methyl-1,3,4,5-tetrahydrobenzo[b]azepin-2-on-8-yl, 2H-benzo[1,4]oxazin-3(4H)-on-6-yl, 2-methyl-(2H)1,4-benzoxazin-3(4H)-on-6-yl, 3,3-difluoro-1-methyl-2-oxoindolin-5-yl, 2-(N,N-dimethylamino)-3-fluoropyridin-5-yl, 3-acetylpyridin-5-yl, 2-(cyclohexanecarbonyl)pyridin-4-yl, 5-oxo-5,6,7,8-tetrahydroquinolin-3-yl, 2,2'-bipyridin-3-yl, 2,2'-bipyridin-4-yl, 2-hydroxymethyl-1,3-benzothiazol-5-yl, 1,3-benzo-dioxol-5-yl, 2,2-difluoro-1,3-benzodioxol-5-yl, 3,4-dihydro-2H-1,5-benzo[b]dioxepin-7-yl, 2-chloropyridin-4-yl, indan-5-yl, 3-fluoro-4-methanesulfonylaminobenzyl, 5-hydroxy-1,2,3,4-tetrahydronaphthalen-1-yl, 5-tert-butyl-2,3-dihydro-1H-inden-1-yl, 5-hydroxy-2-naphthalenyl, 7-hydroxy-1-naphthyl, 2,4-dibromo-7-hydroxy-1-naphthyl, 2,4-dichloro-7-hydroxy-1-naphthyl, 4-chloro-3-(trifluoromethyl)phenyl; 7-hydroxynaphthalen-2-yl, 6-hydroxynaphthalen-1-yl, 5,6,7,8-tetrahydro-7-naphthol-2-yl, indan-2-hydroxy-5-yl, 5,6,7,8-tetrahydro-7-naphthol-1-yl, 5,6,7,8-tetrahydronaphthalen-6,7-diol-1-yl, 5,6,7,8-tetrahydronaphthalen-8-ol-2-yl, 3-acetylphenyl, 3-acetyl-4-methylphenyl, 3-(4-morpholinyl-carbonyl)phenyl, 3-n-butynylphenyl, 3-cyclohexynylphenyl, 3-(picolinyl)phenyl, 8-methoxy-5,6,7,8-tetrahydronaphthalen-2-yl, 8-(N,N-dimethylamino)-5,6,7,8-tetrahydronaphthalen-2-yl, 3-methoxy-5-trifluoromethylphenyl, 4-chloro-3-trifluoromethylphenyl, 4-methanesulfonylphenyl, 3-trifluoromethylphenyl, 3-methanesulfonylphenyl, 4-trifluoromethoxyphenyl, 4-isopropylphenyl, 2-(hydroxyethyl) phenyl, 3-(N,N-dimethylamino)phenyl, 4-(N,N-diethylamino)phenyl; and 2-(2-chlorophenyl)ethyl.

More preferably, specific examples of the "substituted or unsubstituted heteroaryl group" include a 2,3-dihydrobenzo[b][1,4]dioxin-6-yl group, isoquinolin-5-yl group, 5,6,7,8-tetrahydroquinolin-7-yl group, quinolin-7-yl group, quinoxalin-6-yl group, 1,2,3,4-tetrahydro-1-methylquinolin-7-yl group, 2-methyl-1,3-benzothiazolo-5-yl group, 2-morpholinopyridin-3-yl group, 4-methyl-2-oxo-2H-chromen-7-yl group, 6-phenoxypyridin-2-yl group, 1,3-dihydro-1-oxoisobenzofuran-6-yl group, 1-methyl-1H-pyrazolo[3,4-b] pyridin-3-yl group, 1H-indazol-3-yl group, 1-ethyl-1H-benzo[d]imidazolo-2-yl group, [1,2,4]triazolo[1,5-a] pyrimidin-7-yl group, 6,7,8,9-tetrahydro-5H-cyclohepta[b] pyridin-8-yl group, 1-tert-butyl-3-methyl-1H-pyrazolo-5-yl group, 4-phenylthiazolo-2-yl group, 2-hydroxymethyl-1,3-benzothiazol-5-yl group, 3-hydroxy-2-oxo-1,2,3,4-tetrahydroquinolin-5-yl group, 3-hydroxy-1,2,3,4-tetrahydroquinolin-5-yl group, 1-methyl-3-hydroxy-1,2,3,4-tetrahydroquinolin-5-yl group, 1-(2-hydroxyethyl)-1,2,3,4-tetrahydroquinolin-7-yl group, 1-(2-(4-morpholino)ethyl)-1,2,3,4-tetrahydroquinolin-7-yl group, 1-(2-(N,N-dimethylamino)ethyl)-1,2,3,4-tetrahydroquinolin-7-yl group, 3,4-dihydro-1H-quinolin-2-on-7-yl group, 2-quinolon-7-yl group, 5-trifluoromethyl-pyridin-2-yl group, 3,4-dihydro-2H-1,5-benzo[b]dioxepin-7-yl group, 2,2-difluoro-1,3-benzodioxol-5-yl group, 1-methylindol-5-yl group, 1-(2-hydroxyethyl)indol-6-yl group, 1-(1-oxopentyl)-1,2,3,4-tetrahydroquinolin-7-yl group, 1-((1-oxo-2-acetoxy)ethyl)-1,2,3,4-tetrahydroquinolin-7-yl group, 1-trifluoroacetyl-1,2,3,4-tetrahydroquinolin-7-yl group, 3-hydroxymethylindol-4-yl group, 1-(2-hydroxyethyl)indol-5-yl group, 3-hydroxymethyl-2,3-dihydro-1,4-benzodioxin-6-yl group, 2,3-dihydro-isoindol-1-on-6-yl group, 1,2,3,4-tetrahydro-quinolin-7-yl group, (1-(2-hydroxy-1-oxo)ethyl)-1,2,3,4-tetrahydroquinolin-7-yl group, 1a,2,7,7a-tetrahydronaphtho[2,3-b]oxirene-3-yl group, 2-quinolon-8-yl group, 1-methylindol-6-yl group, 1-methyl-2-oxo-1,2,3,4-tetrahydroquinolin-7-yl group, 1,2,3,4-tetrahydroisoquinolin-8-yl group, 2-hydroxyethyl-1,2,3,4-tetrahydroisoquinolin-8-yl group, 3,4-dihydro-2H-isoquinolin-1-on-7-yl group, 2-hydroxyethyl-2,3-dihydro-isoindol-1-on-6-yl group, 3-hydroxy-2,3-dihydro-(1H)-4-benzopyran-5-yl group, 6-hydroxy-2,3-dihydro-(1H)-4-benzopyran-4-yl group, 6-hydroxy-1,2,3,4-tetrahydroquinolin-4-yl group, 2-oxo-1,2,3,4-tetrahydroquinolin-8-yl group, 3-hydroxyquinolin-5-yl group, 6-hydroxyquinolin-4-yl group, 2-acetyl-1,2,3,4-tetrahydroisoquinolin-8-yl group, 4-(2-hydroxyacetyl)-3,4-dihydro-2H-benzo[b][1,4]oxazin-6-yl group, 4-(2-hydroxypropynoyl)-3,4-dihydro-2H-benzo[b][1,4]oxazin-6-yl group, 4-(2-hydroxyethyl)-3,4-dihydro-2H-benzo[b][1,4] oxazin-6-yl group, 2-methylthieno[2,3-c]pyridin-3-yl group, 5-(2-hydroxymethylphenyl)-3-pyridyl group, 2-hydroxymethyl-1,3-benzothiazolo-5-yl group, 3-chloro-5-hydroxymethyl-2-pyridyl group, 6-hydroxychroman-4-yl group, 1H-indazol-4-yl group, 1H-indazol-7-yl group, and 3-amino-1H-pyrrolo[2,3-c]pyridin-3-yl group.

Specific examples of the "substituted or unsubstituted heteroarylalkyl group (aromatic heterocyclic-$C_{1-6}$ alkyl group)" include a 1-(pyridin-4-yl)ethyl group, 1-(pyridin-2-yl)ethyl group, phenyl(pyridin-2-yl)methyl group, (2,3-dihydrobenzo[b][1,4]dioxin-6-yl)methyl group, 1-(2,3-dihydrobenzo[b][1,4]dioxin-6-yl)ethyl group, (2,3-dihydrobenzo[b][1,4]dioxin-3-yl)methyl group, (2,3-dihydrobenzofuran-6-yl) methyl group, (2-(4-chlorophenyl)-4-methylthiazol-5-yl) methyl group, and [1,2,4]triazolo[4,3-a]pyridin-3-yl)methyl group.

Specific examples of the "substituted or unsubstituted aryl group" include a 4-tert-butylphenyl group, 4-(trifluoromethyl)phenyl group, 3-methoxyphenyl group, 7-hydroxynaphthalen-1-yl group, 1,2,3,4-tetrahydro-1-oxonaphthalen-7-yl group, 4-(4-morpholinylcarbonyl)phenyl group, 4-(4-morpholinylsulfonyl)phenyl group, 4-((5-trifluoromethyl)pyridin-2-yloxy)phenyl group, 3-(quinoxalin-2-yl) phenyl group, 3-((pyridin-4-yl)methyl)phenyl group, 2-(hydroxyethyl)phenyl group, 7-oxo-5,6,7,8-tetrahydronaphthalen-1-yl group, 7-hydroxy-5,6,7,8-tetrahydronaphthalen-1-yl group, 5,6,7,8-tetrahydro-trans-6,7-dihydroxynaphthalen-1-yl group, 5,6,7,8-tetrahydro-cis-6,7-dihydroxynaphthalen-1-yl group, 6-hydroxynaphthalen-1-yl group, 7-hydroxynaphthalen-2-yl group, 7-methoxynaphthalen-1-yl group, 3-methoxy-5-trifluoromethylphenyl group, 4-chloro-3-trifluoromethylphenyl group, 5-hydroxynaphthalen-1-yl group, indan-1-on-6-yl group, indan-2-acetoxy-4-yl group, indan-2-ol-4-yl group, 7-dimethylamino-naphthalen-1-yl group, 8-hydroxymethyl-5,6,7,8-tetrahydronaphthalen-2-yl group, 7-hydroxy-7-methyl-5,6,7,8-tetrahydronaphthalen-1-yl group, 7-hydroxy-1,2,3,4-tetrahydronaphthalen-1-yl group, (Z)-7-hydroxyimino-5,6,7,8-tetrahydronaphthalen-1-yl group, (E)-7-hydroxyimino- 5,6,7,8-tetrahydronaphthalen-1-yl group, 1-hydroxy-1,2,3,4-tetrahydronaphthalen-8-yl group, indan-1-ol-6-yl group, 3-hydroxy-2-carboxymethylphenyl group, 3-hydroxy-2-carbamoylmethylphenyl group, 5,6,7,8-tetrahydronaphthalen-1-yl group, 3-((3-hydroxymethyl)-2-pyridyl)phenyl group, 2-(3-hydroxy-2-pyridyl)phenyl group, 2-hydroxy-1,1'-biphenyl-2'-yl group, 2-(3-hydroxypyrrolidin-1-yl)phenyl group, and 3-(2-hydroxymethylpyrrolidin-1-yl)phenyl group.

Specific examples of the "substituted or unsubstituted aralkyl group (aryl-$C_{1-6}$ alkyl group)" include a 2-morpholinophenylmethyl group, 4-(1,2,3-thiadiazolo-4-yl)phenylmethyl group, 4-(1H-pyrazolo-1-yl)phenylmethyl group, 2-(7-hydroxy-5,6,7,8-tetrahydronaphthalen-1-yl)ethyl group, 2-(7-hydroxy-5,6,7,8-tetrahydronaphthalen-1-yl)propyl group, and 2-(2-chlorophenyl)ethyl group.

Further preferable Q is also represented as a bicyclic group by formula (B):

[Ch. 5]

(B)

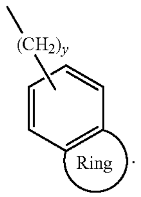

(wherein Ring and y represent the same as the above.) Preferably, y is in the range of 0 to 4, and more preferably, y is 0, 1, 2, or 3.

Specific examples of formula (B) include a 2,3-dihydrobenzo[b][1,4]dioxin-6-yl group, isoquinolin-5-yl group, quinolin-7-yl group, quinoxalin-6-yl group, 1,2,3,4-tetrahydro-1-methylquinolin-7-yl group, 2-methyl-1,3-benzothiazolo-5-yl group, 4-methyl-2-oxo-2H-chromen-7-yl group, 1,3-dihydro-1-oxoisobenzofuran-6-yl group, 2-hydroxymethyl-1,3-benzothiazol-5-yl group, 3-hydroxy-2-oxo-1,2,3,4-tetrahydroquinolin-5-yl group, 3-hydroxy-1,2,3,4-tetrahydroquinolin-5-yl group, 1-methyl-3-hydroxy-1,2,3,4-tetrahydroquinolin-5-yl group, 1-(2-hydroxyethyl)-1,2,3,4-tetrahydroquinolin-7-yl group, 1-(2-(4-morpholino)ethyl)-1,2,3,4-tetrahydroquinolin-7-yl group, 1-(2-(N,N-dimethylamino)ethyl)-1,2,3,4-tetrahydroquinolin-7-yl group, 3,4-dihydro-1H-quinolin-2-on-7-yl group, 2-quinolon-7-yl group, 3,4-dihydro-2H-1,5-benzo[b]dioxepin-7-yl group, 2,2-difluoro-1,3-benzodioxol-5-yl group, 1-methylindol-5-yl group, 1-(2-hydroxyethyl)indol-6-yl group, 1-(1-oxopentyl)-1,2,3,4-tetrahydroquinolin-7-yl group, 1-((1-oxo-2-acetoxy)ethyl)-1,2,3,4-tetrahydroquinolin-7-yl group, 1-trifluoroacetyl-1,2,3,4-tetrahydroquinolin-7-yl group, 3-hydroxymethylindol-4-yl group, 1-(2-hydroxyethyl)indol-5-yl group, 3-hydroxymethyl-2,3-dihydro-1,4-benzodioxin-6-yl group, 2,3-dihydro-isoindol-1-on-6-yl group, 1,2,3,4-tetrahydroquinolin-7-yl group, (1-(2-hydroxy-1-oxo)ethyl)-1,2,3,4-tetrahydroquinolin-7-yl group, 1a,2,7,7a-tetrahydronaphtho[2,3-b]oxirene-3-yl group, 2-quinolon-8-yl group, 1-methylindol-6-yl group, 1-methyl-2-oxo-1,2,3,4-tetrahydroquinolin-7-yl group, 1,2,3,4-tetrahydroisoquinolin-8-yl group, 2-hydroxyethyl-1,2,3,4-tetrahydroisoquinolin-8-yl group, 3,4-dihydro-2H-isoquinolin-1-on-7-yl group, 2-hydroxyethyl-2,3-dihydro-isoindol-1-on-6-yl group, 3-hydroxy-2,3-dihydro-(1H)-4-benzopyran-5-yl group, 6-hydroxy-2,3-dihydro-(1H)-4-benzopyran-4-yl group, 6-hydroxy-1,2,3,4-tetrahydroquinolin-4-yl group, 2-oxo-1,2,3,4-tetrahydroquinolin-8-yl group, 3-hydroxyquinolin-5-yl group, 2-acetyl-1,2,3,4-tetrahydroisoquinolin-8-yl group, 4-(2-hydroxyacetyl)-3,4-dihydro-2H-benzo[b][1,4]oxazin-6-yl group, 4-(2-hydroxypropynoyl)-3,4-dihydro-2H-benzo[b][1,4]oxazin-6-yl group, 4-(2-hydroxyethyl)-3,4-dihydro-2H-benzo[b][1,4]oxazin-6-yl group, 2-hydroxymethyl-1,3-benzothiazolo-5-yl group, 7-hydroxynaphthalen-1-yl group, 1,2,3,4-tetrahydro-1-oxonaphthalen-7-yl group, 7-oxo-5,6,7,8-tetrahydronaphthalen-1-yl group, 1H-indazol-4-yl group, 1H-indazol-7-yl group; (2,3-dihydrobenzo[b][1,4]dioxin-6-yl)methyl group, 1-(2,3-dihydrobenzo[b][1,4]dioxin-6-yl)ethyl group, (2,3-dihydrobenzo[b][1,4]dioxin-3-yl)methyl group, (2,3-dihydrobenzofuran-6-yl)methyl group, (2-(4-chlorophenyl)-4-methylthiazol-5-yl)methyl group, (1,2,4-triazolo[4,3-a]pyridin-3-yl)methyl group; 7-hydroxy-5,6,7,8-tetrahydronaphthalen-1-yl group, 5,6,7,8-tetrahydro-trans-6,7-dihydroxynaphthalen-1-yl group, 5,6,7,8-tetrahydro-cis-6,7-dihydroxynaphthalen-1-yl group, 6-hydroxynaphthalen-1-yl group, 7-hydroxynaphthalen-2-yl group, 7-methoxynaphthalen-1-yl group, 5-hydroxynaphthalen-1-yl group, indan-1-on-6-yl group, indan-2-acetoxy-4-yl group, indan-2-ol-4-yl group, 7-dimethylamino-naphthalen-1-yl group, 8-hydroxymethyl-5,6,7,8-tetrahydronaphthalen-2-yl group, 7-hydroxy-7-methyl-5,6,7,8-tetrahydronaphthalen-1-yl group, (Z)-7-hydroxyimino-5,6,7,8-tetrahydronaphthalen-1-yl group, (E)-7-hydroxyimino-5,6,7,8-tetrahydronaphthalen-1-yl group, 1-hydroxy-1,2,3,4-tetrahydronaphthalen-8-yl group, indan-1-ol-6-yl group, 5,6,7,8-tetrahydronaphthalen-1-yl group, 2-(7-hydroxy-5,6,7,8-tetrahydronaphthalen-1-yl)ethyl group, 2-(7-hydroxy-5,6,7,8-tetrahydronaphthalen-1-yl)propyl group, and 2-(2-chlorophenyl)ethyl group. More preferably, examples thereof include a 2-hydroxymethyl-1,3-benzothiazol-5-yl group, 7-hydroxy-5,6,7,8-tetrahydronaphthalen-1-yl group, 3-hydroxy-2-oxo-1,2,3,4-tetrahydroquinolin-5-yl group, and 3-hydroxy-1,2,3,4-tetrahydroquinolin-5-yl group.

Each of the specific groups of Q described in this embodiment [1-11] may not have further substituents, may be optionally further substituted with 1 to 3 substituents in a class selected from (a-1) to (g-1) described in [1-1-a], or may be optionally exchanged for any substituents in the specific examples. In the groups listed in (a-1) to (g-1) described above, "particularly preferable groups" include substituents such as $C_{1-6}$ alkyl, $C_{2-6}$ alkenyl, $C_{2-6}$ alkynyl, halogen atoms, halogenated $C_{1-6}$ alkyl, cyano, amino, hydroxyl, carbamoyl, $C_{1-6}$ alkoxy, $C_{2-6}$ alkenyloxy, $C_{2-6}$ alkynyloxy, $C_{1-6}$ alkylthio, $C_{1-6}$ alkylsulfinyl, $C_{1-6}$ alkylsulfonyl, mono/di $C_{1-6}$ alkylamino, $C_{1-6}$ alkoxycarbonyl, $C_{2-6}$ alkanoyl, $C_{2-6}$ alkanoylamino, hydroxy-$C_{1-6}$ alkyl, $C_{1-6}$ alkoxy-$C_{1-6}$ alkyl, carboxy-$C_{1-6}$ alkyl, $C_{1-6}$ alkoxycarbonyl-$C_{1-6}$ alkyl, carbamoyl-$C_{1-6}$ alkyl, N—$C_{1-6}$ alkylcarbamoyl-$C_{1-6}$ alkyl, N,N-di $C_{1-6}$ alkylcarbamoyl-$C_{1-6}$ alkyl, phenyl, phenoxy, phenylthio, phenylsulfinyl, phenylsulfonyl, benzyl, benzoyl, morpholino, oxo, morpholinylcarbonyl, morpholinylsulfonyl, 5-trifluoromethylpyridin-2-yloxy, quinoxalin-2-yl, (pyridin-4-yl)methyl, 1,2,3-thiadiazolo-4-yl, 1H-pyrazolo-1-yl, and 4-chlorophenyl. The aromatic rings in these substituents may be further substituted with 1 to 3 substituents selected from halogen atoms, trifluoromethyl, cyano, hydroxyl, amino, nitro, carboxyl, carbamoyl, $C_{1-6}$ alkyl, $C_{1-6}$ alkoxy, mono/di $C_{1-6}$ alkylamino, di-$C_{1-6}$ alkylcarbamoyl, $C_{1-6}$ alkoxycarbonyl, N—$C_{1-6}$ alkylcarbamoyl, N,N-di $C_{1-6}$ alkylcarbamoyl, and $C_{2-6}$ alkenoylamino.

In formula (I), r is an integer of 0 or 1, and preferably, r is 0.

Examples of the Cycle moiety include monocyclic, five- or six-membered rings. Specific examples thereof include a benzene ring, a pyridine ring, and a thiophene ring.

Zero to two $R^1$'s described above can be bonded to the Cycle moiety. More specifically, n represents an integer of 0 to 2. Preferably, n is an integer of 1 or 2, and more preferably, n is 1.

When n is 1, the substitution position of $R^1$ corresponds to the 7th position of a chroman ring, a pyridochroman ring, a 2,3-dihydroquinoline ring, or the like, which belongs to a skeleton in which m=1 and q=0, or an isochroman ring or the like, which belongs to a skeleton in which m=0 and q=1. This position also corresponds to the 8th position of a 3,4-dihydrobenzo[b]oxepine ring or 1,2,3,4-tetrahydrobenzo[b]azepine ring which belongs to a skeleton in which m=2 and q=0, or a 3,4-dihydrobenzo[b]isooxepine ring or the like, which belongs to a skeleton in which m=1 and q=1. In the substitution position of $R^1$, at least one of $R^1$'s is preferably a fluorine atom, a chlorine atom, isobutyl, tert-butyl, trifluoromethyl, or tetrafluoroethoxy. More preferably, at least $R^1$ bonded to $A_2$ or $B_2$ is a fluorine atom, a chlorine atom, isobutyl, tert-butyl, trifluoromethyl, or tetrafluoroethoxy, and particularly preferably, trifluoromethyl.

The wavy line to which "CO—NH-Q" in formula (I) of the present invention is bonded represents a bond of an E-isomer (anti-isomer or trans-isomer) or a Z-isomer (syn-isomer or cis-isomer). This means that the compounds represented by formula (I) include E-isomers and Z-isomers. The compounds represented by formula (I) are preferably E-isomers. Hereinafter, wavy lines in formulae in this description represent the same meaning.

Examples of preferable compounds include:

(E)-2-(chroman-4-ylidene)-N-(2,3-dihydrobenzo[b][1,4]dioxin-6-yl)acetamide (EXAMPLE 1);

(E)-2-(chroman-4-ylidene)-N-(isoquinolin-5-yl)acetamide (EXAMPLE 2);

(E)-2-(7-tert-butyl-chroman-4-ylidene)-N-(5,6,7,8-tetrahydroquinolin-7-yl)acetamide (EXAMPLE 3);

(E)-2-(7-tert-butyl-chroman-4-ylidene)-N-(isoquinolin-5-yl)acetamide (EXAMPLE 4);

(E)-2-(7-tert-butyl-chroman-4-ylidene)-N-(quinolin-7-yl)acetamide (EXAMPLE 5);

(E)-2-(7-(trifluoromethyl)chroman-4-ylidene)-N-(5,6,7,8-tetrahydro-quinolin-7-yl)-acetamide (EXAMPLE 6);

(E)-2-(7-(trifluoromethyl)chroman-4-ylidene)-N-(isoquinolin-5-yl)-acetamide (EXAMPLE 7);

(E)-2-(7-(trifluoromethyl)chroman-4-ylidene)-N-(quinolin-7-yl)-acetamide (EXAMPLE 8);

(E)-2-(8-trifluoromethyl-3,4-dihydrobenzo[b]oxepin-5(2H)-ylidene)-N-(2,3-dihydrobenzo[b][1,4]dioxin-6-yl)acetamide (EXAMPLE 9);

(E)-2-(8-trifluoromethyl-3,4-dihydrobenzo[b]oxepin-5(2H)-ylidene)-N-(5,6,7,8-tetrahydroquinolin-7-yl)acetamide (EXAMPLE 10);

(E)-2-(8-trifluoromethyl-3,4-dihydrobenzo[b]oxepin-5(2H)-ylidene)-N-(isoquinolin-5-yl)acetamide (EXAMPLE 11);

(E)-2-(8-trifluoromethyl-3,4-dihydrobenzo[b]oxepin-5(2H)-ylidene)-N-(quinoxalin-6-yl)acetamide (EXAMPLE 12);

(E)-2-(8-trifluoromethyl-3,4-dihydrobenzo[b]oxepin-5(2H)-ylidene)-N-(quinolin-7-yl)acetamide (EXAMPLE 13);

(E)-N-(4-tert-butylphenyl)-2-(8-trifluoromethyl-3,4-dihydrobenzo[b]oxepin-5(2H)-ylidene)acetamide (EXAMPLE 14);

(E)-2-(8-trifluoromethyl-3,4-dihydrobenzo[b]oxepin-5(2H)-ylidene)-N-(4-(trifluoromethyl)phenyl)acetamide (EXAMPLE 15);

(E)-2-(8-trifluoromethyl-3,4-dihydrobenzo[b]oxepin-5(2H)-ylidene)-N-(3-methoxyphenyl)acetamide (EXAMPLE 16);

(E)-2-(8-trifluoromethyl-3,4-dihydrobenzo[b]oxepin-5(2H)-ylidene)-N-(1,2,3,4-tetrahydro-1-methylquinolin-7-yl)acetamide (EXAMPLE 17);

(E)-2-(8-trifluoromethyl-3,4-dihydrobenzo[b]oxepin-5(2H)-ylidene)-N-(7-hydroxynaphthalen-1-yl)acetamide (EXAMPLE 18);

(E)-2-(8-trifluoromethyl-3,4-dihydrobenzo[b]oxepin-5(2H)-ylidene)-N-(2-methyl-1,3-benzothiazolo-5-yl)acetamide (EXAMPLE 19);

(E)-2-(8-trifluoromethyl-3,4-dihydrobenzo[b]oxepin-5(2H)-ylidene)-N-(2-morpholinopyridin-3-yl)acetamide (EXAMPLE 20);

(E)-2-(8-trifluoromethyl-3,4-dihydrobenzo[b]oxepin-5(2H)-ylidene)-N-(4-methyl-2-oxo-2H-chromen-7-yl)acetamide (EXAMPLE 21);

(E)-2-(8-trifluoromethyl-3,4-dihydrobenzo[b]oxepin-5(2H)-ylidene)-N-(6-phenoxypyridin-3-yl)acetamide (EXAMPLE 22);

(E)-2-(8-trifluoromethyl-3,4-dihydrobenzo[b]oxepin-5(2H)-ylidene)-N-(1,2,3,4-tetrahydro-1-oxonaphthalen-7-yl)acetamide (EXAMPLE 23);

(E)-2-(8-trifluoromethyl-3,4-dihydrobenzo[b]oxepin-5(2H)-ylidene)-N-(1,3-dihydro-1-oxoisobenzofuran-6-yl)acetamide (EXAMPLE 24);

(E)-2-(8-trifluoromethyl-3,4-dihydrobenzo[b]oxepin-5(2H)-ylidene)-N-(4-(4-morpholinylcarbonyl)phenyl)acetamide (EXAMPLE 25);

(E)-2-(8-trifluoromethyl-3,4-dihydrobenzo[b]oxepin-5(2H)-ylidene)-N-(4-(4-morpholinylsulfonyl)phenyl)acetamide (EXAMPLE 26);

(E)-N-(4-(5-trifluoromethyl)pyridin-2-yloxy)phenyl)-2-(8-trifluoromethyl-3,4-dihydrobenzo[b]oxepin-5(2H)-ylidene)acetamide (EXAMPLE 27);

(E)-2-(8-trifluoromethyl-3,4-dihydrobenzo[b]oxepin-5(2H)-ylidene)-N-(3-(quinoxalin-2-yl)phenyl)acetamide (EXAMPLE 28);

(E)-2-(8-trifluoromethyl-3,4-dihydrobenzo[b]oxepin-5(2H)-ylidene)-N-(4-((pyridin-4-yl)methyl)phenyl)acetamide (EXAMPLE 29);

(E)-2-(8-trifluoromethyl-3,4-dihydrobenzo[b]oxepin-5(2H)-ylidene)-N-(1-(pyridin-2-yl)ethyl)acetamide (EXAMPLE 30);

(E)-2-(8-trifluoromethyl-3,4-dihydrobenzo[b]oxepin-5(2H)-ylidene)-N-(phenyl(pyridin-2-yl)methyl)acetamide (EXAMPLE 31);

(E)-2-(8-trifluoromethyl-3,4-dihydrobenzo[b]oxepin-5(2H)-ylidene)-N-((2,3-dihydrobenzo[b][1,4]dioxin-6-yl)methyl)acetamide (EXAMPLE 32);

(E)-2-(8-trifluoromethyl-3,4-dihydrobenzo[b]oxepin-5(2H)-ylidene)-N-(1-(2,3-dihydrobenzo[b][1,4]dioxin-6-yl)ethyl)acetamide (EXAMPLE 33);

(E)-2-(8-trifluoromethyl-3,4-dihydrobenzo[b]oxepin-5(2H)-ylidene)-N-((2,3-dihydrobenzo[b][1,4]dioxin-2-yl)methyl)acetamide (EXAMPLE 34);

(E)-2-(8-trifluoromethyl-3,4-dihydrobenzo[b]oxepin-5(2H)-ylidene)-N-((2,3-dihydrobenzofuran-5-yl)methyl)acetamide (EXAMPLE 35);

(E)-2-(8-trifluoromethyl-3,4-dihydrobenzo[b]oxepin-5(2H)-ylidene)-N-(2-morpholinophenyl)methyl-acetamide (EXAMPLE 36);

(E)-2-(8-trifluoromethyl-3,4-dihydrobenzo[b]oxepin-5(2H)-ylidene)-N-(4-(1,2,3-thiadiazolo-4-yl)phenylmethyl)acetamide (EXAMPLE 37);

(E)-N-(4-(1H-pyrazolo-1-yl)phenylmethyl)-2-(8-trifluoromethyl-3,4-dihydrobenzo[b]oxepin-5(2H)-ylidene)acetamide (EXAMPLE 38);

(E)-N-((2-(4-chlorophenyl)-4-methylthiazol-5-yl)methyl)-2-(8-trifluoromethyl-3,4-dihydrobenzo[b]oxepin-5(2H)-ylidene)acetamide (EXAMPLE 39);

(2E)-N-([1,2,4]triazolo[4,3-a]pyridin-3-yl)methyl)-2-(8-trifluoromethyl-3,4-dihydrobenzo[b]oxepin-5(2H)-ylidene)acetamide (EXAMPLE 40);

(E)-2-(8-trifluoromethyl-3,4-dihydrobenzo[b]oxepin-5(2H)-ylidene)-N-(1-methyl-1H-pyrazolo[3,4-b]pyridin-3-yl)acetamide (EXAMPLE 41);

(E)-2-(8-trifluoromethyl-3,4-dihydrobenzo[b]oxepin-5(2H)-ylidene)-N-(1H-indazol-3-yl)acetamide (EXAMPLE 42);

(E)-N-(1-ethyl-1H-benzo[d]imidazolo-2-yl)-2-(8-trifluoromethyl-3,4-dihydrobenzo[b]oxepin-5(2H)-ylidene)acetamide (EXAMPLE 43);

(2E)-N-([1,2,4]triazolo[1,5-a]pyrimidin-7-yl)-2-(8-trifluoromethyl-3,4-dihydrobenzo[b]oxepin-5(2H)-ylidene)acetamide (EXAMPLE 44);

(E)-2-(8-trifluoromethyl-3,4-dihydrobenzo[b]oxepin-5(2H)-ylidene)-N-(6,7,8,9-tetrahydro-5H-cyclohepta[b]pyridin-8-yl)acetamide (EXAMPLE 45);

(E)-N-(1-tert-butyl-3-methyl-1H-pyrazolo-5-yl)-2-(8-trifluoromethyl-3,4-dihydrobenzo[b]oxepin-5(2H)-ylidene)acetamide (EXAMPLE 46);

(E)-2-(8-trifluoromethyl-3,4-dihydrobenzo[b]oxepin-5(2H)-ylidene)-N-(4-phenylthiazolo-2-yl)acetamide (EXAMPLE 47);

(E)-2-(1-acetyl-7-trifluoromethyl-2,3-dihydroquinolin-4(1H)-ylidene)-N-(quinolin-7-yl)acetamide (EXAMPLE 48);

(E)-2-(7-trifluoromethyl-2,3-dihydroquinolin-4(1H)-ylidene)-N-(5,6,7,8-tetrahydroquinolin-7-yl)acetamide (EXAMPLE 49);

(E)-2-(7-trifluoromethyl-2,3-dihydro-1-pentanoylquinolin-4(1H)-ylidene)-N-(quinolin-7-yl)acetamide (EXAMPLE 50);

(E)-2-(1-(2-ethylbutanoyl)-7-trifluoromethyl-2,3-dihydroquinolin-4(1H)-ylidene)-N-(quinolin-7-yl)acetamide (EXAMPLE 51);

(E)-2-(7-trifluoromethyl-2,3-dihydro-1-cyclohexanecarbonylquinolin-4(1H)-ylidene)-N-(quinolin-7-yl)acetamide (EXAMPLE 52);

(E)-2-(7-trifluoromethyl-2,3-dihydro-1-(4-pyranoyl)quinolin-4(1H)-ylidene)-N-(quinolin-7-yl)acetamide (EXAMPLE 53);

(E)-2-(7-trifluoromethyl-2,3-dihydro-1-benzoylquinolin-4(1H)-ylidene)-N-(quinolin-7-yl)acetamide (EXAMPLE 54);

(E)-2-(7-trifluoromethyl-2,3-dihydro-1-nicotinoylquinolin-4(1H)-ylidene)-N-(quinolin-7-yl)acetamide (EXAMPLE 55);

(E)-2-(1-(4-chlorophenyl)-7-trifluoromethyl-2,3-dihydro-4(1H)-ylidene)-N-(5,6,7,8-tetrahydroquinolin-7-yl)acetamide (EXAMPLE 56);

(E)-2-(1-(4-chlorophenyl)-7-trifluoromethyl-2,3-dihydro-4(1H)-ylidene)-N-(quinolin-7-yl)acetamide (EXAMPLE 57);

(E)-2-(7-trifluoromethyl-2,3-dihydro-1-(pyridin-3-yl)quinolin-4(1H)-ylidene)-N-(quinolin-7-yl)acetamide (EXAMPLE 58);

(E)-2-(8-trifluoromethyl-3,4-dihydrobenzo[b]oxepin-5(2H)-ylidene)-N-(2-hydroxymethyl-1,3-benzothiazolo-5-yl)acetamide (EXAMPLE 59);

(E)-2-(8-trifluoromethyl-3,4-dihydrobenzo[b]oxepin-5(2H)-ylidene)-N-((2-hydroxyethyl)phenyl-1-yl)acetamide (EXAMPLE 60);

(E)-2-(8-trifluoromethyl-3,4-dihydrobenzo[b]oxepin-5(2H)-ylidene)-N-(7-oxo-5,6,7,8-tetrahydronaphthalen-1-yl)acetamide (EXAMPLE 61);

(E)-2-(8-trifluoromethyl-3,4-dihydrobenzo[b]oxepin-5-(2H)-ylidene)-N-(7-hydroxy-5,6,7,8-tetrahydronaphthalen-1-yl)acetamide (EXAMPLE 62);

(E)-2-(8-trifluoromethyl-3,4-dihydrobenzo[b]oxepin-5-(2H)-ylidene)-N-(7-hydroxy-5,6,7,8-tetrahydronaphthalen-1-yl)acetamide (EXAMPLE 63, more polar);

(E)-2-(8-trifluoromethyl-3,4-dihydrobenzo[b]oxepin-5-(2H)-ylidene)-N-(7-hydroxy-5,6,7,8-tetrahydronaphthalen-1-yl)acetamide (EXAMPLE 64, less polar);

(E)-2-(8-trifluoromethyl-3,4-dihydrobenzo[b]oxepin-5-(2H)-ylidene)-N-(trans-6,7-dihydroxy-5,6,7,8-tetrahydronaphthalen-1-yl)acetamide (EXAMPLE 65);

(E)-2-(8-trifluoromethyl-3,4-dihydrobenzo[b]oxepin-5-(2H)-ylidene)-N-(cis-6,7-dihydroxy-5,6,7,8-tetrahydronaphthalen-1-yl)acetamide (EXAMPLE 66);

(E)-2-(8-trifluoromethyl-3,4-dihydrobenzo[b]oxepin-5(2H)-ylidene)-N-(3-hydroxy-2-oxo-1,2,3,4-tetrahydroquinolin-5-yl)acetamide (EXAMPLE 67);

(E)-2-(8-trifluoromethyl-3,4-dihydrobenzo[b]oxepin-5(2H)-ylidene)-N-(3-hydroxy-1,2,3,4-tetrahydroquinolin-5-yl)acetamide (EXAMPLE 68);

(E)-2-(8-trifluoromethyl-3,4-dihydrobenzo[b]oxepin-5(2H)-ylidene)-N-(1-methyl-3-hydroxy-1,2,3,4-tetrahydroquinolin-5-yl)acetamide (EXAMPLE 69);

(E)-2-(7-trifluoromethyl-chroman-4-ylidene)-N-(7-hydroxy-5,6,7,8-tetrahydronaphthalen-1-yl)acetamide (EXAMPLE 70);

(E)-2-(1-cyclopentanecarbonyl-7-trifluoromethyl-2,3-dihydroquinolin-4(1H)-ylidene)-N-(quinolin-7-yl)acetamide (EXAMPLE 73);

(E)-2-(1-pentanoyl-7-trifluoromethyl-2,3-dihydroquinolin-4(1H)-ylidene)-N-(7-hydroxynaphthalen-1-yl)acetamide (EXAMPLE 74);

(E)-2-(1-cyclobutanecarbonyl-7-trifluoromethyl-2,3-dihydroquinolin-4(1H)-ylidene)-N-(quinolin-7-yl)acetamide (EXAMPLE 75);

(E)-2-(1-(3,3-dimethylbutanoyl)-7-trifluoromethyl-2,3-dihydroquinolin-4(1H)-ylidene)-N-(quinolin-7-yl)acetamide (EXAMPLE 76);

(E)-2-(1-(3-methylbutanoyl)-7-trifluoromethyl-2,3-dihydroquinolin-4(1H)-ylidene)-N-(quinolin-7-yl)acetamide (EXAMPLE 77);

(E)-2-(1-(4-methylpentanoyl)-7-trifluoromethyl-2,3-dihydroquinolin-4(1H)-ylidene)-N-(quinolin-7-yl)acetamide (EXAMPLE 78);

(E)-2-(1-(3-methylpentanoyl)-7-trifluoromethyl-2,3-dihydroquinolin-4(1H)-ylidene)-N-(quinolin-7-yl)acetamide (EXAMPLE 79);

(E)-2-(1-(2-methylpentanoyl)-7-trifluoromethyl-2,3-dihydroquinolin-4(1H)-ylidene)-N-(quinolin-7-yl)acetamide (EXAMPLE 80);

(E)-2-(1-(2,2-dimethylpentanoyl)-7-trifluoromethyl-2,3-dihydroquinolin-4(1H)-ylidene)-N-(quinolin-7-yl)acetamide (EXAMPLE 81);

(E)-2-(1-cyclopentanecarbonyl-7-trifluoromethyl-2,3-dihydroquinolin-4(1H)-ylidene)-N-(7-hydroxy-5,6,7,8-tetrahydronaphthalen-1-yl)acetamide (EXAMPLE 82);

(E)-2-(1-pentanoyl-7-trifluoromethyl-2,3-dihydroquinolin-4(1H)-ylidene)-N-(7-hydroxy-5,6,7,8-tetrahydronaphthalen-1-yl)acetamide (EXAMPLE 83);

(E)-2-(1-cyclobutanecarbonyl-7-trifluoromethyl-2,3-dihydroquinolin-4(1H)-ylidene)-N-(7-hydroxy-5,6,7,8-tetrahydronaphthalen-1-yl)acetamide (EXAMPLE 84);

(E)-2-(1-(4,4-difluorocyclohexanecarbonyl)-7-trifluoromethyl-2,3-dihydroquinolin-4(1H)-ylidene)-N-(7-hydroxy-5,6,7,8-tetrahydronaphthalen-1-yl)acetamide (EXAMPLE 85);

(E)-2-(1-(4-methylpentanoyl)-7-trifluoromethyl-2,3-dihydroquinolin-4(1H)-ylidene)-N-(7-hydroxy-5,6,7,8-tetrahydronaphthalen-1-yl)acetamide (EXAMPLE 86);

(E)-2-(1-(3-methylbutanoyl)-7-trifluoromethyl-2,3-dihydroquinolin-4(1H)-ylidene)-N-(7-hydroxy-5,6,7,8-tetrahydronaphthalen-1-yl)acetamide (EXAMPLE 87);

(E)-2-(1-(3-fluorocyclopentanecarbonyl)-7-trifluoromethyl-2,3-dihydroquinolin-4(1H)-ylidene)-N-(7-hydroxy-5,6,7,8-tetrahydronaphthalen-1-yl)acetamide (EXAMPLE 88);

(E)-2-(1-(1-methylcyclopropanecarbonyl)-7-trifluoromethyl-2,3-dihydroquinolin-4(1H)-ylidene)-N-(7-hydroxy-5,6,7,8-tetrahydronaphthalen-1-yl)acetamide (EXAMPLE 89);

(E)-2-(1-(1-methylcyclobutanecarbonyl)-7-trifluoromethyl-2,3-dihydroquinolin-4(1H)-ylidene)-N-(7-hydroxy-5,6,7,8-tetrahydronaphthalen-1-yl)acetamide (EXAMPLE 90);

(E)-2-(1-(4,4,4-trifluorobutanoyl)-7-trifluoromethyl-2,3-dihydroquinolin-4(1H)-ylidene)-N-(7-hydroxy-5,6,7,8-tetrahydronaphthalen-1-yl)acetamide (EXAMPLE 91);

(E)-2-(1-(3,3,3-trifluoropropanoyl)-7-trifluoromethyl-2,3-dihydroquinolin-4(1H)-ylidene)-N-(7-hydroxy-5,6,7,8-tetrahydronaphthalen-1-yl)acetamide (EXAMPLE 92);

(E)-2-(1-(5,5,5-trifluoropentanoyl)-7-trifluoromethyl-2,3-dihydroquinolin-4(1H)-ylidene)-N-(7-hydroxy-5,6,7,8-tetrahydronaphthalen-1-yl)acetamide (EXAMPLE 93);

(E)-2-(1-phenylacetyl-7-trifluoromethyl-2,3-dihydroquinolin-4(1H)-ylidene)-N-(7-hydroxy-5,6,7,8-tetrahydronaphthalen-1-yl)acetamide (EXAMPLE 94);

(E)-2-(1-(2,2-difluorobutanoyl)-7-trifluoromethyl-2,3-dihydroquinolin-4(1H)-ylidene)-N-(7-hydroxy-5,6,7,8-tetrahydronaphthalen-1-yl)acetamide (EXAMPLE 95);

(E)-2-(1-(2-fluoro-2-methylpropanoyl)-7-trifluoromethyl-2,3-dihydroquinolin-4(1H)-ylidene)-N-(7-hydroxy-5,6,7,8-tetrahydronaphthalen-1-yl)acetamide (EXAMPLE 96);

(E)-2-(7-trifluoromethyl-2,3-dihydro-1-cyclohexylquinolin-4(1H)-ylidene)-N-(quinolin-7-yl)acetamide (EXAMPLE 97);

(E)-2-(7-trifluoromethyl-2,3-dihydro-1-(4-methylbenzenesulfonyl)quinolin-4(1H)-ylidene)-N-(quinolin-7-yl)acetamide (EXAMPLE 98);

(E)-2-(7-trifluoromethyl-2,3-dihydro-1-cyclopropanecarbonylquinolin-4(1H)-ylidene)-N-(quinolin-7-yl)acetamide (EXAMPLE 99);

(E)-2-(7-trifluoromethyl-2,3-dihydro-1-(3-methoxypropanoyl)quinolin-4(1H)-ylidene)-N-(quinolin-7-yl)acetamide (EXAMPLE 100);

(E)-2-(7-trifluoromethyl-2,3-dihydro-1-(3-(carbomethoxy)propanoyl)quinolin-4(1H)-ylidene)-N-(quinolin-7-yl)acetamide (EXAMPLE 101);

(E)-2-(7-trifluoromethyl-2,3-dihydro-1-(cyclopentylacetyl)quinolin-4(1H)-ylidene)-N-(quinolin-7-yl)acetamide (EXAMPLE 102);

(E)-2-(7-trifluoromethyl-2,3-dihydro-1-cyclopropanecarbonylquinolin-4(1H)-ylidene)-N-(7-hydroxy-5,6,7,8-tetrahydronaphthalen-1-yl)acetamide (EXAMPLE 105);

(E)-2-(7-trifluoromethyl-2,3-dihydroquinolin-4(1H)-ylidene)-N-(7-hydroxy-5,6,7,8-tetrahydronaphthalen-1-yl)acetamide (EXAMPLE 106);

(E)-2-(7-trifluoromethyl-2,3-dihydro-1-pentanoylquinolin-4(1H)-ylidene)-N-(3,4-dihydro-3-hydroxy(1H)quinolin-2-on-5-yl)acetamide (EXAMPLE 107);

(E)-2-(7-trifluoromethyl-2,3-dihydro-1-pentanoylquinolin-4(1H)-ylidene)-N-(3-hydroxy-1,2,3,4-tetrahydroquinolin-5-yl)acetamide (EXAMPLE 108);

(E)-2-(7-trifluoromethyl-2,3-dihydro-1-((2,2-dimethylcyclopropane)carbonyl)quinolin-4(1H)-ylidene)-N-(7-hydroxy-5,6,7,8-tetrahydronaphthalen-1-yl)acetamide (EXAMPLE 109);

(E)-2-(7-trifluoromethyl-2,3-dihydro-1-((4-(trifluoromethyl)cyclohexane)carbonyl)quinolin-4(1H)-ylidene)-N-(7-hydroxy-5,6,7,8-tetrahydronaphthalen-1-yl)acetamide (EXAMPLE 110);

(E)-2-(7-trifluoromethyl-2,3-dihydro-1-(2-furancarbonyl)quinolin-4(1H)-ylidene)-N-(7-hydroxy-5,6,7,8-tetrahydronaphthalen-1-yl)acetamide (EXAMPLE 111);

(E)-2-(1-(1-hydroxycyclopropanecarbonyl)-7-trifluoromethyl-2,3-dihydroquinolin-4(1H)-ylidene)-N-(7-hydroxy-5,6,7,8-tetrahydronaphthalen-1-yl)acetamide (EXAMPLE 112);

(E)-2-(1-(3,3-difluoroazetidine-1-carbonyl)-7-trifluoromethyl-2,3-dihydroquinolin-4(1H)-ylidene)-N-(7-hydroxy-5,6,7,8-tetrahydronaphthalen-1-yl)acetamide (EXAMPLE 113);

(E)-2-(1-formyl-7-trifluoromethyl-2,3-dihydroquinolin-4(1H)-ylidene)-N-(7-hydroxy-5,6,7,8-tetrahydronaphthalen-1-yl)acetamide (EXAMPLE 114);

(E)-2-(1-(1-fluorocyclopentanecarbonyl)-7-trifluoromethyl-2,3-dihydroquinolin-4(1H)-ylidene)-N-(7-hydroxy-5,6,7,8-tetrahydronaphthalen-1-yl)acetamide (EXAMPLE 115);

(E)-2-(1-(3,3-difluorobutanoyl)-7-trifluoromethyl-2,3-dihydroquinolin-4(1H)-ylidene)-N-(7-hydroxy-5,6,7,8-tetrahydronaphthalen-1-yl)acetamide (EXAMPLE 116);

(E)-2-(1-(3,3-difluoropentanoyl)-7-trifluoromethyl-2,3-dihydroquinolin-4(1H)-ylidene)-N-(7-hydroxy-5,6,7,8-tetrahydronaphthalen-1-yl)acetamide (EXAMPLE 117);

(E)-2-(1-(3,3-difluorocyclobutanecarbonyl)-7-trifluoromethyl-2,3-dihydroquinolin-4(1H)-ylidene)-N-(7-hydroxy-5,6,7,8-tetrahydronaphthalen-1-yl)acetamide (EXAMPLE 118);

(E)-N-(7-oxo-5,6,7,8-tetrahydronaphthalen-1-yl)-2-(7-trifluoromethyl-chroman-4-ylidene)acetamide (EXAMPLE 119);

(E)-N-(7-hydroxynaphthalen-1-yl)-2-(7-trifluoromethyl-chroman-4-ylidene)acetamide (EXAMPLE 120);

(E)-N-(3-hydroxy-2-oxo-1,2,3,4-tetrahydroquinolin-5-yl)-2-(7-trifluoromethyl-chroman-4-ylidene)acetamide (EXAMPLE 121);

(E)-N-(3-hydroxy-1,2,3,4-tetrahydroquinolin-5-yl)-2-(7-trifluoromethyl-chroman-4-ylidene)acetamide (EXAMPLE 122);

(E)-N-(3-hydroxy-chroman-5-yl)-2-(7-trifluoromethyl-chroman-4-ylidene)acetamide (EXAMPLE 125);

(E)-N-(6-hydroxynaphthalen-1-yl)-2-(8-trifluoromethyl-3,4-dihydrobenzo[b]oxepin-5(2H)-ylidene)acetamide (EXAMPLE 126);

(E)-2-(8-trifluoromethyl-3,4-dihydrobenzo[b]oxepin-5(2H)-ylidene)-N-(quinolin-7-yl)acetamide methanesulfonate (EXAMPLE 127);

(E)-2-(8-trifluoromethyl-3,4-dihydrobenzo[b]oxepin-5(2H)-ylidene)-N-(7-hydroxynaphthalen-2-yl)acetamide (EXAMPLE 128);

(E)-2-(8-trifluoromethyl-3,4-dihydrobenzo[b]oxepin-5(2H)-ylidene)-N-(7-methoxynaphthalen-1-yl)acetamide (EXAMPLE 129);

(E)-2-(8-trifluoromethyl-3,4-dihydrobenzo[b]oxepin-5(2H)-ylidene)-N-(1-(2-methoxyethyl)-1,2,3,4-tetrahydroquinolin-7-yl)acetamide (EXAMPLE 130);

(E)-2-(8-trifluoromethyl-3,4-dihydrobenzo[b]oxepin-5(2H)-ylidene)-N-(3,4-dihydro-1H-quinolin-2-on-7-yl)acetamide (EXAMPLE 133);

(E)-2-(8-trifluoromethyl-3,4-dihydrobenzo[b]oxepin-5(2H)-ylidene)-N-(2-quinolon-7-yl)acetamide (EXAMPLE 134);

(E)-2-(8-trifluoromethyl-3,4-dihydrobenzo[b]oxepin-5(2H)-ylidene)-N-(3-methoxy-5-(trifluoromethyl)phenyl)acetamide (EXAMPLE 135);

(E)-2-(8-trifluoromethyl-3,4-dihydrobenzo[b]oxepin-5(2H)-ylidene)-N-(4-chloro-3-(trifluoromethyl)phenyl)acetamide (EXAMPLE 136);

(E)-2-(8-trifluoromethyl-3,4-dihydrobenzo[b]oxepin-5(2H)-ylidene)-N-(indol-6-yl)acetamide (EXAMPLE 137);

(E)-2-(8-trifluoromethyl-3,4-dihydrobenzo[b]oxepin-5(2H)-ylidene)-N-(indol-5-yl)acetamide (EXAMPLE 138);

(E)-2-(8-trifluoromethyl-3,4-dihydrobenzo[b]oxepin-5(2H)-ylidene)-N-(3,4-dihydro-2H-benzo[b]dioxepin-7-yl)acetamide (EXAMPLE 142);

(E)-2-(8-trifluoromethyl-3,4-dihydrobenzo[b]oxepin-5(2H)-ylidene)-N-(2,2-difluoro-1,3-benzodioxol-5-yl)acetamide (EXAMPLE 143);

(E)-2-(8-trifluoromethyl-3,4-dihydrobenzo[b]oxepin-5(2H)-ylidene)-N-(1,3-benzodioxol-5-yl)acetamide (EXAMPLE 144);

(E)-2-(8-trifluoromethyl-3,4-dihydrobenzo[b]oxepin-5(2H)-ylidene)-N-(1-methylindol-5-yl)acetamide (EXAMPLE 149);

(E)-2-(8-trifluoromethyl-3,4-dihydrobenzo[b]oxepin-5(2H)-ylidene)-N-(5-hydroxynaphthalen-1-yl)acetamide (EXAMPLE 150);

(E)-2-(8-trifluoromethyl-3,4-dihydrobenzo[b]oxepin-5(2H)-ylidene)-N-(1-(2-hydroxyethyl)indol-6-yl)acetamide (EXAMPLE 151);

(E)-2-(8-trifluoromethyl-3,4-dihydrobenzo[b]oxepin-5(2H)-ylidene)-N-(1-methylindol-6-yl)acetamide (EXAMPLE 152);

(E)-2-(8-trifluoromethyl-3,4-dihydrobenzo[b]oxepin-5(2H)-ylidene)-N-(indan-1-on-6-yl)acetamide (EXAMPLE 157);

(E)-2-(8-trifluoromethyl-3,4-dihydrobenzo[b]oxepin-5(2H)-ylidene)-N-(indan-1-ol-4-yl)acetamide (EXAMPLE 160);

(E)-2-(8-trifluoromethyl-3,4-dihydrobenzo[b]oxepin-5(2H)-ylidene)-N-(indan-1-acetoxy-4-yl)acetamide (EXAMPLE 161);

(E)-2-(8-trifluoromethyl-3,4-dihydrobenzo[b]oxepin-5(2H)-ylidene)-N-(indan-2-ol-4-yl)acetamide (EXAMPLE 163);

(E)-2-(8-trifluoromethyl-3,4-dihydrobenzo[b]oxepin-5(2H)-ylidene)-N-(1-(2-hydroxyethyl)indol-5-yl)acetamide (EXAMPLE 164);

(E)-2-(8-trifluoromethyl-3,4-dihydrobenzo[b]oxepin-5(2H)-ylidene)-N-(3-hydroxymethyl-2,3-dihydro-1,4-benzodioxin-6-yl)acetamide (EXAMPLE 165);

(E)-2-(8-trifluoromethyl-3,4-dihydrobenzo[b]oxepin-5(2H)-ylidene)-N-(2,3-dihydro-isoindol-1-on-6-yl)acetamide (EXAMPLE 166);

(E)-2-(8-trifluoromethyl-3,4-dihydrobenzo[b]oxepin-5(2H)-ylidene)-N-(1,2,3,4-tetrahydroquinolin-7-yl)acetamide (EXAMPLE 167);

(E)-2-(8-trifluoromethyl-3,4-dihydrobenzo[b]oxepin-5(2H)-ylidene)-N-(1a,2,7,7a-tetrahydronaphtho[b]oxirene-3-yl)acetamide (EXAMPLE 169);

(E)-2-(8-trifluoromethyl-3,4-dihydrobenzo[b]oxepin-5(2H)-ylidene)-N-(1-hydroxy-1,2,3,4-tetrahydronaphthalen-8-yl)acetamide (EXAMPLE 174);

(E)-2-(8-trifluoromethyl-3,4-dihydrobenzo[b]oxepin-5(2H)-ylidene)-N-(indan-1-ol-6-yl)acetamide (EXAMPLE 175);

(E)-2-(8-trifluoromethyl-3,4-dihydrobenzo[b]oxepin-5(2H)-ylidene)-N-(2-hydroxyethyl-2,3-dihydro-isoindol-1-on-6-yl)acetamide (EXAMPLE 176);

(E)-2-(8-trifluoromethyl-3,4-dihydrobenzo[b]oxepin-5(2H)-ylidene)-N-(1-methyl-2-oxo-1,2,3,4-tetrahydroquinolin-7-yl)acetamide (EXAMPLE 178);

(E)-2-(8-trifluoromethyl-3,4-dihydrobenzo[b]oxepin-5(2H)-ylidene)-N-(8-hydroxymethyl-5,6,7,8-tetrahydronaphthalen-2-yl)acetamide (EXAMPLE 179);

(E)-2-(8-trifluoromethyl-3,4-dihydrobenzo[b]oxepin-5(2H)-ylidene)-N-(3-hydroxy-chroman-5-yl)acetamide (EXAMPLE 183);

(E)-2-(1-(2,2-difluorobutanoyl)-7-trifluoromethyl-2,3-dihydroquinolin-4(1H)-ylidene)-N-(3-hydroxy-1,2,3,4-tetrahydroquinolin-5-yl)acetamide (EXAMPLE 184);

(E)-2-(1-(2,2-difluorobutanoyl)-7-trifluoromethyl-2,3-dihydroquinolin-4(1H)-ylidene)-N-(3-hydroxy-2-oxo-1,2,3,4-tetrahydroquinolin-5-yl)acetamide (EXAMPLE 185);

(E)-2-(8-trifluoromethyl-1-pentanoyl-1,2,3,4-tetrahydro-5H-benzo[b]azepin-5-ylidene)-N-(7-hydroxy-5,6,7,8-tetrahydronaphthalen-1-yl)acetamide (EXAMPLE 190);

(E)-2-(8-trifluoromethyl-1,2,3,4-tetrahydro-5H-benzo[b]azepin-5-ylidene)-N-(quinolin-7-yl)acetamide (EXAMPLE 191);

(E)-2-(1-pentanoyl-8-trifluoromethyl-1,2,3,4-tetrahydro-5H-benzo[b]azepin-5-ylidene)-N-(quinolin-7-yl)acetamide (EXAMPLE 192);

(E)-2-(1-cyclopentanecarbonyl-8-trifluoromethyl-1,2,3,4-tetrahydro-5H-benzo[b]azepin-5-ylidene)-N-(quinolin-7-yl)acetamide (EXAMPLE 193);

(E)-2-(1-(4-methylbenzenesulfonyl)-8-trifluoromethyl-1,2,3,4-tetrahydro-5H-benzo[b]azepin-5-ylidene)-N-(quinolin-7-yl)acetamide (EXAMPLE 194);

(E)-2-(1-acetyl-8-trifluoromethyl-1,2,3,4-tetrahydro-5H-benzo[b]azepin-5-ylidene)-N-(quinolin-7-yl)acetamide (EXAMPLE 195);

(E)-2-(1-methyl-8-trifluoromethyl-1,2,3,4-tetrahydro-5H-benzo[b]azepin-5-ylidene)-N-(quinolin-7-yl)acetamide (EXAMPLE 196);

(E)-2-(1-cyclopentylmethyl-8-trifluoromethyl-1,2,3,4-tetrahydro-5H-benzo[b]azepin-5-ylidene)-N-(quinolin-7-yl)acetamide (EXAMPLE 197);

(E)-2-(1-methyl-8-trifluoromethyl-1,2,3,4-tetrahydro-5H-benzo[b]azepin-5-ylidene)-N-(7-hydroxynaphthalen-1-yl)acetamide (EXAMPLE 198);

(E)-2-(1-methyl-8-trifluoromethyl-1,2,3,4-tetrahydro-5H-benzo[b]azepin-5-ylidene)-N-(7-hydroxy-5,6,7,8-tetrahydronaphthalen-1-yl)acetamide (EXAMPLE 199);

(E)-2-(1-(3-chloro-5-hydroxymethyl-pyridin-2-yl)-7-trifluoromethyl-2,3-dihydroquinolin-4(1H)-ylidene)-N-(7-hydroxy-5,6,7,8-tetrahydronaphthalen-1-yl)acetamide (EXAMPLE 200);

(E)-2-(7-trifluoromethyl-chroman-4-ylidene)-N-(5,6,7,8-tetrahydronaphthalen-1-yl)acetamide (EXAMPLE 202);

(E)-2-(7-trifluoromethyl-chroman-4-ylidene)-N-(2-methylthieno[2,3-c]pyridin-3-yl)acetamide (EXAMPLE 204);

(E)-2-(7-isopropyl-chroman-4-ylidene)-N-(7-hydroxy-5,6,7,8-tetrahydronaphthalen-1-yl)acetamide (EXAMPLE 206);

(E)-2-(7-isopropyl-chroman-4-ylidene)-N-(3-hydroxy-1,2,3,4-tetrahydroquinolin-5-yl)acetamide (EXAMPLE 207);

(E)-2-(7-chloro-chroman-4-ylidene)-N-(7-hydroxy-5,6,7,8-tetrahydronaphthalen-1-yl)acetamide (EXAMPLE 208);

(E)-2-(7-chloro-chroman-4-ylidene)-N-(3-hydroxy-1,2,3,4-tetrahydroquinolin-5-yl)acetamide (EXAMPLE 209);

(E)-2-(7-trifluoromethoxy-chroman-4-ylidene)-N-(7-hydroxy-5,6,7,8-tetrahydronaphthalen-1-yl)acetamide (EXAMPLE 210);

(E)-2-(7-trifluoromethoxy-chroman-4-ylidene)-N-(3-hydroxy-1,2,3,4-tetrahydroquinolin-5-yl)acetamide (EXAMPLE 211);

(E)-2-(7-(1,1,2,2-tetrafluoroethoxy)-chroman-4-ylidene)-N-(7-hydroxy-5,6,7,8-tetrahydronaphthalen-1-yl)acetamide (EXAMPLE 212);

(E)-2-(7-(1,1,2,2-tetrafluoroethoxy)-chroman-4-ylidene)-N-(3-hydroxy-1,2,3,4-tetrahydroquinolin-5-yl)acetamide (EXAMPLE 213);

(E)-2-(6-fluoro-7-trifluoromethyl-chroman-4-ylidene)-N-(7-hydroxy-5,6,7,8-tetrahydronaphthalen-1-yl)acetamide (EXAMPLE 214);

(E)-2-(6-fluoro-7-trifluoromethyl-chroman-4-ylidene)-N-(3-hydroxy-1,2,3,4-tetrahydroquinolin-5-yl)acetamide (EXAMPLE 215);

(E)-2-(7-trifluoromethyl-chroman-4-ylidene)-N-(2-hydroxymethyl-1,3-benzothiazolo-5-yl)acetamide (EXAMPLE 216);

(E)-2-(8-trifluoromethyl-3,4-dihydrobenzo[b]oxepin-5(2H)-ylidene)-N-(3-hydroxy-1,2,3,4-tetrahydroquinolin-5-yl)acetamide (EXAMPLE 218 and EXAMPLE 219);

(E)-2-(8-trifluoromethyl-3,4-dihydrobenzo[b]oxepin-5(2H)-ylidene)-N-(7-hydroxy-7-methyl-5,6,7,8-tetrahydronaphthalen-1-yl)acetamide (EXAMPLE 220);

(E)-2-(8-trifluoromethyl-3,4-dihydrobenzo[b]oxepin-5(2H)-ylidene)-N-(2-methylthieno[2,3-c]pyridin-3-yl)acetamide (EXAMPLE 221);

(E)-2-(8-trifluoromethyl-3,4-dihydrobenzo[b]oxepin-5(2H)-ylidene)-N-(3-chloro-5-hydroxymethyl-2-pyridyl)acetamide (EXAMPLE 224);

(E)-2-(8-trifluoromethyl-3,4-dihydrobenzo[b]oxepin-5(2H)-ylidene)-N-(2-(7-hydroxy-5,6,7,8-tetrahydronaphthalen-1-yl)ethyl)acetamide (EXAMPLE 226);

(E)-2-(8-trifluoromethyl-3,4-dihydrobenzo[b]oxepin-5(2H)-ylidene)-N-(2-(7-hydroxy-5,6,7,8-tetrahydronaphthalen-1-yl)propyl)acetamide (EXAMPLE 227);

(E)-2-(8-trifluoromethyl-3,4-dihydrobenzo[b]oxepin-5(2H)-ylidene-N-(3-(2-hydroxymethylpyrrolidin-1-yl)phenyl)acetamide (EXAMPLE 229);

(E)-2-(8-trifluoromethyl-3,4-dihydrobenzo[b]oxepin-5(2H)-ylidene-N-(4-(2-hydroxyacetyl)-3,4-dihydro-2H-benzo[b][1,4]oxazin-6-yl)acetamide (EXAMPLE 231);

(E)-2-(8-trifluoromethyl-3,4-dihydrobenzo[b]oxepin-5(2H)-ylidene-N-(4-(2-hydroxyethyl)-3,4-dihydro-2H-benzo[b][1,4]oxazin-6-yl)acetamide (EXAMPLE 233);

(E)-2-(8-trifluoromethyl-3,4-dihydrobenzo[b]oxepin-5(2H)-ylidene)-N-(4-(2-hydroxyethyl)-2H-1,4-benzoxazin-3(4H)-on-6-yl)acetamide (EXAMPLE 234);

(E)-2-(8-trifluoromethyl-3,4-dihydrobenzo[c]isooxepin-5(1H)-ylidene)-N-(7-hydroxy-5,6,7,8-tetrahydronaphthalen-1-yl)acetamide (EXAMPLE 235);

(E)-2-(8-trifluoromethyl-3,4-dihydrobenzo[c]isooxepin-5(1H)-ylidene)-N-(3-hydroxy-1,2,3,4-tetrahydroquinolin-5-yl)acetamide (EXAMPLE 236);

(E)-2-(7-trifluoromethyl-isochroman-4-ylidene)-N-(7-hydroxy-5,6,7,8-tetrahydronaphthalen-1-yl)acetamide (EXAMPLE 237);

(E)-2-(7-trifluoromethyl-3,4-dihydro-2H-pyrano[2,3-b]pyridin-4-ylidene)-N-(7-hydroxy-5,6,7,8-tetrahydronaphthalen-1-yl)acetamide (EXAMPLE 238);

(E)-2-(8-trifluoromethyl-2,3,4,5-tetrahydrooxepino[2,3-b]pyridin-5-ylidene)-N-(7-hydroxy-5,6,7,8-tetrahydronaphthalen-1-yl)acetamide (EXAMPLE 239);

(Z)-2-(6-trifluoromethyl-3,3-dimethyl-4-oxa-3,4-dihydro-(2H)-isoquinolin-1-ylidene)-N-(7-hydroxy-5,6,7,8-tetrahydronaphthalen-1-yl)acetamide (EXAMPLE 240);

(E)-2-(7-trifluoromethyl-2,2-dimethylchroman-4-ylidene)-N-(7-hydroxy-5,6,7,8-tetrahydronaphthalen-1-yl)acetamide (EXAMPLE 241-A);

(E)-2-(7-trifluoromethyl-2,2-dimethylchroman-4-ylidene)-N-(7-hydroxy-5,6,7,8-tetrahydronaphthalen-1-yl)acetamide (EXAMPLE 242 and EXAMPLE 243);

(E)-2-(7-trifluoromethyl-2,2-dimethylchroman-4-ylidene)-N-(3-hydroxy-1,2,3,4-tetrahydroquinolin-5-yl)acetamide (EXAMPLE 244);

(E)-2-(7-trifluoromethyl-2,2-dimethylchroman-4-ylidene)-N-(3-hydroxy-1,2,3,4-tetrahydroquinolin-5-yl)acetamide (EXAMPLE 245 and EXAMPLE 246);

(Z)-2-(8-trifluoromethyl-3,4-dihydrobenzo[b]oxepin-5(2H)-ylidene)-N-(quinolin-7-yl)acetamide (EXAMPLE 247);

(E)-2-(7-fluoro-8-trifluoromethyl-3,4-dihydrobenzo[b]oxepin-5-(2H)-ylidene)-N-(7-hydroxy-5,6,7,8-tetrahydronaphthalen-1-yl)acetamide (EXAMPLE 248);

(E)-2-(7-trifluoromethyl-2,2-cyclobutylchroman-4-ylidene)-N-(7-hydroxy-5,6,7,8-tetrahydronaphthalen-1-yl)acetamide (EXAMPLE 251);

(E)-N-(3-hydroxy-1,2,3,4-tetrahydroquinolin-5-yl)-2-(7-trifluoromethyl-2,2-cyclobutylchroman-4-ylidene)acetamide (EXAMPLE 252);

(E)-2-(8-trifluoromethyl-3,4-dihydrobenzo[b]oxepin-5(2H)-ylidene)-N-(1H-indazol-4-yl)acetamide (EXAMPLE 253); and (E)-2-(8-trifluoromethyl-3,4-dihydrobenzo[b]oxepin-5(2H)-ylidene)-N-(1H-indazol-7-yl)acetamide (EXAMPLE 254).

Examples of the preferable compounds also include pharmaceutically acceptable salts thereof and solvate thereof.

[1-12] In the compounds represented by formula (I) in embodiment [1], examples of more preferable compounds include compounds represented by formula (I-A).

[Ch. 6]

(I-A)

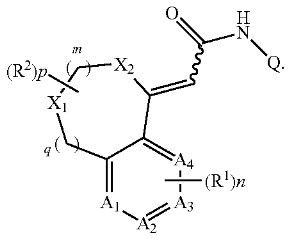

In formula (I-A), $A_1$, $A_2$, $A_3$, and $A_4$ each independently represent —N═ or —CH═, the definitions of $R^1$, $R^2$, $X_1$, $X_2$, m, n, p, q, and Q are the same as those described in one of embodiments [1-1] to [1-11], and preferably, the same as the definitions in embodiment [1-11]. The wavy line to which "CO—NH-Q" is bonded is preferably a bond of an E-isomer.

Here, q is an integer of 0 or 1. When q is 0, the compounds can be represented by formula (I-A-1). When q is 1, the compounds can be represented by formula (I-A-2).

[1-13] In the compounds represented by formula (I) in embodiment [1], examples of more preferable compounds represented by formula (I-A) include compounds represented by formula (I-B).

[Ch. 7]

(I-B)

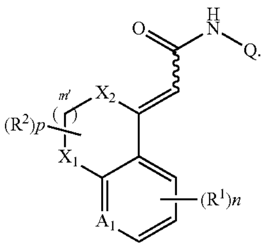

In formula (I-B), $A_1$ represents —N= or —CH=, m' represents an integer of 1 or 2, the definitions of $R^1$, $R^2$, $X_1$, $X_2$, n, p, and Q are the same as those described in one of embodiments [1-1] to [1-11], and preferably, the same as the definitions in embodiment [1-11]. The wavy line to which "CO—NH-Q" is bonded is preferably a bond of an E-isomer. Here, m' is an integer of 1 or 2. When m' is 1, the compounds can be represented by formula (I-B-1). When m' is 2, the compounds can be represented by formula (I-B-2).

[1-14] In the compounds represented by formula (I) in embodiment [1], examples of more preferable compounds represented by formula (I-B) include compounds represented by formula (I-C).

[Ch. 8]

(I-C)

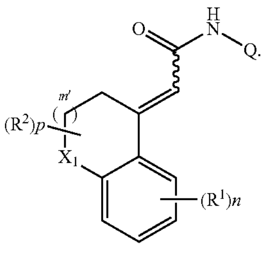

In formula (I-C), m' represents an integer of 1 or 2, the definitions of $R^1$, $R^2$, $X_1$, n, p, and Q are the same as those described in one of embodiments [1-1] to [1-11], and preferably, the same as the definitions in embodiment [1-11]. The wavy line to which "CO—NH-Q" is bonded is preferably a bond of an E-isomer. Here, m' is an integer of 1 or 2. When m' is 1, the compounds can be represented by formula (I-C-1). When m' is 2, the compounds can be represented by formula (I-C-2).

[1-15] In the compounds represented by formula (I) in embodiment [1], examples of more preferable compounds represented by formula (I-C) include compounds represented by formula (I-D).

[Ch. 9]

(I-D)

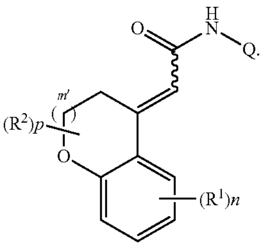

In formula (I-D), m' represents an integer of 1 or 2, the definitions of $R^1$, $R^2$, n, p, Q and the wavy line are the same as those described in one of embodiments [1-1] to [1-11], and preferably, the same as the definitions in embodiment [1-11]. The wavy line to which "CO—NH-Q" is bonded is preferably a bond of an E-isomer. Here, m' is an integer of 1 or 2. When m' is 1, the compounds can be represented by formula (I-D-1). When m' is 2, the compounds can be represented by formula (I-D-2).

[1-16] In the compounds represented by formula (I) in embodiment [1], examples of more preferable compounds represented by formula (I-C) include compounds represented by formula (I-E).

[Ch. 10]

(I-E)

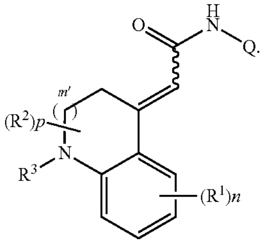

In formula (I-E), m' represents an integer of 1 or 2, the definitions of $R^1$, $R^2$, $R^3$, n, p, Q and the wavy line are the same as those described in one of embodiments [1-1] to [1-11], and preferably, the same as the definitions in embodiment [1-11]. The wavy line to which "CO—NH-Q" is bonded is preferably a bond of an E-isomer. Here, m' is an integer of 1 or 2. When m' is 1, the compounds can be represented by formula (I-E-1). When m' is 2, the compounds can be represented by formula (I-E-2).

[1-17] In the compounds represented by formula (I) in embodiment [1], examples of more preferable compounds represented by formula (I-C) include compounds represented by formula (I-F).

[Ch. 11]

(I-F)

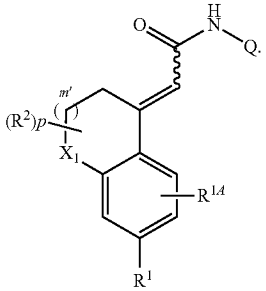

In formula (I-F), $R^{1A}$ is a hydrogen atom or defined the same as $R^1$, the definitions of $R^1$, $R^2$, $X_1$, m, p, and Q are the same as those described in one of embodiments [1-1] to [1-11], and preferably, the same as the definitions in embodiment [1-11]. The wavy line to which "CO—NH-Q" is bonded is preferably a bond of an E-isomer.

Here, m' is an integer of 1 or 2. When m' is 1, the compounds can be represented by formula (I-F-1). When m' is 2, the compounds can be represented by formula (I-F-2).

In this description, in particular, in the first embodiment of the present invention, the "TRPV1 receptor antagonist" is an embodiment of a "TRPV1 receptor regulator". The term "TRPV1 receptor regulator" means an agent comprising a compound that modulates the function of the TRPV1 receptor. More specifically, the term "TRPV1 receptor regulator" means an agent comprising a compound that suppresses activation of the TRPV1 receptor. The compound may be a compound (TRPV1 receptor antagonist) that is combined with the TRPV1 receptor and that antagonizes an endogenous ligand, thereby suppressing activation of the TRPV1 receptor, or a compound (TRPV1 receptor agonist) that continuously activates the TRPV1 receptor and that desensitizes nerves in which the receptor is present, thereby suppressing activation of the receptor thereafter. Accordingly, the term "TRPV1 receptor regulator" is a generic name for the TRPV1 receptor antagonists and the TRPV1 receptor agonists. The TRPV1 receptor regulator of the present invention is preferably a TRPV1 receptor antagonist. It is expected that the TRPV1 antagonist of the present invention has a promising effect of preventing or curing various diseases and conditions. Examples thereof include acute pain; chronic pain; neuropathic pain; postherpetic neuralgia; trigeminal neuralgia; lower-back pain; pain after spinal cord injury; leg pain; causalgia; diabetic neuralgia; pain caused by edema, burns, sprains, bone fractures, and the like; pain after surgical operations; scapulohumeral periarthritis; osteoarthritis; arthritis; rheumatic arthritis pain; inflammatory pain; cancer pain; migraines; headaches; toothaches; neuralgia; muscle pain; hyoeralgesia; pain caused by angina pectoris, menstruation, and the like; neuropathy; nerve damage; neurodegeneration; chronic obstructive pulmonary disease (COPD); asthma; airway hypersensitivity; stridor; cough; rhinitis; inflammation of mucosa such as eyes; nervous dermatitis; inflammatory skin complaint such as psoriasis and eczema; edema; allergic diseases; gastroduodenal ulcer; ulcerative colitis; irritable colon syndrome; Crohn disease; urinary incontinence; urinary urge incontinence; overactive bladder; cystitis; nephritis; pancreatitis; uveitis; splanchnopathy; ischemia; apoplexy; dystonia; obesity; septicemia; and pruritus. In particular, a promising effect for neuropathic pain, inflammatory pain, and urinary incontinence can be expected.

[2] A second embodiment of the present invention provides compounds represented by formula (I'), salts thereof, and solvates thereof.

[Ch. 12]

(I')

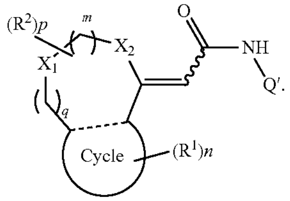

(wherein m, n, and p each independently represent an integer of 0 to 2; q represents an integer of 0 or 1; $R^1$ represents a group optionally selected from a halogen atom, a substituted or unsubstituted hydrocarbon group, a substituted or unsubstituted heterocyclic group, a substituted or unsubstituted $C_{1-6}$ alkoxy group, a substituted or unsubstituted $C_{1-6}$ alkoxycarbonyl group, an amino group which may be mono- or di-substituted with a substituted or unsubstituted $C_{1-6}$ alkyl group, a protected or unprotected hydroxyl group, a protected or unprotected carboxyl group, a carbamoyl group which is optionally mono- or di-substituted with a substituted or unsubstituted $C_{1-6}$ alkyl group, a $C_{1-6}$ alkanoyl group, a $C_{1-6}$ alkylthio group, a $C_{1-6}$ alkylsulfinyl group, a $C_{1-6}$ alkylsulfonyl group, a sulfamoyl group which may be mono- or di-substituted with a substituted or unsubstituted $C_{1-6}$ alkyl group, a cyano group, and a nitro group; $R^2$ represents a group optionally selected from a halogen atom, a substituted or unsubstituted amino group, a substituted or unsubstituted hydrocarbon group, a substituted or unsubstituted aromatic heterocyclic group, and an oxo group, or two geminal or vicinal $R^2$'s may bind to each other to form a $C_{2-6}$ alkylene group, and form a cyclo ring group together with the carbon atom to which the two $R^2$'s are bonded; $X_1$ represents an oxygen atom, —$NR^3$— (wherein $R^3$ is a hydrogen atom, a substituted or unsubstituted hydrocarbon group, a substituted or unsubstituted heterocyclic group, or a substituted or unsubstituted acyl group), or —S(O)r- (wherein r is an integer of 0 to 2); $X_2$ represents a methylene group, an oxygen atom, —$NR^3$— (wherein $R^3$ is a hydrogen atom, a substituted or unsubstituted hydrocarbon group, a substituted or unsubstituted heterocyclic group, or a substituted or unsubstituted acyl group) or —S(O)r- (wherein r is an integer of 0 to 2); Q' represents a substituted or unsubstituted heteroaryl group, a substituted or unsubstituted heteroarylalkyl group, a substituted aryl group, or a substituted or unsubstituted aralkyl group; Cycle moiety represents a five- or six-membered aryl ring or heteroaryl ring; the broken line represents a condensation of two rings; and the wavy line represents an E-isomer or a Z-isomer; however, the case where m is 2, $X_1$ is —$NR^3$—, $X_2$ is a methylene group, $R^2$ is a fluorine atom, and p is 2; the case where $X_1$ is —S(O)r- (wherein r is an integer of 0 to 2), r is 2, and $X_2$ is —$NR^3$—; the case where p is 2, $R^2$'s are an oxo group and a sec-butyl group, and q is 1; the case where $R^2$ is an oxo group and m is 0 or 2; and the case where m is 2, $X_1$ is —$NR^3$—, $X_2$ is a methylene group, and n is 0; are eliminated.)

In the formula, the definitions of $R^1$, $R^2$, $X_1$, $X_2$, m, n, p, q, the Cycle moiety, and the wavy line are the same as those described in embodiment [1], and Q' represents a substituted or unsubstituted heteroaryl group, a substituted or unsubstituted heteroarylalkyl group, a substituted aryl group, or a substituted or unsubstituted aralkyl group (however, the case where m is 2, $X_1$ is —$NR^3$—, $X_2$ is a methylene group, $R^2$ is a fluorine atom, and p is 2; the case where $X_1$ is —S(O)r- (wherein r is an integer of 0 to 2), r is 2, and $X_2$ is —$NR^3$—; the case where p is 2, $R^2$'s are an oxo group and a sec-butyl group, and q is 1; the case where $R^2$ is an oxo group and m is 0 or 2; and the case where m is 2, $X_1$ is —$NR^3$—, $X_2$ is a methylene group, and n is 0 are eliminated). The definition of $R^3$ is included in the definitions of $X_1$ and $X_2$.

More specifically, in formula (I'), the definitions of $R^1$, $R^2$, $X_1$, $X_2$, m, n, p, q, the Cycle moiety, and the wavy line are the same as those described in one of embodiments [1-1] to [1-11]. The definition of Q' is also the same as the definition of Q described in one of embodiments [1-1] to [1-11] except that only an unsubstituted aryl group is eliminated from Q. Preferably, the definitions of $R^1$, $R^2$, $X_1$, $X_2$, m, n, p, q, the Cycle moiety, and the wavy line, and Q' follow the definitions given in embodiment [1-11]. The wavy line to which "CO—NH-Q'" is bonded is preferably a bond of an E-isomer.

More specifically, the following embodiments are preferred.

[2-1]

An embodiment 2-1 of the present invention provides compounds represented by formula (I'-A), salts thereof, and solvates thereof.

[Ch. 13]

(I'-A)

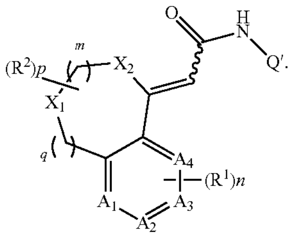

(wherein $A_1$, $A_2$, $A_3$, and $A_4$ each independently represent —N═ or —CH═, the definitions of $R^1$, $R^2$, $X_1$, $X_2$, m, n, p, q, Q', and the wavy line are the same as those described in embodiment [2] above (however, the case where m is 2, $X_1$ is —$NR^3$—, $X_2$ is a methylene group, $R^2$ is a fluorine atom, and p is 2; the case where $X_1$ is —S(O)r- (wherein r is an integer of 0 to 2), r is 2, and $X_2$ is —$NR^3$—; the case where p is 2, $R^2$'s are an oxo group and a sec-butyl group, and q is 1; the case where $R^2$ is an oxo group and m is 0 or 2; and the case where m is 2, $X_1$ is —$NR^3$—, $X_2$ is a methylene group, and n is 0; are eliminated)).

More specifically, in formula (I'-A), the definitions of $R^1$, $R^2$, $X_1$, $X_2$, m, n, p, q, and the wavy line are the same as those described in one of embodiments [1-1] to [1-11]. The definition of Q' is also the same as the definition of Q described in one of embodiments [1-1] to [1-11] except that only an unsubstituted aryl group is eliminated from Q. Preferably, the definitions of $R^1$, $R^2$, $X_1$, $X_2$, m, n, p, q, the Cycle moiety, and the wavy line, and Q' follow the definitions given in embodiment [1-11]. The wavy line to which "CO—NH-Q'" is bonded is preferably a bond of an E-isomer.

Here, q is an integer of 0 or 1. When q is 0, the compounds are referred to as formula (I'-A-1). When q is 1, the compounds are referred to as formula (I'-A-2).

In any one of formulae (I'-A), (I'-A-1), and (I'-A-2), compounds in which n is 1 or 2 and at least one $R^1$ is located at the $A_2$ position are more preferred. In such a case, for example, formula (I'-A) can be represented by the following formula.

[Ch. 14]

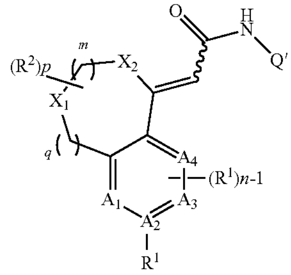

[2-2]

An embodiment 2-2 of the present invention provides compounds represented by formula (I'-B), salts thereof, and solvates thereof.

[Ch. 15]

(I'-B)

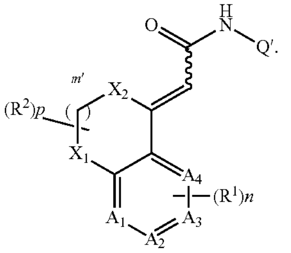

(wherein $A_1$, $A_2$, $A_3$, and $A_4$ each independently represent —N═ or —CH═, m' represents an integer of 1 or 2, the definitions of $R^1$, $R^2$, $X_1$, $X_2$, n, p, and Q' are the same as those described in embodiment [2] above (however, the case where m' is 2, $X_1$ is —$NR^3$—, $X_2$ is a methylene group, $R^2$ is a fluorine atom, and p is 2; the case where $R^2$ is an oxo group and m' is 2; and the case where m' is 2, $X_1$ is —$NR^3$—, $X_2$ is a methylene group, and n is 0; are eliminated)).

More specifically, in formula (I'-B), the definitions of $R^1$, $R^2$, $X_1$, $X_2$, m, n, p and the wavy line are the same as those described in one of embodiments [1-1] to [1-11]. The definition of Q' is also the same as the definition of Q described in one of embodiments [1-1] to [1-11] except that only an unsubstituted aryl group is eliminated from Q.

Preferably, the definitions of $R^1$, $R^2$, $X_1$, $X_2$, m, n, p, and the wavy line, and Q' follow the definitions given in embodiment [1-11]. The wavy line to which "CO—NH-Q'" is bonded is preferably a bond of an E-isomer.

More preferably, $A_1$ represents —N═ or —C═, and each of $A_2$, $A_3$, and $A_4$ represents —CH═.

Here, m' is an integer of 1 or 2. When m' is 1, the compounds are referred to as formula (I'-B-1). When m' is 2, the compounds are referred to as formula (I'-B-2).

In any one of formulae (I'-B), (I'-B-1), and (I'-B-2), compounds in which n is 1 or 2 and at least one $R^1$ is located at the $A_2$ position are further preferred.

[2-3]

An embodiment 2-3 of the present invention provides compounds represented by formula (I'-C), salts thereof, and solvates thereof.

[Ch. 16]

(I'-C)

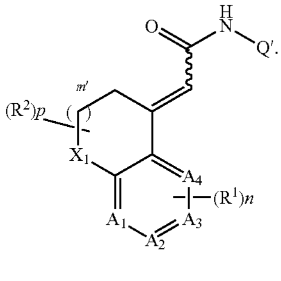

(wherein $A_1$, $A_2$, $A_3$, and $A_4$ each independently represent —N═ or —CH═, m' represents an integer of 1 or 2, and $R^1$, $R^2$, $X_1$, n, p, and Q' are the same as those described above (however, the case where m' is 2, $X_1$ is —$NR^3$—, $R^2$ is a fluorine atom, and p is 2; and the case where m' is 2, $X_1$ is —$NR^3$—, and n is 0 are eliminated)).

More specifically, in formula (I'-C), the definitions of $R^1$, $R^2$, $X_1$, $X_2$, m, n, p and the wavy line are the same as those described in one of embodiments [1-1] to [1-11]. The definition of Q' is also the same as the definition of Q described in one of embodiments [1-1] to [1-11] except that only an unsubstituted aryl group is eliminated from Q. Preferably, the definitions of $R^1$, $R^2$, $X_1$, $X_2$, m, n, p, and the wavy line, and Q' follow the definitions given in embodiment [1-11]. The wavy line to which "CO—NH-Q'" is bonded is preferably a bond of an E-isomer.

More preferably, each of $A_1$, $A_2$, $A_3$, and $A_4$ represents —CH═.

Here, m' is an integer of 1 or 2. When m' is 1, the compounds are referred to as formula (I'-C-1). When m' is 2, the compounds are referred to as formula (I'-C-2).

In any one of formulae (I'-C), (I'-C-1), and (I'-C-2), compounds in which n is 1 or 2 and at least one $R^1$ is located at the $A_2$ position are further preferred.

[2-4]

An embodiment 2-4 of the present invention provides compounds represented by formula (I'-D), salts thereof, and solvates thereof.

[Ch. 17]

(I'-D)

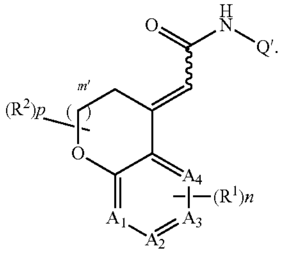

(wherein $A_1$, $A_2$, $A_3$, and $A_4$ each independently represent —N═ or —CH═, m' represents an integer of 1 or 2, and $R^1$, $R^2$, n, p, and Q' are the same as those described above).

More specifically, in formula (I'-D), the definitions of $R^1$, $R^2$, $X_1$, $X_2$, m, n, p and the wavy line are the same as those described in one of embodiments [1-1] to [1-11]. The definition of Q' is also the same as the definition of Q described in one of embodiments [1-1] to [1-11] except that only an unsubstituted aryl group is eliminated from Q. Preferably, the definitions of $R^1$, $R^2$, $X_1$, $X_2$, m, n, p, and the wavy line, and Q' follow the definitions given in embodiment [1-11]. The wavy line to which "CO—NH-Q'" is bonded is preferably a bond of an E-isomer.

More preferably, each of $A_1$, $A_2$, $A_3$, and $A_4$ represents —CH═.

Here, m' is an integer of 1 or 2. When m' is 1, the compounds are referred to as formula (I'-D-1). When m' is 2, the compounds are referred to as formula (I'-D-2).

In any one of formulae (I'-D), (I'-D-1), and (I'-D-2), compounds in which n is 1 or 2 and at least one $R^1$ is located at the $A_2$ position are further preferred.

[2-5]

An embodiment 2-5 of the present invention provides compounds represented by formula (I'-E), salts thereof, and solvates thereof.

[Ch. 18]

(I'-E)

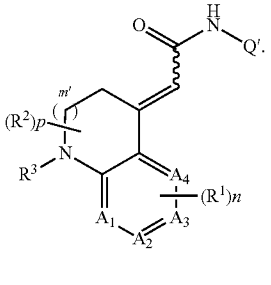

(wherein $A_1$, $A_2$, $A_3$, and $A_4$ each independently represent —N═ or —CH═, m' represents an integer of 1 or 2, and the definitions of $R^1$, $R^2$, $R^3$, n, p, and Q' are the same as those described in embodiment [1] above (however, the case where m' is 2, $R^2$ is a fluorine atom, and p is 2; and the case where m' is 2 and n is 0 are eliminated)).

More specifically, in formula (I'-E), the definitions of $R^1$, $R^2$, $X_1$, $X_2$, m, n, p, the Cycle moiety, and the wavy line are the same as those described in one of embodiments [1-1] to [1-11]. The definition of Q' is also the same as the definition of Q described in one of embodiments [1-1] to [1-11] except that only an unsubstituted aryl group is eliminated from Q. Preferably, the definitions of $R^1$, $R^2$, $X_1$, $X_2$, m, n, p, q, the Cycle moiety, and the wavy line; and Q' replace the definitions given in embodiment [1-11]. The wavy line to which "CO—NH-Q'" is bonded is preferably a bond of an E-isomer.

More preferably, each of $A_1$, $A_2$, $A_3$, and $A_4$ represents —CH═.

Here, m' is an integer of 1 or 2. When m' is 1, the compounds are referred to as formula (I'-E-1). When m' is 2, the compounds are referred to as formula (I'-E-2).

In any one of formulae (I'-E), (I'-E-1), and (I'-E-2), compounds in which n is 1 or 2 and at least one $R^1$ is located at the $A_2$ position are further preferred.

[2-6]

An embodiment 2-6 of the present invention provides compounds represented by formula (I'-F), salts thereof, and solvates thereof.

[Ch. 19]

(I'-F)

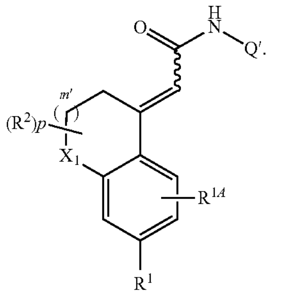

(wherein $R^{1A}$ is a hydrogen atom or defined the same as $R^1$, m' represents an integer of 1 or 2, and $R^1$, $R^2$, p, and Q' are the same as those described above (however, the case where m' is 2, $X_1$ is —$NR^3$—, $R^2$ is a fluorine atom, and p is 2 is eliminated)).

More specifically, in formula (I'-F), the definitions of $R^1$, $R^2$, $X_1$, m, p, and the wavy line are the same as those described in one of embodiments [1-1] to [1-11]. The definition of Q' is also the same as the definition of Q described in one of embodiments [1-1] to [1-11] except that only an unsubstituted aryl group is eliminated from Q.

Preferably, the definitions of $R^1$, $R^2$, $X_1$, m, p, and the wavy line; and Q' replace the definitions given in embodiment [1-11]. The wavy line to which "CO—NH-Q'" is bonded is preferably a bond of an E-isomer.

Here, m' is an integer of 1 or 2. When m' is 1, the compounds are referred to as formula (I'-F-1). When m' is 2, the compounds are referred to as formula (I'-F-2).

[2-7]

An embodiment 2-7 of the present invention provides the compounds described as the preferable compounds in embodiment [1-11], salts thereof, and solvates thereof.

[2-8]

More preferably, Q' in the formulae described in the second embodiment and embodiments 2-1 to 2-6 of the present invention is represented as the following bicyclic group by formula (B):

[Ch. 19a]

(B)

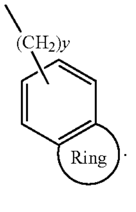

(wherein Ring and y are the same as those described above.) Preferably, y is in the range of 0 to 4, and more preferably in the range of 0 to 3. Specific examples of formula (B) can be selected from the group consisting of a 2,3-dihydrobenzo[b][1,4]dioxin-6-yl group, isoquinolin-5-yl group, quinolin-7-yl group, quinoxalin-6-yl group, 1,2,3,4-tetrahydro-1-methylquinolin-7-yl group, 2-methyl-1,3-benzothiazolo-5-yl group, 4-methyl-2-oxo-2H-chromen-7-yl group, 1,3-dihydro-1-oxoisobenzofuran-6-yl group, 2-hydroxymethyl-1,3-benzothiazol-5-yl group, 3-hydroxy-2-oxo-1,2,3,4-tetrahydroquinolin-5-yl group, 3-hydroxy-1,2,3,4-tetrahydroquinolin-5-yl group, 1-methyl-3-hydroxy-1,2,3,4-tetrahydroquinolin-5-yl group, 1-(2-hydroxyethyl)-1,2,3,4-tetrahydroquinolin-7-yl group, 1-(2-(4-morpholino)ethyl)-1,2,3,4-tetrahydroquinolin-7-yl group, 1-(2-(N,N-dimethylamino)ethyl)-1,2,3,4-tetrahydroquinolin-7-yl group, 3,4-dihydro-1H-quinolin-2-on-7-yl group, 2-quinolon-7-yl group, 3,4-dihydro-2H-1,5-benzo[b]dioxepin-7-yl group, 2,2-difluoro-1,3-benzodioxol-5-yl group, 1-methylindol-5-yl group, 1-(2-hydroxyethyl)indol-6-yl group, 1-(1-oxopentyl)-1,2,3,4-tetrahydroquinolin-7-yl group, 1-((1-oxo-2-acetoxy)ethyl)-1,2,3,4-tetrahydroquinolin-7-yl group, 1-trifluoroacetyl-1,2,3,4-tetrahydroquinolin-7-yl group, 3-hydroxymethylindol-4-yl group, 1-(2-hydroxyethyl)indol-5-yl group, 3-hydroxymethyl-2,3-dihydro-1,4-benzodioxin-6-yl group, 2,3-dihydro-isoindol-1-on-6-yl group, 1,2,3,4-tetrahydroquinolin-7-yl group, (1-(2-hydroxy-1-oxo)ethyl)-1,2,3,4-tetrahydroquinolin-7-yl group, 1a,2,7,7a-tetrahydronaphtho[2,3-b]oxirene-3-yl group, 2-quinolon-8-yl group, 1-methylindol-6-yl group, 1-methyl-2-oxo-1,2,3,4-tetrahydroquinolin-7-yl group, 1,2,3,4-tetrahydroisoquinolin-8-yl group, 2-hydroxyethyl-1,2,3,4-tetrahydroisoquinolin-8-yl group, 3,4-dihydro-2H-isoquinolin-1-on-7-yl group, 2-hydroxyethyl-2,3-dihydro-isoindol-1-on-6-yl group, 3-hydroxy-2,3-dihydro-(1H)-4-benzopyran-5-yl group, 6-hydroxy-2,3-dihydro-(1H)-4-benzopyran-4-yl group, 6-hydroxy-1,2,3,4-tetrahydroquinolin-4-yl group, 2-oxo-1,2,3,4-tetrahydroquinolin-8-yl group, 3-hydroxyquinolin-5-yl group, 2-acetyl-1,2,3,4-tetrahydroisoquinolin-8-yl group, 4-(2-hydroxyacetyl)-3,4-dihydro-2H-benzo[b][1,4]oxazin-6-yl group, 4-(2-hydroxypropynoyl)-3,4-dihydro-2H-benzo[b][1,4]oxazin-6-yl group, 4-(2-hydroxyethyl)-3,4-dihydro-2H-benzo[b][1,4]oxazin-6-yl group, 2-hydroxymethyl-1,3-benzothiazolo-5-yl group, 1H-indazol-4-yl group, 1H-indazol-7-yl group; (2,3-dihydrobenzo[b][1,4]dioxin-6-yl)methyl group, 1-(2,3-dihydrobenzo[b][1,4]dioxin-6-yl)ethyl group, (2,3-dihydrobenzo[b][1,4]dioxin-3-yl)methyl group, (2,3-dihydrobenzofuran-6-yl)methyl group, (2-(4-chlorophenyl)-4-methylthiazol-5-yl)methyl group, (1,2,4-triazolo[4,3-a]pyridin-3-yl)methyl group; 7-hydroxynaphthalen-1-yl group, 1,2,3,4-tetrahydro-1-oxonaphthalen-7-yl group, 7-oxo-5,6,7,8-tetrahydronaphthalen-1-yl group, 7-hydroxy-5,6,7,8-tetrahydronaphthalen-1-yl group, 5,6,7,8-tetrahydro-trans-6,7-dihydroxynaphthalen-1-yl group, 5,6,7,8-tetrahydro-cis-6,7-dihydroxynaphthalen-1-yl group, 6-hydroxynaphthalen-1-yl group, 7-hydroxynaphthalen-2-yl group, 7-methoxynaphthalen-1-yl group, 5-hydroxynaphthalen-1-yl group, indan-1-on-6-yl group, indan-2-acetox-4-yl group, indan-2-ol-4-yl group, 7-dimethylamino-naphthalen-1-yl group, 8-hydroxymethyl-5,6,7,8-tetrahydronaphthalen-2-yl group, 7-hydroxy-7-methyl-5,6,7,8-tetrahydronaphthalen-1-yl group, (Z)-7-hydroxyimino-5,6,7,8-tetrahydronaphthalen-1-yl group, (E)-7-hydroxyimino-5,6,7,8-tetrahydronaphthalen-1-yl group, 1-hydroxy-1,2,3,4-tetrahydronaphthalen-8-yl group, indan-1-ol-6-yl group, 5,6,7,8-tetrahydronaphthalen-1-yl group, 2-(7-hydroxy-5,6,7,8-tetrahydronaphthalen-1-yl)ethyl group, 2-(7-hydroxy-5,6,7,8-tetrahydronaphthalen-1-yl)propyl group, and 2-(2-chlorophenyl)ethyl group. More preferably, examples of formula (B) include a 2-hydroxymethyl-1,3-benzothiazol-5-yl group, 7-hydroxy-5,6,7,8-tetrahydronaphthalen-1-yl group, 3-hydroxy-2-oxo-1,2,3,4-tetrahydroquinolin-5-yl group, and 3-hydroxy-1,2,3,4-tetrahydroquinolin-5-yl group.

[2-9]

Each of the specific groups of Q described in embodiment [2-8] may not have further substituents, may be optionally further substituted with 1 to 3 substituents in a class selected from (a-1) to (g-1) described in [1-1-a], or may be optionally exchanged for any substituents in the specific examples. In the groups listed in (a-1) to (g-1), "particularly preferable groups" include substituents such as $C_{1-6}$ alkyl, $C_{2-6}$ alkenyl, $C_{2-6}$ alkynyl, halogen atoms, halogenated $C_{1-6}$ alkyl, cyano, amino, hydroxyl, carbamoyl, $C_{1-6}$ alkoxy, $C_{2-6}$ alkenyloxy, $C_{2-6}$ alkynyloxy, $C_{1-6}$ alkylthio, $C_{1-6}$ alkylsulfinyl, $C_{1-6}$ alkylsulfonyl, mono/di $C_{1-6}$ alkylamino, $C_{1-6}$ alkoxycarbonyl, $C_{2-6}$ alkanoyl, $C_{2-6}$ alkanoylamino, hydroxy-$C_{1-6}$ alkyl, $C_{1-6}$ alkoxy-$C_{1-6}$ alkyl, carboxy-$C_{1-6}$ alkyl, $C_{1-6}$ alkoxycarbonyl-$C_{1-6}$ alkyl, carbamoyl-$C_{1-6}$ alkyl, N—$C_{1-6}$ alkylcarbamoyl-$C_{1-6}$ alkyl, N,N-di $C_{1-6}$-alkylcarbamoyl-$C_{1-6}$ alkyl, phenyl, phenoxy, phenylthio, phenylsulfinyl, phenylsulfonyl, benzyl, benzoyl, morpholino, oxo, morpholinylcarbonyl, morpholinylsulfonyl, 5-trifluoromethylpyridin-2-yloxy, quinoxalin-2-yl, (pyridin-4-yl)methyl, 1,2,3-thiadiazolo-4-yl, 1H-pyrazolo-1-yl, and 4-chlorophenyl. The aromatic rings in these substituents may be optionally further optionally substituted with 1 to 3 substituents selected from halogen atoms, trifluoromethyl, cyano, hydroxyl, amino, nitro, carboxyl, carbamoyl, $C_{1-6}$ alkyl, $C_{1-6}$ alkoxy, mono/di $C_{1-6}$ alkylamino, di-$C_{1-6}$ alkylcarbamoyl, $C_{1-6}$ alkoxycarbonyl, N—$C_{1-6}$ alkylcarbamoyl, N,N-di $C_{1-6}$ alkylcarbamoyl, and $C_{2-6}$ alkenoylamino.

[3] A third embodiment of the present invention provides a pharmaceutical composition comprising the compounds represented by formula (I'), pharmaceutically acceptable salts thereof, or solvates thereof as an active ingredient.

More specifically, the following embodiments are preferred.

[3-1]

An embodiment 3-1 of the present invention provides a pharmaceutical composition comprising at least one of the compounds represented by formula (I'-A), pharmaceutically acceptable salts thereof, and solvates thereof as an active ingredient.

[3-2]

An embodiment 3-2 of the present invention provides a pharmaceutical composition comprising at least one of the compounds represented by formula (I'-B), pharmaceutically acceptable salts thereof, and solvates thereof as an active ingredient.

[3-3]

An embodiment 3-3 of the present invention provides a pharmaceutical composition comprising at least one of the compounds represented by formula (I'-C), pharmaceutically acceptable salts thereof, and solvates thereof as an active ingredient.

[3-4]

An embodiment 3-4 of the present invention provides a pharmaceutical composition comprising at least one of the compounds represented by formula (I'-D), pharmaceutically acceptable salts thereof, and solvates thereof as an active ingredient.

[3-5]

An embodiment 3-5 of the present invention provides a pharmaceutical composition comprising at least one of the compounds represented by formula (I'-E), pharmaceutically acceptable salts thereof, and solvates thereof as an active ingredient.

[3-6]

An embodiment 3-6 of the present invention provides a pharmaceutical composition comprising at least one of the compounds represented by formula (I'-F), pharmaceutically acceptable salts thereof, and solvates thereof as an active ingredient.

[3-7]

An embodiment 3-7 of the present invention provides a pharmaceutical composition comprising at least one of the compounds described as the preferable compounds in embodiment [1-11], pharmaceutically acceptable salts thereof, and solvates thereof as an active ingredient.

[4] A fourth embodiment of the present invention provides an agent for preventing or treating pain comprising at least one of the compounds represented by formula (I'), pharmaceutically acceptable salts thereof, and solvates thereof as an active ingredient.

More specifically, the following embodiments are preferred.

[4-1]

An embodiment 4-1 of the present invention provides an agent for preventing or treating pain comprising at least one of the compounds represented by formula (I'-A), pharmaceutically acceptable salts thereof, and solvates thereof as an active ingredient.

[4-2]

An embodiment 4-2 of the present invention provides an agent for preventing or treating pain comprising at least one of the compounds represented by formula (I'-B), pharmaceutically acceptable salts thereof, and solvates thereof as an active ingredient.

[4-3]

An embodiment 4-3 of the present invention provides an agent for preventing or treating pain comprising at least one of the compounds represented by formula (I'-C), pharmaceutically acceptable salts thereof, and solvates thereof as an active ingredient.

[4-4]

An embodiment 4-4 of the present invention provides an agent for preventing or treating pain comprising at least one of the compounds represented by formula (I'-D), pharmaceutically acceptable salts thereof, and solvates thereof as an active ingredient.

[4-5]

An embodiment 4-5 of the present invention provides an agent for preventing or treating pain comprising at least one of the compounds represented by formula (I'-E), pharmaceutically acceptable salts thereof, and solvates thereof as an active ingredient.

[4-6]

An embodiment 4-6 of the present invention provides an agent for preventing or treating pain comprising at least one of the compounds represented by formula (I'-F), pharmaceutically acceptable salts thereof, and solvates thereof as an active ingredient.

[4-7]

An embodiment 4-7 of the present invention provides an agent for preventing or treating pain comprising at least one of the compounds described as the preferable compounds in embodiment [1-11], pharmaceutically acceptable salts thereof, and solvates thereof as an active ingredient.

[5] A fifth embodiment of the present invention provides an agent for preventing or treating neuropathic pain comprising at least one of the compounds represented by formula (I'), pharmaceutically acceptable salts thereof, and solvates thereof as an active ingredient.

More specifically, the following embodiments are preferred.

[5-1]

An embodiment 5-1 of the present invention provides an agent for preventing or treating neuropathic pain comprising at least one of the compounds represented by formula (I'-A), pharmaceutically acceptable salts thereof, and solvates thereof as an active ingredient.

[5-2]

An embodiment 5-2 of the present invention provides an agent for preventing or treating neuropathic pain comprising at least one of the compounds represented by formula (I'-B), pharmaceutically acceptable salts thereof, and solvates thereof as an active ingredient.

[5-3]

An embodiment 5-3 of the present invention provides an agent for preventing or treating neuropathic pain comprising at least one of the compounds represented by formula (I'-C), pharmaceutically acceptable salts thereof, and solvates thereof as an active ingredient.

[5-4]

An embodiment 5-4 of the present invention provides an agent for preventing or treating neuropathic pain comprising at least one of the compounds represented by formula (I'-D), pharmaceutically acceptable salts thereof, and solvates thereof as an active ingredient.

[5-5]

An embodiment 5-5 of the present invention provides an agent for preventing or treating neuropathic pain comprising at least one of the compounds represented by formula (I'-E), pharmaceutically acceptable salts thereof, and solvates thereof as an active ingredient.

[5-6]

An embodiment 5-6 of the present invention provides an agent for preventing or treating neuropathic pain comprising at least one of the compounds represented by formula (I'-F), pharmaceutically acceptable salts thereof, and solvates thereof as an active ingredient.

[5-7]

An embodiment 5-7 of the present invention provides an agent for preventing or treating neuropathic pain comprising at least one of the compounds described as the preferable compounds in embodiment [1-11], pharmaceutically acceptable salts thereof, and solvates thereof as an active ingredient.

[6] A sixth embodiment of the present invention provides an agent for preventing or treating inflammatory pain comprising at least one of the compounds represented by formula (I'), pharmaceutically acceptable salts thereof, and solvates thereof as an active ingredient.

More specifically, the following embodiments are preferred.

[6-1]

An embodiment 6-1 of the present invention provides an agent for preventing or treating inflammatory pain comprising at least one of the compounds represented by formula (I'-A), pharmaceutically acceptable salts thereof, and solvates thereof as an active ingredient.

[6-2]

An embodiment 6-2 of the present invention provides an agent for preventing or treating inflammatory pain comprising at least one of the compounds represented by formula (I'-B), pharmaceutically acceptable salts thereof, and solvates thereof as an active ingredient.

[6-3]

An embodiment 6-3 of the present invention provides an agent for preventing or treating inflammatory pain comprising at least one of the compounds represented by formula (I'-C), pharmaceutically acceptable salts thereof, and solvates thereof as an active ingredient.

[6-4]

An embodiment 6-4 of the present invention provides an agent for preventing or treating inflammatory pain comprising at least one of the compounds represented by formula (I'-D), pharmaceutically acceptable salts thereof, and solvates thereof as an active ingredient.

[6-5]

An embodiment 6-5 of the present invention provides an agent for preventing or treating inflammatory pain comprising at least one of the compounds represented by formula (I'-E), pharmaceutically acceptable salts thereof, and solvates thereof as an active ingredient.

[6-6]

An embodiment 6-6 of the present invention provides an agent for preventing or treating inflammatory pain comprising at least one of the compounds represented by formula (I'-F), pharmaceutically acceptable salts thereof, and solvates thereof as an active ingredient.

[6-7]

An embodiment 6-7 of the present invention provides an agent for preventing or treating inflammatory pain comprising at least one of the compounds described as the preferable compounds in embodiment [1-11], pharmaceutically acceptable salts thereof, and solvates thereof as an active ingredient.

In any one of the second embodiment to the sixth embodiment, and preferable embodiments thereof, in the compounds represented by formulae (I'), (I'-A), (I'-B), (I'-C), (I'-D), (I'-E), and (I'-F), preferable substituents and combinations thereof are described in the first embodiment.

In the embodiments described in [1] to [6] of the present invention, compounds having TRPV1 receptor antagonistic activity (determined by, for example, experimental example (2) described below: a measurement of Ca-influx using FDSS-6000) of 1 μM or less, preferably 100 nM or less, and more preferably 30 nM or less in terms of an A2 value are preferably used.

[7] A seventh embodiment of the present invention provides compounds represented by formula (VIII-b), salts thereof, and solvates thereof.

[Ch. 20]

(VIII-b)

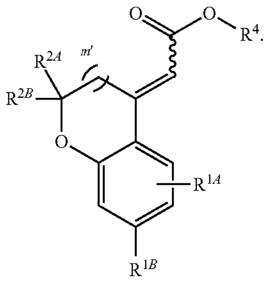

(wherein m' represents an integer of 1 or 2; $R^{1A}$ is a hydrogen atom or defined the same as the above; $R^1$B represents a halogen atom, or a $C_{1-4}$ alkyl or $C_{1-4}$ alkoxy group which may be substituted with 1 to 5 halogen atoms; $R^{2A}$ and $R^{2B}$ each independently represent a hydrogen atom or a $C_{1-4}$ alkyl group, $R^{2A}$ and $R^{2B}$ may form a ring together with the carbon atom to which $R^{2A}$ and $R^{2B}$ are bonded; and $R^4$ represents a hydrogen atom or a $C_{1-6}$ alkyl group.)

$R^{1A}$ is preferably a hydrogen atom, a halogen atom or a $C_{1-4}$ alkyl or $C_{1-4}$ alkoxy group which may be substituted with 1 to 5 halogen atoms. More specifically, examples of $R^{1A}$ include a fluorine atom, a chlorine atom, methyl, ethyl, propyl, isopropyl, butyl, isobutyl, sec-butyl, tert-butyl, trifluoromethyl, methoxy, ethoxy, propoxy, isopropoxy, butoxy, sec-butoxy, tert-butoxy, trifluoromethoxy, and tetrafluoroethoxy. More preferably, $R^{1A}$ is a fluorine atom, a chlorine atom, isobutyl, tert-butyl, trifluoromethyl, or tetrafluoroethoxy.

Specific examples of $R^{1B}$ include a fluorine atom, a chlorine atom, methyl, ethyl, propyl, isopropyl, butyl, isobutyl, sec-butyl, tert-butyl, trifluoromethyl, methoxy, ethoxy, propoxy, isopropoxy, butoxy, sec-butoxy, tert-butoxy, trifluoromethoxy, and tetrafluoroethoxy. More preferably, $R^{1B}$ is a fluorine atom, a chlorine atom, isobutyl, tert-butyl, trifluoromethyl, or, tetrafluoroethoxy. Particularly preferably, $R^{1B}$ is trifluoromethyl.

Each of $R^{2A}$ and $R^{2B}$ is independently a hydrogen atom or methyl, ethyl, propyl, isopropyl, butyl, isobutyl, sec-butyl, tert-butyl, or the like. Each of $R^{2A}$ and $R^{2B}$ is preferably methyl or ethyl. $R^{2A}$ and $R^{2B}$ may form a ring together with the carbon atom to which $R^{2A}$ and $R^{2B}$ are bonded. An example of such a ring is a cyclobutyl ring.

Examples of $R^4$ include a hydrogen atom or $C_{1-6}$ alkyl groups (in particular, $C_{1-4}$ alkyl groups such as methyl, ethyl, propyl, isopropyl, butyl, isobutyl, sec-butyl, and tert-butyl).

In all the above embodiments, when the term compound is used, the term also refers to pharmaceutically acceptable salts thereof. The compounds of the present invention may have an asymmetric carbon atom. Accordingly, the compounds of the present invention include mixtures of various stereoisomers, such as geometrical isomers, tautomers, and optical isomers, and isolated isomers. The isolation and the purification of such stereoisomers can be performed by those skilled in the art with a known technique such as optical resolution using preferential crystallization or column chromatography, or asymmetric synthesis.

The compounds represented by formulae (I), (I-A), (I-B), (I-C), (I-D), (I-E), (I-F), (I'), (I'-A), (I'-B), (I'-C), (I'-D), (I'-E), and (I'-F) of the present invention may form acid addition salts. Alternatively, these compounds may form salts with a base according to the type of substituent. These salts are not particularly limited as long as the salts are pharmaceutically acceptable salts. Specific examples of the salts include acid addition salts with a mineral acid such as hydrochloric acid, hydrobromic acid, hydroiodic acid, sulfuric acid, nitric acid, or phosphoric acid; an organic carboxylic acid such as an aliphatic monocarboxylic acid, e.g., formic acid, acetic acid, propionic acid, butyric acid, valeric acid, enanthic acid, capric acid, myristic acid, palmitic acid, stearic acid, lactic acid, sorbic acid, or mandelic acid, an aromatic monocarboxylic acid, e.g., benzoic acid or salicylic acid, an aliphatic dicarboxylic acid, e.g., oxalic acid, malonic acid, succinic acid, fumaric acid, maleic acid, malic acid, or tartaric acid, and an aliphatic tricarboxylic acid e.g., citric acid; an organic sulfonic acid such as an aliphatic sulfonic acid, e.g., methanesulfonic acid, ethanesulfonic acid, or 2-hydroxyethanesulfonic acid, or an aromatic sulfonic acid, e.g., benzenesulfonic acid or p-toluenesulfonic acid; or an acidic amino acid, e.g., aspartic acid or glutamic acid; salts with a metal such as an alkali metal, e.g., sodium or potassium, or an alkaline earth metal, e.g., magnesium or calcium; salts with an organic base such as methylamine, ethylamine, ethanolamine, pyridine, lysine, arginine, or ornithine; and ammonium salts.

These salts can be obtained by a known method, for example, by mixing a compound of the present invention with an equivalent amount and a solution comprising a desired acid, base, or the like, and then collecting the desired salt by filtering the salt or distilling off the solvent. The compounds of the present invention and salts thereof can form solvates with a solvent such as water, ethanol, or glycerol.

The salts of a compound of the present invention include mono-salts and di-salts. The compounds of the present invention can form an acid addition salt and a salt with a base at the same time according to the type of substituent of the side chain.

Furthermore, the present invention includes hydrates, pharmaceutically acceptable various solvates, and crystal polymorphism of the compounds represented by formulae (I), (I-A), (I-B), (I-C), (I-D), (I-E), (I-F), (I'), (I'-A), (I'-B), (I'-C), (I'-D), (I'-E), and (I'-F) of the present invention. The present invention is not limited to the compounds described in examples below and includes all compounds represented by formulae (I), (I-A), (I-B), (I-C), (I-D), (I-E), (I-F), (I'), (I'-A), (I'-B), (I'-C), (I'-D), (I'-E), and (I'-F) of the present invention and pharmaceutically acceptable salts thereof.

[Process of Producing Compound of the Present Invention]

Compounds represented by formulae (I), (I-A), (I-B), (I-C), (I-D), (I-E), (I-F), (I'), (I'-A), (I'-B), (I'-C), (I'-D), (I'-E), (I'-F), (I''), (I'''), (I''''), (II), (IV), (V), (V-a), (V-a-1), (V-a-2), (V-b), (VI), (VI-a), (VIII), and (IX), which are used in the present invention, and related compounds represented by formulae in (Reaction scheme) or Production processes A to J below can be obtained by production processes described below. Each of reaction steps will now be described.

Unless otherwise stated, the reaction conditions employed in the production processes are as described below. The reaction temperature is in the range of −78° C. to the solvent-reflux temperature, and the reaction time is the time sufficient for required progress of the reaction. Examples of solvents which are inactive to the reaction include aromatic hydrocarbon solvents such as toluene, xylene, and benzene; polar solvents such as alcohols, e.g., methanol and ethanol, N,N-dimethylformamide, dimethyl sulfoxide, acetonitrile, and water; basic solvents such as triethylamine and pyridine; organic acid solvents such as acetic acid; halogenated solvents such as chloroform, dichloromethane, and 1,2-dichloroethane; ether solvents such as diethyl ether, tetrahydrofuran, dioxane, and dimethoxyethane; and mixed solvents thereof, and the solvent used may be adequately selected according to the reaction conditions. Examples of bases include inorganic bases such as potassium carbonate, sodium carbonate, cesium carbonate, sodium hydroxide, potassium hydroxide, sodium hydride, and sodium hydrogencarbonate; and organic bases such as triethylamine, diethylamine, pyridine, N,N-dialkylanilines, lithium diisopropylamide, and lithium bis(trimethylsilyl)amide. Examples of acids include inorganic acids such as hydrochloric acid and sulfuric acid; and organic acids such as acetic acid, trifluoroacetic acid, methanesulfonic acid, and p-toluenesulfonic acid. The solvents, the bases, and the acids are not necessarily limited to those mentioned above.

The compounds represented by formula (I) and salts thereof, which are the compounds of the present invention can be readily produced from known compounds or commercially available compounds by, for example, known processes described in published documents, and produced by production processes described below.

The present invention is not limited to the production processes described below.

The production processes will now be described in detail.

In the description below, unless otherwise stated, the definitions of $R^1$, $R^2$, $R^3$, Q, $X_1$, $X_1'$, $X_2$, m, m', n, and p in formulae of the compounds represented by formula (I), (I''), (I'''), (I''''), (II), (IV), (V), (V-a), (V-a-1), (V-a-2), (V-b), (VI), (VI-a), (VIII), or (IX), and related compounds represented by formulae in (Reaction scheme) or Production processes A to J below are the same as those in formula (I). $R^4$ represents a hydrogen atom or a $C_{1-6}$ alkyl group (in particular, a $C_{1-4}$ alkyl group such as methyl, ethyl, propyl, isopropyl, butyl, isobutyl, sec-butyl, or tert-butyl); $R^5$ represents an alkyl group, $R^6$ represents a protective group such as an arylsulfonyl group, an acyl group, a carbamoyl group (for example, a tert-butoxy-carbonyl group or a benzyloxycarbonyl group), or a p-toluenesulfonyl group; Y and Z each represent an leaving groups such as halogen; and M represents a metal such as Li, Na, or K.

A compound represented by formula (I) can be obtained by a condensation reaction of a carboxylic acid represented by formula (VIII) and an amine ($Q-NH_2$) represented by formula (IX).

(Reaction scheme ).

[Ch. 21]

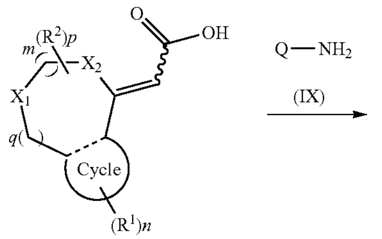

(VIII)

-continued

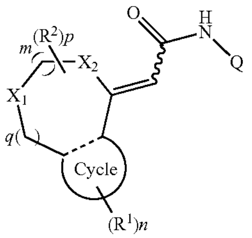

(I)

<The case where q is 0 and $X_2$ is $CH_2$, and $X_1$' is O, N—$R^3$, or S.>

[Ch. 22]

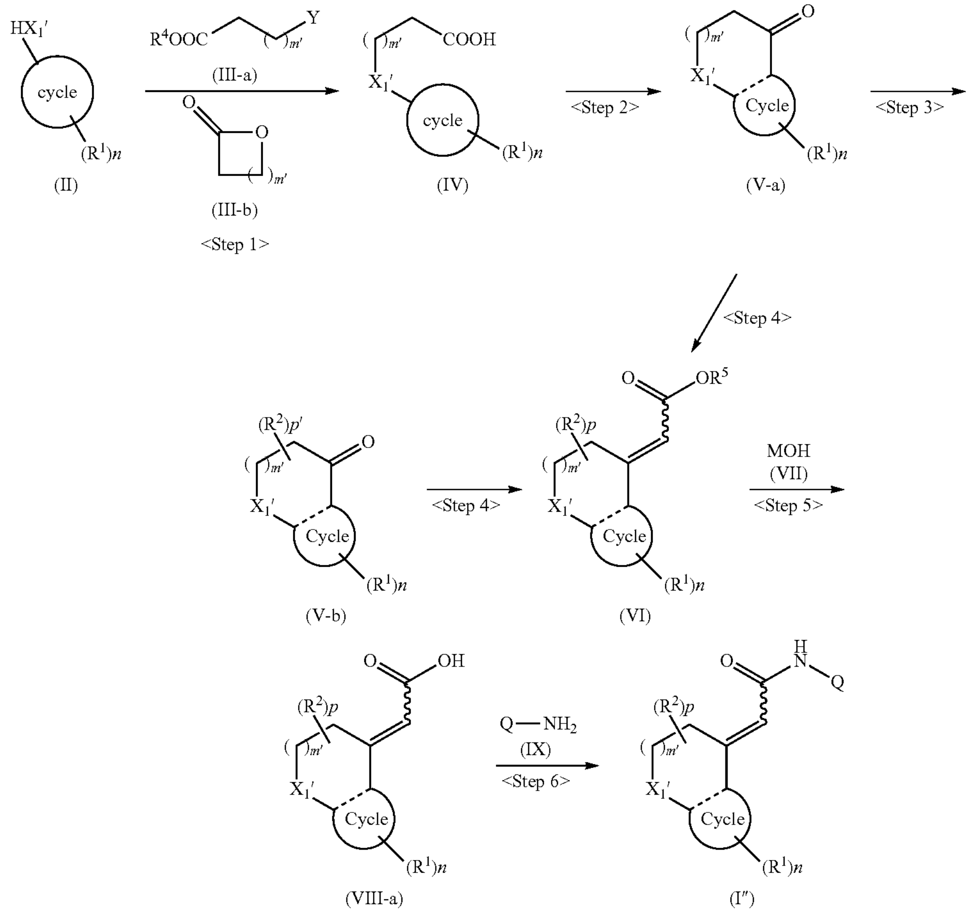

(Reaction Scheme) <Step 1>

When $R^4$ is H (a hydrogen atom), a compound represented by formula (IV) can be produced by allowing a compound represented by formula (II) to react with a compound represented by formula (III-a) by a process similar to that described in published documents, for example, Journal of Medicinal Chemistry, 31(1), pp. 230-243, 1988, in the presence of a base such as sodium hydride, lithium hydroxide, sodium hydroxide, potassium hydroxide, lithium carbonate, sodium carbonate, or potassium carbonate using a solvent which is inactive to the reaction, such as methanol, ethanol, acetone, N,N-dimethylformamide, dioxane, tetrahydrofuran, or water, or a mixed solvent thereof at a temperature in the range of room temperature to the solvent-reflux temperature.

Alternatively, the compound represented by formula (IV) can be produced by conducting a reaction using a compound represented by formula (III-b) by a process similar to that described in published documents, for example, PCT Publication No. 01/036381 pamphlet, pp. 360-361, in the presence of a base such as sodium hydride, lithium hydroxide, sodium hydroxide, potassium hydroxide, lithium carbonate, sodium carbonate, or potassium carbonate with a solvent which is inactive to the reaction, such as methanol, ethanol, acetone, N,N-dimethylformamide, dioxane, tetrahydrofuran, or water, or a mixed solvent thereof at a temperature in the range of room temperature to the solvent-reflux temperature.

When $R^4$ is an alkyl group (e.g., a methyl group or an ethyl group), the compound represented by formula (IV) can be produced from an ester produced by the same reaction as that conducted in the case where $R^4$ is H by a process similar to that described in published documents, for example, Jikken Kagaku Koza (Experimental Chemistry Series), 4th edition, 22, Organic synthesis IV, Acids, amino acids, and peptides, pp. 1-43, 1992, Maruzen Co., Ltd., in the presence of a base such as lithium hydroxide, sodium hydroxide, potassium hydroxide, lithium carbonate, sodium carbonate, or potassium carbonate using a solvent which is inactive to the reaction, such as water, methanol, ethanol, 2-propanol, N,N-dimethylformamide, dioxane, or tetrahydrofuran, or a mixed solvent thereof at a temperature in the range of 0° C. to the solvent-reflux temperature.

(Reaction Scheme) <Step 2>

A compound represented by formula (V-a) can be produced by conducting a reaction using the compound represented by formula (IV) by a process similar to that described in published documents, for example, Journal of Medicinal Chemistry, 31(1), pp. 230-243, 1988, in a cyclization-dehydrating agent such as polyphosphoric acid (PPA), polyphosphoric acid ethyl ester (PPE), diphosphorus pentaoxide ($P_2C_5$), or Eaton's reagent (a mixture of methanesulfonic acid and phosphorus pentoxide) or in the presence of such a cyclization-dehydrating agent, and in a solvent which would not take part in the reaction, such as a halogenated solvent, e.g., dichloromethane or chloroform, an ether solvent, e.g., diethyl ether or tetrahydrofuran, or an aromatic hydrocarbon solvent, e.g., toluene or benzene at a temperature in the range of 0° C. to the solvent-reflux temperature. Alternatively, the compound represented by formula (V-a) can be similarly produced by conducting the reaction in the presence of a Lewis acid such as aluminum trichloride or tin tetrachloride in a solvent which would not take part in the reaction, such as a halogenated solvent, e.g., dichloromethane or chloroform at a temperature in the range of 0° C. to the solvent-reflux temperature.

(Reaction Scheme) <Step 3>

A compound represented by formula (V-b) (wherein p' represents 1 or 2) can be produced as follows. When $R^2$ is a halogen atom, for example, a fluorine atom (F), the compound represented by formula (V-a) is converted to a trimethylsilyl enol ether by a process similar to that described in published documents, for example, Tetrahedron Letters, 25(51), pp. 5953-5956, 1984. The resulting compound is then treated by a process similar to that described in published documents, for example, Organic Letters, 1(10), pp. 1591-1594, 1998, in the presence of a fluorinating reagent such as xenon difluoride ($XeF_2$), fluorine ($F_2$), 1-fluoro-4-methyl-1,4-diazabicyclo[2,2,2]octane trifluoromethanesulfonate, N-fluoro-β-benzenesulfonimide, N-fluorobenzenesulfonimide, hypofluorous acid trifluoromethyl ether, or 1-fluoropyridine trifluoromethanesulfonate in a solvent which would not take part in the reaction, such as a halogenated solvent, e.g., dichloromethane or chloroform, an ether solvent, e.g., diethyl ether or tetrahydrofuran, or an aromatic hydrocarbon solvent, e.g., toluene or benzene at a temperature in the range of −78° C. to the solvent-reflux temperature, thereby producing the compound represented by formula (V-b). When $R^2$ is an amino group, the above-mentioned trimethylsilyl enol ether is allowed to react with sodium azide by a process similar to that described in published documents, for example, Tetrahedron, 51(41), pp. 11075-11086, 1995, in the presence of diammonium cerium hexanitrate in a solvent which would not take part in the reaction, such as a halogenated solvent, e.g., dichloromethane or chloroform, an ether solvent, e.g., diethyl ether or tetrahydrofuran, a polar solvent, e.g., acetonitrile, or an aromatic hydrocarbon solvent, e.g., toluene or benzene to produce an azide compound. Subsequently, hydrogen gas is added to the azide compound by a process similar to that described in published documents, for example, Jikken Kagaku Koza (Experimental Chemistry Series), 4th edition, 26, Organic synthesis VIII, Asymmetric synthesis, reduction, sugar, and labeled compound, pp. 251-266, 1992, Maruzen Co., Ltd., in the presence of a catalyst such as palladium-carbon (Pd—C), Raney-Ni, or platinum oxide ($PtO_2$) in a solvent which would not take part in the reaction, such as an alcohol solvent, e.g., methanol, ethanol, or 2-propanol, a halogenated solvent, e.g., dichloromethane or chloroform, an ether solvent, e.g., diethyl ether or tetrahydrofuran, a polar solvent, e.g., ethyl acetate or acetonitrile, an aromatic hydrocarbon solvent, e.g., toluene or benzene, or an acid solvent, e.g., acetic acid at a temperature in the range of room temperature to the solvent-reflux temperature, thereby producing the compound represented by formula (V-b). When $R^2$ is an oxo group, the above-mentioned trimethylsilyl enol ether is allowed to react with 3-chloroperbenzoic acid, aqueous hydrogen peroxide, or the like by a process similar to that described in published documents, for example, Jikken Kagaku Koza (Experimental Chemistry Series), 4th edition, 26, Organic synthesis V, Oxidative reaction, pp. 225-298, 1992, Maruzen Co., Ltd., in a solvent which would not take part in the reaction, such as water, an alcohol solvent, e.g., methanol, ethanol, or 2-propanol, a halogenated solvent, e.g., dichloromethane or chloroform, or an aromatic hydrocarbon solvent, e.g., toluene or benzene to produce an epoxy compound. Subsequently, the trimethylsilyl group is removed by a process described in published textbooks, for example, Greene et al., Protective Groups in Organic Synthesis, (the United States), 3rd edition, 1999, thereby producing the compound represented by formula (V-b).

(Reaction Scheme) <Step 4>

A compound represented by formula (VI) can be produced by conducting a reaction using the compound represented by formula (V-a) or (V-b) by a process similar to that described in published documents, for example, Jikken Kagaku Koza (Experimental Chemistry Series), 4th edition, 19, Organic synthesis I, Hydrocarbons and halogenated compounds, pp. 53-298, 1992, Maruzen Co., Ltd., in the presence of a Wittig reagent or a Horner-Emmons reagent, such as (ethoxycarbonylmethyl)triphenylphosphonium chloride, (ethoxycarbonylmethyl)triphenylphosphonium bromide, ethyl triphenylphosphoranylidene acetate, bis-2,2,2-trifluoroethoxy phosphinyl acetate, ethyl di-ortho-tolylphosphonoacetate, ethyl dimethylphosphonoacetate, ethyl diethylphosphonoacetate, or ethyl 1-trimethylsilyl acetate, and a base such as sodium hydride, butyllithium, piperazine, morpholine, triethylamine, lithium diisopropylamide, lithium bis(trimethylsilyl)amide, sodium bis(trimethylsilyl)amide, potassium bis (trimethylsilyl)amide, or phosphazene base-P4-tert-butyl, using a solvent which is inactive to the reaction, such as methanol, ethanol, N,N-dimethylformamide, dioxane, tetrahydrofuran, or an aromatic hydrocarbon solvent, e.g., benzene, toluene, or xylene, or a mixed solvent thereof at a temperature in the range of −78° C. to the solvent-reflux temperature.

(Reaction Scheme) <Step 5>

A compound represented by formula (VIII-a) can be produced by conducting a reaction by the same process as that used in <Step 1> of (Reaction scheme) (in the case where $R^4$ is an alkyl group (e.g., a methyl group or an ethyl group)) using the compound represented by formula (VI) and a compound represented by formula (VII).

(Reaction Scheme) <Step 6>

A compound represented by formula (I") can be produced by conducting a reaction using the compound represented by formula (VIII-a) and a compound represented by formula (IX) (for example, a known amine) as follows. When the compound represented by formula (VIII-a) is a carboxylic acid, the compound represented by formula (I") can be produced by allowing the compound represented by formula (VIII-a) to react with the compound represented by formula (IX) by a process similar to that described in published documents, for example, Jikken Kagaku Koza (Experimental Chemistry Series), 4th edition, 22, Organic synthesis IV, Acids, amino acids, and peptides, pp. 191-309, 1992, Maruzen Co., Ltd., in the presence of a condensing agent such as 1,3-dicyclohexylcarbodiimide (DCC), 1-ethyl-3-(3'-dimethylaminopropyl)carbodiimide hydrochloride (WSC.HCl), benzotriazol-1-yloxy tris(dimethylamino)phosphonium hexafluorophosphate (BOP reagent), bis(2-oxo-3-oxazolidinyl)phosphinic chloride (BOP-Cl), 2-chloro-1,3-dimethylimidazolinium hexafluorophosphate (CIP), or 4-(4,6-dimethoxy-1,3,5-triazin-2-yl)-4-methylmorpholinium chloride, in a solvent which would not take part in the reaction, such as a halogenated solvent, e.g., dichloromethane or chloroform, an ether solvent, e.g., diethyl ether or tetrahydrofuran, an aromatic hydrocarbon solvent, e.g., toluene or benzene, a polar solvent, e.g., N,N-dimethylformamide, or an alcohol solvent, e.g., methanol, ethanol, or 2-propanol, in the presence or absence of a base such as triethylamine or pyridine at a temperature in the range of 0° C. to the solvent-reflux temperature. When the compound represented by formula (VIII-a) is converted to an acid halide, the compound represented by formula (I") can be similarly produced by conducting a reaction by a process similar to that described in, for example, Jikken Kagaku Koza (Experimental Chemistry Series), 4th edition, 22, Organic synthesis IV, Acids, amino acids, and peptides, pp. 144-146, 1992, Maruzen Co., Ltd., in the presence of a base such as triethylamine or pyridine in a solvent which would not take part in the reaction, such as a halogenated solvent, e.g., dichloromethane or chloroform, an ether solvent, e.g., diethyl ether or tetrahydrofuran, an aromatic hydrocarbon solvent, e.g., toluene or benzene, or a polar solvent, e.g., N,N-dimethylformamide at a temperature in the range of 0° C. to the solvent-reflux temperature.

The compound represented by formula (V-a) or a compound represented by formula (VI-a) (a compound in which p is 0 in formula (VI)), which is an intermediate in the above reaction scheme, can also be produced by Production processes A to D described below. In the formulae, $X_1'$ is O, N—$R^3$, or S.

(Production Process A)

[Ch. 23]

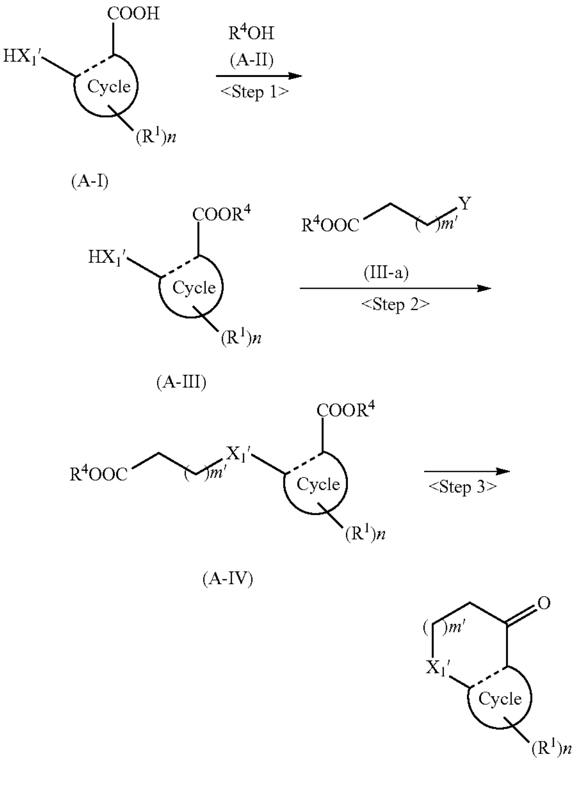

(A-I)

(A-III)

(A-IV)

(V-a)

<Step 1>

A compound represented by formula (A-III) can be produced by allowing a compound represented by formula (A-I) to react with a compound represented by formula (A-II) by a process similar to that described in published documents, for example, Jikken Kagaku Koza (Experimental Chemistry Series), 4th edition, 22, Organic synthesis IV, Acids, amino acids, and peptides, pp. 1-82, 1992, Maruzen Co., Ltd., in the presence of an acidic reagent such as hydrochloric acid, sulfuric acid, thionyl chloride, or acetyl chloride, using a solvent such as methanol, ethanol, or 2-propanol at a temperature in the range of 0° C. to the solvent-reflux temperature.

<Step 2>

A compound represented by formula (A-IV) can be produced by the same process as that used in <Step 1> of (Reaction scheme) using the compound represented by formula (A-III) and a compound represented by formula (III-a).

<Step 3>

The compound represented by formula (V-a) can be produced by conducting a reaction using the compound represented by formula (A-IV) by a process similar to that described in published documents, for example, Organic Reactions, 1, p. 274, 1942, in the presence of a basic reagent such as sodium methoxide, sodium ethoxide, potassium tert-butoxide, sodium hydride, sodium hydroxide, or potassium hydroxide with a solvent which would not take part in the reaction, such as methanol, ethanol, dimethyl sulfoxide, benzene, toluene, or xylene at a temperature in the range of 0° C. to the solvent-reflux temperature, followed by a reaction in a mixed solvent containing a solvent which would not take part in the reaction, such as dimethyl sulfoxide, benzene, toluene, or xylene, and water or an acidic aqueous solution such as an aqueous hydrochloric acid solution or an aqueous acetic acid solution at a temperature in the range of room temperature to the solvent-reflux temperature.

(Production process B)

[Ch. 24]

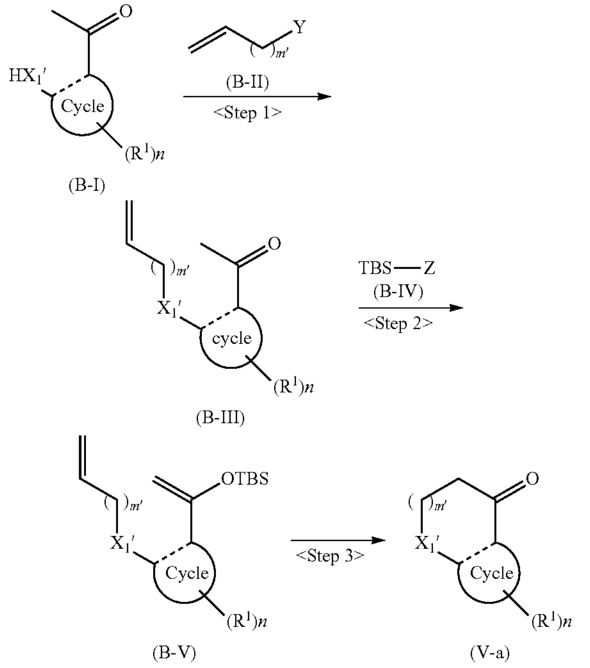

<Step 1>

A compound represented by formula (B-III) can be produced by the same process as that used in <Step 1> of (Reaction scheme) using a compound represented by formula (B-I) and a compound represented by formula (B-II).

<Step 2>

A compound represented by formula (B-V) can be produced by allowing the compound represented by formula (B-III) to react with a compound represented by formula (B-IV) by a process similar to that described in published documents, for example, Tetrahedron Letters, 25(51), pp. 5953-5956, 1984, in the presence of a silylation agent such as tert-butyldimethylsilyl chloride (TBSCl) or tert-butyldimethylsilyl trifluoromethanesulfonate (TBSOTf) and a base such as sodium hydride, piperazine, morpholine, triethylamine, lithium diisopropylamide, lithium bis(trimethylsilyl) amide, sodium bis(trimethylsilyl)amide, or potassium bis(trimethylsilyl)amide using a solvent which is inactive to the reaction, such as a halogen-containing solvent, e.g., methylene chloride or chloroform, an ether solvent, e.g., dioxane or tetrahydrofuran, or an aromatic hydrocarbon solvent, e.g., benzene, toluene, or xylene, or a mixed solvent thereof at a temperature in the range of −78° C. to the solvent-reflux temperature.

<Step 3>

The compound represented by formula (V-a) can be produced by conducting a reaction using the compound represented by formula (B-V) by a process similar to that described in published documents, for example, Tetrahedron, 60(13), pp. 3017-3035, 2004, in the presence of a ruthenium catalyst such as benzylidene bistricyclohexylphosphineruthenium dichloride, tricyclohexylphosphine-1,3-bis-2,4,6-trimethylphenyl-4,5-dihydroimidazol-2-ylidene benzylideneruthenium dichloride, or ruthenium-1,3-bis-2,4,6-trimethylphenyl-2-imidazolidinylylidenedichloro-2-1-methylethoxy phenyl methylene with a solvent which is inactive to the reaction, such as a halogenated solvent, e.g., dichloromethane or chloroform, an ether solvent, e.g., dioxane or tetrahydrofuran, or an aromatic hydrocarbon solvent, e.g., benzene, toluene, or xylene, or a mixed solvent thereof at a temperature in the range of room temperature to the solvent-reflux temperature.

(Production process C)

[Ch. 25]

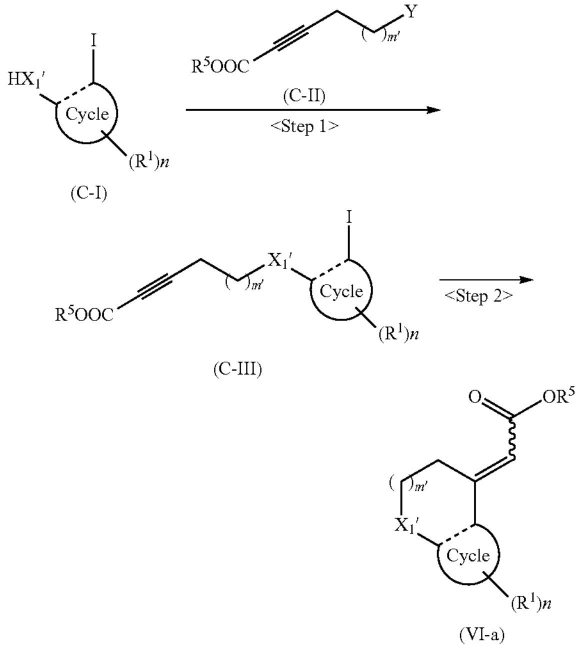

<Step 1>

A compound represented by formula (C-III) can be produced by the same process as that used in <Step 1> of (Reaction scheme) using a compound represented by formula (C-I) and a compound represented by formula (C-II).

<Step 2>

A compound represented by formula (VI-a) (a compound in which p is 0 in formula (VI)) can be produced by conducting a reaction using the compound represented by formula (C-III) by a process similar to that described in published documents, for example, Tetrahedron Letters, 28(44), pp. 5291-5294, 1987, in the presence of a palladium catalyst such as palladium diacetate, tetrakis triphenylphosphine palladium, or tris dibenzylideneacetone dipalladium with a solvent which is inactive to the reaction, such as acetonitrile, dioxane, tetrahydrofuran, benzene, toluene, dimethyl sulfoxide, or N,N-dimethylformamide, or a mixed solvent thereof at a temperature in the range of room temperature to the solvent-reflux temperature.

(Production Process D)

[Ch. 26]

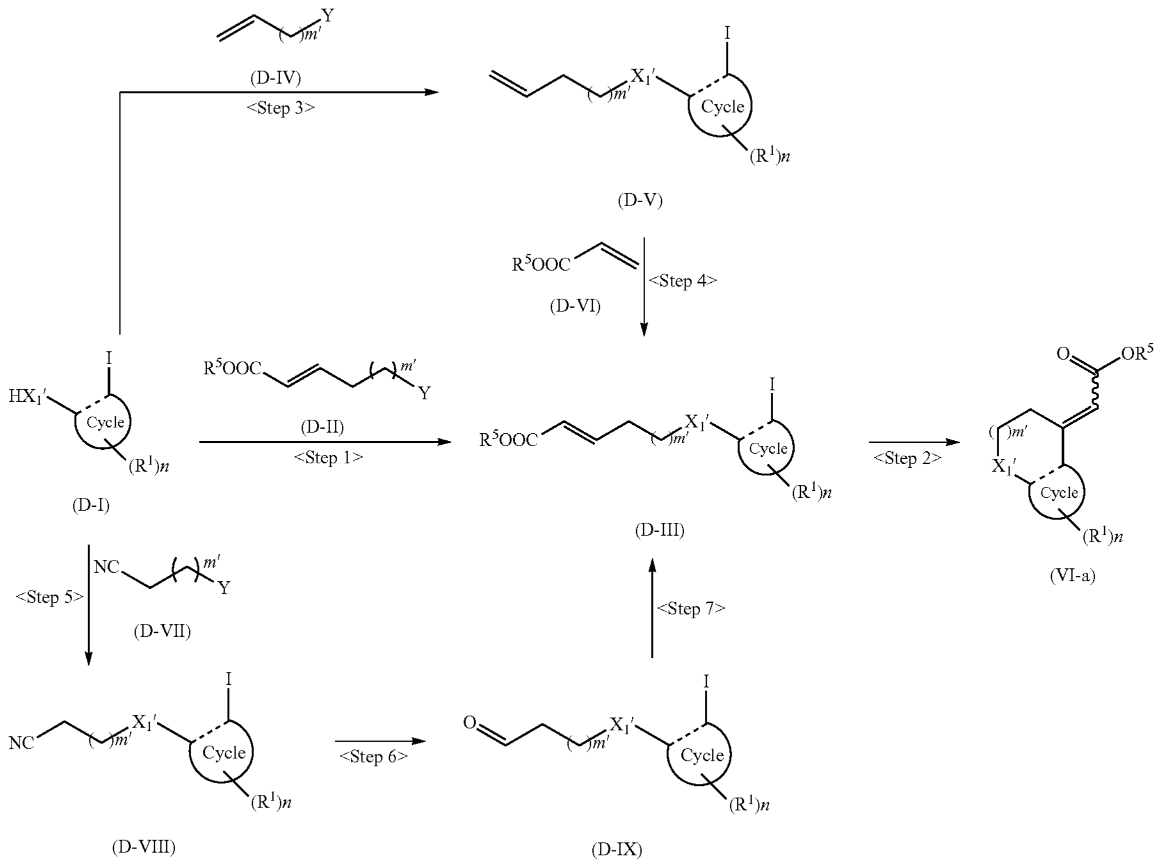

(D-IV) (D-V) (D-VI) (D-I) (D-II) (D-III) (VI-a) (D-VII) (D-VIII) (D-IX)

<Step 1>

A compound represented by formula (D-III) can be produced by the same process as that used in <Step 1> of (Reaction scheme) using a compound represented by formula (D-I) and a compound represented by formula (D-II).

<Step 2>

The compound represented by formula (VI-a) (the compound in which p is 0 in formula (VI)) can be produced by conducting a reaction using the compound represented by formula (D-III) by a process similar to that described in published documents, for example, Synlett, No. 6, pp. 848-850, 2001, in the presence of a palladium catalyst such as palladium diacetate, tetrakis triphenylphosphine palladium, or tris dibenzylideneacetone dipalladium, and a base such as silver carbonate with a solvent which is inactive to the reaction, such as acetonitrile, dioxane, tetrahydrofuran, benzene, toluene, dimethyl sulfoxide, or N,N-dimethylformamide, or a mixed solvent thereof at a temperature in the range of room temperature to the solvent-reflux temperature.

Alternatively, the compound represented by formula (D-III), which is an intermediate, can be produced by the following process.

<Step 3>

A compound represented by formula (D-V) can be produced by the same process as that used in <Step 1> of (Reaction scheme) using the compound represented by formula (D-I) and a compound represented by formula (D-IV).

<Step 4>

The compound represented by formula (D-III) can be produced by the same process as that used in <Step 3> of (Production process B) using the compound represented by formula (D-V) and a compound represented by formula (D-VI).

<Step 5>

A compound represented by formula (D-VIII) can be produced by the same process as that used in <Step 1> of (Reaction scheme) using the compound represented by formula (D-I) and a compound represented by formula (D-VII).

<Step 6>

A compound represented by formula (D-IX) can be produced by conducting a reaction using the compound represented by formula (D-VIII) by a process similar to that described in published documents, for example, Jikken Kagaku Koza (Experimental Chemistry Series), 4th edition, 26, Organic synthesis VIII, Asymmetric synthesis, reduction, sugar, and labeled compound, pp. 159-266, 1992, Maruzen Co., Ltd., in the presence of a reducing agent such as diisopropylaluminum hydride (DIBAH), lithium triethoxyaluminum hydride, sodium bis-2-methoxyethoxy aluminum hydride, or Raney-Ni-formic acid, with a solvent which is inactive to the reaction, such as diethyl ether, 1,2-dimethoxyethane, dioxane, tetrahydrofuran, benzene, or toluene, or a mixed solvent thereof at a temperature in the range of −78° C. to the solvent-reflux temperature.

<Step 7>

The compound represented by formula (D-III) can be produced by the same process as that used in <Step 4> of (Reaction scheme) using the compound represented by formula (D-IX).

A compound represented by formula (V-a-1), in which m' is 1 and $X_1$' is NH in the compound represented by formula (V-a), or a compound represented by formula (V-a-2), in which m' is 1 and $X_1$' is N—$R^{3'}$ (wherein $R^{3'}$ is a substituted or unsubstituted hydrocarbon group, a substituted or unsubstituted heterocyclic group, or a substituted or unsubstituted acyl group which is defined in $R^3$) in the compound represented by formula (V-a) can also be produced by Production process E below.

(Production Process E)

[Ch. 27]

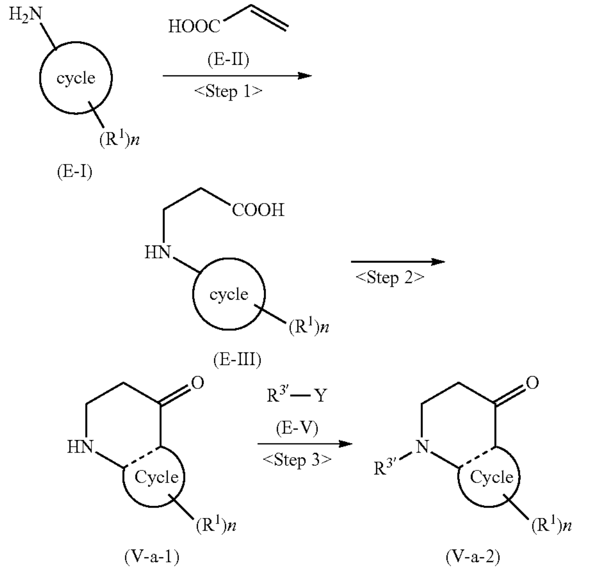

<Step 1>

A compound represented by formula (E-III) can be produced by allowing a compound represented by formula (E-I) to react with a compound represented by formula (E-II) by a process similar to that described in published documents, for example, Jikken Kagaku Koza (Experimental Chemistry Series), 4th edition, 20, Organic synthesis II, Alcohols and amines, pp. 280-372, 1992, Maruzen Co., Ltd., using a solvent which is inactive to the reaction, such as acetonitrile, dioxane, tetrahydrofuran, benzene, toluene, dimethyl sulfoxide, N,N-dimethylformamide, or water, or a mixed solvent thereof at a temperature in the range of room temperature to the solvent-reflux temperature.

<Step 2>

The compound represented by formula (V-a-1) (the compound in which $X_1$ is N—$R^3$, $R^3$ is H, and m' is 1 in the compound represented by formula (V-a)) can be produced by the same process as that used in <Step 2> of (Reaction scheme) using the compound represented by formula (E-III).

<Step 3>

The compound represented by formula (V-a-2) (compound in which X is N—$R^{3'}$, $R^{3'}$ is a substituted or unsubstituted hydrocarbon group, a substituted or unsubstituted heterocyclic group, or a substituted or unsubstituted acyl group which is defined in $R^3$, and m' is 1 in the compound represented by formula (V-a)) can be produced using the compound represented by formula (V-a-1) and a compound represented by formula (E-V) (for example, a desired alkyl halide, acyl halide, aryl halide, or heteroaryl halide, wherein $R^{3'}$ is a substituted or unsubstituted hydrocarbon group, a substituted or unsubstituted heterocyclic group, or a substituted or unsubstituted acyl group which is defined in $R^3$). For example, when $R^{3'}$ is alkyl, the compound represented by formula (V-a-2) can be produced by conducting a reaction by a process similar to that described in published documents, for example, Jikken Kagaku Koza (Experimental Chemistry Series), 4th edition, 20, Organic synthesis II, Alcohols and amines, pp. 280-372, 1992, Maruzen Co., Ltd., using a solvent which is inactive to the reaction, such as acetonitrile, dioxane, tetrahydrofuran, benzene, toluene, dimethyl sulfoxide, or N,N-dimethylformamide, or a mixed solvent thereof at a temperature in the range of room temperature to the solvent-reflux temperature. When $R^{3'}$ is acyl, the compound represented by formula (V-a-2) can be produced by the same process as that used in <Step 6> of (Reaction scheme). When $R^{3'}$ is aryl or a heterocycle, the compound represented by formula (V-a-2) can be produced by conducting a reaction by a process similar to that described in published documents, for example, Jikken Kagaku Koza (Experimental Chemistry Series), 4th edition, 20, Organic synthesis II, Alcohols and amines, pp. 187-243, 1992, Maruzen Co., Ltd., using a solvent which is inactive to the reaction, such as acetonitrile, dioxane, tetrahydrofuran, benzene, toluene, dimethyl sulfoxide, or N,N-dimethylformamide, or a mixed solvent thereof at a temperature in the range of room temperature to the solvent-reflux temperature.

In the above reaction scheme, the compound represented by formula (VIII-a) can also be produced from a compound represented by formula (V) (including the compounds represented by formulae (V-a) and (V-b) in the reaction scheme) by Production process F below.

(Production Process F)

[Ch. 28]

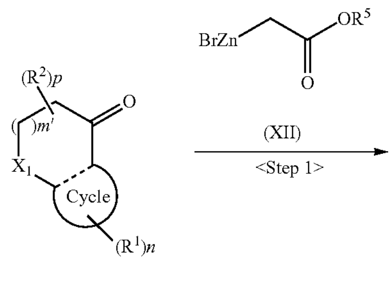

(V)

-continued

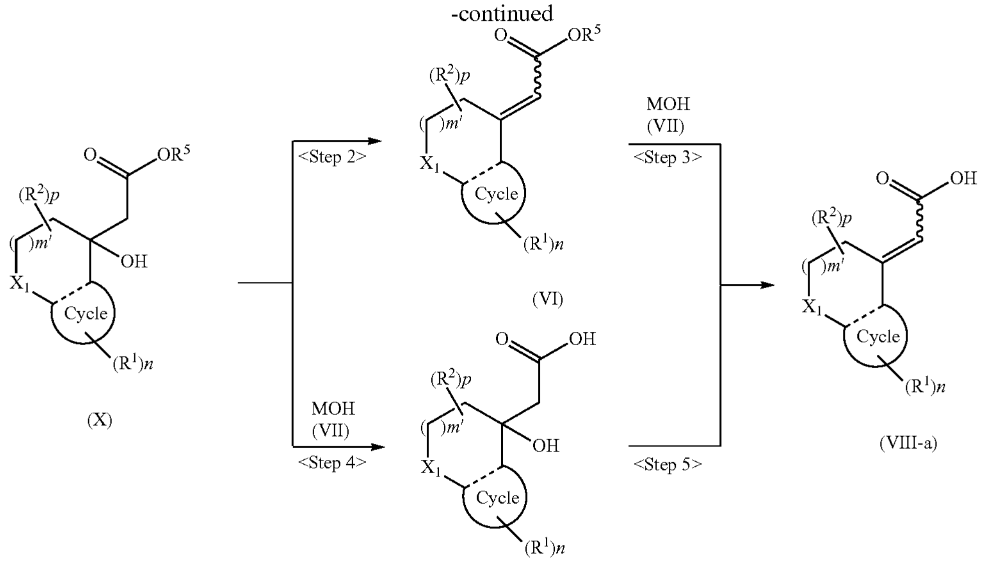

(X) (VI) (XI) (VIII-a)

<Step 1>

A compound represented by formula (X) can be produced by a process similar to that described in published documents, for example, Jikken Kagaku Koza (Experimental Chemistry Series), 4th edition, 20, Organic synthesis II, Alcohols, pp. 82-94, 1992, Maruzen Co., Ltd., by allowing the compound represented by formula (V) to react with a Reformatsky reagent (a compound represented by formula (XII)), which is prepared from an α-haloacetate such as ethyl bromoacetate or tert-butyl bromoacetate in the presence of zinc, or by allowing the compound represented by formula (V) to react with a silyl acetate such as ethyl (trimethylsilyl)acetate in the presence of a base such as phosphazene base-P4-tert-butyl using a solvent which is inactive to the reaction, such as an ether solvent, e.g., dioxane or tetrahydrofuran, or an aromatic hydrocarbon solvent, e.g., benzene, toluene, or xylene, or a mixed solvent thereof at a temperature in the range of −78° C. to the solvent-reflux temperature.

<Step 2>

The compound represented by formula (VI) can be produced by performing a reaction using the compound represented by formula (X) by a process similar to that described in published documents, for example, Jikken Kagaku Koza (Experimental Chemistry Series), 4th edition, 19, Organic synthesis I, Hydrocarbons, pp. 194-236, 1992, Maruzen Co., Ltd., in the presence of a dehydrating agent such as potassium hydrogensulfate; an inorganic acid, e.g., concentrated sulfuric acid; an organic acid, e.g., p-toluenesulfonic acid, methanesulfonic acid, or trifluoroacetic acid; thionyl chloride; or phosphorus oxychloride using a solvent which is inactive to the reaction, such as an ether solvent, e.g., dioxane or tetrahydrofuran, or an aromatic hydrocarbon solvent, e.g., benzene, toluene, or xylene, or a mixed solvent thereof at a temperature in the range of −78° C. to the solvent-reflux temperature.

<Step 3>

The compound represented by formula (VIII) can be produced by conducting a reaction by the same process as that used in <Step 5> of (Reaction scheme) (in the case where $R^5$ is an alkyl group (e.g., a methyl group or an ethyl group)) using the compound represented by formula (VI) and the compound represented by formula (VII). When $R^5$ is a tert-butyl group, the compound represented by formula (VIII-a) can be produced by conducting a reaction using an acid such as hydrochloric acid or trifluoroacetic acid.

<Step 4>

A compound represented by formula (XI) can be produced by conducting a reaction by the same process as that used in <Step 5> of (Reaction scheme) using the compound represented by formula (X) and the compound represented by formula (VII).

<Step 5>

The compound represented by formula (VIII-a) can be produced by conducting a reaction by the same process as that used in <Step 2> of (Production process F) using the compound represented by formula (XI).

A compound represented by formula (I)-e-1, in which $X_1$' is N—$R^3$, $R^3$ is H, and m' is 1 in the compound represented by formula (I") in the reaction scheme, and a compound represented by formula (I)-e-2, in which $X_1$' is N—$R^{3'}$, $R^{3'}$ is a substituted or unsubstituted hydrocarbon group, a substituted or unsubstituted heterocyclic group, or a substituted or unsubstituted acyl group which is defined in $R^3$, and m' is 1 in the compound represented by formula (I"), can also be produced by Production process G below.

(Production Process G)

[Ch. 29]

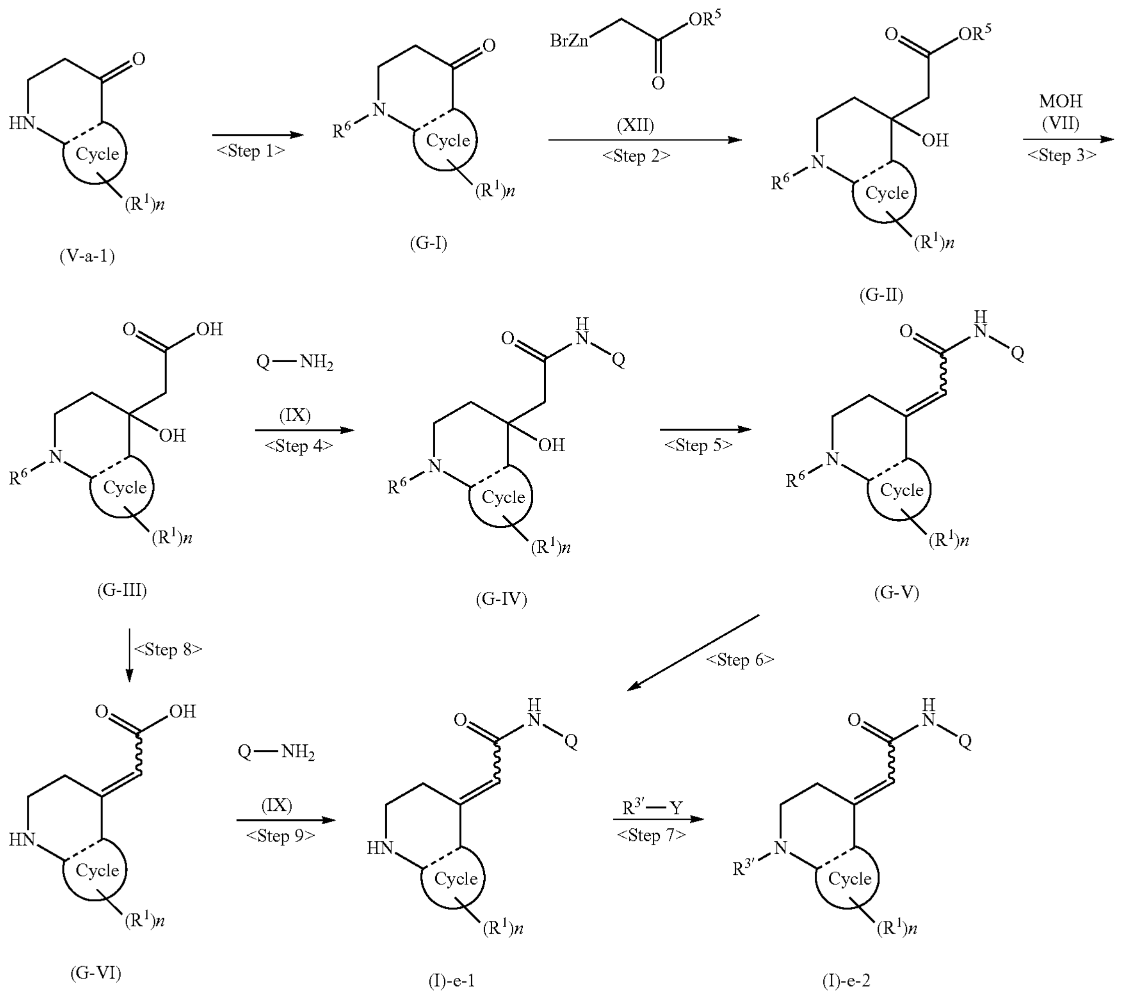

(V-a-1) (G-I) (G-II) (G-III) (G-IV) (G-V) (G-VI) (I)-e-1 (I)-e-2

<Step 1>

A compound represented by formula (G-I) can be produced by introducing a protective group such as a tert-butoxycarbonyl group, a benzyloxycarbonyl group, or a p-toluenesulfonyl group into the compound represented by formula (V-a-1) by a process described in published textbooks, for example, Greene et al., Protective Groups in Organic Synthesis, (the United States), 3rd edition, 1999.

<Step 2>

A compound represented by formula (G-II) can be produced in accordance with the process described in <Step 1> of (Production process F) using the compound represented by formula (G-I).

<Step 3>

A compound represented by formula (G-III) can be produced in accordance with the process described in <Step 3> of (Production process F) using the compound represented by formula (G-II) and the compound represented by formula (VII).

<Step 4>

A compound represented by formula (G-IV) can be produced in accordance with the process described in <Step 6> of (Reaction scheme) using the compound represented by formula (G-III) and the compound represented by formula (IX).

<Step 5>

A compound represented by formula (G-V) can be produced by the same process as that used in <Step 5> of (Production process F) using the compound represented by formula (G-IV).

<Step 6>

The compound represented by formula (I)-e-1 can be produced by removing the introduced protective group from the compound represented by formula (G-V) by a process described in published textbooks, for example, Greene et al., Protective Groups in Organic Synthesis, (the United States), 3rd edition, 1999.

<Step 7>

The compound represented by formula (I)-e-2 can be produced by the same process as that used in <Step 3> of (Production process E) using the compound represented by formula (I)-e-1.

<Step 8>

A compound represented by formula (G-VI) can be produced by conducting a reaction as in <Step 5> of (Production process G) using the compound represented by formula (G-III).

<Step 9>

The compound represented by formula (I)-e-1 can be produced by conducting a reaction as in <Step 4> of (Production process G) using the compound represented by formula (G-VI).

<In formula (I), the case where $X_1$ is O, N—$R^3$, or S (which is represented by $X_1$'), $X_2$ is $CH_2$, and p is 0.>

(Production Process H)

[Ch. 30]

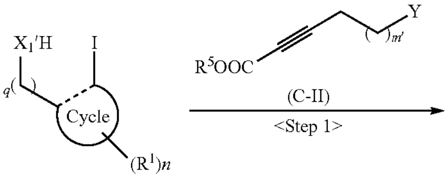

(H-I)

-continued

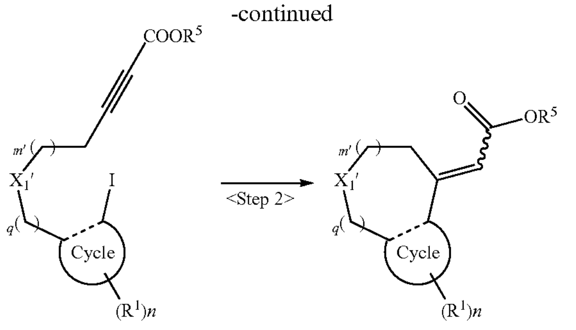

(H-II) (H-III)

<Step 1>

A compound represented by formula (H-II) can be produced by the same process as that used in <Step 1> of (Reaction scheme) using a compound represented by formula (H-I) and the compound represented by formula (C-II).

<Step 2>

A compound represented by formula (H-III) can be produced by the same process as that used in <Step 2> of (Production process C) using the compound represented by formula (H-II).

Alternatively, the compound represented by formula (H-III) can be produced by the following process.

[Ch. 31]

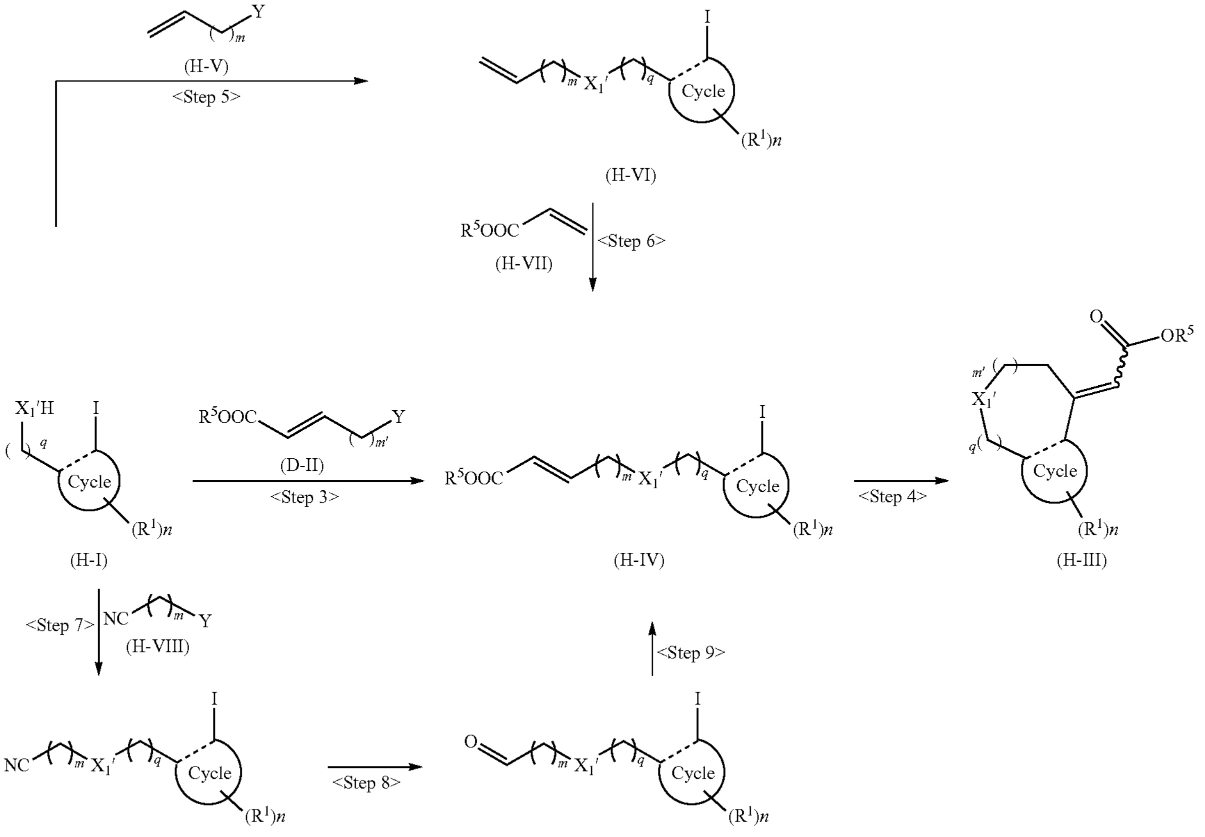

(H-IX) (H-X)

<Step 3>

A compound represented by formula (H-IV) can be produced by the same process as that used in <Step 1> of (Reaction scheme) using the compound represented by formula (H-I) and the compound represented by formula (D-II).

<Step 4>

The compound represented by formula (H-III) can be produced by the same process as that used in <Step 2> of (Production process D) using the compound represented by formula (H-IV).

Furthermore, the compound represented by formula (H-IV), which is an intermediate, can be produced by the following process.

<Step 5>

<Step 8>

A compound represented by formula (H—X) can be produced by the same process as that used in <Step 6> of (Production process D) using the compound represented by formula (H-IX).

<Step 9>

The compound represented by formula (H-IV) can be produced by the same process as that used in <Step 4> of (Reaction scheme) using the compound represented by formula (H—X).

(Production Process I)

<In formula (I), the case where $X_1$ is O, N—$R^3$, or S (which is represented by $X_1$'), $X_2$ is $CH_2$, q is 0, m is 1, $R^2$ is alkyl, and p is 2.>

[Ch. 32]

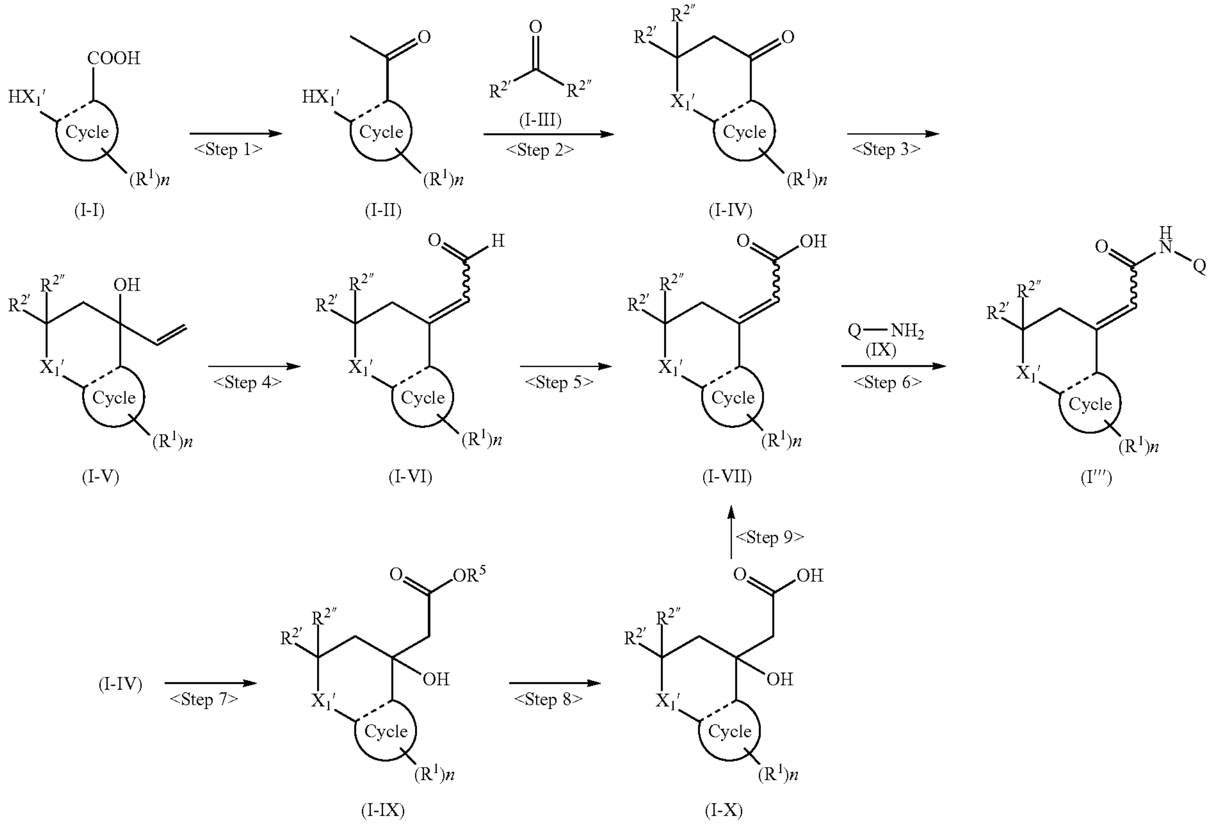

A compound represented by formula (H-VI) can be produced by the same process as that used in <Step 1> of (Reaction scheme) using the compound represented by formula (H-I) and a compound represented by formula (H-V).

<Step 6>

The compound represented by formula (H-IV) can be produced by the same process as that used in <Step 3> of (Production process B) using the compound represented by formula (H-VI) and a compound represented by formula (H-VII).

<Step 7>

A compound represented by formula (H-IX) can be produced by the same process as that used in <Step 1> of (Reaction scheme) using the compound represented by formula (H-I) and a compound represented by formula (H-VIII).

<Step 1>

A compound represented by formula (I-II) can be produced by conducting a reaction using a compound represented by formula (I-I) by a process similar to that described in published documents, for example, Journal of Medicinal Chemistry, 46(13), pp. 2683-2696, 2003, in the presence of methyllithium (MeLi) with a solvent which is inactive to the reaction, such as diethyl ether, 1,2-dimethoxyethane, dioxane, or tetrahydrofuran, or a mixed solvent thereof at a temperature in the range of −78° C. to the solvent-reflux temperature.

<Step 2>

A compound represented by formula (I-IV) can be produced by reacting the compound represented by formula (I-II) with a compound represented by formula (I-III) by a process similar to that described in published documents, for example, Journal of Heterocyclic Chemistry, 32, pp. 1393-

1395, 1995, in the presence of a base such as pyrrolidine, piperazine, morpholine, triethylamine, N,N-diisopropylethylamine, or pyridine using a solvent which would not take part in the reaction, such as an alcohol solvent, e.g., methanol, ethanol, or 2-propanol, or a mixed solvent thereof at a temperature in the range of 0° C. to the solvent-reflux temperature. In the formulae, each of $R^{2'}$ and $R^{2''}$ is an alkyl group such as methyl, ethyl, propyl, or isopropyl, and $R^{2'}$ and $R^{2''}$ may be the same or independent each other. $R^{2'}$ and $R^{2''}$ may form a ring such as cyclopropyl, cyclobutyl, cyclopentyl, or cyclohexyl, and the ring may include a heteroatom such as S, O, or N.

<Step 3>

A compound represented by formula (I-V) can be produced by conducting a reaction using the compound represented by formula (I-IV) by a process similar to that described in published documents, for example, Jikken Kagaku Koza (Experimental Chemistry Series), 4th edition, 25, Organic synthesis VII, Synthesis using organometallic reagent, pp. 59-72, 1992, Maruzen Co., Ltd., in the presence of vinyl magnesium chloride or vinyl magnesium bromide with a solvent which is inactive to the reaction, such as diethyl ether, 1,2-dimethoxyethane, dioxane, or tetrahydrofuran, or a mixed solvent thereof at a temperature in the range of −78° C. to the solvent-reflux temperature.

<Step 4>

A compound represented by formula (I-VI) can be produced by conducting a reaction using the compound represented by formula (I-V) by a process similar to that described in published documents, for example, Tetrahedron Letters, 30(9), pp. 1033-1036, 1989, in the presence of an oxidizing agent such as pyridinium dichromate (PDC), pyridinium chlorochromate (PCC), or chromium oxide ($CrO_3$) with a solvent which is inactive to the reaction, such as dichloromethane, 1,2-dichloroethane, or benzene, or a mixed solvent thereof at a temperature in the range of 0° C. to the solvent-reflux temperature.

<Step 5>

A compound represented by formula (I-VII) can be produced by conducting a reaction using the compound represented by formula (I-VI) by a process similar to that described in published documents, for example, Jikken Kagaku Koza (Experimental Chemistry Series), 4th edition, 23, Organic synthesis V, Oxidative reaction, pp. 472-513, 1992, Maruzen Co., Ltd., in the presence of an oxidizing agent such as sodium hypochlorite or calcium hypochlorite with a solvent which is inactive to the reaction, such as dichloromethane, 1,2-dichloroethane, acetonitrile, or water, or a mixed solvent thereof at a temperature in the range of 0° C. to the solvent-reflux temperature.

<Step 6>

A compound represented by formula (I''') can be produced by the same process as that used in <Step 6> of (Reaction scheme) using the compound represented by formula (I-VII) and the compound represented by formula (IX).

Alternatively, the compound represented by formula (I-VII), which is an intermediate, can be produced by the following process.

<Step 7>

A compound represented by formula (I-IX) can be produced by a process similar to that described in <Step 1> of (Production process F) using the compound represented by formula (I-IV).

<Step 8>

A compound represented by formula (I-X) can be produced by the same process as that used in <Step 4> of (Production process F) using the compound represented by formula (I-IX).

<Step 9>

The compound represented by formula (I-VII) can be produced by the same process as that used in <Step 2> of (Production process F) using the compound represented by formula (I-X).

(Production Process J)

<In formula (I), the case where $X_1$ is O, N—$R^3$, or S (which is represented by $X_1$'), $X_2$ is NH, m is 1, $R^2$ is alkyl, and p is 2.>

[Ch. 33]

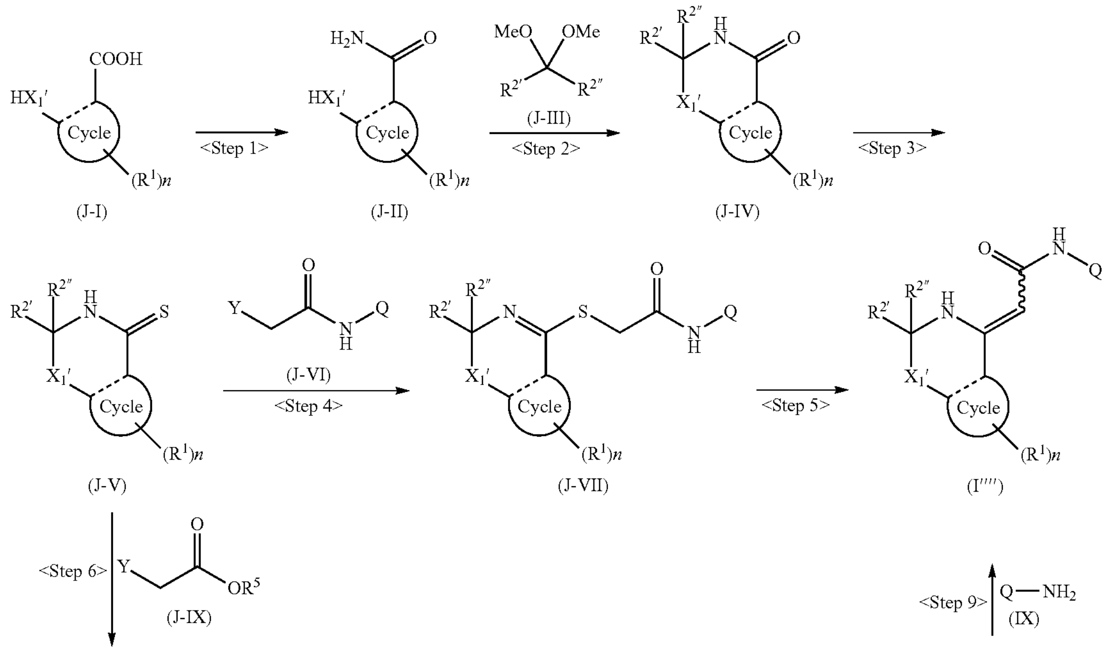

(J-I) (J-II) (J-III) (J-IV) (J-V) (J-VI) (J-VII) (I'''') (J-IX) (IX)

-continued

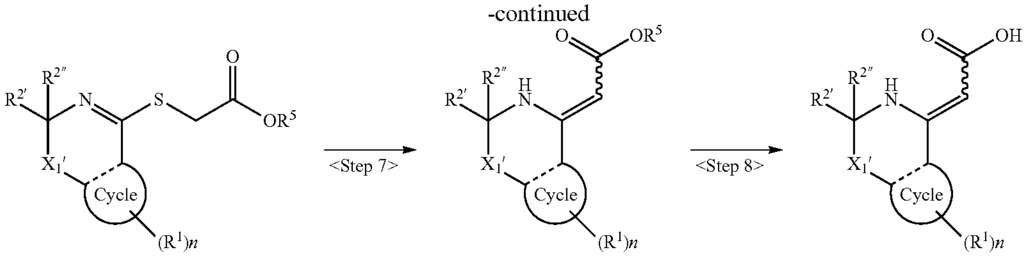

(J-X) (J-XI) (J-XII)

<Step 1>

A compound represented by formula (J-II) can be produced by a process similar to that described in <Step 6> of (Reaction scheme) using a compound represented by formula (J-I).

<Step 2>

A compound represented by formula (J-IV) can be produced by allowing the compound represented by formula (J-II) to react with a compound represented by formula (J-III) by a process described in published textbooks, for example, Greene et al., Protective Groups in Organic Synthesis, (the United States), 3rd edition, 1999. In the formulae, each of $R^{2'}$ and $R^{2''}$ is an alkyl group such as methyl, ethyl, propyl, or isopropyl, and $R^{2'}$ and $R^{2''}$ may be the same or independent each other. $R^{2'}$ and $R^{2''}$ may form a ring such as cyclopropyl, cyclobutyl, cyclopentyl, or cyclohexyl, and the ring may include a heteroatom such as S, O, or N.

<Step 3>

A compound represented by formula (J-V) can be produced by conducting a reaction using the compound represented by formula (J-IV) by a process similar to that described in published documents, for example, Bulletin des Societes Chimiques Belges, 87, p. 229, 1978, in the presence of the Lawesson's reagent (2,4-bis(4-methoxyphenyl)-1,3,2,4-dithiadiphosphetane-2,4-disulfide) with a solvent which is inactive to the reaction, such as toluene, benzene, xylene, 1,2-dimethoxyethane, dichloromethane, 1,2-dichloroethane, chloroform, or hexamethylphosphoric triamide, or a mixed solvent thereof at a temperature in the range of 0° C. to the solvent-reflux temperature.

<Step 4>

A compound represented by formula (J-VII) can be produced by allowing the compound represented by formula (J-V) to react with a compound represented by formula (J-VI) by a process similar to that described in published documents, for example, Synlett, No. 11, pp. 1117-1118, 1996, in the presence of a base such as triethylamine, N,N-diisopropylethylamine, or N,N-dimethylaminopyridine using a solvent which is inactive to the reaction, such as acetonitrile, dioxane, tetrahydrofuran, benzene, toluene, dichloromethane, 1,2-dichloroethane, or chloroform, or a mixed solvent thereof at a temperature in the range of room temperature to the solvent-reflux temperature.

<Step 5>

A compound represented by formula (I"") can be produced by conducting a reaction using the compound represented by formula (J-VII) by a process similar to that described in published documents, for example, Synlett, No. 11, pp. 1117-1118, 1996, in the presence of a phosphine reagent such as triphenylphosphine or tributylphosphine; a phosphite reagent such as trimethyl phosphite, triethyl phosphite, tripropyl phosphite, or tributyl phosphite; and a base such as triethylamine, N,N-diisopropylethylamine, or N,N-dimethylaminopyridine at a temperature in the range of room temperature to the solvent-reflux temperature.

<Step 6>

A compound represented by formula (J-X) can be produced by the same process as that used in <Step 4> of (Production process J) using the compound represented by formula (J-V) and a compound represented by formula (J-IX).

<Step 7>

A compound represented by formula ($J-X_1$) can be produced by the same process as that used in <Step 5> of (Production process J) using the compound represented by formula (J-X).

<Step 8>

A compound represented by formula (J-XII) can be produced by the same process as that used in <Step 5> of (Reaction scheme) using the compound represented by formula (J-XI).

<Step 9>

A compound represented by formula (J-VIII) can be produced by the same process as that used in <Step 6> of (Reaction scheme) using the compound represented by formula (J-XII) and the compound represented by formula (IX).

As described above, the compound represented by formula (I), a salt thereof, and a solvate thereof, which are used in the present invention, can be produced by (Reaction scheme) above and the processes described in Production processes A to J, or processes similar to these processes.

The compound represented by formula (I) can be obtained by a condensation reaction of a carboxylic acid represented by formula (VIII) and an amine ($Q-NH_2$) represented by formula (IX).

[Ch. 34]

(IX)

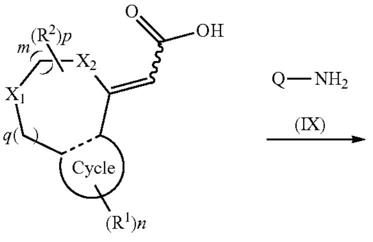

(VIII)

-continued

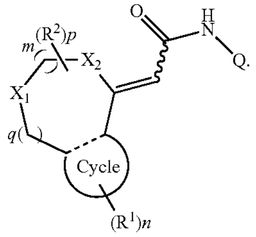

(I)

Various carboxylic acid derivatives included in general formula (VIII) can be synthesized by the above-described processes. Alternatively, these carboxylic acid derivatives can be readily produced from known compounds or commercially available compounds by, for example, methods described in published documents or methods which are normally employed by those skilled in the art. Examples of the carboxylic acid derivatives represented by formula (VIII) and compounds used as the starting materials thereof will now be described.

In the following formulae, Me represents a methyl group, Et represents an ethyl group, and Ph represents a phenyl group.

[Ch. 35]

Formula (1)

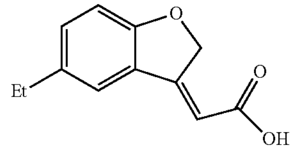

RN = 879935-06-5

Formula (2)

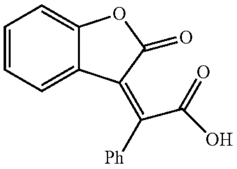

RN = 374919-95-6

Formula (3)

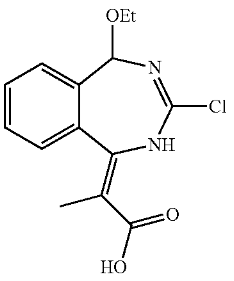

RN = 300695-65-2

-continued

Formula (4)

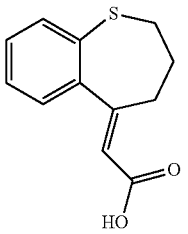

RN = 14861-92-8

Formula (5)

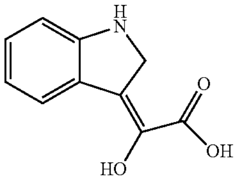

RN = 5818-74-6

Formula (6)

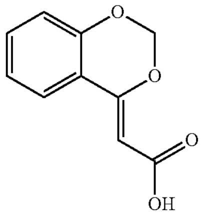

RN = 4442-50-6

Formula (7)

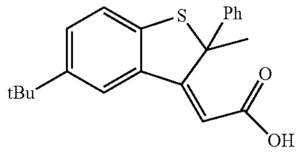

RN = 869593-14-6

Formula (8)

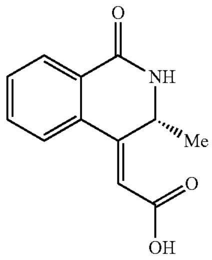

RN = 496802-73-4

Formula (9)

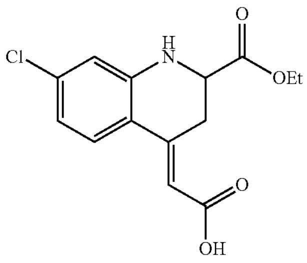

RN = 294626-49-6

-continued

Formula (10)

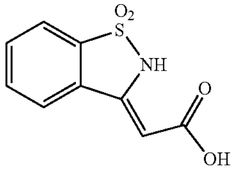

RN = 34981-46-9

Formula (11)

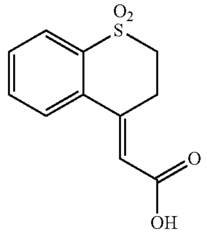

RN = 134997-72-1

Formula (12)

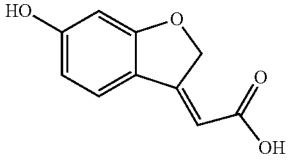

RN = 855221-04-4

Formula (13)

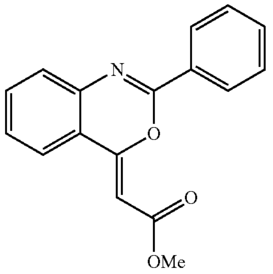

RN = 685110-67-2

Formula (14)

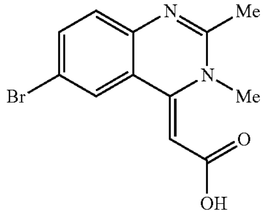

RN = 221198-87-4

Formula (15)

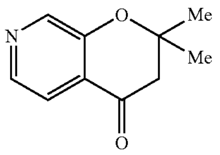

RN = 122262-34-4

The carboxylic acid represented by formula (I) is listed as 5-ethyl-3(2H)-benzofuranylideneacetic acid (Registry No. (RN)=879935-06-5) in the CHEMCATS file of a commercial database, STN international.

The carboxylic acid represented by formula (2) is listed as α-(2-oxo-3(2H)-benzofuranylidene)-benzeneacetic acid (Registry No. (RN)=374919-95-6) in the CHEMCATS file of a commercial database, STN international.

The carboxylic acid represented by formula (3) is listed as 2-(3-chloro-5-ethoxy-2,5-dihydro-1H-2,4-benzodiazepin-1-ylidene)-propanoic acid (Registry No. (RN)=300695-65-2) in the CHEMCATS file of a commercial database, STN international.

The carboxylic acid represented by formula (4) is listed as 3,4-dihydro-1-benzothiepin-Δ5(2H)-α-acetic acid (Registry No. (RN)=14861-92-8) in the CHEMCATS file of a commercial database, STN international.

The carboxylic acid represented by formula (5) is listed as (1,2-dihydro-3H-indol-3-ylidene)hydroxyacetic acid (Registry No. (RN)=5818-74-6) in the CHEMCATS file of a commercial database, STN international.

The carboxylic acid represented by formula (6) is listed as 1,3-benzodioxan-Δ4,α-acetic acid (Registry No. (RN) =4442-50-6) in the CHEMCATS file of a commercial database, STN international.

The carboxylic acid represented by formula (7) is disclosed as [5-(1,1-dimethylethyl)-2-methyl-2-phenylbenzo[b]thien-3(2H)-ylidene]acetic acid (Registry No. (RN)=869593-14-6) of compound 117 in p. 26 of PCT Publication No. 06/108355 pamphlet, which discloses dihydrobenzothiophene used as an antineoplastic agent.

The carboxylic acid represented by formula (8) is disclosed as [(3S)-2,3-dihydro-3-methyl-1-oxo-4(1H)-isoquinolinylidene]acetic acid (Registry No. (RN)=496802-73-4) of a starting material in Advanced Synthesis & Catalysis, 344(8), pp. 855-867, 2002, which is related to a novel peptide having a hybridized heterocycle.

The carboxylic acid represented by formula (9) is disclosed as 4(E)-4-(carboxymethylene)-7-chloro-1,2,3,4-tetrahydro-2-quinolinecarboxylic acid 2-ethyl ester (Registry No. (RN) =294626-49-6) of a starting material in Canadian Journal of Chemistry, 78(6), pp. 809-815, 2000, which is related to a glycine antagonist.

The carboxylic acid represented by formula (10) is disclosed as (1,1-dioxide-1,2-benzisothiazol-3(2H)-ylidene) acetic acid (Registry No. (RN)=34981-46-9) in U.S. Pat. No. 5,849,450, which discloses a novel charge-control agent for electrostatographic toners.

The carboxylic acid represented by formula (11) is disclosed as (2,3-dihydro-1,1-dioxide-4H-1-benzothiopyran-4-ylidene)acetic acid (Registry No. (RN)=134997-72-1) in production example D5(c) in Japanese Patent Application Laid-open No. Hei 3-41090, which discloses a renin inhibitor.

The carboxylic acid represented by formula (12) is disclosed as 6-hydroxy-Δ3(2H)-α-benzofuranacetic acid (Registry No. (RN)=855221-04-4) in Journal of Scientific & Industrial Research, 12B, pp. 346-9, 1953, which is related to benzopyran derivatives.

The carboxylic acid derivative (ester) represented by example (13) is disclosed as methyl (2-phenyl-4H-3,1-benzoxazin-4-ylidene)acetate (Registry No. (RN)=68510-67-2) in Journal of Organic Chemistry, 69(7), pp. 2469-2477, 2004, which is related to the synthesis of benzoxazine derivatives, quinazolin-2-one derivatives, and quinolin-4-ones.

The carboxylic acid represented by example (14) is disclosed as (6-bromo-2,3-dimethyl-4(3H)-quinazolinylidene)-acetic acid (Registry No. (RN)=221198-87 -4) of a starting material in Bulletin of the Polish Academy of Science, Chemistry, 46(4), pp. 353-359, 1998, which is related to the synthesis of novel spiroquinazoline derivatives.

The compound represented by example (15) is disclosed as 2,3-dihydro-2,2-dimethyl-4H-pyrano[2,3-c]pyridin-4-one (Registry No. (RN)=122262-34-4) in Japanese Patent Application Laid-open No. Hei 1-102080, which is related to pyridonyl azachromene derivatives.

When the compound synthesized by any of the above-described production processes has a reactive group such as a hydroxyl group, an amino group, or carboxyl group, as a substituent, the compound can be produced by appropriately protecting the reactive group with a protective group in the production processes and then removing the protective group in an appropriate stage. The processes of the introduction and the removal of such a protective group are appropriately selected according to the type of group to be protected or the type of protective group. The introduction and the removal of the protective group can be performed by a process described in published textbooks, for example, Greene et al., Protective Groups in Organic Synthesis, (the United States), 3rd edition, 1999.

Examples of Pharmacological Experiment

The present invention will now be described more specifically using experimental examples. However, the present invention is not limited to these experimental examples.

[Measurement of Capsaicin-Induced Ca Influx in Human TRPV1 Transformed CHO Cell Line]

(1) Establishment of Human TRPV1 Transformed CHO Cell Line

Human vanilloid receptor 1 (hTRPV1) cDNA was cloned from a human brain. The cloned hTRPV1 cDNA was incorporated in a pCAGGS vector. The gene of the vector was introduced to a CHO-K1 cell line, thus performing transformation. Clones obtained by limiting dilution were stimulated with capsaicin. Clones with a high responsiveness were selected using an increase in the Ca concentration as an indicator. The selected clones were used for the following experiment.

(2) Measurement of Ca Influx Using FDSS-6000

The human TRPV1 transformed CHO cells were seeded in a 96-well plate (with black walls and transparent bottoms, manufactured by Greiner) at a density of 40,000 cells per well. The cells were cultured at 37° C. in 5% $CO_2$ for one night. A loading solution of FLIPR Calcium 3 assay kit (manufactured by Molecular Devices Corporation) containing 2.5 mmol/L of probenecid was then added to each of the wells in the same amount as the culture medium, and the cells were cultured at 37° C. for 60 minutes. After the cells were stimulated with capsaicin (1 nmol/L to 1 μmol/L), the change in the Ca concentration in the cells was measured using FDSS-6000 (λex: 480 nm, λem: 540 nm, manufactured by Hamamatsu Photonics K.K.) for three minutes. The integrated values of the increase rate of the Ca concentration in the cells were calculated for a group treated with the compounds of the present invention and a group treated with a medium, thus allowing capsaicin concentration-reaction curves to be obtained. A concentration (A2 value) of each of the compounds of the present invention, at which the capsaicin concentration-reaction curve obtained when the cells were treated with the medium was shifted two times to the right side, was calculated. The inhibiting effects of the test compounds were compared using this value as an indicator.

In the case where a compound of the present invention is an agonist, when the cells are treated with the compound of the present invention prior to the capsaicin stimulation, the Ca influx is observed. In Table 1, compounds of the present invention having an A2 value of less than 100 nM are represented by A, and compounds having an A2 value of 100 nM or more are represented by B. When the A2 values of the compounds of the present invention were measured by the above-described method, the compounds have an intensity of 1 μM or less.

(3) Effect of Compound on CFA-Induced Rat Inflammatory Pain Model

A CFA-induced rat inflammatory pain model is prepared by a general method, for example, the method used by Pomonis J D et al. (The Journal of Pharmacology and Experimental Therapeutics, Vol. 306, pp. 387-393). More specifically, 100 μL of CFA is administered into the sole of a rat's paw, thus inducing inflammation.

A compound of the present invention was orally administered to rats one day or one week after the administration of CFA. Thereby, a decrease in the threshold of pain was suppressed, that is, the effectiveness as a curative medicine for inflammatory pain was verified.

(4) Effect of Compound on Neuropathic Pain Model Rat

A compound of the present invention was orally administered to a Chung model rat, a Seltzer model rat, or a STZ-induced diabetic pain model rat. Thereby, a decrease in the threshold of pain was suppressed, that is, the effectiveness as a curative medicine for neuropathic pain was verified.

(5) Safety Test

When a compound of the present invention was orally administered to rats at a dosage of 100 mg/kg for two weeks, no rats died. Thus, the safety of the present invention was verified.

The above results show that the compound of the present invention had an antagonism to the TRPV1 receptor. Furthermore, an analgetic effect was observed in the inflammatory pain model and the neuropathic pain model in vivo. In addition, no particular effect was observed in the safety test, which demonstrated the low toxicity of the present invention.

Furthermore, the compound of the present invention does not have an inhibitory action of a hERG channel. The compound of the present invention has high metabolic stability and satisfactory pharmacokinetics.

Accordingly, the compound of the present invention serves as a TRPV1 receptor antagonist and is expected as an agent for preventing or treating pain, in particular, as an agent for preventing or treating inflammatory pain or neuropathic pain.

It is expected that the compound of the present invention has a promising effect of preventing or curing the above various diseases and conditions. More specifically, the compound of the present invention can be used for treating acute pain; chronic pain; neuropathic pain; postherpetic neuralgia; trigeminal neuralgia; lower-back pain; pain after spinal cord injury; leg pain; causalgia; diabetic neuralgia; pain caused by edema, burns, sprains, bone fractures, and the like; pain after surgical operations; scapulohumeral periarthritis; osteoarthritis; arthritis; rheumatic arthritis pain; inflammatory pain; cancer pain; migraines; headaches; toothaches; neuralgia; muscle pain; hyperalgesia; pain caused by angina pectoris, menstruation, and the like; neuropathy; nerve damage; neurodegeneration; chronic obstructive pulmonary disease (COPD); asthma; airway hypersensitivity; stridor; cough; rhinitis; inflammation of mucosa such as eyes; nervous dermatitis; inflammatory skin complaint such as psoriasis and eczema; edema; allergic diseases; gastroduodenal ulcer; ulcerative colitis; irritable colon syndrome; Crohn's disease; urinary incontinence; urge incontinence; overactive bladder; cystitis; nephritis; pancreatitis; uveitis; splanchnopathy; ischemia; apoplexy; dystonia; obesity; septicemia; and pruritus. In particular, a promising effect for treating neuropathic pain, inflammatory pain, and urinary incontinence can be expected.

The compound of the present invention can be used in combination with other drugs.

Examples of the drugs include analgetic drugs such as opioid agonists, e.g., morphine; gabapentin; Pregabalin; antidepressant drugs such as Duloxetine and amitriptyline; antiepileptic drugs such as carbamazepine and phenyloin; antiarrhythmic drugs, such as mexiletine, which are alternatively used and prescribed for neuropathic pain; NSAIDs such as diclofenac, indomethacin, ibuprofen, and naproxen; and anti-inflammatory drugs such as COX-2 inhibitors, e.g., Celebrex. Among these, preferable examples of the drugs include morphine, gabapentin or Pregabalin, diclofenac, and Celebrex.

In addition to the use of the compound of the present invention in combination with other drugs, the medical treatment can be performed in combination with other treatments. Examples of the other treatments include acupuncture, laser therapy, and nerve block therapy.

For diseases or conditions in which TRPV1 is involved other than pain, the compound of the present invention can be used in combination with drugs used in the corresponding field. For example, for chronic rheumatic arthritis, the compound of the present invention can be used in combination with generally used NSAIDs, disease-modifying antirheumatic drugs (DMARDs), anti-TNF-α antibodies, soluble TNF-α receptors, steroids, immunosuppressants, or the like. For COPD or allergic diseases, the compound of the present invention can be used in combination with general curative medicines such as β2-receptor agonists or steroids. For an overactive bladder or urinary incontinence, the compound of the present invention can be used in combination with an anticholinergic drug.

When the compound of the present invention is used for treating the above diseases and conditions in combination with an existing drug, the dosage of the existing drug can be decreased, and thus, side effects of the existing drug can be reduced. The method of using the drugs in combinations is not limited to the above-mentioned diseases and conditions, and the drugs used in combinations are not limited to the above compounds listed as examples.

When the compound of the present invention is used in combination with another drug, the drugs may be prepared separately or as a medical mixture. In the case of separate drugs, both drugs may be administered at the same time. Alternatively, one drug may be administered in advance, and another drug may then be administered some time later.

A medicine of the present invention is administered in the form of a pharmaceutical composition.

It is sufficient that the pharmaceutical composition of the present invention contains at least one compound represented by formula (I), (I-A), (I-B), (I-C), (I-D), (I-E), (I-F), (I'), (I'-A), (I'-B), (I'-C), (I'-D), (I'-E), (I'-F), (I''), (I'''), or (I''''). The pharmaceutical composition of the present invention is prepared by being combined with pharmaceutically acceptable additives. In more detail, the compound of the present invention may be appropriately combined with the following additives to prepare various formulations. Examples of the additives include excipients (for example, lactose, sucrose, mannitel, crystalline cellulose, silicic acid, corn starch, and potato starch); binders (for example, celluloses (hydroxypropyl cellulose (HPC) and hydroxypropylmethyl cellulose (HPMC)), crystalline cellulose, sugars (lactose, mannitel, sucrose, sorbitol, erythritol, and xylitol), starches (corn starch and potato starch), α-starch, dextrine, polyvinylpyrrolidone (PVP), macrogol, and polyvinyl alcohol (PVA)); lubricants (for example, magnesium stearate, calcium stearate, talc, and carboxymethyl cellulose); disintegrants (for example, starches (corn starch and potato starch), sodium carboxymethyl starch, carmellose, carmellose calcium, crosscarmellose sodium, and crosspovidone); coating agents (for example, celluloses (hydroxypropyl cellulose (HPC) and hydroxypropylmethyl cellulose (HPMC)), aminoalkyl methacrylate copolymer E, and methacrylic acid copolymer LD); plasticizers (for example, triethyl citrate, and macrogol); masking agents (for example, titanium oxide); colorants; flavoring agents; antiseptics (benzalkonium chloride and parahydroxybenzoates); isotonic agents (for example, glycerol, sodium chloride, calcium chloride, mannitol, and glucose); pH adjusting agents (sodium hydroxide, potassium hydroxide, sodium carbonate, hydrochloric acid, sulfuric acid, and a buffer solution such as a phosphate buffer); stabilizers (for example, sugars, sugar alcohols, and xanthan gum); dispersion agents; antioxidants (for example, ascorbic acid, butylhydroxyanisole (BHA), propyl gallate, and dl-α-tocopherol); buffers; preservatives (for example, paraben, benzyl alcohol, and benzalkonium chloride); aromatics (for example, vanilin, 1-menthol, and rose oil); dissolution aids (for example, polyoxyethylene hardened castor oil, Polysorbate 80, polyethylene glycol, phospholipid cholesterol, and triethanolamine); absorption accelerators (for example, sodium glycolate, disodium edetate, sodium caprate, acylcarnitines, and limonene); gelation agents; suspending agents; emulsifying agents; and suitable additives and solvents which are normally used.

Such formulations include tablets, capsules, granules, powders, pills, aerosols, inhalants, ointments, plasters, suppositories, injections, troches, liquids, spirits, suspensions, extracts, and elixirs. These formulations may be administered to a patient by oral administration, subcutaneous administration, intramuscular administration, intranasal administration, percutaneous administration, intravenous administration, intraarterial administration, perineural administration, epidural administration, subdural administration, intraventricular administration, intrarectal administration, inhalation, or the like.

The dosage of the compound of the present invention is usually in the range of 0.005 mg to 3.0 g per day for an adult, preferably 0.05 mg to 2.5 g, and more preferably 0.1 mg to 1.5 g. The dosage may be appropriately increased or decreased in accordance with the progress of the disease and administration routes.

The entire quantity may be orally or parenterally given in one dose or given in two to six doses, or may be continuously administered by intravenous drip or the like.

Formulation Examples

Examples of pharmaceutical compositions of the present invention will be described below.

TABLE 1

| Formulation example 1 | Tablet |
|---|---|
| Compound of Example 3 | 100 g |
| Lactose | 137 g |
| Crystalline cellulose | 30 g |
| Hydroxypropyl cellulose | 15 g |
| Sodium carboxymethyl starch | 15 g |
| Magnesium stearate | 3 g |

The above ingredients are weighed and then mixed homogeneously. The resulting mixture is compressed to prepare a tablet having a weight of 150 mg.

TABLE 2

| Formulation example 2 | Film coating |
|---|---|
| Hydroxypropylmethyl cellulose | 9 g |
| Macrogol 6000 | 1 g |
| Titanium oxide | 2 g |

The above ingredients are weighed. Hydroxypropylmethyl cellulose and Macrogol 6000 are then dissolved in water, and titanium oxide is dispersed in the solution. The resulting liquid is coated on the surfaces of 300 g of the tablets prepared in Formulation example 1 to form a film. Thus, film-coated tablets are obtained.

TABLE 3

| Formulation example 3 | Capsule |
|---|---|
| Compound of Example 7 | 50 g |
| Lactose | 435 g |
| Magnesium stearate | 15 g |

The above ingredients are weighed and then mixed homogeneously. Subsequently, 300 mg of the resulting mixture is filled in an appropriate hard capsule with a capsule enclosing device, thus allowing a capsule to be prepared.

TABLE 4

| Formulation example 4 | Capsule |
|---|---|
| Compound of Example 9 | 100 g |
| Lactose | 63 g |
| Corn starch | 25 g |
| Hydroxypropyl cellulose | 10 g |
| Talc | 2 g |

The above ingredients are weighed. The compound of Example 9, lactose, and corn starch are then mixed homogeneously, and an aqueous solution of hydroxypropyl cellulose is added to the mixture. Granules are produced by a wet granulation method. Talc is then homogeneously mixed with the granules. Subsequently, 200 mg of the resulting mixture is filled in an appropriate hard capsule, thus allowing a capsule to be prepared.

TABLE 5

| Formulation example 5 | Powder |
|---|---|
| Compound of Example 25 | 200 g |
| Lactose | 790 g |
| Magnesium stearate | 10 g |

The above ingredients are weighed and then mixed homogeneously. Thus, 20% powder medicine is prepared.

TABLE 6

| Formulation example 6 | Granules and fine granules |
|---|---|
| Compound of Example 48 | 100 g |
| Lactose | 200 g |
| Crystalline cellulose | 100 g |
| Partially α-converted starch | 50 g |
| Hydroxypropyl cellulose | 50 g |

The above ingredients are weighed. The compound of Example 48, lactose, crystalline cellulose, and partially α-converted starch are then homogeneously mixed, and an aqueous solution of hydroxypropyl cellulose (HPC) is added to the mixture. Granules or fine granules are produced by a wet granulation method. The granules or fine granules are dried, thus allowing a granular medicine or a fine granular medicine to be prepared.

TABLE 7

| Formulation example 7 | Cream |
|---|---|
| Compound of Example 51 | 0.5 g |
| dl-α-Tocopherol acetate | 0.1 g |
| Stearyl glycyrrhetinate | 0.05 g |
| Stearic acid | 3 g |
| Higher alcohol | 1 g |
| Squalane | 10 g |
| Octyldodecyl myristate | 3 g |
| Trimethylglycine | 7 g |
| Antiseptic | Proper quantity |
| Saponifier | Proper quantity |

The above ingredients are weighed. The compound of Example 51 is then mixed with other ingredients and dissolved. A proper amount of purified water is added so that the total weight reaches 50 g, thus allowing a cream formulation to be prepared.

TABLE 8

| Formulation example 8 | Suppository |
|---|---|
| Compound of Example 57 | 100 g |
| Polyethylene glycol 1500 | 180 g |
| Polyethylene glycol 4000 | 720 g |

The compound of Example 57 is sufficiently ground with a mortar to prepare a fine powder. The powder is then formed into a suppository having a weight of 1 g by a fusion method.

EXAMPLES

The present invention will now be described in more detail using examples, but the present invention is not limited to the examples.

The measurement of nuclear magnetic resonance (NMR) spectrum was performed using a JEOL JNM-LA300 FT-NMR (manufactured by JEOL Ltd.) or a JEOL JNM-EX270 FT-NMR (manufactured by JEOL Ltd.). Liquid chromatography-mass spectrometry (LC-MS) was performed using a Waters FractionLynx MS system (manufactured by Waters Corporation). A SunFire column (4.6 mm×5 cm, 5 μm) (manufactured by Waters Corporation) was used. Acetonitrile and a 0.05% aqueous acetic acid solution were used as the mobile phase. The analysis was performed under the following gradient conditions: (Method A) acetonitrile:0.05% aqueous acetic acid solution=1:9 (0 minutes), 1:1 (6 minutes), 9:1 (9 minutes), and 9:1 (9.5 minutes). (Method B) acetonitrile: 0.05% aqueous acetic acid solution=1:9 (0 minutes), 9:1 (5 minutes), and 9:1 (9.5 minutes). (Method C) acetonitrile: 0.05% aqueous acetic acid solution=1:9 (0 minutes), 9:1 (5 minutes), and 9:1 (7 minutes). (In tables below, Method A and Method B in the measurement are denoted by A and B, respectively, at the upper right of example numbers, and Method C is not denoted.)

Example 1

Synthesis of (E)-2-(chroman-4-ylidene)-N-(2,3-dihydrobenzo[b][1,4]dioxin-6-yl)acetamide <Step 1> Synthesis of ethyl (E)-chroman-4-ylidene acetate A tetrahydrofuran (10 mL) solution of triethylphosphonoacetate (5.9 mL) was added to a tetrahydrofuran (40 mL) suspension of 60% sodium hydride (1.2 g) at an inner temperature of 20° C. or lower, and the reaction mixture was then stirred at room temperature for one hour. A tetrahydrofuran (10 mL) solution of 4-chromanone (2.0 g) was added to the mixture under ice cooling, and the mixture was then stirred overnight at room temperature. The solvent was then distilled off under reduced pressure. The residue was purified by silica gel column chromatography (eluate; n-hexane:ethyl acetate=10:1). The title compound (1.24 g) was obtained as colorless crystals.

<Step 2> Synthesis of chroman-4-ylideneacetic acid

Water (6 mL) and lithium hydroxide (0.35 g) were added to a tetrahydrofuran (20 mL) solution of the compound (1.2 g) prepared in <Step 1>, and the reaction mixture was then refluxed for six hours. The solvent was distilled off under reduced pressure. The reaction mixture was then neutralized with 1 N hydrochloric acid and was extracted with ethyl acetate. The organic layer was washed with a saturated brine and then dried over anhydrous sodium sulfate. The solvent was then distilled off under reduced pressure. Ethyl acetate was added to the residue to solidify the resulting product. The title compound (0.55 g) was obtained as a white solid.

<Step 3> Synthesis of (E)-2-(chroman-4-ylidene)-N-(2,3-dihydrobenzo[b][1,4]dioxin-6-yl)acetamide 1,4-Benzodioxan-6-amine (40 mg) and 1-ethyl-3-(3-dimethylaminopropyl)carbodiimide hydrochloride (53 mg) were added to a dichloromethane (2 mL) solution of the compound (50 mg) prepared in <Step 2> under ice cooling. The reaction mixture was stirred at room temperature overnight. Water was added to the solution, and the resulting solution was extracted with ethyl acetate. The organic layer was sequentially washed with water, a 10% aqueous citric acid solution, a saturated aqueous sodium hydrogencarbonate solution, and a saturated brine, and then dried over anhydrous sodium sulfate. The solvent was then distilled off under reduced pressure. Ethyl acetate was added to the residue to solidify the resulting product. The product was washed with diethyl ether. The title compound (47 mg) was obtained as brown-white crystals.

Example 2

Synthesis of (E)-2-(chroman-4-ylidene)-N-(isoquinolin-5-yl)acetamide

The title compound (21 mg) was obtained as pale yellow-white crystals from the compound (50 mg) prepared in <Step 2> of Example 1 by the same process as that used in <Step 3> of Example 1.

Example 3

Synthesis of (E)-2-(7-tert-butyl-chroman-4-ylidene)-N-(5,6,7,8-tetrahydroquinolin-7-yl)acetamide <Step 1> Synthesis of ethyl (E)-2-(7-tert-butyl-chroman-4-ylidene)acetate The title compound (0.56 g) was obtained as colorless oil from 7-tert-butyl-chroman-4-one (1.5 g) by the same process as that used in <Step 1> of Example 1.

<Step 2> Synthesis of (E)-2-(7-tert-butyl-chroman-4-ylidene)acetic acid

The title compound (0.22 g) was obtained as colorless crystals from the compound (0.56 g) prepared in <Step 1> of Experimental example 3 by the same process as that used in <Step 2> of Example 1.

<Step 3> Synthesis of (E)-2-(7-tert-butyl-chroman-4-ylidene)-N-(5,6,7,8-tetrahydroquinolin-7-yl)acetamide The title compound (35 mg) was obtained as pale yellow crystals from the compound (50 mg) prepared in <Step 2> of Experimental example 3 by the same process as that used in <Step 3> of Example 1.

The following compounds of Examples 4 and 5 were synthesized by a process the same as or similar to the process used in Example 1.

Example 4

(E)-2-(7-tert-butyl-chroman-4-ylidene)-N-(isoquinolin-5-yl)acetamide

Example 5

(E)-2-(7-tert-butyl-chroman-4-ylidene)-N-(quinolin-7-yl)acetamide

Example 6

Synthesis of (E)-2-(7-trifluoromethyl-chroman-4-ylidene)-N-(5,6,7,8-tetrahydroquinolin-7-yl)acetamide <Step 1-Process A> Synthesis of 3-(3-trifluoromethylphenoxy)propionic acid 3-Chloropropionic acid (25 g) was added dropwise to a 2 N aqueous sodium hydroxide solution (120 mL) of 3-hydroxybenzotrifluoride (25 g). The reaction mixture was refluxed for one hour while the pH was maintained at 10 or more with a 5 N aqueous sodium hydroxide solution. The reaction mixture was cooled to room temperature and was then washed with diethyl ether. Subsequently, 1 N hydrochloric acid was added thereto so that the solution became acidic. The reaction mixture was extracted with ethyl acetate. The organic layer was sequentially washed with water and a saturated brine and then dried over anhydrous sodium sulfate. The solvent was distilled off under reduced pressure, and n-hexane was then added to the residue to perform crystallization. The title compound (6.1 g) was obtained as colorless crystals.

<Step 1-Process B> Synthesis of 3-(3-trifluoromethylphenoxy)propionic acid

Sodium hydride (550 mg) was added to an N,N-dimethylformamide (20.0 mL) solution of 3-hydroxybenzotrifluoride (2.0 g), and the reaction mixture was stirred at room temperature for one hour. β-Propiolactone (1.0 mL) was added thereto, and the solution was stirred at room temperature for 2.5 hours. Water was then added to the solution, and the pH was adjusted to 2 with 2 N hydrochloric acid. The solution was extracted with ethyl acetate. The organic layer was sequentially washed with water and a saturated brine and then dried over anhydrous sodium sulfate. The solvent was distilled off under reduced pressure, and n-hexane was then added to the residue to perform crystallization. The title compound (2.2 g) was obtained as colorless crystals.

<Step 2> Synthesis of 7-trifluoromethylchroman-4-one

The compound (4.7 g) prepared in <Step 1> of Example 6 was dissolved in polyphosphoric acid (100 g), and the reaction mixture was stirred at an outer temperature in the range of 100° C. to 120° C. for one hour. The reaction mixture was poured into ice water and then extracted with ethyl acetate. The organic layer was washed with a saturated brine and then dried over anhydrous sodium sulfate. The solvent was distilled off under reduced pressure. The residue was purified by silica gel column chromatography (eluate; n-hexane:ethyl acetate=10:1). The title compound (4.2 g) was obtained as colorless crystals.

<Step 3> Synthesis of ethyl (E)-2-(7-trifluoromethyl-chroman-4-ylidene) acetate

The title compound (1.36 g) was obtained as colorless crystals from the compound (4.2 g) prepared in <Step 2> of Example 6 by the same process as that used in <Step 1> of Example 1.

<Step 4> Synthesis of (E)-2-(7-trifluoromethyl-chroman-4-ylidene)acetic acid

The title compound (0.35 g) was obtained as colorless crystals from the compound (1.0 g) prepared in <Step 3> of Example 6 by the same process as that used in <Step 2> of Example 1.

<Step 5> Synthesis of (E)-2-(7-trifluoromethyl-chroman-4-ylidene)-N-(5,6,7,8-tetrahydroquinolin-7-yl) acetamide The title compound (108 mg) was obtained as colorless crystals from the compound (100 mg) prepared in <Step 4> of Example 6 by the same process as that used in <Step 3> of Example 1.

The following compounds of Examples 7 and 8 were synthesized by a process the same as or similar to the process used in <Step 5> of Example 6.

Example 7

(E)-2-(7-trifluoromethyl-chroman-4-ylidene)-N-(isoquinolin-5-yl)acetamide

Example 8

(E)-2-(7-trifluoromethyl-chroman-4-ylidene)-N-(quinolin-7-yl)acetamide

Example 9

Synthesis of (E)-2-(8-trifluoromethyl-3,4-dihydrobenzo[b]oxepin-5(2H)-ylidene)-N-(2,3-dihydrobenzo[b][1,4]dioxin-6-yl)acetamide <Step 1> Synthesis of methyl 4-trifluoromethyl-2-hydroxy benzoate Thionyl chloride (11 mL) was added dropwise to methanol (200 mL) under ice cooling. After the dropwise addition, 4-trifluoromethyl-2-hydroxy-benzoic acid (10 g) was added to the solution, and the reaction mixture was then refluxed for eight hours. The solution was cooled to room temperature. The reaction solvent was distilled off under reduced pressure, and the solution was then extracted with diethyl ether. The organic layer was sequentially washed with water and a saturated brine and then dried over anhydrous sodium sulfate. The solvent was distilled off under reduced pressure. The residue was purified by silica gel column chromatography (eluate; n-hexane:ethyl acetate=20:1). The title compound (9.4 g) was obtained as a colorless liquid.

<Step 2> Synthesis of methyl 2-(3-(methoxycarbonyl)propanoxy)-4-trifluoromethyl benzoate Potassium carbonate (7.7 g), potassium iodide (0.7 g), and methyl 4-bromobutyrate (9.25 g) were added to an acetone (300 mL) solution of the compound (9.4 g) prepared in <Step 1> of Example 9. The reaction mixture was refluxed for 12 hours. The reaction mixture was cooled to room temperature. The reaction solvent was distilled off under reduced pressure, and the solution was then extracted with ethyl acetate. The organic layer was washed with a saturated brine and then dried over anhydrous sodium sulfate. The solvent was distilled off under reduced pressure. The residue was purified by silica gel column chromatography (eluate; n-hexane:ethyl acetate=20:1). The title compound (13.1 g) was obtained as a colorless liquid.

<Step 3> Synthesis of 8-trifluoromethyl-3,4-dihydro-2H-benzo[b]oxepin-5-one

A dimethyl sulfoxide (15 mL) solution of the compound (2.0 g) prepared in <Step 2> of Example 9 was added dropwise to a dimethyl sulfoxide (15 mL) solution of 60% sodium hydride (260 mg) under ice cooling over a period of one hour. The reaction mixture was stirred at the same temperature for two hours. Water was added to the solution, and the solution was extracted with ethyl acetate. The organic layer was washed with a saturated brine and then dried over anhydrous sodium sulfate. The solvent was distilled off under reduced pressure. The residue was again dissolved in dimethyl sulfoxide (5 mL) and water (1 mL), and the solution was refluxed at 150° C. for 10 hours. The solution was cooled to room temperature and was then extracted with ethyl acetate. The organic layer was washed with a saturated brine and then dried over anhydrous sodium sulfate. The solvent was distilled off under reduced pressure. The residue was purified by silica gel column chromatography (eluate; n-hexane:ethyl acetate=90:10). The title compound (0.4 g) was obtained as colorless oil.

<Step 4> Synthesis of ethyl (E)-(8-trifluoromethyl-3,4-dihydro-2H-benzo[b]oxepin-5-ylidene)acetate and ethyl (Z)-(8-trifluoromethyl-3,4-dihydro-2H-benzo[b]oxepin-5-ylidene)acetate Ethyl (E)-(8-trifluoromethyl-3,4-dihydro-2H-benzo[b]oxepin-5-ylidene)acetate (170 mg) and ethyl (Z)-(8-trifluoromethyl-3,4-dihydro-2H-benzo[b]oxepin-5-ylidene)acetate (3.2 g) were obtained as colorless crystals and pale yellow oil, respectively, from the compound (2.8 g) prepared in <Step 3> of Example 9 by the same process as that used in <Step 1> of Example 1.

<Step 5> Synthesis of (E)-(8-trifluoromethyl-3,4-dihydro-2H-benzo[b]oxepin-5-ylidene)acetic acid The title compound (120 mg) was obtained as pale yellow-white crystals from the (E)-isomer (160 mg) prepared in <Step 4> of Example 9 by the same process as that used in <Step 2> of Example 1.

<Step 6> Synthesis of (E)-2-(8-trifluoromethyl-3,4-dihydrobenzo[b]oxepin-5(2H)-ylidene)-N-(2,3-dihydrobenzo[b][1,4]dioxin-6-yl)acetamide The title compound (101 mg) was obtained as pale yellow-white crystals from the compound (100 mg) prepared in <Step 5> of Example 9 by the same process as that used in <Step 3> of Example 1.

Example 9

Alternative Process A

Step 1> Synthesis of 2-iodo-5-trifluoromethylphenol

A toluene (200.0 mL) solution of 3-trifluoromethylphenol (16.6 g) was added dropwise to a toluene (300.0 mL) suspension of sodium hydride (7.1 g) under ice cooling. The reaction mixture was stirred at the same temperature for 30 minutes, and iodine (26.0 g) was then added thereto. The solution was stirred at room temperature for 12 hours. Subsequently, 3 N hydrochloric acid was added to the solution so that the pH of the solution was adjusted to 2. The solution was extracted with ethyl acetate. The organic layer was sequentially washed with water and a saturated brine and then dried over anhydrous sodium sulfate. The solvent was distilled off under reduced pressure. The title crude compound (30.8 g) was obtained as pale yellow oil.

<Step 2> Synthesis of 3-(5-methoxycarbonyl-4-penten)oxy-4-iodo-tri fluoromethylbenzene Potassium carbonate (52.8 mg), 6-bromo-2-hexenoic acid methyl ester (57.5 mg), and 18-crown ether (a catalyst amount) were added to an N,N-dimethylformamide (10.0 mL) solution of the compound (100.0 mg) prepared in <Step 1> of Alternative process A in Example 9. The reaction mixture was stirred at room temperature for 12 hours. Water was added to the solution, and the solution was then extracted with ethyl acetate. The organic layer was sequentially washed with water and a saturated brine and then dried over anhydrous sodium sulfate. The solvent was distilled off under reduced pressure. The title crude compound (66.0 mg) was obtained as colorless oil.

<Step 3> Synthesis of methyl (E)-(8-trifluoromethyl-3,4-dihydro-2H-benzo[b]oxepin-5-ylidene)acetate Palladium acetate (3.7 mg), triphenylphosphine (8.6 mg), and silver carbonate (45.0 mg) were added to a tetrahydrofuran (1.0 mL) solution of the compound (65.0 mg) prepared in <Step 2> of Alternative process A in Example 9. The reaction mixture was refluxed for eight hours under nitrogen atmosphere. The reaction mixture was subjected to Celite filtration. Water was then added to the solution, and the solution was extracted with ethyl acetate. The organic layer was sequentially washed with water and a saturated brine and then dried over anhydrous sodium sulfate. The solvent was distilled off under reduced pressure. The title compound (47.0 mg) was obtained as colorless crystals.

<Step 4> Synthesis of (E)-(8-trifluoromethyl-3,4-dihydro-2H-benzo[b]oxepin-5-ylidene)acetic acid The title compound (7.0 mg) was obtained as colorless crystals from the compound (47.0 mg) prepared in <Step 3> of Alternative process A in Example 9 by the same process as that used in <Step 2> of Example 1.

Example 9

Alternative Process B

<Step 1> Synthesis of 3-(3-cyanopropan)oxy-4-iodo-trifluoromethylbenzene

The title crude compound (72.4 g) was obtained as pale yellow crystals from the compound (60.0 g) prepared in <Step 1> of Alternative process A in Example 9 and 4-bromobutyronitrile (31.5 g) by the same process as that used in <Step 2> of Alternative process A in Example 9.

<Step 2> Synthesis of 3-(5-ethoxycarbonyl-4-penten)oxy-4-iodo-trifluoromethylbenzene Diisobutylaluminum hydride (a toluene solution, 341 mL) was added dropwise to a toluene (600.0 mL) solution of the compound (100.0 g) prepared in <Step 1> of Alternative process B in Example 9 at −78° C. The reaction mixture was stirred at the same temperature for 30 minutes and at room temperature for one hour. Subsequently, 0.5 N sulfuric acid (1.4 L) was added thereto, and the solution was extracted with hexane. The organic layer was sequentially washed with water and a saturated brine and then dried over anhydrous sodium sulfate. The solvent was distilled off under reduced pressure. Thus, an intermediate (aldehyde) was obtained as a pale yellow liquid. Ethyl diethylphosphonoacetate (25.8 g) was added to a tetrahydrofuran (1.0 L) solution of the aldehyde. A tetrahydrofuran (200.0 mL) suspension of potassium hydroxide (7.9 g) was added to the solution under ice cooling, and the reaction mixture was stirred at room temperature for eight hours. Water was then added to the mixture, and the mixture was extracted with hexane. The organic layer was sequentially washed with water and a saturated brine and then dried over anhydrous sodium sulfate. The solvent was distilled off under reduced pressure. The title compound (111.6 g) was obtained as pale yellow oil.

Example 9

Alternative Process C

<Step 1> Synthesis of 3-(4-penten)oxy-4-iodo-trifluoromethylbenzene

The title compound (3.1 g) was obtained as colorless oil from the compound (5.0 g) prepared in <Step 1> of Alternative process A in Example 9 and 5-bromo-1-pentene (2.5 mL) by the same process as that used in <Step 2> of Alternative process A in Example 9.

<Step 2> Synthesis of 3-(5-methoxycarbonyl-4-penten)oxy-4-iodo-trifluoromethylbenzene Tricyclohexylphosphine-1,3-bis-2,4,6-trimethylphenyl-4,5-dihydroimidazol-2-ylidene benzylidene ruthenium dichloride (0.18 g) was added to a methylene chloride (10.0 mL) solution of the compound (1.5 g) prepared in <Step 1> of Alternative process C in Example 9 and methyl acrylate (7.6 mL), and the reaction mixture was stirred for 12 hours. The solvent was distilled off under reduced pressure. The residue was purified by silica gel column chromatography (eluate; n-hexane:ethyl acetate=100:0 to 80:20). The title compound (1.15 g) was obtained as colorless crystals.

The following compounds of Examples 10 to 47 were synthesized by a process the same as or similar to the process used in Example 9.

Example 10

(E)-2-(8-trifluoromethyl-3,4-dihydrobenzo[b]oxepin-5(2H)-ylidene)-N-(5,6,7,8-tetrahydroquinolin-7-yl)acetamide Example 11

(E)-2-(8-trifluoromethyl-3,4-dihydrobenzo[b]oxepin-5(2H)-ylidene)-N-(isoquinolin-5-yl)acetamide Example 12

(E)-2-(8-trifluoromethyl-3,4-dihydrobenzo[b]oxepin-5(2H)-ylidene)-N-(quinoxalin-6-yl)acetamide Example 13

(E)-2-(8-trifluoromethyl-3,4-dihydrobenzo[b]oxepin-5(2H)-ylidene)-N-(quinolin-7-yl)acetamide Example 14

(E)-N-(4-tert-butylphenyl)-2-(8-trifluoromethyl-3,4-dihydrobenzo[b]oxepin-5(2H)-ylidene)acetamide Example 15

(E)-2-(8-trifluoromethyl-3,4-dihydrobenzo[b]oxepin-5(2H)-ylidene)-N-(4-trifluoromethylphenyl)acetamide Example 16

(E)-2-(8-trifluoromethyl-3,4-dihydrobenzo[b]oxepin-5(2H)-ylidene)-N-(3-methoxyphenyl)acetamide Example 17

(E)-2-(8-trifluoromethyl-3,4-dihydrobenzo[b]oxepin-5(2H)-ylidene)-N-(1,2,3,4-tetrahydro-1-methylquinolin-7-yl)acetamide Example 18

(E)-2-(8-trifluoromethyl-3,4-dihydrobenzo[b]oxepin-5(2H)-ylidene)-N-(7-hydroxynaphthalen-1-yl)acetamide Example 19

(E)-2-(8-trifluoromethyl-3,4-dihydrobenzo[b]oxepin-5(2H)-ylidene)-N-(2-methyl-1,3-benzothiazolo-5-yl)acetamide Example 20

(E)-2-(8-trifluoromethyl-3,4-dihydrobenzo[b]oxepin-5(2H)-ylidene)-N-(2-morpholinopyridin-3-yl)acetamide Example 21

(E)-2-(8-trifluoromethyl-3,4-dihydrobenzo[b]oxepin-5(2H)-ylidene)-N-(4-methyl-2-oxo-2H-chromen-7-yl)acetamide Example 22

(E)-2-(8-trifluoromethyl-3,4-dihydrobenzo[b]oxepin-5(2H)-ylidene)-N-(6-phenoxypyridin-3-yl)acetamide Example 23

(E)-2-(8-trifluoromethyl-3,4-dihydrobenzo[b]oxepin-5(2H)-ylidene)-N-(1,2,3,4-tetrahydro-1-oxonaphthalen-7-yl)acetamide Example 24

(E)-2-(8-trifluoromethyl-3,4-dihydrobenzo[b]oxepin-5(2H)-ylidene)-N-(1,3-dihydro-1-oxoisobenzofuran-6-yl)acetamide Example 25

(E)-2-(8-trifluoromethyl-3,4-dihydrobenzo[b]oxepin-5(2H)-ylidene)-N-(4-(4-morpholinylcarbonyl)phenyl)acetamide Example 26

(E)-2-(8-trifluoromethyl-3,4-dihydrobenzo[b]oxepin-5(2H)-ylidene)-N-(4-(4-morpholinylsulfonyl)phenyl)acetamide Example 27

(E)-N-(4-(5-trifluoromethyl)pyridin-2-yloxy)phenyl)-2-(8-trifluoromethyl-3,4-dihydrobenzo[b]oxepin-5(2H)-ylidene)acetamide Example 28

(E)-2-(8-trifluoromethyl-3,4-dihydrobenzo[b]oxepin-5(2H)-ylidene)-N-(3-(quinoxalin-2-yl)phenyl)acetamide Example 29

(E)-2-(8-trifluoromethyl-3,4-dihydrobenzo[b]oxepin-5(2H)-ylidene)-N-(4-((pyridin-4-yl)methyl)phenyl)acetamide Example 30

(E)-2-(8-trifluoromethyl-3,4-dihydrobenzo[b]oxepin-5(2H)-ylidene)-N-(1-(pyridin-2-yl)ethyl)acetamide Example 31

(E)-2-(8-trifluoromethyl-3,4-dihydrobenzo[b]oxepin-5(2H)-ylidene)-N-(phenyl(pyridin-2-yl)methyl)acetamide Example 32

(E)-2-(8-trifluoromethyl-3,4-dihydrobenzo[b]oxepin-5(2H)-ylidene)-N-((2,3-dihydrobenzo[b][1,4]dioxin-6-yl)methyl)acetamide Example 33

(E)-2-(8-trifluoromethyl-3,4-dihydrobenzo[b]oxepin-5(2H)-ylidene)-N-(1-(2,3-dihydrobenzo[b][1,4]dioxin-6-yl)ethyl)acetamide Example 34

(E)-2-(8-trifluoromethyl-3,4-dihydrobenzo[b]oxepin-5(2H)-ylidene)-N-((2,3-dihydrobenzo[b][1,4]dioxin-2-yl)methyl)acetamide Example 35

(E)-2-(8-trifluoromethyl-3,4-dihydrobenzo[b]oxepin-5(2H)-ylidene)-N-((2,3-dihydrobenzofuran-5-yl)methyl)acetamide Example 36

(E)-2-(8-trifluoromethyl-3,4-dihydrobenzo[b]oxepin-5(2H)-ylidene)-N-(2-morpholinophenyl)methyl-acetamide Example 37

(E)-2-(8-trifluoromethyl-3,4-dihydrobenzo[b]oxepin-5(2H)-ylidene)-N-(4-(1,2,3-thiadiazolo-4-yl)phenylmethyl)acetamide Example 38

(E)-N-(4-(1H-pyrazolo-1-yl)phenylmethyl)-2-(8-trifluoromethyl-3,4-dihydrobenzo[b]oxepin-5(2H)-ylidene)acetamide Example 39

(E)-N-((2-(4-chlorophenyl)-4-methylthiazol-5-yl)methyl)-2-(8-trifluoromethyl-3,4-dihydrobenzo[b]oxepin-5(2H)-ylidene)acetamide Example 40

(E)-N-([1,2,4]triazolo[4,3-a]pyridin-3-yl)methyl)-2-(8-trifluoromethyl-3,4-dihydrobenzo[b]oxepin-5(2H)-ylidene)acetamide Example 41

(E)-2-(8-trifluoromethyl-3,4-dihydrobenzo[b]oxepin-5(2H)-ylidene)-N-(1-methyl-1H-pyrazolo[3,4-b]pyridin-3-yl)acetamide Example 42

(E)-2-(8-trifluoromethyl-3,4-dihydrobenzo[b]oxepin-5(2H)-ylidene)-N-(1H-indazol-3-yl)acetamide Example 43

(E)-N-(1-ethyl-1H-benzo[d]imidazolo-2-yl)-2-(8-trifluoromethyl-3,4-dihydrobenzo[b]oxepin-5(2H)-ylidene)acetamide Example 44

(E)-N-([1,2,4]triazolo[1,5-a]pyrimidin-7-yl)-2-(8-trifluoromethyl-3,4-dihydrobenzo[b]oxepin-5(2H)-ylidene)acetamide Example 45

(E)-2-(8-trifluoromethyl-3,4-dihydrobenzo[b]oxepin-5(2H)-ylidene)-N-(6,7,8,9-tetrahydro-5H-cyclohepta[b]pyridin-8-yl)acetamide Example 46

(E)-N-(1-tert-butyl-3-methyl-1H-pyrazolo-5-yl)-2-(8-trifluoromethyl-3,4-dihydrobenzo[b]oxepin-5(2H)-ylidene)acetamide Example 47

(E)-2-(8-trifluoromethyl-3,4-dihydrobenzo[b]oxepin-5(2H)-ylidene)-N-(4-phenylthiazolo-2-yl)acetamide Example 48

Synthesis of (E)-2-(1-acetyl-7-trifluoromethyl-2,3-dihydroquinolin-4(1H)-ylidene)-N-(quinolin-7-yl)acetamide <Step 1> Synthesis of 3-(3-(trifluoromethyl)phenylamino)propionic acid Water (150 mL) and acrylic acid (48 g) were added to 3-aminobenzotrifluoride (75 g). The reaction mixture was stirred at 100° C. for one hour. The solution was cooled to room temperature. The pH of the solution was then adjusted to 10 with a 1 N aqueous sodium hydroxide solution. The solution was washed with diethyl ether, and the pH of the solution was then adjusted to 3 with 1 N hydrochloric acid. The solution was extracted with diethyl ether. The organic layer was washed with a saturated brine and then dried over anhydrous sodium sulfate. The solvent was distilled off under reduced pressure. The residue was purified by silica gel column chromatography (eluate; n-hexane:ethyl acetate=2:1). The title compound (82 g) was obtained as a white solid.

<Step 2> Synthesis of 7-trifluoromethyl-2,3-dihydroquinolin-4(1H)-one

The title compound (29 g) was obtained as yellow crystals from the compound (70 g) prepared in <Step 1> of Example 48 by the same process as that used in <Step 2> of Example 6.

<Step 3> Synthesis of 1-acetyl-7-trifluoromethyl-2,3-dihydroquinolin-4(1H)-one

Pyridine (0.6 mL) and acetyl chloride (0.4 mL) were added to a methylene chloride (20 mL) solution of the compound (1.0 g) prepared in <Step 2> of Example 48 under ice cooling. The reaction mixture was stirred at room temperature for one hour. Water was added to the reaction mixture, and the reaction mixture was then extracted with methylene chloride. The organic layer was sequentially washed with 1 N hydrochloric acid, water, a 1 N aqueous sodium hydroxide solution, and a saturated brine and then dried over anhydrous sodium sulfate. The solvent was then distilled off under reduced pressure. Subsequently, n-hexane was added to the residue to solidify the resulting product. The title compound (1.2 g) was obtained as a yellow solid.

<Step 4> Synthesis of ethyl 1-acetyl-7-trifluoromethyl-2,3-dihydroquinoline-4-(trimethylsilyloxy)-4-acetate A hexane (0.4 mL) solution of phosphazene base-P4-tert-butyl was added to a tetrahydrofuran (25 mL) solution of the compound (1.1 g) prepared in <Step 3> of Example 48 and ethyl trimethylsilylacetate (1.6 mL) at −78° C. The reaction mixture was stirred at room temperature for three hours. Water was added to the reaction mixture, and the solution was then extracted with ethyl acetate. The organic layer was washed with a saturated brine and then dried over anhydrous sodium sulfate. The solvent was distilled off under reduced pressure. The residue was purified by silica gel column chromatography (eluate; n-hexane:ethyl acetate=2:1). The title compound (530 mg) was obtained as a yellow solid.

<Step 5> Synthesis of 1-acetyl-7-trifluoromethyl-2,3-dihydroquinoline-4-hydroxy-4-acetic acid A 1 N aqueous sodium hydroxide solution (2 mL) was added to an ethanol (7 mL) solution of the compound (0.7 g) prepared in <Step 4> of Example 48, and the reaction mixture was stirred at room temperature for one hour. The ethanol was distilled off under reduced pressure. The reaction mixture was then neutralized with 1 N hydrochloric acid and extracted with ethyl acetate. The organic layer was washed with a saturated brine and then dried over anhydrous sodium sulfate. The solvent was distilled off under reduced pressure. Subsequently, n-hexane was added to the residue to solidify the resulting product. The title compound (0.5 g) was obtained as a white solid.

<Step 6> Synthesis of (E)-2-(1-acetyl-7-trifluoromethyl-2,3-dihydroquinolin-4(1H)-ylidene)acetic acid Concentrated sulfuric acid (one drop) was added to a toluene (40 mL) solution of the compound (0.5 g) prepared in <Step 5> of Example 48, and the reaction mixture was stirred at 60° C. for 30 minutes. The solution was left to cool. Water was then added to the solution, and the solution was extracted with ethyl acetate. The organic layer was washed with a saturated brine and then dried over anhydrous sodium sulfate. The solvent was distilled off under reduced pressure. The residue was purified by silica gel column chromatography (eluate; n-hexane:ethyl acetate=100:0 to 70:30). The title compound (70 mg) was obtained as a white solid.

<Step 7> Synthesis of (E)-2-(1-acetyl-7-trifluoromethyl-2,3-dihydroquinolin-4(1H)-ylidene)-N-(quinolin-7-yl)acetamide The title compound (29 mg) was obtained as pale yellow-white crystals from the compound (50 mg) prepared in <Step 6> of Example 48 and 7-aminoquinoline by the same process as that used in <Step 3> of Example 1.

The following compounds of Examples 49 to 58 were synthesized by a process the same as or similar to the process used in Example 48, using an alkyl halide, an acyl halide, an aryl halide, a heteroaryl halide, or the like.

Example 49

(E)-2-(7-trifluoromethyl-2,3-dihydroquinolin-4(1H)-ylidene)-N-(5,6,7,8-tetrahydroquinolin-7-yl)acetamide Example 50

(E)-2-(7-trifluoromethyl-2,3-dihydro-1-pentanoylquinolin-4(1H)-ylidene)-N-(quinolin-7-yl)acetamide Example 51

(E)-2-(1-(2-ethylbutanoyl)-7-trifluoromethyl-2,3-dihydroquinolin-4(1H)-ylidene)-N-(quinolin-7-yl)acetamide Example 52

(E)-2-(7-trifluoromethyl-2,3-dihydro-1-cyclohexanecarbonylquinolin-4(1H)-ylidene)-N-(quinolin-7-yl)acetamide Example 53

(E)-2-(7-trifluoromethyl-2,3-dihydro-1-(4-pyranoyl)quinolin-4(1H)-ylidene)-N-(quinolin-7-yl)acetamide Example 54

(E)-2-(7-trifluoromethyl-2,3-dihydro-1-benzoylquinolin-4(1H)-ylidene)-N-(quinolin-7-yl)acetamide Example 55

(E)-2-(7-trifluoromethyl-2,3-dihydro-1-nicotinoylquinolin-4(1H)-ylidene)-N-(quinolin-7-yl)acetamide Example 56

(E)-2-(1-(4-chlorophenyl)-7-trifluoromethyl-2,3-dihydro-4(1H)-ylidene)-N-(5,6,7,8-tetrahydroquinolin-7-yl)acetamide Example 57

(E)-2-(1-(4-chlorophenyl)-7-trifluoromethyl-2,3-dihydro-4(1H)-ylidene)-N-(quinolin-7-yl)acetamide Example 58

(E)-2-(7-trifluoromethyl-2,3-dihydro-1-(pyridin-3-yl)quinolin-4(1H)-ylidene)-N-(quinolin-7-yl)acetamide Example 59

Synthesis of (E)-2-(8-trifluoromethyl-3,4-dihydrobenzo[b]oxepin-5(2H)-ylidene)-N-(2-hydroxymethyl-1,3-benzothiazolo-5-yl)acetamide The title compound (27 mg) was obtained as a pale yellow solid from the compound (50 mg) prepared in <Step 5> of Example 9 and 2-hydroxymethyl-5-amino-1,3-benzothiazole by a process similar to the process used in Example 9.

Example 60

Synthesis of (E)-2-(8-trifluoromethyl-3,4-dihydrobenzo[b]oxepin-5(2H)-ylidene)-N-((2-hydroxyethyl)phenyl-1-yl)acetamide The title compound (48 mg) was obtained as a white solid from the compound (70 mg) prepared in <Step 5> of Example 9 and 2-(2-aminophenyl)ethyl alcohol by a process similar to the process used in Example 9.

Example 61

Synthesis of (E)-2-(8-trifluoromethyl-3,4-dihydrobenzo[b]oxepin-5(2H)-ylidene)-N-(7-oxo-5,6,7,8-tetrahydronaphthalen-1-yl)acetamide The title compound (102.1 mg) was obtained as a pale brown solid from 8-amino-3,4-dihydro-1H-naphthalen-2-one (50.6 mg) synthesized in accordance with the process described in PCT Publication No. 05/40100 pamphlet and the compound (110 mg) prepared in <Step 5> of Example 9 by a process similar to the process used in Example 9.

Example 62

Synthesis of (E)-2-(8-trifluoromethyl-3,4-dihydrobenzo[b]oxepin-5-(2H)-ylidene)-N-(7-hydroxy-5,6,7,8-tetrahydronaphthalen-1-yl)acetamide Sodium borohydride (2.5 mg) was added to a methanol solution of the compound (50 mg) obtained in Example 61 under ice cooling, and the reaction mixture was stirred for one hour. Water was added to the solution, and the solution was then extracted with ethyl acetate. The organic layer was washed with a saturated brine and then dried over anhydrous sodium sulfate. The solvent was distilled off under reduced pressure. Subsequently, n-hexane was added to the residue to solidify the resulting product. The title compound (43.6 mg) was obtained as a gray solid.

Examples 63 and 64

Optical resolution of (E)-2-(8-trifluoromethyl-3,4-dihydrobenzo[b]oxepin-5-(2H)-ylidene)-N-(7-hydroxy-5,6,7,8-tetrahydronaphthalen-1-yl)acetamide Optical resolution of the compound (140 mg) obtained in Example 62 was performed by preparative chromatography (column; CHIRALPAK AD-H manufactured by Daicel Chemical Industries, Ltd., solvent; EtOH:$Et_2NH$=100:0.1). Accordingly, enantiomers of the title compound were obtained as a first fraction (62 mg, white solid, 99.9% ee, retention time: 8.9 minutes, Example 63) and a second fraction (51 mg, white solid, 99.4% ee, retention time: 14.5 minutes, Example 64).

Example 65

Synthesis of (E)-2-(8-trifluoromethyl-3,4-dihydrobenzo[b]oxepin-5-(2H)-ylidene)-N-(trans-6,7-dihydroxy-5,6,7,8-tetrahydronaphthalen-1-yl)acetamide <Step 1> Synthesis of 1a,2,7,7a-tetrahydronaphtho[2,3-b]oxirene-3-amine The title compound was obtained by allowing N-(1a,2,7,7a-tetrahydronaphtho[2,3-b]oxiren-3-yl)trifluoroacetamide synthesized in accordance with the process described in Journal of Medicinal Chemistry, (1989), 32(6), pp. 1217-1230 to react with potassium carbonate in methanol.

<Step 2> Synthesis of (E)-2-(8-trifluoromethyl-3,4-dihydrobenzo[b]oxepin-5-(2H)-ylidene)-N-(1a,2,7,7a-tetrahydronaphtho[2,3-b]oxiren-3-yl)acetamide The title compound was obtained from the compound prepared in <Step 5> of Example 9 and the compound prepared in <Step 1> of Example 65 by a process similar to the process used in Example 9.

<Step 3> Synthesis of (E)-2-(8-trifluoromethyl-3,4-dihydrobenzo[b]oxepin-5-(2H)-ylidene)-N-(trans-6,7-dihydroxy-5,6,7,8-tetrahydronaphthalen-1-yl)acetamide Water (3.0 mL) and concentrated sulfuric acid (one drop) were added to a tetrahydrofuran (3.0 mL) solution of the compound (50 mg) prepared in <Step 2> of Example 65, and the reaction mixture was stirred at room temperature for eight hours. A saturated aqueous sodium hydrogencarbonate solution was added thereto, and the reaction mixture was then extracted with ethyl acetate. The organic layer was sequentially washed with water and a saturated brine and then dried over anhydrous sodium sulfate. The solvent was distilled off under reduced pressure. The residue was purified by silica gel column chromatography (eluate; n-hexane:ethyl acetate=70:30 to 30:70). Furthermore, diethyl ether was added to the purified product to solidify the product. The title compound (44 mg) was obtained as colorless crystals.

Example 66

Synthesis of (E)-2-(8-trifluoromethyl-3,4-dihydrobenzo[b]oxepin-5-(2H)-ylidene)-N-(cis-6,7-dihydroxy-5,6,7,8-tetrahydronaphthalen-1-yl)acetamide The title compound (54 mg) was obtained from the compound (50 mg) prepared in <Step 5> of Example 9 and 1-amino-cis-6,7-dihydroxy-5,6,7,8-tetrahydronaphthalene by the same process as that used in <Step 3> of Example 1.

Example 67

Synthesis of (E)-2-(8-trifluoromethyl-3,4-dihydrobenzo[b]oxepin-5(2H)-ylidene)-N-(3-hydroxy-2-oxo-1,2,3,4-tetrahydroquinolin-5-yl)acetamide The title compound (25.8 mg) was obtained as a white solid by conducting a reaction using 5-amino-3-hydroxy-3,4-dihydroquinolin-2(1H)-one (25.2 mg) synthesized in accordance with the process described in PCT Publication No. 05/044802 pamphlet and the compound (50 mg) prepared in <Step 5> of Example 9 by the same process as that used in <Step 3> of Example 1.

Example 68

Synthesis of (E)-2-(8-trifluoromethyl-3,4-dihydrobenzo[b]oxepin-5(2H)-ylidene)-N-(3-hydroxy-1,2,3,4-tetrahydroquinolin-5-yl)acetamide The title compound (13.9 mg) was obtained as a pale yellow solid from 5-amino-1,2,3,4-tetrahydroquinolin-3-ol (9.05 mg) synthesized in accordance with the process described in PCT Publication No. 05/044802 pamphlet and the compound (10 mg) prepared in <Step 5> of Example 9 by the same process as that used in <Step 3> of Example 1.

Example 69

Synthesis of (E)-2-(8-trifluoromethyl-3,4-dihydrobenzo[b]oxepin-5-(2H)-ylidene)-N-(1-methyl-3-hydroxy-1,2,3,4-tetrahydroquinolin-5-yl)acetamide First, a 36% aqueous formaldehyde solution (32 μL) and sodium triacetoxyborohydride (22.8 mg) were added to a dichloroethane (1 mL) solution of the compound (30 mg) obtained in Example 68 under ice cooling. The reaction mixture was stirred under ice cooling for one hour and at room temperature for 30 minutes. A saturated aqueous sodium hydrogencarbonate solution was added thereto, and the reaction mixture was then extracted with ethyl acetate. The organic layer was washed with a saturated brine and then dried over anhydrous sodium sulfate. The solvent was distilled off under reduced pressure. The residue was purified by silica gel column chromatography (eluate; n-hexane:ethyl acetate=3:2 to 1:1). The title compound (13.7 mg) was obtained as a pale yellow solid.

Example 70

Synthesis of (E)-2-(7-trifluoromethyl-chroman-4-ylidene)-N-(7-hydroxy-5,6,7,8-tetrahydronaphthalen-1-yl)acetamide Example 70

Process A

<Step 1> Synthesis of (E)-2-(7-trifluoromethyl-chroman-4-ylidene)-N-(5,6,7,8-tetrahydro-7-oxonaphthalen-1-yl)acetamide The title compound (52.0 mg) was obtained as a gray solid by conducting a reaction using 8-amino-3,4-dihydro-1H-naphthalen-2-one (59.2 mg) synthesized in accordance with the process described in PCT Publication No. 05/040100 pamphlet and the compound (100 mg) prepared in <Step 4> of Example 6 by a process similar to the process used in Example 9.

<Step 2> Synthesis of (E)-2-(7-trifluoromethyl-chroman-4-ylidene)-N-(7-hydroxy-5,6,7,8-tetrahydronaphthalen-1-yl)acetamide The title compound (30.3 mg) was obtained as a gray solid by conducting a reaction using the compound (40 mg) prepared in <Step 1> of Process A in Example 70 by the same process as that used in Example 62.

Example 70

Process B

<Step 1> Synthesis of 7-trifluoromethylchroman-4-one

Diphosphorus pentoxide (2.0 g) was added to methanesulfonic acid (18.0 g) little by little, and the mixture was stirred at room temperature for 2.5 hours. The compound (2.0 g) prepared in <Step 1> of Example 6 was added to the mixture over a period of 10 minutes at an outer temperature in the range of 70° C. to 80° C. The reaction mixture was stirred at the same temperature for 30 minutes and was then left to cool. The reaction mixture was poured into ice water (100 mL). The reaction mixture was extracted with ethyl acetate (100 mL and 20 mL). The combined organic layers were washed with water (15 mL), a half-saturated aqueous sodium hydrogencarbonate solution (15 mL), water (10 mL), and a saturated brine (10 mL). The organic layer was dried over anhydrous sodium sulfate and then concentrated under reduced pressure. The residue was purified by silica gel column chromatography (eluate; n-hexane:ethyl acetate=95:5). The title compound (1.7 g) was obtained as a yellow solid.

<Step 2> Synthesis of ethyl 7-trifluoromethyl-chroman-4-hydroxy-4-acetate

Zinc (300 mg) was suspended in tetrahydrofuran (4 mL). A toluene (8 mL) solution of the compound (500 mg) prepared in <Step 1> of Example 70 and ethyl bromoacetate (590 mg) were added dropwise to the suspension at an outer temperature of 70° C. The reaction mixture was refluxed for 30 minutes, and zinc (300 mg) and ethyl bromoacetate (590 mg) were added thereto. The reaction mixture was refluxed for 30 minutes and left to cool. Subsequently, 1 N hydrochloric acid was added to the reaction mixture. The reaction mixture was separated, and the resulting aqueous layer was then extracted with ethyl acetate. The organic layers were combined and washed with a saturated brine. The resulting organic layer was dried over anhydrous sodium sulfate and then concentrated under reduced pressure. The title compound (700 mg) was obtained as brown oil.

<Step 3> Synthesis of 7-trifluoromethyl-chroman-4-hydroxy-4-acetic acid

The title compound (590 mg) was obtained as a deep orange amorphous product from the compound (700 mg) prepared in <Step 2> of Example 70 by the same process as that used in <Step 5> of Example 48.

<Step 4> Synthesis of (E)-2-(7-trifluoromethyl-chroman-4-ylidene)acetic acid

The compound (120 mg) prepared in <Step 3> of Example 70 was suspended in toluene (1 mL), and concentrated sulfuric acid (one drop) was added thereto. The mixture was stirred at room temperature for 30 minutes. Water was added to the mixture, and the resulting mixture was extracted with ethyl acetate. The organic layers were combined and washed with a saturated brine. The resulting organic layer was dried over anhydrous sodium sulfate and then concentrated under reduced pressure. The product was solidified with diethyl ether and n-hexane, and then collected by filtration. The title compound (22 mg) was obtained as a pale yellow powder.

<Step 5> Synthesis of (E)-2-(7-trifluoromethyl-chroman-4-ylidene)-N-(5,6,7,8-tetrahydro-7-oxonaphthalen-1-yl)acetamide The title compound (52.0 mg) was obtained as a gray solid from 8-amino-3,4-dihydro-1H-naphthalen-2-one (59.2 mg) synthesized in accordance with the process described in PCT Publication No. 05/040100 pamphlet and the compound (100 mg) prepared in <Step 4> in Process B of Example 70 by a process similar to the process used in Example 9.

<Step 6> Synthesis of (E)-2-(7-trifluoromethyl-chroman-4-ylidene)-N-(7-hydroxy-5,6,7,8-tetrahydronaphthalen-1-yl)acetamide The title compound (30.3 mg) was obtained as a gray solid by conducting a reaction using the compound (40 mg) prepared in <Step 5> in Process B of Example 70 by the same process as that used in Example 62.

Examples 71 and 72

Optical resolution of (E)-2-(7-trifluoromethyl-chroman-4-ylidene)-N-(7-hydroxy-5,6,7,8-tetrahydronaphthalen-1-yl) acetamide Optical resolution of the compound (160 mg) obtained in Example 70 was performed by preparative chromatography (column; CHIRALPAK AD-H manufactured by Daicel Chemical Industries, Ltd., solvent; EtOH:$Et_2NH$=100:0.1). Accordingly, enantiomers of the title compound were obtained as a first fraction (69 mg, white solid, 99.9% ee, retention time: 9.9 minutes, Example 71) and a second fraction (71 mg, white solid, 99.3% ee, retention time: 17.3 minutes, Example 72).

Example 73

Synthesis of (E)-2-(1-cyclopentanecarbonyl-7-trifluoromethyl-2,3-dihydroquinolin-4(1H)-ylidene)-N-(quinolin-7-yl)acetamide <Step 1> Synthesis of 1-(tert-butoxycarbonyl)-7-trifluoromethyl-2,3-dihydroquinolin-4-(1H)-one Di-tert-butyl dicarbonate (9.23 g) and N,N-dimethylaminopyridine (0.20 g) were added to an acetonitrile (253 mL) solution of the compound (7.00 g) prepared in <Step 2> of Example 48, and the reaction mixture was stirred at an outer temperature of 40° C. for 1.5 hours. The solvent was distilled off under reduced pressure. The residue was purified by silica gel column chromatography (eluate; n-hexane:ethyl acetate). The title compound (8.73 g) was obtained as a white solid.

<Step 2> Synthesis of ethyl 1-(tert-butoxycarbonyl)-7-trifluoromethyl-2,3-dihydroquinoline-4-trimethylsilyloxy-4-acetate The title compound (10.00 g) was obtained as a pale yellow liquid from the compound (8.37 g) prepared in <Step 1> of Example 73 by the same process as that used in <Step 4> of Example 48.

<Step 3> Synthesis of 1-(tert-butoxycarbonyl)-7-trifluoromethyl-2,3-dihydroquinoline-4-hydroxy-4-acetic acid The title compound (7.95 g) was obtained as a yellow amorphous product from the compound (10.00 g) prepared in <Step 2> of Example 73 by the same process as that used in <Step 5> of Example 48.

<Step 4> Synthesis of (E)-2-(7-trifluoromethyl-2,3-dihydroquinolin-4(1H)-ylidene)-N-(quinolin-7-yl) acetamide A condensation product (1.6 g) was obtained using the compound (2.00 g) prepared in <Step 3> of Example 73 by the same process as that used in <Step 3> of Example 1. Furthermore, the title compound (647 mg) was obtained as a yellow powder by conducting a reaction by the same process as that used in <Step 4> of Example 48.

<Step 5> Synthesis of (E)-2-(1-cyclopentanecarbonyl-7-trifluoromethyl-2,3-dihydroquinolin-4(1H)-ylidene)-N-(quinolin-7-yl)acetamide The compound (20 mg) prepared in <Step 4> of Example 73 was dissolved in pyridine (1.2 mL), and N,N-dimethylaminopyridine was added in a catalitic amount thereto. Cyclopentanecarbonyl chloride (28 μL) was added to the reaction mixture at an outer temperature of 80° C. The reaction mixture was stirred at the same temperature for one hour. Water (1 mL) and a saturated aqueous sodium hydrogencarbonate solution (1 mL) were added to the reaction mixture, and the solution was extracted with ethyl acetate (20 mL). The organic layer was washed with a saturated brine and then dried over anhydrous sodium sulfate. The solvent was distilled off under reduced pressure. The residue was purified by column chromatography (eluate; n-hexane:ethyl acetate). The title compound (16.6 mg) was obtained as a pale yellow powder.

The following compounds of Examples 74 to 96 were synthesized by a process the same as or similar to the process used in Example 73.

Example 74

(E)-2-(1-pentanoyl-7-trifluoromethyl-2,3-dihydroquinolin-4(1H)-ylidene)-N-(7-hydroxynaphthalen-1-yl)acetamide Example 75

(E)-2-(1-cyclobutanecarbonyl-7-trifluoromethyl-2,3-dihydroquinolin-4(1H)-ylidene)-N-(quinolin-7-yl)acetamide Example 76

(E)-2-(1-(3,3-dimethylbutanoyl)-7-trifluoromethyl-2,3-dihydroquinolin-4(1H)-ylidene)-N-(quinolin-7-yl)acetamide Example 77

(E)-2-(1-(3-methylbutanoyl)-7-trifluoromethyl-2,3-dihydroquinolin-4(1H)-ylidene)-N-(quinolin-7-yl)acetamide Example 78

(E)-2-(1-(4-methylpentanoyl)-7-trifluoromethyl-2,3-dihydroquinolin-4(1H)-ylidene)-N-(quinolin-7-yl)acetamide Example 79

(E)-2-(1-(3-methylpentanoyl)-7-trifluoromethyl-2,3-dihydroquinolin-4(1H)-ylidene)-N-(quinolin-7-yl)acetamide Example 80

(E)-2-(1-(2-methylpentanoyl)-7-trifluoromethyl-2,3-dihydroquinolin-4(1H)-ylidene)-N-(quinolin-7-yl)acetamide Example 81

(E)-2-(1-(2,2-dimethylpentanoyl)-7-trifluoromethyl-2,3-dihydroquinolin-4(1H)-ylidene)-N-(quinolin-7-yl)acetamide Example 82

(E)-2-(1-cyclopentanecarbonyl-7-trifluoromethyl-2,3-dihydroquinolin-4(1H)-ylidene)-N-(7-hydroxy-5,6,7,8-tetrahydronaphthalen-1-yl)acetamide Example 83

(E)-2-(1-pentanoyl-7-trifluoromethyl-2,3-dihydroquinolin-4(1H)-ylidene)-N-(7-hydroxy-5,6,7,8-tetrahydronaphthalen-1-yl)acetamide Example 84

(E)-2-(1-cyclobutanecarbonyl-7-trifluoromethyl-2,3-dihydroquinolin-4(1H)-ylidene)-N-(7-hydroxy-5,6,7,8-tetrahydronaphthalen-1-yl)acetamide Example 85

(E)-2-(1-(4,4-difluorocyclohexanecarbonyl)-7-trifluoromethyl-2,3-dihydroquinolin-4(1H)-ylidene)-N-(7-hydroxy-5,6,7,8-tetrahydronaphthalen-1-yl)acetamide Example 86

(E)-2-(1-(4-methylpentanoyl)-7-trifluoromethyl-2,3-dihydroquinolin-4(1H)-ylidene)-N-(7-hydroxy-5,6,7,8-tetrahydronaphthalen-1-yl)acetamide Example 87

(E)-2-(1-(3-methylbutanoyl)-7-trifluoromethyl-2,3-dihydroquinolin-4(1H)-ylidene)-N-(7-hydroxy-5,6,7,8-tetrahydronaphthalen-1-yl)acetamide Example 88

(E)-2-(1-(3-fluorocyclopentanecarbonyl)-7-trifluoromethyl-2,3-dihydroquinolin-4(1H)-ylidene)-N-(7-hydroxy-5,6,7,8-tetrahydronaphthalen-1-yl)acetamide Example 89

(E)-2-(1-(1-methylcyclopropanecarbonyl)-7-trifluoromethyl-2,3-dihydroquinolin-4(1H)-ylidene)-N-(7-hydroxy-5,6,7,8-tetrahydronaphthalen-1-yl)acetamide Example 90

(E)-2-(1-(1-methylcyclobutanecarbonyl)-7-trifluoromethyl-2,3-dihydroquinolin-4(1H)-ylidene)-N-(7-hydroxy-5,6,7,8-tetrahydronaphthalen-1-yl)acetamide Example 91

(E)-2-(1-(4,4,4-trifluorobutanoyl)-7-trifluoromethyl-2,3-dihydroquinolin-4(1H)-ylidene)-N-(7-hydroxy-5,6,7,8-tetrahydronaphthalen-1-yl)acetamide Example 92

(E)-2-(1-(3,3,3-trifluoropropanoyl)-7-trifluoromethyl-2,3-dihydroquinolin-4(1H)-ylidene)-N-(7-hydroxy-5,6,7,8-tetrahydronaphthalen-1-yl)acetamide Example 93

(E)-2-(1-(5,5,5-trifluoropentanoyl)-7-trifluoromethyl-2,3-dihydroquinolin-4(1H)-ylidene)-N-(7-hydroxy-5,6,7,8-tetrahydronaphthalen-1-yl)acetamide Example 94

(E)-2-(1-phenylacetyl-7-trifluoromethyl-2,3-dihydroquinolin-4(1H)-ylidene)-N-(7-hydroxy-5,6,7,8-tetrahydronaphthalen-1-yl)acetamide Example 95

(E)-2-(1-(2,2-difluorobutanoyl)-7-trifluoromethyl-2,3-dihydroquinolin-4(1H)-ylidene)-N-(7-hydroxy-5,6,7,8-tetrahydronaphthalen-1-yl)acetamide Example 96

(E)-2-(1-(2-fluoro-2-methylpropanoyl)-7-trifluoromethyl-2,3-dihydroquinolin-4(1H)-ylidene)-N-(7-hydroxy-5,6,7,8-tetrahydronaphthalen-1-yl)acetamide The following compounds of Examples 97 to 189 were also synthesized by a process the same as or similar to the process used in one of Examples 1 to 96.

Example 97

(E)-2-(7-trifluoromethyl-2,3-dihydro-1-cyclohexylquinolin-4(1H)-ylidene)-N-(quinolin-7-yl)acetamide Example 98

(E)-2-(7-trifluoromethyl-2,3-dihydro-1-(4-methylbenzenesulfonyl)quinolin-4(1H)-ylidene)-N-(quinolin-7-yl)acetamide Example 99

(E)-2-(7-trifluoromethyl-2,3-dihydro-1-cyclopropanecarbonylquinolin-4(1H)-ylidene)-N-(quinolin-7-yl)acetamide Example 100

(E)-2-(7-trifluoromethyl-2,3-dihydro-1-(3-methoxypropanoyl)quinolin-4(1H)-ylidene)-N-(quinolin-7-yl)acetamide Example 101

(E)-2-(7-trifluoromethyl-2,3-dihydro-1-(3-(carbomethoxy)propanoyl)quinolin-4(1H)-ylidene)-N-(quinolin-7-yl)acetamide Example 102

(E)-2-(7-trifluoromethyl-2,3-dihydro-1-(cyclopentylacetyl)quinolin-4(1H)-ylidene)-N-(quinolin-7-yl)acetamide Example 103

(E)-2-(7-trifluoromethyl-2,3-dihydro-1-(4-(N,N-dimethylamino)butanoyl)quinolin-4(1H)-ylidene)-N-(quinolin-7-yl)acetamide Example 104

(E)-2-(7-trifluoromethyl-2,3-dihydro-1-(3-pyrrolidinecarbonyl)quinolin-4(1H)-ylidene)-N-(quinolin-7-yl)acetamide Example 105

(E)-2-(7-trifluoromethyl-2,3-dihydro-1-cyclopropanecarbonylquinolin-4(1H)-ylidene)-N-(7-hydroxy-5,6,7,8-tetrahydronaphthalen-1-yl)acetamide Example 106

(E)-2-(7-trifluoromethyl-2,3-dihydroquinolin-4(1H)-ylidene)-N-(7-hydroxy-5,6,7,8-tetrahydronaphthalen-1-yl)acetamide Example 107

(E)-2-(7-trifluoromethyl-2,3-dihydro-1-pentanoylquinolin-4(1H)-ylidene)-N-(3,4-dihydro-3-hydroxy(1H)quinolin-2-on-5-yl)acetamide Example 108

(E)-2-(7-trifluoromethyl-2,3-dihydro-1-pentanoylquinolin-4(1H)-ylidene)-N-(3-hydroxy-1,2,3,4-tetrahydroquinolin-5-yl)acetamide Example 109

(E)-2-(7-trifluoromethyl-2,3-dihydro-1-((2,2-dimethylcyclopropane)carbonyl)quinolin-4(1H)-ylidene)-N-(7-hydroxy-5,6,7,8-tetrahydronaphthalen-1-yl)acetamide Example 110

(E)-2-(7-trifluoromethyl-2,3-dihydro-1-((4-(trifluoromethyl)cyclohexane)carbonyl)quinolin-4(1H)-ylidene)-N-(7-hydroxy-5,6,7,8-tetrahydronaphthalen-1-yl)acetamide Example 111

(E)-2-(7-trifluoromethyl-2,3-dihydro-1-(2-furancarbonyl)quinolin-4(1H)-ylidene)-N-(7-hydroxy-5,6,7,8-tetrahydronaphthalen-1-yl)acetamide Example 112

(E)-2-(1-(1-hydroxycyclopropanecarbonyl)-7-trifluoromethyl-2,3-dihydroquinolin-4(1H)-ylidene)-N-(7-hydroxy-5,6,7,8-tetrahydronaphthalen-1-yl)acetamide Example 113

(E)-2-(1-(3,3-difluoroazetidine-1-carbonyl)-7-trifluoromethyl-2,3-dihydroquinolin-4(1H)-ylidene)-N-(7-hydroxy-5,6,7,8-tetrahydronaphthalen-1-yl)acetamide Example 114

(E)-2-(1-formyl-7-trifluoromethyl-2,3-dihydroquinolin-4(1H)-ylidene)-N-(7-hydroxy-5,6,7,8-tetrahydronaphthalen-1-yl)acetamide Example 115

(E)-2-(1-(1-fluorocyclopentanecarbonyl)-7-trifluoromethyl-2,3-dihydroquinolin-4(1H)-ylidene)-N-(7-hydroxy-5,6,7,8-tetrahydronaphthalen-1-yl)acetamide Example 116

(E)-2-(1-(3,3-difluorobutanoyl)-7-trifluoromethyl-2,3-dihydroquinolin-4(1H)-ylidene)-N-(7-hydroxy-5,6,7,8-tetrahydronaphthalen-1-yl)acetamide Example 117

(E)-2-(1-(3,3-difluoropentanoyl)-7-trifluoromethyl-2,3-dihydroquinolin-4(1H)-ylidene)-N-(7-hydroxy-5,6,7,8-tetrahydronaphthalen-1-yl)acetamide Example 118

(E)-2-(1-(3,3-difluorocyclobutanecarbonyl)-7-trifluoromethyl-2,3-dihydroquinolin-4(1H)-ylidene)-N-(7-hydroxy-5,6,7,8-tetrahydronaphthalen-1-yl)acetamide Example 119

(E)-N-(7-oxo-5,6,7,8-tetrahydronaphthalen-1-yl)-2-(7-trifluoromethyl-chroman-4-ylidene)acetamide Example 120

(E)-N-(7-hydroxynaphthalen-1-yl)-2-(7-trifluoromethyl-chroman-4-ylidene)acetamide Example 121

(E)-N-(3-hydroxy-2-oxo-1,2,3,4-tetrahydroquinolin-5-yl)-2-(7-trifluoromethyl-chroman-4-ylidene)acetamide Example 122

(E)-N-(3-hydroxy-1,2,3,4-tetrahydroquinolin-5-yl)-2-(7-trifluoromethyl-chroman-4-ylidene)acetamide Example 123

(E)-N-((Z)-7-hydroxyimino-5,6,7,8-tetrahydronaphthalen-1-yl)-2-(7-trifluoromethyl-chroman-4-ylidene)acetamide Example 124

(E)-N-((E)-7-hydroxyimino-5,6,7,8-tetrahydronaphthalen-1-yl)-2-(7-trifluoromethyl-chroman-4-ylidene)acetamide Example 125

(E)-N-(3-hydroxy-chroman-5-yl)-2-(7-trifluoromethyl-chroman-4-ylidene)acetamide

Example 126

(E)-N-(6-hydroxynaphthalen-1-yl)-2-(8-trifluoromethyl-3,4-dihydrobenzo[b]oxepin-5(2H)-ylidene)acetamide Example 127

(E)-2-(8-trifluoromethyl-3,4-dihydrobenzo[b]oxepin-5(2H)-ylidene)-N-(quinolin-7-yl)acetamide methanesulfonate Example 128

(E)-2-(8-trifluoromethyl-3,4-dihydrobenzo[b]oxepin-5(2H)-ylidene)-N-(7-hydroxynaphthalen-2-yl)acetamide Example 129

(E)-2-(8-trifluoromethyl-3,4-dihydrobenzo[b]oxepin-5(2H)-ylidene)-N-(7-methoxynaphthalen-1-yl)acetamide Example 130

(E)-2-(8-trifluoromethyl-3,4-dihydrobenzo[b]oxepin-5(2H)-ylidene)-N-(1-(2-methoxyethyl)-1,2,3,4-tetrahydroquinolin-7-yl)acetamide Example 131

(E)-2-(8-trifluoromethyl-3,4-dihydrobenzo[b]oxepin-5(2H)-ylidene)-N-(1-(2-(4-morpholino)ethyl)-1,2,3,4-tetrahydroquinolin-7-yl)acetamide Example 132

(E)-2-(8-trifluoromethyl-3,4-dihydrobenzo[b]oxepin-5(2H)-ylidene)-N-(1-(2-(N,N-dimethylamino)ethyl)-1,2,3,4-tetrahydroquinolin-7-yl)acetamide Example 133

(E)-2-(8-trifluoromethyl-3,4-dihydrobenzo[b]oxepin-5(2H)-ylidene)-N-(3,4-dihydro-1H-quinolin-2-on-7-yl)acetamide Example 134

(E)-2-(8-trifluoromethyl-3,4-dihydrobenzo[b]oxepin-5(2H)-ylidene)-N-(2-quinolon-7-yl)acetamide Example 135

(E)-2-(8-trifluoromethyl-3,4-dihydrobenzo[b]oxepin-5(2H)-ylidene)-N-(3-methoxy-5-(trifluoromethyl)phenyl)acetamide Example 136

(E)-2-(8-trifluoromethyl-3,4-dihydrobenzo[b]oxepin-5(2H)-ylidene)-N-(4-chloro-3-(trifluoromethyl)phenyl)acetamide Example 137

(E)-2-(8-trifluoromethyl-3,4-dihydrobenzo[b]oxepin-5(2H)-ylidene)-N-(indol-6-yl)acetamide Example 138

(E)-2-(8-trifluoromethyl-3,4-dihydrobenzo[b]oxepin-5(2H)-ylidene)-N-(indol-5-yl)acetamide Example 139

(E)-2-(8-trifluoromethyl-3,4-dihydrobenzo[b]oxepin-5(2H)-ylidene)-N-(4-methanesulfonylphenyl)acetamide Example 140

(E)-2-(8-trifluoromethyl-3,4-dihydrobenzo[b]oxepin-5(2H)-ylidene)-N-(3-methanesulfonylphenyl)acetamide Example 141

(E)-2-(8-trifluoromethyl-3,4-dihydrobenzo[b]oxepin-5(2H)-ylidene)-N-(5-(trifluoromethyl)pyridin-2-yl)acetamide Example 142

(E)-2-(8-trifluoromethyl-3,4-dihydrobenzo[b]oxepin-5(2H)-ylidene)-N-(3,4-dihydro-2H-benzo[b]dioxepin-7-yl)acetamide Example 143

(E)-2-(8-trifluoromethyl-3,4-dihydrobenzo[b]oxepin-5(2H)-ylidene)-N-(2,2-difluoro-1,3-benzodioxol-5-yl)acetamide Example 144

(E)-2-(8-trifluoromethyl-3,4-dihydrobenzo[b]oxepin-5(2H)-ylidene)-N-(1,3-benzodioxol-5-yl)acetamide Example 145

(E)-2-(8-trifluoromethyl-3,4-dihydrobenzo[b]oxepin-5(2H)-ylidene)-N-(2-oxoindolin-6-yl)acetamide Example 146

(E)-2-(8-trifluoromethyl-3,4-dihydrobenzo[b]oxepin-5(2H)-ylidene)-N-(2H-benzo[1,4]oxazin-3(4H)-on-6-yl)acetamide Example 147

(E)-2-(8-trifluoromethyl-3,4-dihydrobenzo[b]oxepin-5(2H)-ylidene)-N-(2-(2-chlorophenyl)ethyl)acetamide Example 148

(E)-2-(8-trifluoromethyl-3,4-dihydrobenzo[b]oxepin-5(2H)-ylidene)-N-(4H-1,3-benzodioxin-6-yl)acetamide Example 149

(E)-2-(8-trifluoromethyl-3,4-dihydrobenzo[b]oxepin-5(2H)-ylidene)-N-(1-methylindol-5-yl)acetamide Example 150

(E)-2-(8-trifluoromethyl-3,4-dihydrobenzo[b]oxepin-5(2H)-ylidene)-N-(5-hydroxynaphthalen-1-yl)acetamide Example 151

(E)-2-(8-trifluoromethyl-3,4-dihydrobenzo[b]oxepin-5(2H)-ylidene)-N-(1-(2-hydroxyethyl)indol-6-yl)acetamide Example 152

(E)-2-(8-trifluoromethyl-3,4-dihydrobenzo[b]oxepin-5 (2H)-ylidene)-N-(1-methylindol-6-yl)acetamide Example 153

(E)-2-(8-trifluoromethyl-3,4-dihydrobenzo[b]oxepin-5 (2H)-ylidene)-N-(1-(1-oxopentyl)-1,2,3,4-tetrahydroquinolin-7-yl)acetamide Example 154

(E)-2-(8-trifluoromethyl-3,4-dihydrobenzo[b]oxepin-5 (2H)-ylidene)-N-(1-((1-oxo-2-acetoxy)ethyl)-1,2,3,4-tetrahydroquinolin-7-yl)acetamide Example 155

(E)-2-(8-trifluoromethyl-3,4-dihydrobenzo[b]oxepin-5 (2H)-ylidene)-N-(1-trifluoroacetyl-1,2,3,4-tetrahydroquinolin-7-yl)acetamide Example 156

(E)-2-(8-trifluoromethyl-3,4-dihydrobenzo[b]oxepin-5 (2H)-ylidene)-N-(3-(hydroxymethyl)indol-4-yl)acetamide Example 157

(E)-2-(8-trifluoromethyl-3,4-dihydrobenzo[b]oxepin-5 (2H)-ylidene)-N-(indan-1-on-6-yl)acetamide Example 158

(E)-2-(8-trifluoromethyl-3,4-dihydrobenzo[b]oxepin-5 (2H)-ylidene)-N-(indan-1-on-4-yl)acetamide Example 159

(E)-2-(8-trifluoromethyl-3,4-dihydrobenzo[b]oxepin-5 (2H)-ylidene)-N-(3,4-dihydro-1H-quinolin-2-on-6-yl)acetamide Example 160

(E)-2-(8-trifluoromethyl-3,4-dihydrobenzo[b]oxepin-5 (2H)-ylidene)-N-(indan-1-ol-4-yl)acetamide Example 161

(E)-2-(8-trifluoromethyl-3,4-dihydrobenzo[b]oxepin-5 (2H)-ylidene)-N-(indan-1-acetoxy-4-yl)acetamide Example 162

(E)-2-(8-trifluoromethyl-3,4-dihydrobenzo[b]oxepin-5 (2H)-ylidene)-N-(indan-2-acetoxy-4-yl)acetamide Example 163

(E)-2-(8-trifluoromethyl-3,4-dihydrobenzo[b]oxepin-5 (2H)-ylidene)-N-(indan-2-ol-4-yl)acetamide Example 164

(E)-2-(8-trifluoromethyl-3,4-dihydrobenzo[b]oxepin-5 (2H)-ylidene)-N-(1-(2-hydroxyethyl)indol-5-yl)acetamide)

Example 165

(E)-2-(8-trifluoromethyl-3,4-dihydrobenzo[b]oxepin-5 (2H)-ylidene)-N-(3-hydroxymethyl-2,3-dihydro-1,4-benzodioxin-6-yl)acetamide Example 166

(E)-2-(8-trifluoromethyl-3,4-dihydrobenzo[b]oxepin-5 (2H)-ylidene)-N-(2,3-dihydro-isoindol-1-on-6-yl)acetamide Example 167

(E)-2-(8-trifluoromethyl-3,4-dihydrobenzo[b]oxepin-5 (2H)-ylidene)-N-(1,2,3,4-tetrahydroquinolin-7-yl)acetamide Example 168

(E)-2-(8-trifluoromethyl-3,4-dihydrobenzo[b]oxepin-5 (2H)-ylidene)-N-(1-(2-hydroxyacetyl)-1,2,3,4-tetrahydroquinolin-7-yl)acetamide Example 169

(E)-2-(8-trifluoromethyl-3,4-dihydrobenzo[b]oxepin-5 (2H)-ylidene)-N-(1a,2,7,7a-tetrahydronaphtho[b]oxiren-3-yl)acetamide Example 170

(E)-2-(8-trifluoromethyl-3,4-dihydrobenzo[b]oxepin-5 (2H)-ylidene)-N-(7-dimethylamino-5,6,7,8-tetrahydronaphthalen-1-yl)acetamide Example 171

(E)-2-(8-trifluoromethyl-3,4-dihydrobenzo[b]oxepin-5 (2H)-ylidene)-N-(2-quinolon-8-yl)acetamide Example 172

(E)-2-(8-trifluoromethyl-3,4-dihydrobenzo[b]oxepin-5 (2H)-ylidene)-N-(2-oxo-1,2,3,4-tetrahydroquinolin-8-yl)acetamide Example 173

(E)-2-(8-trifluoromethyl-3,4-dihydrobenzo[b]oxepin-5 (2H)-ylidene)-N-(3-hydroxyquinolin-5-yl)acetamide Example 174

(E)-2-(8-trifluoromethyl-3,4-dihydrobenzo[b]oxepin-5 (2H)-ylidene)-N-(1-hydroxy-1,2,3,4-tetrahydronaphthalen-8-yl)acetamide Example 175

(E)-2-(8-trifluoromethyl-3,4-dihydrobenzo[b]oxepin-5 (2H)-ylidene)-N-(indan-1-ol-6-yl)acetamide Example 176

(E)-2-(8-trifluoromethyl-3,4-dihydrobenzo[b]oxepin-5 (2H)-ylidene)-N-(2-hydroxyethyl-2,3-dihydro-isoindol-1-on-6-yl)acetamide Example 177

(E)-2-(8-trifluoromethyl-3,4-dihydrobenzo[b]oxepin-5(2H)-ylidene)-N-(3,4-dihydro-(2H)-isoquinolin-1-on-7-yl)acetamide Example 178

(E)-2-(8-trifluoromethyl-3,4-dihydrobenzo[b]oxepin-5(2H)-ylidene)-N-(1-methyl-2-oxo-1,2,3,4-tetrahydroquinolin-7-yl)acetamide Example 179

(E)-2-(8-trifluoromethyl-3,4-dihydrobenzo[b]oxepin-5(2H)-ylidene)-N-(8-hydroxymethyl-5,6,7,8-tetrahydronaphthalen-2-yl)acetamide Example 180

(E)-2-(8-trifluoromethyl-3,4-dihydrobenzo[b]oxepin-5(2H)-ylidene)-N-(6-hydroxyquinolin-4-yl)acetamide Example 181

(E)-2-(8-trifluoromethyl-3,4-dihydrobenzo[b]oxepin-5(2H)-ylidene)-N-(7-hydroxy-1,2,3,4-tetrahydronaphthalen-1-yl)acetamide Example 182

(E)-2-(8-trifluoromethyl-3,4-dihydrobenzo[b]oxepin-5(2H)-ylidene)-N-(7-(4,6-dimethoxy-[1,3,5]triazin-2-yloxy))-1,2,3,4-tetrahydronaphthalen-1-yl)acetamide Example 183

(E)-2-(8-trifluoromethyl-3,4-dihydrobenzo[b]oxepin-5(2H)-ylidene)-N-(3-hydroxy-chroman-5-yl)acetamide Example 184

(E)-2-(1-(2,2-difluorobutanoyl)-7-trifluoromethyl-2,3-dihydroquinolin-4(1H)-ylidene)-N-(3-hydroxy-1,2,3,4-tetrahydroquinolin-5-yl)acetamide Example 185

(E)-2-(1-(2,2-difluorobutanoyl)-7-trifluoromethyl-2,3-dihydroquinolin-4(1H)-ylidene)-N-(3-hydroxy-2-oxo-1,2,3,4-tetrahydroquinolin-5-yl)acetamide Example 186

(E)-2-(7-trifluoromethyl-chroman-4-ylidene)-N-(2-acetyl-1,2,3,4-tetrahydroisoquinolin-8-yl)acetamide Example 187

(E)-2-(7-trifluoromethyl-chroman-4-ylidene)-N-(1,2,3,4-tetrahydroisoquinolin-8-yl)acetamide Example 188

(E)-2-(7-trifluoromethyl-chroman-4-ylidene)-N-(3-hydroxy-2-carboxymethylphenyl-1-yl)acetamide Example 189

(E)-2-(7-trifluoromethyl-chroman-4-ylidene)-N-(3-hydroxy-2-carbamoylmethylphenyl-1-yl)acetamide Example 190

(E)-2-(8-trifluoromethyl-1-pentanoyl-1,2,3,4-tetrahydro-5H-benzo[b]azepin-5-ylidene)-N-(7-hydroxy-5,6,7,8-tetrahydronaphthalen-1-yl)acetamide <Step 1> Synthesis of methyl 2-nitro-4-trifluoromethyl benzoate Thionyl chloride (19 mL) was added to a methanol (150 mL) solution of 2-nitro-4-trifluoromethylbenzoic acid (25.0 g), and the reaction mixture was refluxed for 27 hours. The solvent was distilled off under reduced pressure. Water was added to the residue, and the solution was extracted with diethyl ether. The organic layer was sequentially washed with water and a saturated brine and then dried over anhydrous sodium sulfate. The solvent was distilled off under reduced pressure. The title compound (24.6 g) was obtained as colorless oil.

<Step 2> Synthesis of methyl 2-amino-4-trifluoromethyl benzoate

First, 10% Pd—C (2.5 g) was added to a methanol (490 mL) solution of the compound (24.6 g) prepared in <Step 1> of Example 190, and the mixture was stirred in a hydrogen atmosphere at room temperature for 20 hours. The reaction mixture was subjected to Celite filtration. The solvent was then distilled off under reduced pressure. The title compound (21.3 g) was obtained as gray-white crystals.

<Step 3> Synthesis of 4-methyl-N-(2-methoxycarbonyl-5-trifluoromethylphenyl)benzenesulfonylamide Tosyl chloride (12.4 g) was added to a pyridine (40 mL) solution of the compound (13.0 g) prepared in <Step 2> of Example 190. The reaction mixture was stirred at room temperature for two hours. Water was added to the reaction mixture, and the reaction mixture was extracted with ethyl acetate. The organic layer was sequentially washed with water, 1 N hydrochloric acid, and a saturated brine and then dried over anhydrous sodium sulfate. The solvent was distilled off under reduced pressure. Subsequently, n-hexane was added to the residue to solidify the resulting product. The title compound (18.9 g) was obtained as pale yellow crystals.

<Step 4> Synthesis of 4-methyl-N,N'-(3-methoxycarbonylpropyl)-(2-methoxycarbonyl-5-trifluoromethylphenyl)benzenesulfonylamide The compound (132 g) prepared in <Step 3> of Example 190 was added to an N,N-dimethylformamide (1.2 L) suspension of sodium hydride (15.6 g) under ice cooing, and the mixture was stirred at room temperature for 30 minutes and at 40° C. for 10 minutes. Methyl-4-bromobutyrate (75 g) was added to the mixture, and the reaction mixture was stirred at 90° C. for two hours. Water was added to the reaction mixture, and the mixture was extracted with diethyl ether. The organic layer was sequentially washed with water and a saturated brine and then dried over anhydrous sodium sulfate. The solvent was distilled off under reduced pressure. Subsequently, n-hexane was added to the residue to solidify the resulting product. The title compound (99.0 g) was obtained as colorless crystals.

<Step 5> Synthesis of 1-(toluene-4-sulfonyl)-8-trifluoromethyl-1,2,3,4-tetrahydrobenzo[b]azepin-5-one A toluene (500 mL) solution of the compound (89.0 g) prepared in <Step 4> of Example 190 was added dropwise to a toluene (1.0 L) suspension of potassium tert-butoxide (42.0 g) over a period of three hours, and the reaction mixture was then stirred for 10 minutes. The reaction mixture was neutralized with 1 N hydrochloric acid under ice cooling and then extracted with ethyl acetate. The organic layer was sequentially washed with water and a saturated brine and then dried over anhydrous sodium sulfate. The solvent was distilled off under reduced pressure, and a residue was obtained. Dimethyl sulfoxide (1.0 L) and water (35 mL) were added to the residue, and the mixture was stirred in an argon atmosphere at 150° C. for 90 minutes. A saturated brine (2.5 L) was added to the mixture, and the mixture was then extracted with ethyl acetate. The organic layer was sequentially washed with water and a saturated brine and then dried over anhydrous sodium sulfate. The solvent was distilled off under reduced pressure. The residue was purified by silica gel column chromatography (eluate; n-hexane:ethyl acetate=100:0 to 75:25). The title compound (50.0 g) was obtained as brown-white crystals.

<Step 6> Synthesis of 8-trifluoromethyl-1,2,3,4-tetrahydrobenzo[b]azepin-5-one

Polyphosphoric acid (60 g) was added to the compound (5.9 g) prepared in <Step 5> of Example 190, and the reaction mixture was stirred at 80° C. for 30 minutes. The reaction mixture was poured into water (2.5 L), and the solution was extracted with diethyl ether. The organic layer was sequentially washed with water, a saturated aqueous sodium hydrogencarbonate solution, and a saturated brine and then dried over anhydrous sodium sulfate. The solvent was distilled off under reduced pressure. The residue was purified by silica gel column chromatography (eluate; n-hexane:ethyl acetate=100:0 to 50:50). The title compound (3.0 g) was obtained as green-white crystals.

<Step 7> Synthesis of 1-pentanoyl-8-trifluoromethyl-1,2,3,4-tetrahydrobenzo[b]azepin-5-one The title compound (280 mg) was obtained as pale yellow oil from the compound (200 mg) prepared in <Step 6> of Example 190 and valeroyl chloride (0.12 mL) by the same process as that used in <Step 3> of Example 48.

<Step 8> Synthesis of ethyl (E)-2-(1-pentanoyl-8-trifluoromethyl-1,2,3,4-tetrahydro-5H-benzo[b]azepin-5-ylidene)acetate The title compound (47 mg) was obtained as colorless oil from the compound (280 mg) prepared in <Step 7> of Example 190 and ethyl diphenylphosphonoacetate (570 mg) by the same process as that used in <Step 4> of Example 9.

<Step 9> Synthesis of (E)-2-(1-pentanoyl-8-trifluoromethyl-1,2,3,4-tetrahydro-5H-benzo[b]azepin-5-ylidene)acetic acid The title compound (74 mg) was obtained as colorless crystals from the compound (134 mg) prepared in <Step 8> of Example 190 and lithium hydroxide (22 mg) by the same process as that used in <Step 5> of Example 9.

<Step 10> Synthesis of (E)-2-(1-pentanoyl-8-trifluoromethyl-1,2,3,4-tetrahydro-5H-benzo[b]azepin-5-ylidene)-N-(7-oxo-5,6,7,8-tetrahydronaphthalen-1-yl)acetamide The title compound (20.0 mg) was obtained as colorless crystals from the compound (37.3 mg) prepared in <Step 9> of Example 190 and 7-oxo-5,6,7,8-tetrahydro-1-naphthylamine (17.5 mg) by a process similar to the process used in <Step 3> of Example 1.

<Step 11> Synthesis of (E)-2-(1-pentanoyl-8-trifluoromethyl-1,2,3,4-tetrahydro-5H-benzo[b]azepin-5-ylidene)-N-(7-hydroxy-5,6,7,8-tetrahydronaphthalen-1-yl)acetamide The title compound (8.0 mg) was obtained as a colorless amorphous product from the compound (20.0 mg) prepared in <Step 10> of Example 190 and sodium borohydride (1.0 mg) by the same process as that used in Example 62.

Example 191

(E)-2-(8-trifluoromethyl-1,2,3,4-tetrahydro-5H-benzo[b]azepin-5-ylidene)-N-(quinolin-7-yl)acetamide <Step 1> Synthesis of ethyl (E)-2-(8-trifluoromethyl-1,2,3,4-tetrahydro-5H-benzo[b]azepin-5-ylidene)acetate The title compound (1.0 g) was obtained as colorless crystals from the compound (4.0 g) prepared in <Step 6> of Example 190 and ethyl diphenylphosphonoacetate (5.9 g) by the same process as that used in <Step 4> of Example 9.

<Step 2> Synthesis of (E)-2-(8-trifluoromethyl-1,2,3,4-tetrahydro-5H-benzo[b]azepin-5-ylidene)acetic acid The title compound (820 mg) was obtained as colorless crystals from the compound (1.0 g) prepared in <Step 1> of Example 191 and lithium hydroxide (210 mg) by the same process as that used in <Step 5> of Example 9.

<Step 3> Synthesis of (E)-2-(8-trifluoromethyl-1,2,3,4-tetrahydro-5H-benzo[b]azepin-5-ylidene)-N-(quinolin-7-yl)acetamide The title compound (200 mg) was obtained as yellow-white crystals from the compound (220 mg) prepared in <Step 2> of Example 191 and 7-aminoquinoline (130 mg) by a process similar to the process used in <Step 3> of Example 1.

Example 192

(E)-2-(1-pentanoyl-8-trifluoromethyl-1,2,3,4-tetrahydro-5H-benzo[b]azepin-5-ylidene)-N-(quinolin-7-yl)acetamide The title compound (3.8 mg) was obtained as pale yellow crystals from the compound (20.0 mg) prepared in <Step 3> of Example 191 and valeroyl chloride (7.2 μL) by the same process as that used in <Step 3> of Example 48.

Example 193

(E)-2-(1-cyclopentanecarbonyl-8-trifluoromethyl-1,2,3,4-tetrahydro-5H-benzo[b]azepin-5-ylidene)-N-(quinolin-7-yl)acetamide The title compound (12.3 mg) was obtained as pale yellow crystals from the compound (20.0 mg) prepared in <Step 3> of Example 191 and cyclopentanecarbonyl chloride (7.3 μL) by the same process as that used in <Step 3> of Example 48.

Example 194

(E)-2-(1-(4-methylbenzenesulfonyl)-8-trifluoromethyl-1,2,3,4-tetrahydro-5H-benzo[b]azepin-5-ylidene)-N-(quinolin-7-yl)acetamide The title compound (7.6 mg) was obtained as colorless crystals from the compound (20.0 mg) prepared in <Step 3> of Example 191 and tosyl chloride (11.5 mg) by the same process as that used in <Step 3> of Example 48.

Example 195

(E)-2-(1-acetyl-8-trifluoromethyl-1,2,3,4-tetrahydro-5H-benzo[b]azepin-5-ylidene)-N-(quinolin-7-yl)acetamide The title compound (8.5 mg) was obtained as colorless crystals from the compound (20.0 mg) prepared in <Step 3> of Example 191 and acetyl chloride (18 μL) by the same process as that used in <Step 3> of Example 48.

Example 196

(E)-2-(1-methyl-8-trifluoromethyl-1,2,3,4-tetrahydro-5H-benzo[b]azepin-5-ylidene)-N-(quinolin-7-yl)acetamide Concentrated sulfuric acid (123.0 mg) was added to an aqueous solution prepared by adding water (0.4 mL) to a 37% aqueous formalin solution (8.1 mg) under ice cooling. A tetrahydrofuran (1.0 mL) solution of the compound (20.0 mg) prepared in <Step 3> of Example 191 and sodium borohydride (9.6 mg) was added dropwise to the reaction mixture at the same temperature. The reaction mixture was neutralized with a saturated aqueous sodium hydrogencarbonate solution and extracted with ethyl acetate. The organic layer was sequentially washed with water, a saturated aqueous sodium hydrogencarbonate solution, and a saturated brine and then dried over anhydrous sodium sulfate. The solvent was distilled off under reduced pressure. Subsequently, n-hexane was added to the residue to solidify the resulting product. The title compound (13.3 mg) was obtained as yellow crystals.

Example 197

(E)-2-(1-cyclopentylmethyl-8-trifluoromethyl-1,2,3,4-tetrahydro-5H-benzo[b]azepin-5-ylidene)-N-(quinolin-7-yl)acetamide The title compound (25.0 mg) was obtained as yellow-white crystals from the compound (30.0 mg) prepared in <Step 3> of Example 191 and cyclopentanecarbaldehyde (14.8 mg) by the same process as that used in Example 196.

Example 198

(E)-2-(1-methyl-8-trifluoromethyl-1,2,3,4-tetrahydro-5H-benzo[b]azepin-5-ylidene)-N-(7-hydroxynaphthalen-1-yl)acetamide <Step 1> Synthesis of (E)-2-(1-methyl-8-trifluoromethyl-1,2,3,4-tetrahydro-5H-benzo[b]azepin-5-ylidene)acetic acid The title compound (360.0 mg) was obtained as yellow crystals from (E)-2-(8-trifluoromethyl-1,2,3,4-tetrahydro-5H-benzo[b]azepin-5-ylidene)acetic acid (400 mg) and a 37% aqueous formalin solution (88.5 mg) by the same process as that used in Example 196.

<Step 2> Synthesis of (E)-2-(1-methyl-8-trifluoromethyl-1,2,3,4-tetrahydro-5H-benzo[b]azepin-5-ylidene)-N-(7-hydroxynaphthalen-1-yl)acetamide The title compound (57.0 mg) was obtained as yellow-white crystals from the compound (100 mg) prepared in <Step 1> of Example 198 and 7-hydroxy-1-naphthylamine (95.0 mg) by a process similar to the process used in <Step 3> of Example 1.

Example 199

(E)-2-(1-methyl-8-trifluoromethyl-1,2,3,4-tetrahydro-5H-benzo[b]azepin-5-ylidene)-N-(7-hydroxy-5,6,7,8-tetrahydronaphthalen-1-yl)acetamide The title compound (40.0 mg) was obtained as yellow-white crystals from the compound (100 mg) prepared in <Step 1> of Example 198 and 8-amino-1,2,3,4-tetrahydro-2-naphthol (56.0 mg) by a process similar to the process used in <Step 3> of Example 1.

Example 200

(E)-2-(1-(3-chloro-5-hydroxymethyl-pyridin-2-yl)-7-trifluoromethyl-2,3-dihydroquinolin-4(1H)-ylidene)-N-(7-hydroxy-5,6,7,8-tetrahydronaphthalen-1-yl)acetamide <Step 1> Synthesis of 2,3-dichloro-5-(((tetrahydro-2H-pyran-2-yl)oxy)methyl)pyridine 3,4-Dihydro-2H-pyran (1.1 mL) and tin (II) chloride dihydrate (0.38 g) were added to a chloroform solution of 2,3-dichloro-5-hydroxymethylpyridine (1.5 g), and the reaction mixture was stirred at room temperature for 63 hours. The reaction mixture was filtered, and the solvent was then distilled off under reduced pressure. The residue was purified by silica gel column chromatography (eluate; n-hexane:ethyl acetate=100:0 to 90:10). The title compound (1.7 g) was obtained as colorless oil.

<Step 2> Synthesis of (E)-2-(7-trifluoromethyl-2,3-dihydroquinolin-4(1H)-ylidene)-N-(7-tert-butyldimethylsilyloxy-5,6,7,8-tetrahydronaphthalen-1-yl)acetamide First, tert-butyldimethylsilyl chloride (800.0 mg), imidazole (360.0 mg), and N,N-dimethylaminopyridine (25.8 mg) were added to an N,N-dimethylformamide (17.0 mL) solution of the compound (850 mg) of Example 106. The reaction mixture was stirred at room temperature for one hour. Water was added to the solution, and the solution was extracted with ethyl acetate. The organic layer was sequentially washed with water and a saturated brine and then dried over anhydrous sodium sulfate. The solvent was distilled off under reduced pressure. The residue was purified by silica gel column chromatography (eluate; n-hexane:ethyl acetate=100:0 to 90:10). The title compound (700.0 mg) was obtained as a yellow amorphous product.

<Step 3> Synthesis of (E)-2-(1-(3-chloro-5-hydroxymethyl-pyridin-2-yl)-7-trifluoromethyl-2,3-dihydroquinolin-4(1H)-ylidene)-N-(7-tert-butyldimethylsilyloxy-5,6,7,8-tetrahydronaphthalen-1-yl) acetamide A compound (55.8 mg) prepared in <Step 1> of Example 247, palladium acetate (8.7 mg), cesium carbonate (130.0 mg), and 2,2'-bis(diphenylphosphino)-1,1'-binaphthyl (BINAP) (36.2 mg) were added to a toluene (2.0 mL) solution of the compound (100.0 mg) prepared in <Step 2> of Example 200, and the reaction mixture was refluxed for two hours. The reaction mixture was subjected to Celite filtration. The solvent was then distilled off under reduced pressure. The residue was purified by silica gel column chromatography (eluate; n-hexane:ethyl acetate=100:0 to 50:50). The title compound (69.0 mg) was obtained as a pale yellow amorphous product.

<Step 4> Synthesis of (E)-2-(1-(3-chloro-5-hydroxymethyl-pyridin-2-yl)-7-trifluoromethyl-2,3-dihydroquinolin-4(1H)-ylidene)-N-(7-hydroxy-5,6,7,8-tetrahydronaphthalen-1-yl)acetamide A 4 N hydrogen chloride-ethyl acetate solution (1.0 mL) was added to an ethyl acetate (3.0 mL) solution of the compound (60.0 mg) prepared in <Step 3> of Example 200, and the reaction mixture was stirred at room temperature. Methanol (0.5 mL) was added thereto, and the reaction mixture was neutralized with a saturated aqueous sodium hydrogencarbonate solution. The reaction mixture was then extracted with ethyl acetate. The organic layer was sequentially washed with water and a saturated brine and then dried over anhydrous sodium sulfate. The solvent was distilled off under reduced pressure. The residue was purified by silica gel column chromatography (eluate; n-hexane:ethyl acetate=100:0 to 0:100). The title compound (33.0 mg) was obtained as pale yellow crystals.

The following compounds of Examples 201 to 216 were synthesized by a process the same as or similar to the process used in Example 1.

Example 201

(E)-2-(7-trifluoromethyl-chroman-4-ylidene)-N-(2-hydroxyethyl-1,2,3,4-tetrahydroisoquinolin-8-yl)acetamide Example 202

(E)-2-(7-trifluoromethyl-chroman-4-ylidene)-N-(5,6,7,8-tetrahydronaphthalen-1-yl)acetamide Example 203

(E)-2-(7-trifluoromethyl-chroman-4-ylidene)-N-(3-(3-hydroxymethyl)-pyridin-2-yl)phenyl)acetamide Example 204

(E)-2-(7-trifluoromethyl-chroman-4-ylidene)-N-(2-methylthieno[2,3-c]pyridin-3-yl)acetamide Example 205

(E)-2-(7-trifluoromethyl-chroman-4-ylidene)-N-(5-(2-hydroxymethylphenyl)-pyridin-3-yl)acetamide Example 206

(E)-2-(7-isopropyl-chroman-4-ylidene)-N-(7-hydroxy-5,6,7,8-tetrahydronaphthalen-1-yl)acetamide Example 207

(E)-2-(7-isopropyl-chroman-4-ylidene)-N-(3-hydroxy-1,2,3,4-tetrahydroquinolin-5-yl)acetamide Example 208

(E)-2-(7-chloro-chroman-4-ylidene)-N-(7-hydroxy-5,6,7,8-tetrahydronaphthalen-1-yl)acetamide Example 209

(E)-2-(7-chloro-chroman-4-ylidene)-N-(3-hydroxy-1,2,3,4-tetrahydroquinolin-5-yl)acetamide Example 210

(E)-2-(7-trifluoromethoxy-chroman-4-ylidene)-N-(7-hydroxy-5,6,7,8-tetrahydronaphthalen-1-yl)acetamide Example 211

(E)-2-(7-trifluoromethoxy-chroman-4-ylidene)-N-(3-hydroxy-1,2,3,4-tetrahydroquinolin-5-yl)acetamide Example 212

(E)-2-(7-(1,1,2,2-tetrafluoroethoxy)-chroman-4-ylidene)-N-(7-hydroxy-5,6,7,8-tetrahydronaphthalen-1-yl)acetamide Example 213

(E)-2-(7-(1,1,2,2-tetrafluoroethoxy)-chroman-4-ylidene)-N-(3-hydroxy-1,2,3,4-tetrahydroquinolin-5-yl)acetamide Example 214

(E)-2-(6-fluoro-7-trifluoromethyl-chroman-4-ylidene)-N-(7-hydroxy-5,6,7,8-tetrahydronaphthalen-1-yl)acetamide Example 215

(E)-2-(6-fluoro-7-trifluoromethyl-chroman-4-ylidene)-N-(3-hydroxy-1,2,3,4-tetrahydroquinolin-5-yl)acetamide Example 216

(E)-2-(7-trifluoromethyl-chroman-4-ylidene)-N-(2-hydroxymethyl-1,3-benzothiazolo-5-yl)acetamide Example 217

(E)-2-(7-trifluoromethyl-3,3-difluorochroman-4-ylidene)-N-(7-hydroxy-5,6,7,8-tetrahydronaphthalen-1-yl) acetamide <Step 1> Synthesis of 7-trifluoromethyl-3,3-difluorochroman-4-one Manganese bromide (9.9 g) was added to potassium bis (trimethylsilyl)amide (69.0 mL, 0.5 M toluene solution) at −78° C., and the reaction mixture was stirred at the same temperature for 15 minutes. A tetrahydrofuran (120 mL) solution of the compound (2.49 g) prepared in <Step 2> of Example 6 was added dropwise to the reaction mixture, and the reaction mixture was further stirred at the same temperature for 30 minutes. Subsequently, N-fluorobenzenesulfonimide (14.5 g) was added thereto, and the temperature of the reaction mixture was increased to 0° C. over a period of four hours. The reaction mixture was then neutralized with 1 N hydrochloric acid and extracted with diethyl ether. The organic layer was sequentially washed with water and a saturated brine and then dried over anhydrous sodium sulfate. The solvent was distilled off under reduced pressure. The residue was purified by silica gel column chromatography (eluate; n-hexane:ethyl acetate=100:0 to 90:10). The title compound (1.0 g) was obtained as pale yellow oil.

<Step 2> Synthesis of ethyl (E)-2-(7-trifluoromethyl-3,3-difluorochroman-4-ylidene)acetate The title compound (348 mg) was obtained as pale yellow oil from the compound (1.0 g) prepared in <Step 1> of Example 217 and triethylphosphonoacetate (1.7 mL) by the same process as that used in <Step 1> of Example 1.

<Step 3> Synthesis of (E)-2-(7-trifluoromethyl-3,3-difluorochroman-4-ylidene)acetic acid The title compound (174 mg) was obtained as pale yellow crystals from the compound (330 mg) prepared in <Step 2> of Example 217 by the same process as that used in <Step 2> of Example 1.

<Step 4> Synthesis of (E)-2-(7-trifluoromethyl-3,3-difluorochroman-4-ylidene)-N-(7-hydroxy-5,6,7,8-tetrahydronaphthalen-1-yl)acetamide The title compound (67.7 mg) was obtained as colorless crystals from the compound (30.0 mg) prepared in <Step 3> of Example 217 and 8-amino-1,2,3,4-tetrahydro-2-naphthol (41.6 mg) by the same process as that used in <Step 3> of Example 1.

Example 218 and Example 219

Optical resolution of (E)-2-(8-trifluoromethyl-3,4-dihydrobenzo[b]oxepin-5(2H)-ylidene)-N-(3-hydroxy-1,2,3,4-tetrahydroquinolin-5-yl)acetamide Optical resolution of the compound (200.0 mg) obtained in Example 68 was performed by preparative chromatography (column; CHIRALPAK AD-H manufactured by Daicel Chemical Industries, Ltd., solvent; EtOH). Accordingly, enantiomers of the title compound were obtained as a first fraction (88 mg, pale yellow solid, 99.9% ee, retention time: 8.1 minutes, Example 218) and a second fraction (94 mg, pale yellow solid, 99.2% ee, retention time: 15.0 minutes, Example 219).

The following compounds of Examples 220 to 234 were synthesized by a process the same as or similar to the process used in Example 9.

Example 220

(E)-2-(8-trifluoromethyl-3,4-dihydrobenzo[b]oxepin-5(2H)-ylidene)-N-(7-hydroxy-7-methyl-5,6,7,8-tetrahydronaphthalen-1-yl)acetamide Example 221

(E)-2-(8-trifluoromethyl-3,4-dihydrobenzo[b]oxepin-5(2H)-ylidene)-N-(2-methylthieno[2,3-c]pyridin-3-yl)acetamide Example 222

(E)-2-(8-trifluoromethyl-3,4-dihydrobenzo[b]oxepin-5(2H)-ylidene)-N-(6-hydroxychroman-4-yl)acetamide Example 223

(E)-2-(8-trifluoromethyl-3,4-dihydrobenzo[b]oxepin-5(2H)-ylidene)-N-(2-(3-hydroxy-pyridin-2-yl)phenyl)acetamide Example 224

(E)-2-(8-trifluoromethyl-3,4-dihydrobenzo[b]oxepin-5(2H)-ylidene)-N-(3-chloro-5-hydroxymethyl-2-pyridyl)acetamide Example 225

(E)-2-(8-trifluoromethyl-3,4-dihydrobenzo[b]oxepin-5(2H)-ylidene)-N-(2-hydroxy-1,1'-biphenyl-2'-yl)acetamide Example 226

(E)-2-(8-trifluoromethyl-3,4-dihydrobenzo[b]oxepin-5(2H)-ylidene)-N-(2-(7-hydroxy-5,6,7,8-tetrahydronaphthalen-1-yl)ethyl)acetamide Example 227

(E)-2-(8-trifluoromethyl-3,4-dihydrobenzo[b]oxepin-5(2H)-ylidene)-N-(2-(7-hydroxy-5,6,7,8-tetrahydronaphthalen-1-yl)propyl)acetamide Example 228

(E)-2-(8-trifluoromethyl-3,4-dihydrobenzo[b]oxepin-5(2H)-ylidene-N-(2-(3-hydroxypyrrolidin-1-yl)phenyl)acetamide Example 229

(E)-2-(8-trifluoromethyl-3,4-dihydrobenzo[b]oxepin-5(2H)-ylidene-N-(3-(2-hydroxymethylpyrrolidin-1-yl)phenyl)acetamide Example 230

(E)-2-(8-trifluoromethyl-3,4-dihydrobenzo[b]oxepin-5(2H)-ylidene-N-(6-hydroxy-1,2,3,4-tetrahydroquinolin-4-yl)acetamide Example 231

(E)-2-(8-trifluoromethyl-3,4-dihydrobenzo[b]oxepin-5(2H)-ylidene-N-(4-(2-hydroxyacetyl)-3,4-dihydro-2H-benzo[b][1,4]oxazin-6-yl)acetamide Example 232

(E)-2-(8-trifluoromethyl-3,4-dihydrobenzo[b]oxepin-5(2H)-ylidene-N-(4-(2-hydroxypropanoyl)-3,4-dihydro-2H-benzo[b][1,4]oxazin-6-yl)acetamide Example 233

(E)-2-(8-trifluoromethyl-3,4-dihydrobenzo[b]oxepin-5(2H)-ylidene-N-(4-(2-hydroxyethyl)-3,4-dihydro-2H-benzo[b][1,4]oxazin-6-yl)acetamide Example 234

(E)-2-(8-trifluoromethyl-3,4-dihydrobenzo[b]oxepin-5(2H)-ylidene)-N-(4-(2-hydroxyethyl)-2H-1,4-benzoxazin-3(4H)-on-6-yl)acetamide Example 235

Synthesis of (E)-2-(8-trifluoromethyl-3,4-dihydrobenzo[c]isooxepin-5(1H)-ylidene)-N-(7-hydroxy-5,6,7,8-tetrahydronaphthalen-1-yl)acetamide <Step 1> Synthesis of 4-trifluoromethyl-tert-butylphenyl carbamate First, di-tert-butyl dicarbamate (30 mL) was added to a tetrahydrofuran (50 mL) solution of 4-trifluoromethylaniline (10 mL). The reaction mixture was then refluxed for 10 hours. The solvent was distilled off under reduced pressure. Water was added to the residue to solidify the resulting product. The product was then washed with hexane. The title compound (18.7 g) was obtained as colorless crystals.

<Step 2> Synthesis of 4-trifluoromethyl-2-(tert-butoxycarbonylamino)benzoic acid Tetramethylethylenediamine (32 mL) and n-butyllithium (131 mL) were added to a tetrahydrofuran (190 mL) solution of the compound (18.5 g) prepared in <Step 1> of Example 235 at −78° C. The temperature of the reaction mixture was increased to −30° C., and the reaction mixture was stirred at the same temperature for five hours. The temperature of the reaction mixture was again decreased to −78° C., and dry ice (32 g) was added thereto. The temperature of the reaction mixture was increased to room temperature, and the reaction mixture was stirred for 12 hours. The reaction mixture was neutralized with 1 N hydrochloric acid and was extracted with ethyl acetate. The organic layer was washed with a saturated brine and then dried over anhydrous sodium sulfate. The solvent was distilled off under reduced pressure. The residue was purified by silica gel column chromatography (eluate; n-hexane:methanol=100:0 to 90:10). The title compound (18.7 g) was obtained as a white solid.

<Step 3> Synthesis of 4-trifluoromethylanthranilic acid

First, 1 N hydrochloric acid (60 mL) was added to an ethanol (230 mL) solution of the compound (26.0 g) prepared in <Step 2> of Example 235, and the reaction mixture was refluxed for three hours. The reaction mixture was neutralized with 1 N aqueous sodium hydroxide solution and was extracted with ethyl acetate. The organic layer was washed with a saturated brine and then dried over anhydrous sodium sulfate. The solvent was distilled off under reduced pressure. The title compound (13.2 g) was obtained as yellow crystals.

<Step 4> Synthesis of 2-iodo-5-trifluoromethylbenzoic acid

Sodium hypochlorite (5.25 g) dissolved in water (12 mL) was added dropwise to a suspension prepared by suspending the compound (13.0 g) prepared in <Step 3> of Example 235 in concentrated hydrochloric acid (15 mL) and water (80 mL) under ice cooling. The reaction mixture was stirred at the same temperature for 30 minutes and then added to an aqueous solution prepared by dissolving potassium iodide (21 g) in water (30 mL) and concentrated sulfuric acid (5 mL). The reaction mixture was stirred at 100° C. for two hours. The reaction mixture was then extracted with ethyl acetate. The organic layer was sequentially washed with a saturated aqueous sodium sulfite solution and a saturated brine and then dried over anhydrous sodium sulfate. The solvent was distilled off under reduced pressure. The title compound (19.1 g) was obtained as yellow crystals.

<Step 5> Synthesis of 2-iodo-5-(trifluoromethyl)phenyl methanol

A borane-tetrahydrofuran solution (120 mL) was added to a tetrahydrofuran (50 mL) solution of the compound (17.2 g) prepared in <Step 4> of Example 235 under ice cooling, and the reaction mixture was then stirred at room temperature for three hours. Water (200 mL) was added to the reaction mixture, and the solvent was distilled off under reduced pressure. The residue was extracted with ethyl acetate. The organic layer was washed with a saturated brine and then dried over anhydrous sodium sulfate. The solvent was distilled off under reduced pressure. The title compound (16.0 g) was obtained as yellow crystals.

<Step 6> Synthesis of 2-bromomethyl-1-iodo-4-trifluoromethylbenzene

Phosphorus tribromide (5 mL) was added to a diethyl ether (130 mL) solution of the compound (16.0 g) prepared in <Step 5> of Example 235 under ice cooling, and the solution was then stirred at room temperature for 12 hours. Water (200 mL) was added to the solution, and the solution was then extracted with diethyl ether. The organic layer was sequentially washed with a saturated aqueous sodium hydrogencarbonate solution and a saturated brine, and then dried over anhydrous sodium sulfate. The solvent was distilled off under reduced pressure. The title compound (16.0 g) was obtained as yellow crystals.

<Step 7> Synthesis of 2-(3-butenoxy)methyl-1-iodo-4-trifluoromethylbenzene

Sodium hydride (2.3 g) was added to a tetrahydrofuran (200 mL) solution of 3-buten-1-ol (5.2 mL) under ice cooling, and the reaction mixture was then stirred at the same temperature for 30 minutes. The compound (14.8 g) prepared in <Step 6> of Example 235 and tetra-n-butylammonium iodide (1.5 g) were added thereto, and the reaction mixture was stirred at room temperature for 12 hours. Water was added to the reaction mixture, and the reaction mixture was then extracted with ethyl acetate. The organic layer was washed with a saturated brine and then dried over anhydrous sodium sulfate. The solvent was distilled off under reduced pressure. The residue was purified by silica gel column chromatography (eluate; n-hexane:ethyl acetate=100:0 to 95:5). The title compound (13.9 g) was obtained as yellow oil.

<Step 8> Synthesis of 2-(4-(1,1-dimethylethyloxy-carbonyl)-3-butenoxy)methyl-1-iodo-4-trifluoromethylbenzene The title compound (11.9 g) was obtained as yellow oil from the compound (12.8 g) prepared in <Step 7> of Example 235 and tert-butyl acrylate (53 mL) by the same process as that used in <Step 2> of Alternative process C in Example 9.

<Step 9> Synthesis of tert-butyl (E)-(8-trifluoromethyl-3,4-dihydro-1H-benzo[c]isooxepin-5-ylidene) acetate Palladium acetate (1.74 g), triphenylphosphine (4.1 g), and silver carbonate (7.1 g) were added to a tetrahydrofuran (130 mL) solution of the compound (11.8 g) prepared in <Step 8> of Example 235. The reaction mixture was stirred at 60° C. for four hours. The reaction mixture was subjected to Celite filtration, and the solvent was then distilled off under reduced pressure. The residue was purified by silica gel column chromatography (eluate; n-hexane:ethyl acetate=100:0 to 95:5). The title compound (7.6 g) was obtained as yellow oil.

<Step 10> Synthesis of (E)-(8-trifluoromethyl-3,4-dihydro-1H-benzo[c]isooxepin-5-ylidene)acetic acid The compound (7.5 g) prepared in <Step 9> of Example 235 was dissolved in formic acid (100 mL), and the solution was stirred for two hours. Water (300 mL) was added to the reaction mixture. The precipitate was collected by filtration and was then dried under reduced pressure. The title compound (5.5 g) was obtained as colorless crystals.

<Step 11> Synthesis of (E)-2-(8-trifluoromethyl-3,4-dihydrobenzo[c]isooxepin-5(1H)-ylidene)-N-(7-hydroxy-5,6,7,8-tetrahydronaphthalen-1-yl)acetamide The title compound (3.0 g) was obtained as pale pink crystals from the compound (3.0 g) prepared in <Step 10> of Example 235 and 8-amino-1,2,3,4-tetrahydro-2-naphthol (1.8 g) by a process similar to the process used in <Step 3> of Example 1.

Example 236

(E)-2-(8-trifluoromethyl-3,4-dihydrobenzo[c]isooxepin-5(1H)-ylidene)-N-(3-hydroxy-1,2,3,4-tetrahydroquinolin-5-yl)acetamide The title compound (41 mg) was obtained as colorless crystals from the compound (100 mg) prepared in <Step 10> of Example 235 and 5-amino-1,2,3,4-tetrahydroquinolin-3-ol (60 mg) by a process similar to the process used in <Step 3> of Example 1.

Example 237

(E)-2-(7-trifluoromethyl-isochroman-4-ylidene)-N-(7-hydroxy-5,6,7,8-tetrahydronaphthalen-1-yl)acetamide <Step 1> Synthesis of 2-(3-propenoxy)methyl-1-iodo-4-trifluoromethylbenzene Sodium hydride (100 mg) was added to a tetrahydrofuran (20.0 mL) solution of the compound (500 mg) prepared in <Step 6> of Example 235, and the reaction mixture was stirred at room temperature for 30 minutes. Allyl bromide (0.2 mL) and tetra-n-butylammonium iodide (62 mg) were added thereto, and the reaction mixture was stirred at 40° C. for two hours. Water was added to the reaction mixture, and the reaction mixture was then extracted with ethyl acetate. The organic layer was washed with a saturated brine and then dried over anhydrous sodium sulfate. The solvent was distilled off under reduced pressure. The residue was purified by silica gel column chromatography (eluate; n-hexane:ethyl acetate=100:0 to 95:5). The title compound (430 mg) was obtained as colorless oil.

<Step 2> Synthesis of 2-(4-methoxycarbonyl-3-propenoxy)methyl-1-iodo-4-trifluoromethylbenzene The title compound (280 mg) was obtained as colorless oil from the compound (350 mg) prepared in <Step 1> of Example 237 and methyl acrylate (1.9 mL) by the same process as that used in <Step 2> of Alternative process C in Example 9.

<Step 3> Synthesis of 2-(4-hydroxycarbonyl-3-propenoxy)methyl-1-iodo-4-trifluoromethylbenzene The title compound (253 mg) was obtained as colorless crystals from the compound (280 mg) prepared in <Step 2> of Example 237 by the same process as that used in <Step 2> of Example 1.

<Step 4> Synthesis of (E)-(7-trifluoromethyl-isochroman-4-ylidene)acetic acid

The title crude compound (270 mg) was obtained as a green solid from the compound (240 mg) prepared in <Step 3> of Example 237 by the same process as that used in <Step 9> of Example 235.

<Step 5> Synthesis of (E)-2-(7-trifluoromethyl-isochroman-4-ylidene)-N-(7-hydroxy-5,6,7,8-tetrahydronaphthalen-1-yl)acetamide The title compound (35 mg) was obtained as colorless crystals from the crude compound (120 mg) prepared in <Step 4> of Example 237 and 8-amino-1,2,3,4-tetrahydro-2-naphthol (77.6 mg) by the same process as that used in <Step 3> of Example 1.

Example 238

(E)-2-(7-trifluoromethyl-3,4-dihydro-2H-pyrano[2,3-b]pyridin-4-ylidene)-N-(7-hydroxy-5,6,7,8-tetrahydronaphthalen-1-yl)acetamide <Step 1> Synthesis of 2-chloro-3-iodo-6-trifluoromethylpyridine A hexane solution of n-butyl lithium (3.8 mL) was added to a tetrahydrofuran (10 mL) solution of 2,2,6,6-tetramethylpyrrolidine (0.93 mL) at −78° C. The reaction mixture was stirred at the same temperature for 30 minutes. A tetrahydrofuran (5 mL) solution of 2-chloro-6-trifluoromethylpyridine (1.0 g) was added dropwise to the reaction mixture, and the solution was further stirred at −78° C. for 30 minutes. A tetrahydrofuran (5 mL) solution of iodine (1.54 g) was added to the solution, and the temperature of the solution was increased to the room temperature. An aqueous sodium sulfite solution was added to the solution, and the solution was extracted with diethyl ether. The organic layer was sequentially washed with an aqueous sodium sulfite solution, an aqueous sodium hydrogencarbonate solution, and a saturated brine and then dried over anhydrous sodium sulfate. The solvent was distilled off under reduced pressure. The residue was purified by silica gel column chromatography (eluate; n-hexane:ethyl acetate=100:0 to 95:5). The title compound (750 mg) was obtained as pale yellow oil.

<Step 2> Synthesis of 2-(3-butenoxy)-3-iodo-6-trifluoromethylpyridine

The title compound (220 mg) was obtained as pale yellow oil from the compound (300 mg) prepared in <Step 1> of Example 238 and 3-buten-1-ol (0.13 mL) by a process the same as or similar to the process used in <Step 7> of Example 235.

<Step 3> Synthesis of 2-(4-(1,1-dimethylethyloxycarbonyl)-3-butenoxy)-3-iodo-6-trifluoromethylpyridine The title compound (390 mg) was obtained as pale yellow oil from the compound (220 mg) prepared in <Step 2> of Example 238 and tert-butyl acrylate (1.9 mL) by the same process as that used in <Step 2> of Alternative process C in Example 9.

<Step 4> Synthesis of 5-(3-iodo-6-trifluoromethylpyridin-2-yl)-oxy-2-pentenoic acid The title compound (110 mg) was obtained as colorless crystals from the compound (280 mg) prepared in <Step 3> of Example 238 by a process the same as or similar to the process used in <Step 10> of Example 235.

<Step 5> Synthesis of (E)-2-(7-trifluoromethyl-3,4-dihydro-2H-pyrano[2,3-b]pyridin-4-ylidene)acetic acid The title compound (7 mg) was obtained as colorless crystals from the compound (110 mg) prepared in <Step 4> of Example 238 by a process the same as or similar to the process used in <Step 9> of Example 235.

<Step 6> Synthesis of (E)-2-(7-trifluoromethyl-3,4-dihydro-2H-pyrano[2,3-b]pyridin-4-ylidene)-N-(7-hydroxy-5,6,7,8-tetrahydronaphthalen-1-yl)acetamide The title compound (6 mg) was obtained as colorless crystals from the compound (7 mg) prepared in <Step 5> of Example 238 and 8-amino-1,2,3,4-tetrahydro-2-naphthol (7 mg) by a process the same as or similar to the process used in <Step 3> of Example 1.

Example 239

Synthesis of (E)-2-(8-trifluoromethyl-2,3,4,5-tetrahydrooxepino[2,3-b]pyridin-5-ylidene)-N-(7-hydroxy-5,6,7,8-tetrahydronaphthalen-1-yl)acetamide <Step 1> Synthesis of 2-(4-pentenoxy)-3-iodo-6-trifluoromethylpyridine The title compound (700 mg) was obtained as pale yellow oil from the compound (1.2 g) prepared in <Step 1> of Example 238 and 4-penten-1-ol (0.5 g) by a process the same as or similar to the process used in <Step 7> of Example 235.

<Step 2> Synthesis of 2-((1,1-dimethylethyloxycarbonyl)-3-butenoxy)-3-iodo-6-trifluoromethylpyridine The title compound (680 mg) was obtained as colorless oil from the compound (700 mg) prepared in <Step 1> of Example 239 and methyl acrylate (3.5 mL) by the same process as that used in <Step 2> of Alternative process C in Example 9

<Step 3> Synthesis of methyl (E)-2-(8-trifluoromethyl-2,3,4,5-tetrahydrooxepino[2,3-b]pyridin-5-ylidene)acetate The title compound (37 mg) was obtained as pale yellow crystals from the compound (100 mg) prepared in <Step 2> of Example 239 by a process the same as or similar to the process used in <Step 9> of Example 235.

<Step 4> Synthesis of (E)-2-(8-trifluoromethyl-2,3,4,5-tetrahydrooxepino[2,3-b]pyridin-5-ylidene)acetic acid The title compound (30.0 mg) was obtained as pale yellow crystals from the compound (35.0 mg) prepared in <Step 3> of Example 239 by the same process as that used in <Step 2> of Example 1.

<Step 5> Synthesis of (E)-2-(8-trifluoromethyl-2,3,4,5-tetrahydrooxepino[2,3-b]pyridin-5-ylidene)-N-(7-hydroxy-5,6,7,8-tetrahydronaphthalen-1-yl)acetamide The title compound (23.0 mg) was obtained as pale brown crystals from the compound (30.0 mg) prepared in <Step 4> of Example 239 and 8-amino-1,2,3,4-tetrahydro-2-naphthol by the same process as that used in <Step 3> of Example 1.

Example 240

(Z)-2-(6-trifluoromethyl-3,3-dimethyl-4-oxa-3,4-dihydro-(2H)-isoquinolin-1-ylidene)-N-(7-hydroxy-5,6,7,8-tetrahydronaphthalen-1-yl)acetamide <Step 1> Synthesis of 2-hydroxy-4-trifluoromethyl-benzamide Thionyl chloride (2.7 mL) and N,N-dimethylformamide (0.1 mL) were added to a toluene (50.0 mL) solution of 4-trifluoromethylsalicylic acid (5.0 g), and the reaction mixture was refluxed for 30 minutes. The reaction mixture was left to cool. The reaction mixture was then added dropwise to aqueous ammonia (50.0 mL) under ice cooling, and the reaction mixture was stirred at the same temperature for 10 minutes. The pH of the reaction mixture was adjusted to 3 with concentrated hydrochloric acid, and the reaction mixture was then extracted with ethyl acetate. The organic layer was sequentially washed with water and a saturated brine and then dried over anhydrous sodium sulfate. The solvent was distilled off under reduced pressure. The residue was purified by silica gel column chromatography (eluate; n-hexane:ethyl acetate=100:0 to 50:50). The title compound (1.84 g) was obtained as pale beige crystals.

<Step 2> Synthesis of 2,2-dimethyl-7-trifluoromethyl-2,3-dihydro-4H-1,3-benzoxazin-4-one 2,2-Dimethoxypropane (4.3 mL) and concentrated sulfuric acid (0.4 mL) were added to a chloroform (20.0 mL) solution of the compound (1.78 g) prepared in <Step 1> of Example 240, and the reaction mixture was refluxed for eight hours. The reaction mixture was neutralized with a saturated aqueous sodium hydrogencarbonate solution and was then extracted with ethyl acetate. The organic layer was sequentially washed with water and a saturated brine and then dried over anhydrous sodium sulfate. The solvent was distilled off under reduced pressure. The residue was purified by silica gel column chromatography (eluate; n-hexane:ethyl acetate=100:0 to 50:50). The title compound (1.12 g) was obtained as pale yellow crystals.

<Step 3> Synthesis of 2,2-dimethyl-7-trifluoromethyl-2,3-dihydro-4H-1,3-benzoxazine-4-thione The Lawesson's reagent (1.17 g) was added to a toluene (58.0 mL) solution of the compound (1.15 g) prepared in <Step 2> of Example 240, and the reaction mixture was refluxed for one hour. The reaction mixture was left to cool and was then purified by silica gel column chromatography (eluate; n-hexane:ethyl acetate=90:10 to 88:12). The title compound (1.42 g) was obtained as yellow crystals.

<Step 4> Synthesis of 2-bromo-N-(7-hydroxy-5,6,7,8-tetrahydronaphthyl)acetamide

The title compound (590 mg) was obtained as pale purple crystals from 8-amino-1,2,3,4-tetrahydro-2-naphthol (500 mg) and bromoacetic acid (470 mg) by the same process as that used in <Step 3> of Example 1.

<Step 5> Synthesis of 2-(2,2-dimethyl-7-trifluoromethyl-2H-1,3-benzoxazin-4-ylthio)-N-(7-hydroxy-5,6,7,8-tetrahydronaphthyl)acetamide A 1,4-dioxane (10.0 mL) solution of the compound (150 mg) prepared in <Step 3> of Example 240 and the compound (240 mg) prepared in <Step 4> of Example 240 was stirred at room temperature for 15 hours and then refluxed for three hours. The solvent was distilled off under reduced pressure. The residue was purified by silica gel column chromatography (eluate; n-hexane:ethyl acetate=67:33 to 0:100). The title compound (37.0 mg) was obtained as a purple amorphous product.

<Step 6> Synthesis of (Z)-2-(6-trifluoromethyl-3,3-dimethyl-4-oxa-3,4-dihydro-(2H)-isoquinolin-1-ylidene)-N-(7-hydroxy-5,6,7,8-tetrahydronaphthalen-1-yl)acetamide N,N-Diisopropylethylamine (2.0 mL) and triphenylphosphine (96.0 mg) were added to the compound (34.0 mg) prepared in <Step 5> of Example 240, and the reaction mixture was refluxed for 20 hours. The solvent was distilled off under reduced pressure. The residue was purified by preparative chromatography (solvent system; n-hexane:ethyl acetate=50:50). The title compound (1.1 mg) was obtained as a colorless amorphous product.

<Step 7> Synthesis of 2,2-dimethyl-7-trifluoromethyl-4-(ethoxycarbonylmethylthio)-2H-1,3-benzoxazine A toluene (10.0 mL) solution of the compound (500.0 mg) prepared in <Step 3> of Example 240 and ethyl bromoacetate (0.64 mL) was stirred at room temperature for 24 hours. The solvent was distilled off under reduced pressure. The residue was purified by silica gel column chromatography (eluate; n-hexane:ethyl acetate=100:0 to 90:10). The title compound (540.0 mg) was obtained as yellow oil.

<Step 8> Synthesis of ethyl (Z)-2-(6-trifluoromethyl-3,3-dimethyl-4-oxa-3,4-dihydro-(2H)-isoquinolin-1-ylidene)acetate N,N-Diisopropylethylamine (3.6 mL) and triphenylphosphine (1.36 g) were added to the compound (360.0 mg) prepared in <Step 7> of Example 240, and the reaction mixture was refluxed for three hours. The solvent was distilled off under reduced pressure. The residue was purified by preparative chromatography (solvent system; n-hexane:ethyl acetate=88:12). The title compound (190.0 mg) was obtained as a pale beige solid.

Example 241-A (E)-2-(7-trifluoromethyl-2,2-dimethylchroman-4-ylidene)-N-(7-hydroxy-5,6,7,8-tetrahydronaphthalen-1-yl)acetamide <Step 1> Synthesis of 2-hydroxy-4-trifluoromethyl-acetophenone Methyllithium (1.0 M diethyl ether solution, 98.0 mL) was added to a tetrahydrofuran (60.0 mL) solution of 4-trifluoromethylsalicylic acid (6.0 g) under ice cooling, and the reaction mixture was stirred at room temperature for two hours. Trimethylsilyl chloride (37.0 mL) and 1 N hydrochloric acid (100 mL) were added to the reaction mixture under ice cooling. The reaction mixture was extracted with ethyl acetate. The organic layer was sequentially washed with water and a saturated brine and then dried over anhydrous sodium sulfate. The solvent was distilled off under reduced pressure. The residue was purified by silica gel column chromatography (eluate; n-hexane:ethyl acetate=100:0 to 95:5). The title compound (5.86 g) was obtained as pale yellow oil.

<Step 2> Synthesis of 7-trifluoromethyl-2,2-dimethylchroman-4-one

Acetone (3.3 mL) and pyrrolidine (3.7 mL) were added to a methanol (140.0 mL) solution of the compound (5.71 g) prepared in <Step 1> of Example 241-A, and the reaction mixture was stirred at room temperature for 12 hours. The solvent was distilled off under reduced pressure. A 10% aqueous citric acid solution (50.0 mL) and water (50.0 mL) were added to the residue, and the resulting solution was extracted with ethyl acetate. The organic layer was sequentially washed with water and a saturated brine and then dried over anhydrous sodium sulfate. The solvent was distilled off under reduced pressure. The title crude compound (6.27 g) was obtained as orange oil.

<Step 3> Synthesis of 4-hydroxy-4-vinyl-7-trifluoromethyl-2,2-dimethylchroman

Vinyl magnesium chloride (38.0 mL) was added to a tetrahydrofuran (120.0 mL) solution of the crude compound (6.14 g) prepared in <Step 2> of Example 241-A under ice cooling, and the reaction mixture was stirred at room temperature for five hours. Water was added to the reaction mixture, and the reaction mixture was then extracted with ethyl acetate. The organic layer was sequentially washed with water and a saturated brine and then dried over anhydrous sodium sulfate. The solvent was distilled off under reduced pressure. The residue was purified by silica gel column chromatography (eluate; n-hexane:ethyl acetate=100:0 to 90:10). The title compound (2.35 g) was obtained as yellow oil.

<Step 4> Synthesis of (E)-2-(7-trifluoromethyl-2,2-dimethylchroman-4-ylidene)aldehyde Pyridinium dichromate (5.22 g) was added to a dichloromethane (35.0 mL) solution of the compound (1.89 g) prepared in <Step 3> of Example 241-A and molecular sieves 4A (10.0 g) under ice cooling, and the reaction mixture was stirred at room temperature for two hours. Diethyl ether was added to the reaction mixture, and the reaction mixture was subjected to Celite filtration. The solvent was distilled off under reduced pressure. The residue was purified by silica gel column chromatography (eluate; n-hexane:ethyl acetate=100:0 to 90:10). The title compound (440 mg) was obtained as yellow oil.

<Step 5> Synthesis of (E)-2-(7-trifluoromethyl-2,2-dimethylchroman-4-ylidene)acetic acid Sodium hydrogenphosphate (180 mg), 2-methyl-2-butene (0.63 mL), and water (2.0 mL) were added to a tert-butanol (8.0 mL) solution of the compound (400 mg) prepared in <Step 4> of Example 241-A. Sodium hypochlorite (400 mg) was added to the reaction mixture under ice cooling, and the reaction mixture was stirred at the same temperature for two hours. The reaction mixture was neutralized with 1 N hydrochloric acid and then extracted with ethyl acetate. The organic layer was sequentially washed with water and a saturated brine and then dried over anhydrous sodium sulfate. The solvent was distilled off under reduced pressure. The title crude compound (477 mg) was obtained as colorless crystals.

<Step 6> Synthesis of (E)-2-(7-trifluoromethyl-2,2-dimethylchroman-4-ylidene)-N-(7-hydroxy-5,6,7,8-tetrahydronaphthalen-1-yl)acetamide The title compound (42.0 mg) was obtained as colorless crystals from the compound (100.0 mg) prepared in <Step 5> of Example 241-A and 8-amino-1,2,3,4-tetrahydro-2-naphthol (57.0 mg) by the same process as that used in <Step 3> of Example 1.

Example 241

Process B

<Step 1> Synthesis of ethyl 7-trifluoromethyl-2,2-dimethylchroman-4-hydroxy-4-acetate The title compound (180.0 mg) was obtained as yellow oil from the compound (200.0 mg) prepared in <Step 2> of Example 241-A by the same process as that used in <Step 2> of Example 70.

<Step 2> Synthesis of 7-trifluoromethyl-2,2-dimethylchroman-4-hydroxy-4-acetic acid The title compound (154.5 mg) was obtained as pale yellow crystals from the compound (180.0 mg) prepared in <Step 1> of Example 241-Process B by the same process as that used in <Step 5> of Example 48.

<Step 3> Synthesis of (E)-2-(7-trifluoromethyl-2,2-dimethylchroman-4-ylidene)acetic acid The title compound (115.0 mg) was obtained as pale yellow crystals from the compound (140.0 mg) prepared in <Step 2> of Example 241-Process B by the same process as that used in <Step 4> of Example 70.

Examples 242 and 243

Optical resolution of (E)-2-(7-trifluoromethyl-2,2-dimethylchroman-4-ylidene)-N-(7-hydroxy-5,6,7,8-tetrahydronaphthalen-1-yl)acetamide Optical resolution of the compound (32.0 mg) obtained in Example 241 was performed by preparative chromatography (column; CHIRALPAK AD-H manufactured by Daicel Chemical Industries, Ltd., solvent; n-hexane:EtOH=75:25). Accordingly, enantiomers of the title compound were obtained as a first fraction (12.3 mg, white solid, >99% ee, retention time: 10.9 minutes, Example 242) and a second fraction (15.4 mg, white solid, >99% ee, retention time: 16.1 minutes, Example 243).

Example 244

(E)-2-(7-trifluoromethyl-2,2-dimethylchroman-4-ylidene)-N-(3-hydroxy-1,2,3,4-tetrahydroquinolin-5-yl)acetamide The title compound (47.9 mg) was obtained as a yellow amorphous product from the compound (100.0 mg) prepared in <Step 5> of Example 241 and 5-amino-1,2,3,4-tetrahydroquinolin-3-ol (57.0 mg) by the same process as that used in <Step 3> of Example 1.

Examples 245 and 246

Optical resolution of (E)-2-(7-trifluoromethyl-2,2-dimethylchroman-4-ylidene)-N-(3-hydroxy-1,2,3,4-tetrahydroquinolin-5-yl)acetamide Optical resolution of the compound (37.0 mg) obtained in Example 244 was performed by preparative chromatography (column; CHIRALPAK AD-H manufactured by Daicel Chemical Industries, Ltd., solvent; n-hexane:EtOH=75:25). Accordingly, enantiomers of the title compound were obtained as a first fraction (15.3 mg, yellow solid, >99% ee, retention time: 13.5 minutes, Example 245) and a second fraction (15.7 mg, yellow solid, >99% ee, retention time: 19.4 minutes, Example 246).

Example 247

(Z)-2-(8-trifluoromethyl-3,4-dihydrobenzo[b]oxepin-5(2H)-ylidene)-N-(quinolin-7-yl)acetamide <Step 1> Synthesis of (Z)-(8-trifluoromethyl-3,4-dihydro-2H-benzo[b]oxepin-5-ylidene)acetic acid The title compound (83.5 mg) was obtained as pale beige crystals from the (Z)-isomer (100.0 mg) prepared in <Step 4> of Example 9 by the same process as that used in <Step 2> of Example 1.

<Step 2> Synthesis of (Z)-2-(8-trifluoromethyl-3,4-dihydrobenzo[b]oxepin-5(2H)-ylidene)-N-(quinolin-7-yl)acetamide The title compound (30.0 mg) was obtained as colorless crystals from the compound (114 mg) prepared in <Step 1> of Example 247 by the same process as that used in <Step 3> of Example 1.

Example 248

Synthesis of (E)-2-(7-fluoro-8-trifluoromethyl-3,4-dihydrobenzo[b]oxepin-5-(2H)-ylidene)-N-(7-hydroxy-5,6,7,8-tetrahydronaphthalen-1-yl)acetamide The title compound (96.8 mg) was obtained as colorless crystals from (E)-(7-fluoro-8-trifluoromethyl-3,4-dihydro-2H-benzo[b]oxepin-5-ylidene)acetic acid (100.0 mg) obtained by a process similar to the process used in Example 9 and 8-amino-1,2,3,4-tetrahydro-2-naphthol (56.2 mg) by the same process as that used in <Step 3> of Example 1.

The following compounds of Examples 249 and 250 were synthesized by a process similar to the process used in Example 70. The following compounds of Examples 251 and 252 were synthesized by a process similar to the process used in Example 241-A. The following compounds of Examples 253 to 255 were synthesized by a process similar to the process used in Example 1.

Example 249

(E)-2-(6-trifluoromethyl-chroman-4-ylidene)-N-(7-hydroxy-5,6,7,8-tetrahydronaphthalen-1-yl)acetamide Example 250

(E)-N-(3-hydroxy-1,2,3,4-tetrahydroquinolin-5-yl)-2-(6-trifluoromethyl-chroman-4-ylidene)acetamide Example 251

(E)-2-(7-trifluoromethyl-2,2-cyclobutylchroman-4-ylidene)-N-(7-hydroxy-5,6,7,8-tetrahydronaphthalen-1-yl) acetamide Example 252

(E)-N-(3-hydroxy-1,2,3,4-tetrahydroquinolin-5-yl)-2-(7-trifluoromethyl-2,2-cyclobutylchroman-4-ylidene)acetamide Example 253

(E)-2-(8-trifluoromethyl-3,4-dihydrobenzo[b]oxepin-5(2H)-ylidene)-N-(1H-indazol-4-yl)acetamide Example 254

(E)-2-(8-trifluoromethyl-3,4-dihydrobenzo[b]oxepin-5(2H)-ylidene)-N-(1H-indazol-7-yl)acetamide Example 255

(E)-2-(8-trifluoromethyl-3,4-dihydrobenzo[b]oxepin-5(2H)-ylidene)-N-(1H-pyrrolo[2,3-c]pyridin-3-yl)acetamide The structures of the compound synthesized in Examples 1 to 255 are shown in Table 2. The data of liquid chromatography-mass spectrometry (LC-MS) of these examples are shown in Table 3. The NMR data of typical compounds are shown in Table 4 (300 MHz: no mark, 270 MHz: marked with *). The structures of the intermediate compounds are shown in Table 5. The NMR data of these intermediate compounds are shown in Table 6 (300 MHz: no mark, 270 MHz: marked with *).

TABLE 1

| EXAMPLE | A2 VALUE |
|---|---|
| 1 | B |
| 2 | B |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | B |
| 16 | A |
| 17 | A |
| 18 | A |
| 19 | A |
| 20 | B |
| 21 | B |
| 22 | B |
| 23 | A |
| 24 | A |
| 25 | B |
| 26 | B |
| 27 | B |
| 28 | B |
| 29 | B |
| 30 | B |
| 31 | B |
| 32 | B |
| 33 | B |
| 34 | B |
| 35 | B |
| 36 | B |
| 37 | B |
| 38 | B |
| 39 | B |
| 40 | B |
| 41 | B |
| 42 | B |
| 43 | B |
| 44 | B |
| 45 | B |
| 46 | B |
| 47 | B |
| 48 | A |
| 49 | B |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |

TABLE 1-continued

| EXAMPLE | A 2 VALUE |
|---|---|
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |
| 99 | A |
| 100 | A |
| 101 | A |
| 102 | A |
| 105 | A |
| 106 | A |
| 107 | A |
| 108 | A |
| 109 | A |
| 110 | A |
| 111 | A |
| 112 | B |
| 113 | A |
| 114 | A |
| 115 | A |
| 116 | A |
| 117 | A |
| 118 | A |
| 119 | A |
| 120 | A |
| 121 | A |
| 122 | A |
| 125 | A |
| 126 | A |
| 127 | A |
| 128 | A |
| 129 | B |
| 130 | A |
| 133 | A |
| 134 | A |
| 135 | A |
| 136 | A |
| 137 | A |
| 138 | A |
| 142 | A |
| 143 | B |
| 144 | A |
| 149 | A |
| 150 | A |
| 151 | A |
| 152 | A |
| 157 | A |
| 160 | A |
| 161 | B |
| 163 | A |
| 164 | A |
| 165 | A |

TABLE 1-continued

| EXAMPLE | A 2 VALUE |
|---|---|
| 166 | A |
| 167 | A |
| 169 | A |
| 174 | A |
| 175 | A |
| 176 | B |
| 178 | A |
| 179 | A |
| 183 | A |
| 184 | A |
| 185 | A |
| 190 | A |
| 191 | A |
| 192 | A |
| 193 | A |
| 194 | B |
| 195 | B |
| 196 | A |
| 197 | A |
| 198 | A |
| 199 | A |
| 200 | A |
| 202 | A |
| 204 | A |
| 206 | A |
| 207 | A |
| 208 | A |
| 209 | A |
| 210 | A |
| 211 | A |
| 212 | A |
| 213 | A |
| 214 | A |
| 215 | A |
| 216 | A |
| 218 | A |
| 219 | A |
| 220 | A |
| 221 | A |
| 224 | B |
| 226 | A |
| 227 | A |
| 229 | B |
| 231 | B |
| 233 | A |
| 234 | A |
| 235 | A |
| 236 | A |
| 237 | A |
| 238 | A |
| 239 | A |
| 240 | A |
| 241 | A |
| 242 | A |
| 243 | A |
| 244 | A |
| 245 | A |
| 246 | A |
| 247 | A |
| 248 | A |
| 251 | A |
| 252 | A |
| 253 | A |
| 254 | A |

TABLE 2
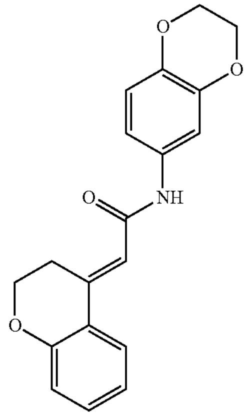
EXAMPLE 1
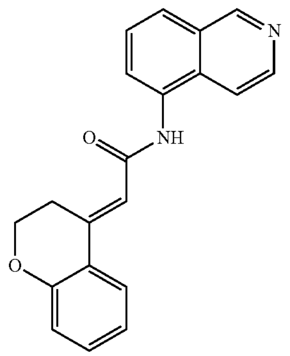
EXAMPLE 2
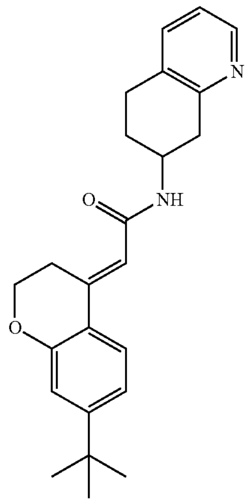
EXAMPLE 3
TABLE 2-continued
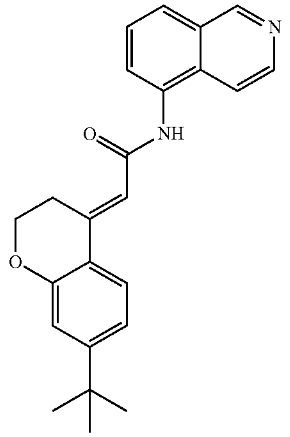
EXAMPLE 4
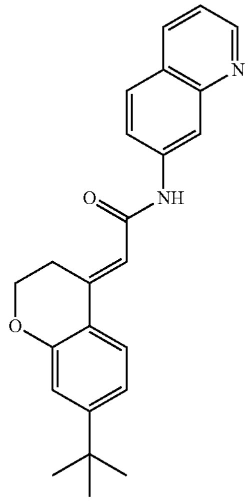
EXAMPLE 5
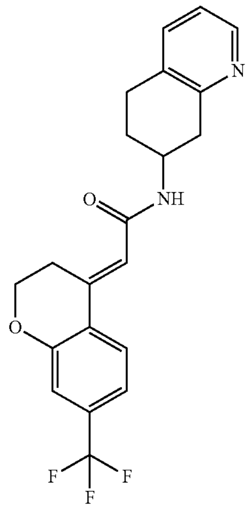
EXAMPLE 6

TABLE 2-continued
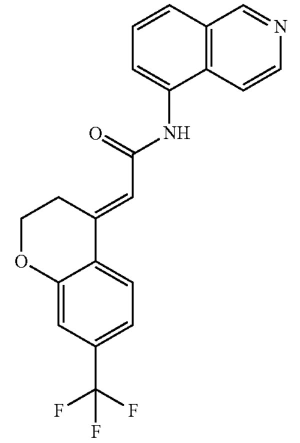
EXAMPLE 7
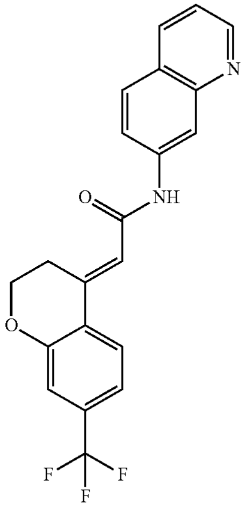
EXAMPLE 8
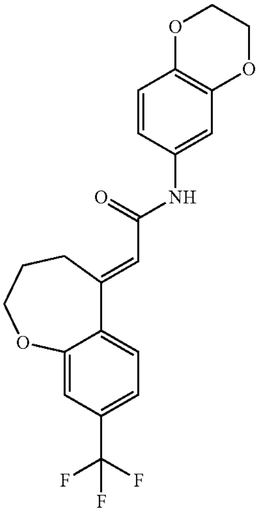
EXAMPLE 9
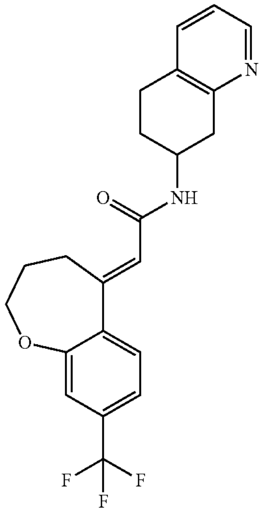
EXAMPLE 10
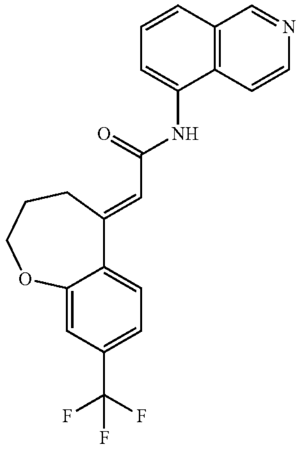
EXAMPLE 11
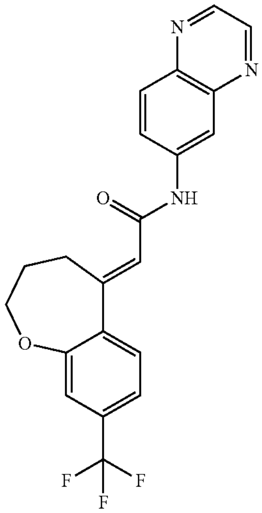
EXAMPLE 12

TABLE 2-continued
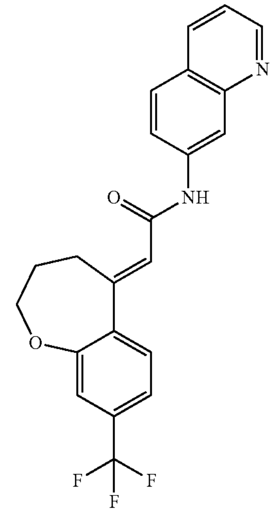
EXAMPLE 13
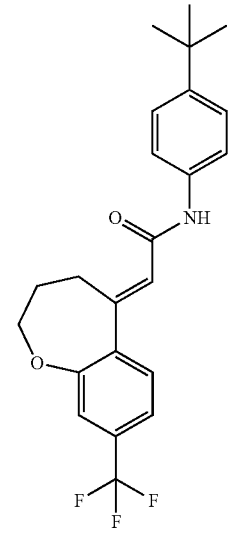
EXAMPLE 14
TABLE 2-continued
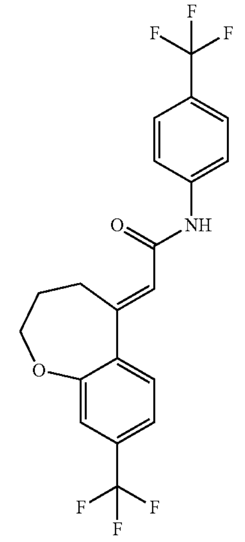
EXAMPLE 15
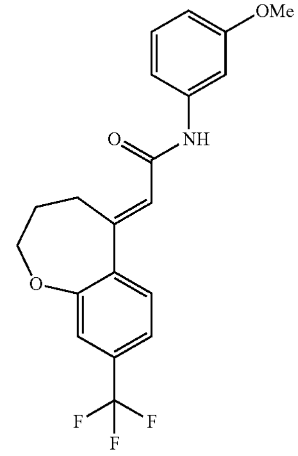
EXAMPLE 16
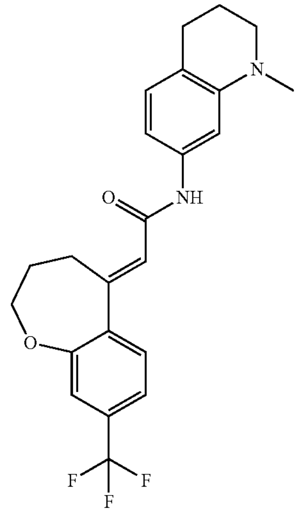
EXAMPLE 17

TABLE 2-continued
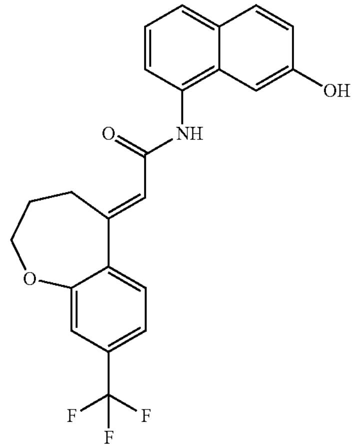
EXAMPLE 18
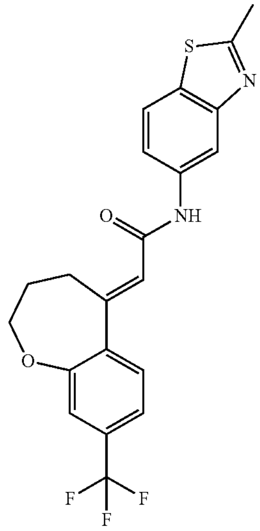
EXAMPLE 19
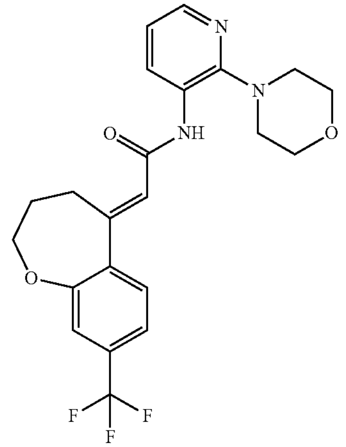
EXAMPLE 20
TABLE 2-continued
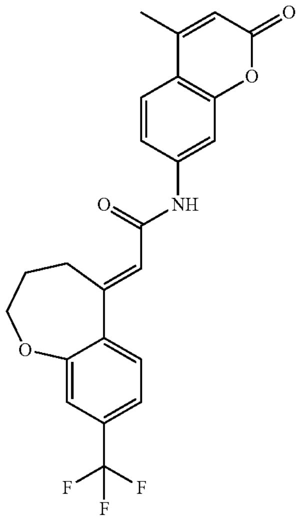
EXAMPLE 21
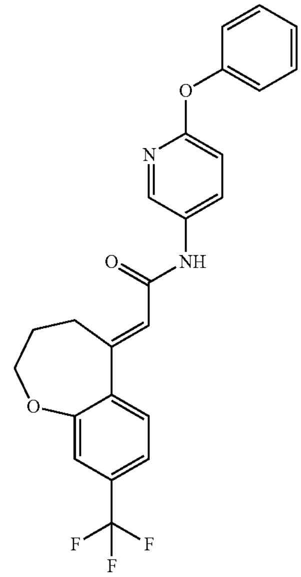
EXAMPLE 22

TABLE 2-continued
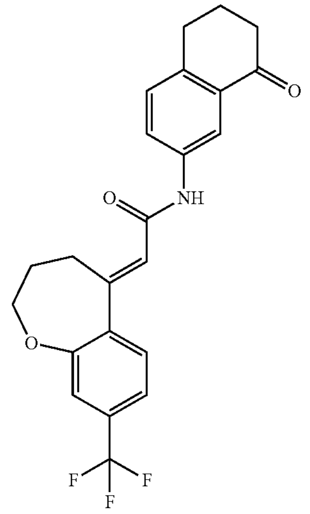
EXAMPLE 23
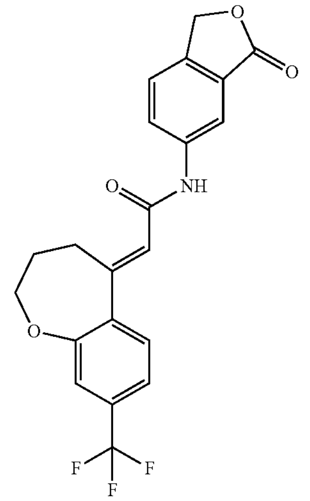
EXAMPLE 24
TABLE 2-continued
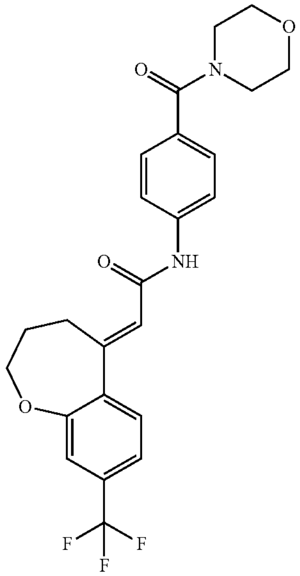
EXAMPLE 25
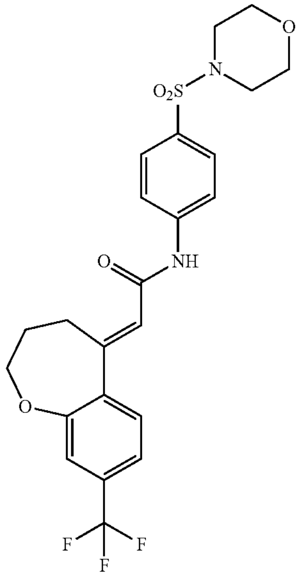
EXAMPLE 26

TABLE 2-continued
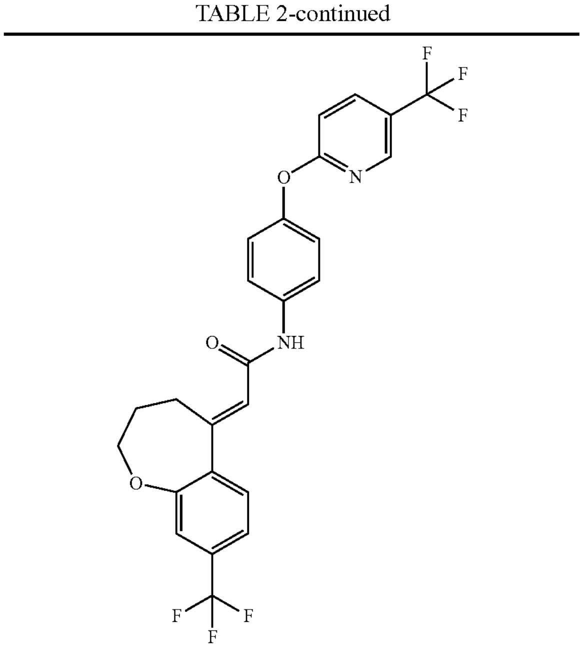
EXAMPLE 27
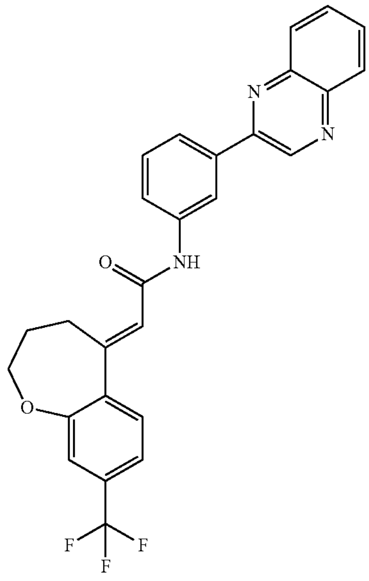
EXAMPLE 28
TABLE 2-continued
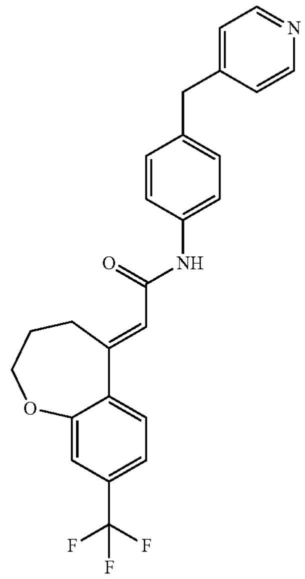
EXAMPLE 29
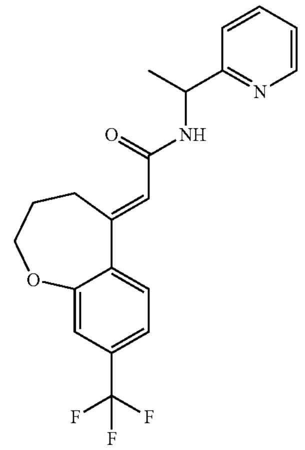
EXAMPLE 30
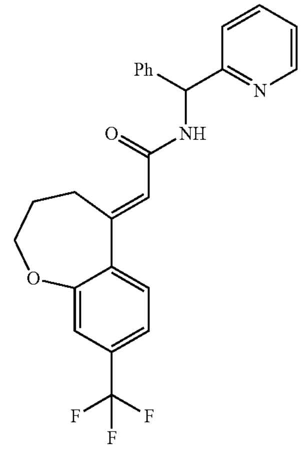
EXAMPLE 31

TABLE 2-continued
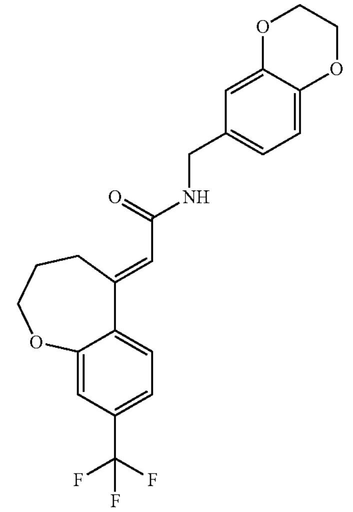
EXAMPLE 32
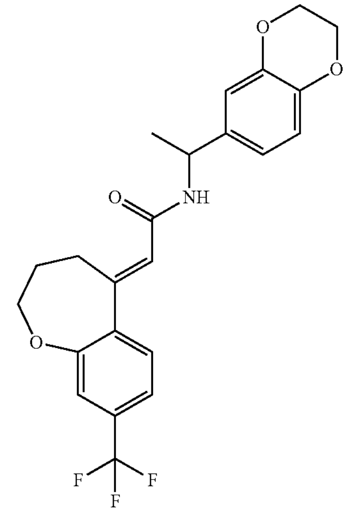
EXAMPLE 33
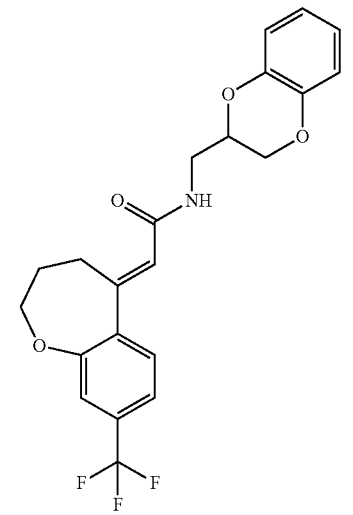
EXAMPLE 34
TABLE 2-continued
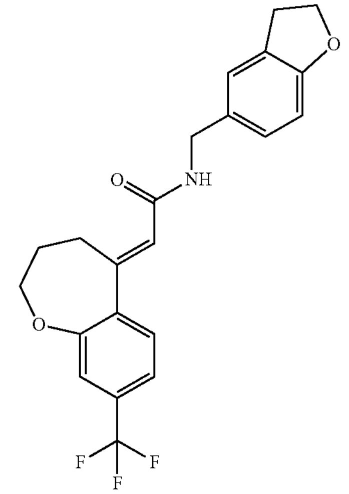
EXAMPLE 35
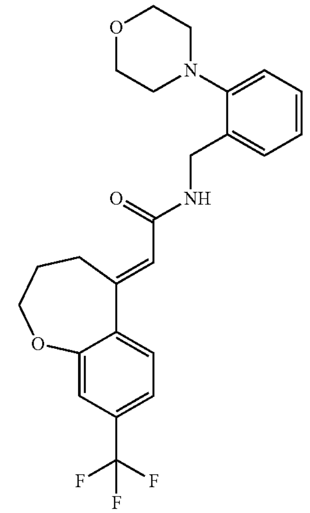
EXAMPLE 36
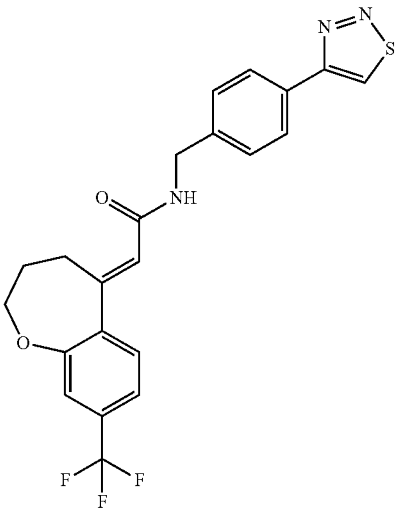
EXAMPLE 37

TABLE 2-continued
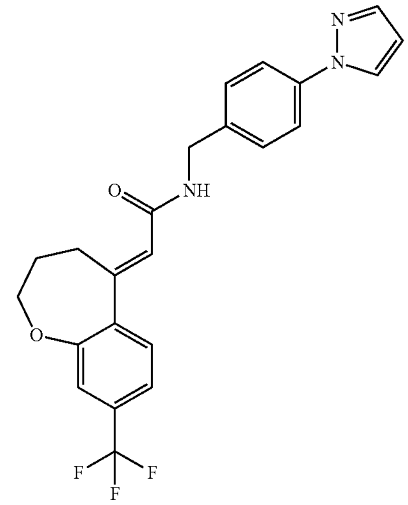
EXAMPLE 38
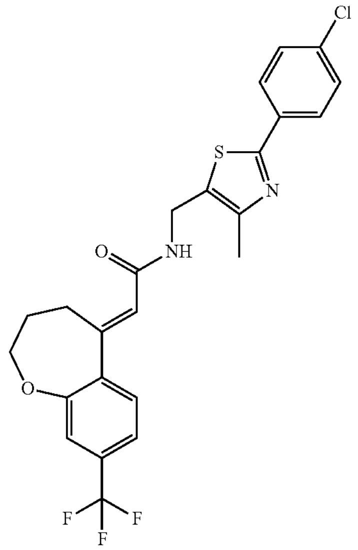
EXAMPLE 39
TABLE 2-continued
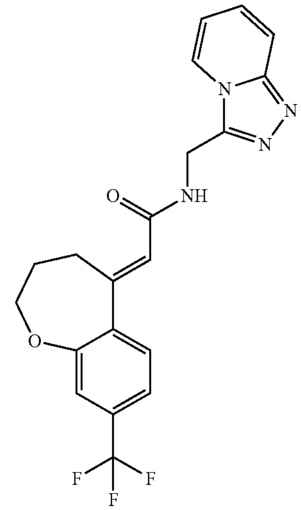
EXAMPLE 40
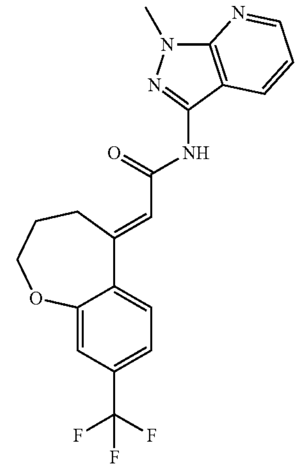
EXAMPLE 41
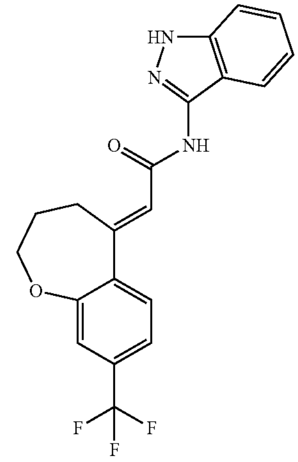
EXAMPLE 42

TABLE 2-continued
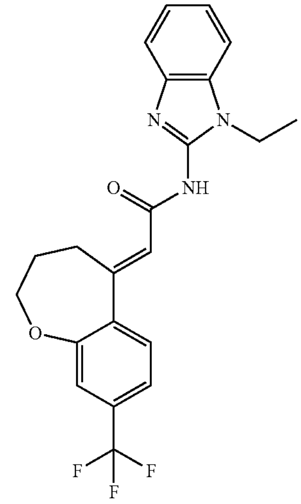
EXAMPLE 43
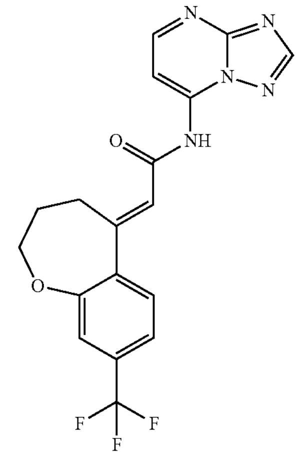
EXAMPLE 44
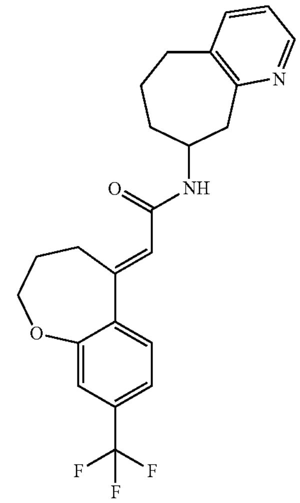
EXAMPLE 45
TABLE 2-continued
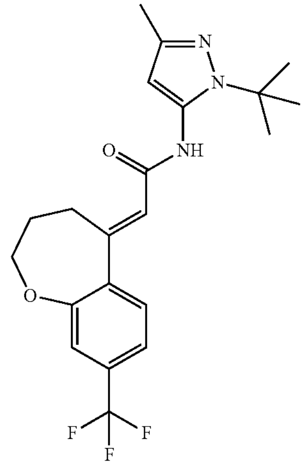
EXAMPLE 46
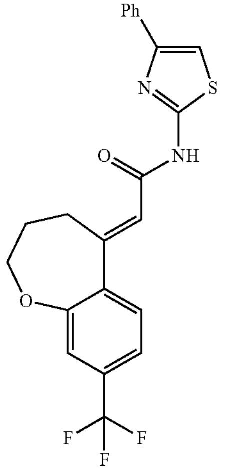
EXAMPLE 47
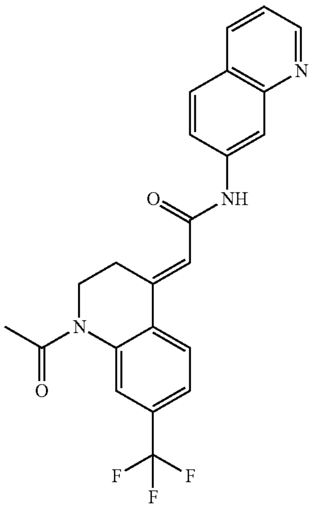
EXAMPLE 48

TABLE 2-continued
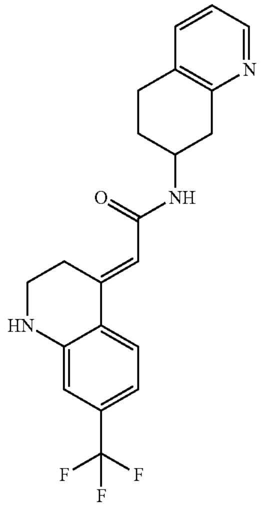
EXAMPLE 49
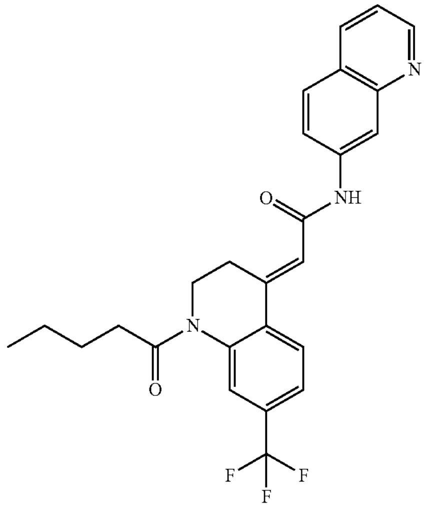
EXAMPLE 50
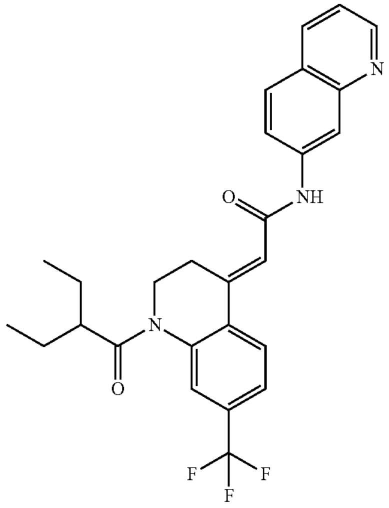
EXAMPLE 51
TABLE 2-continued
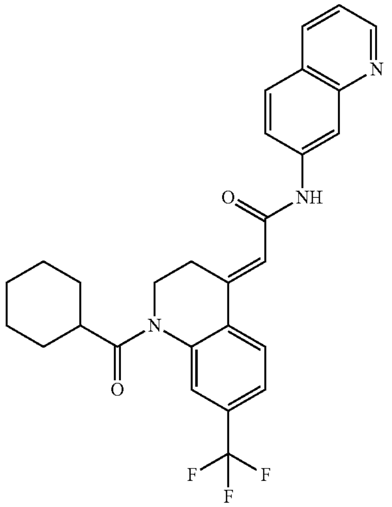
EXAMPLE 52
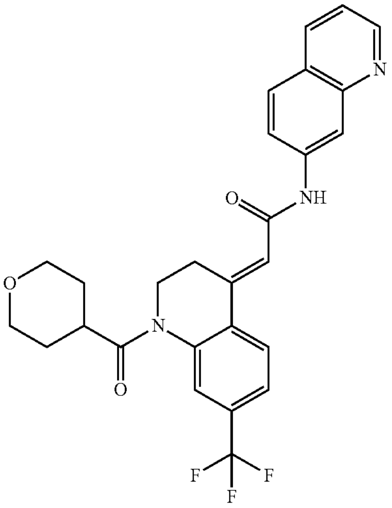
EXAMPLE 53
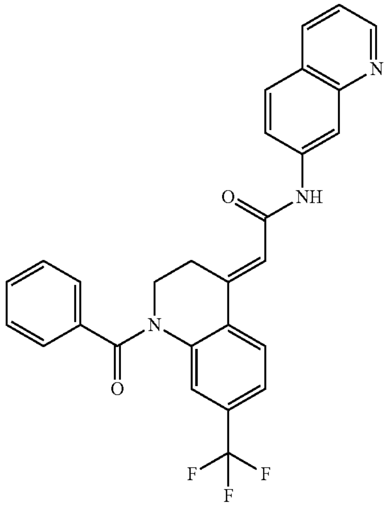
EXAMPLE 54

TABLE 2-continued
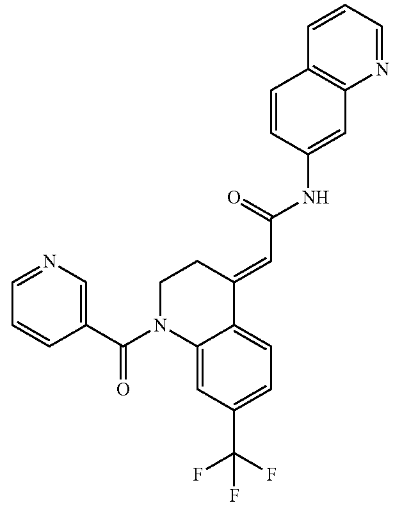
EXAMPLE 55
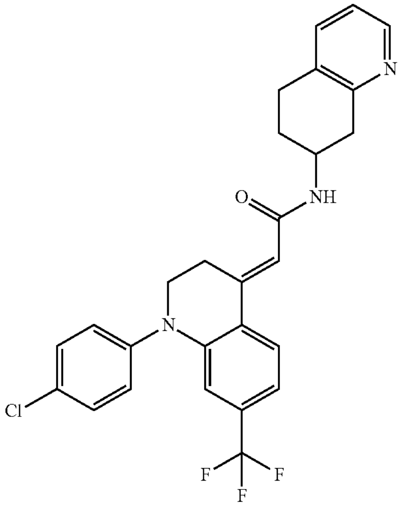
EXAMPLE 56
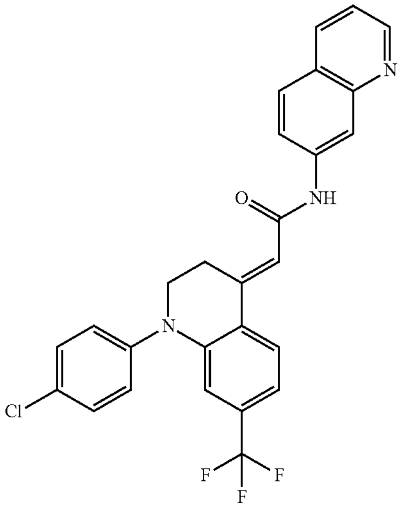
EXAMPLE 57
TABLE 2-continued
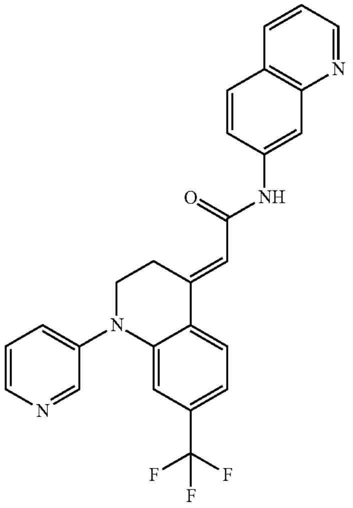
EXAMPLE 58
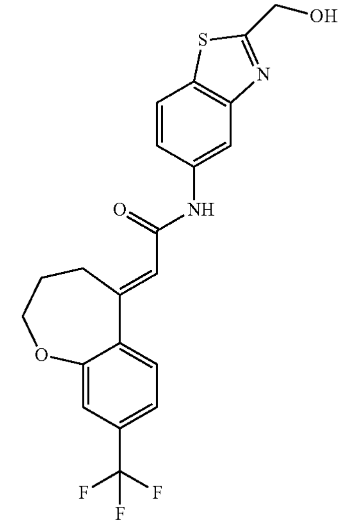
EXAMPLE 59
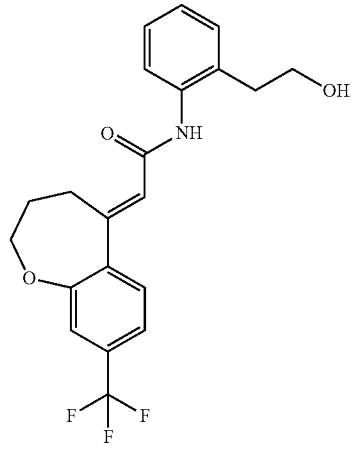
EXAMPLE 60

TABLE 2-continued
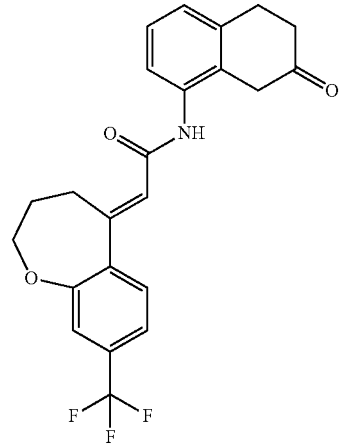
EXAMPLE 61
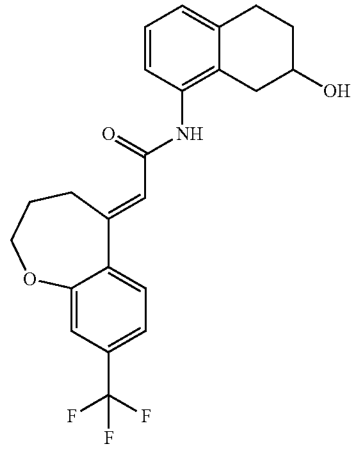
EXAMPLE 62
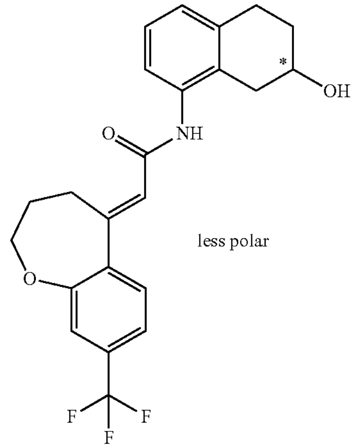
EXAMPLE 63
TABLE 2-continued
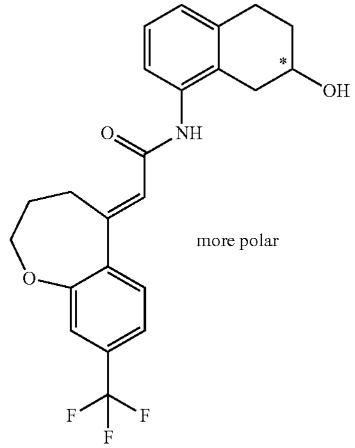
EXAMPLE 64
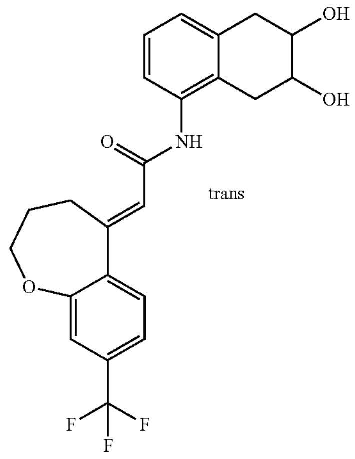
EXAMPLE 65
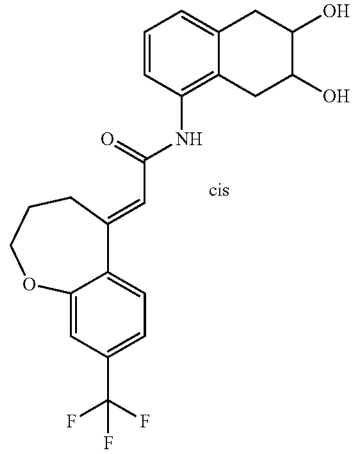
EXAMPLE 66

TABLE 2-continued
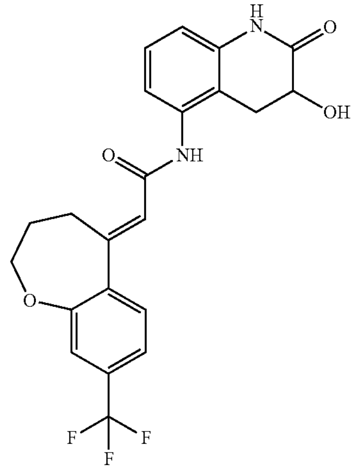
EXAMPLE 67
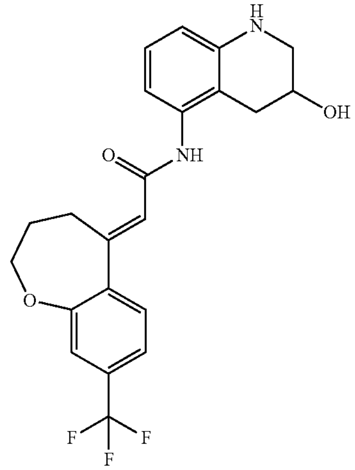
EXAMPLE 68
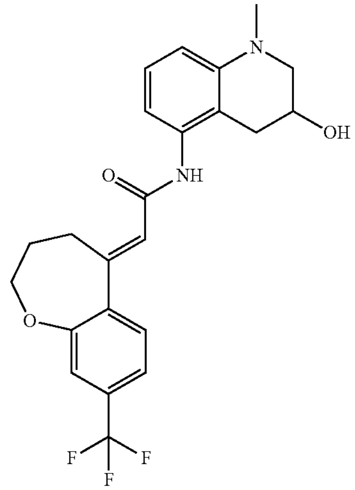
EXAMPLE 69
TABLE 2-continued
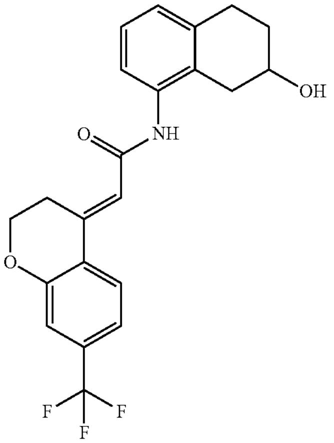
EXAMPLE 70
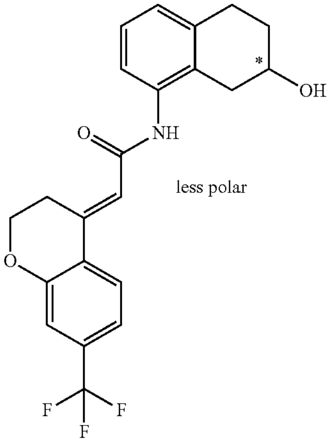
EXAMPLE 71
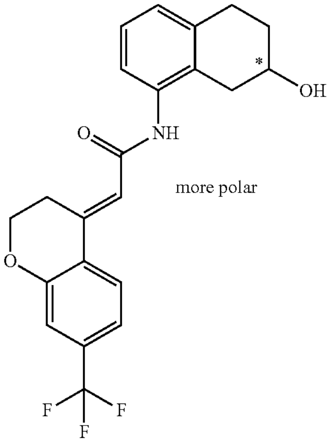
EXAMPLE 72

TABLE 2-continued
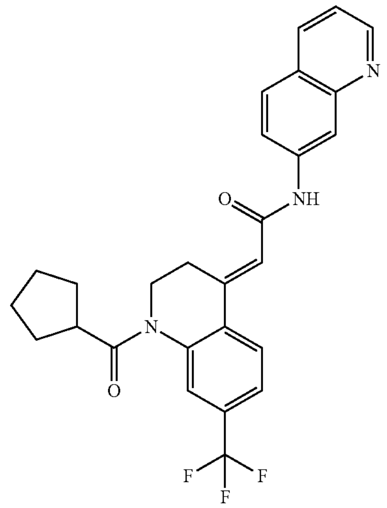
EXAMPLE 73
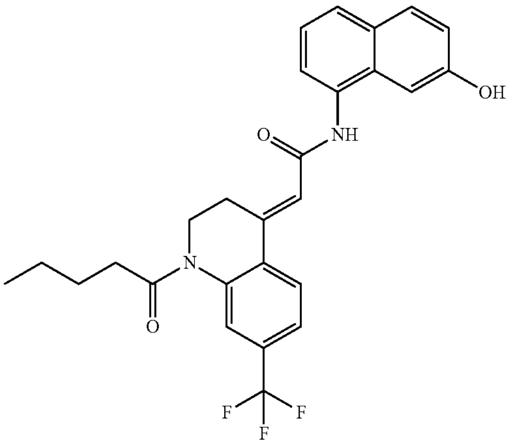
EXAMPLE 74
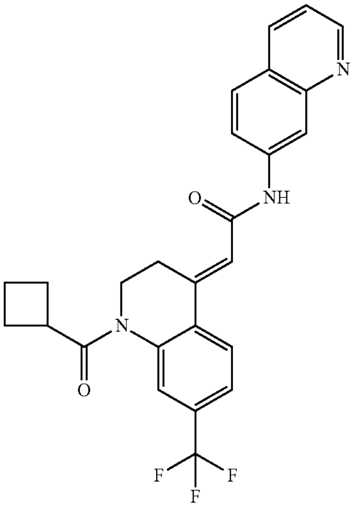
EXAMPLE 75
TABLE 2-continued
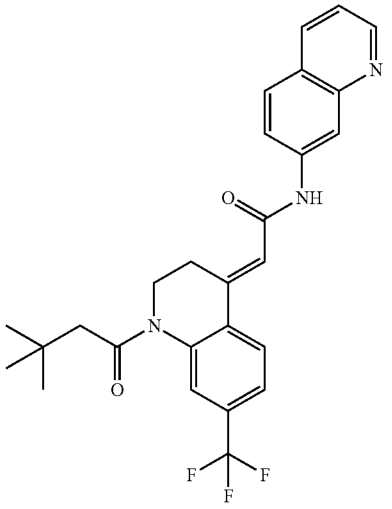
EXAMPLE 76
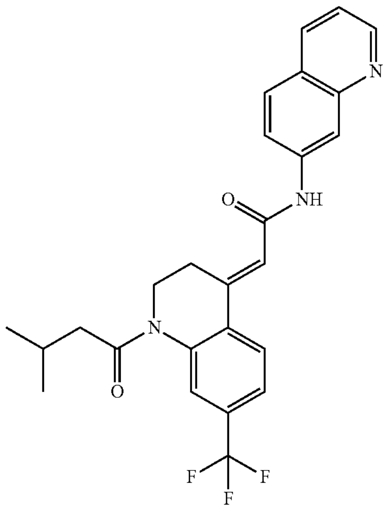
EXAMPLE 77
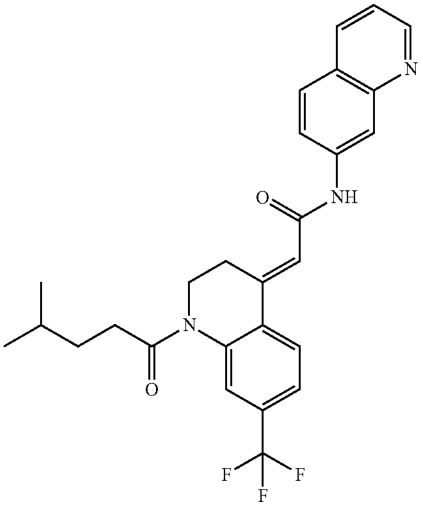
EXAMPLE 78

TABLE 2-continued
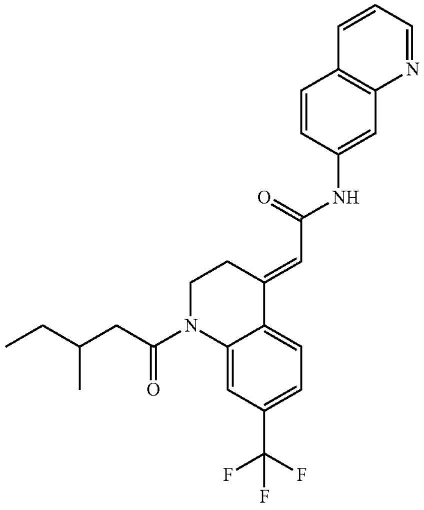
EXAMPLE 79
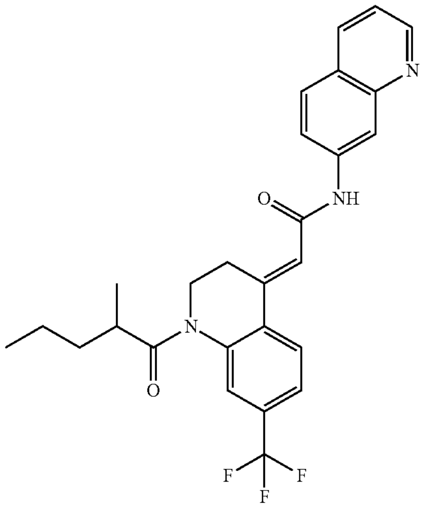
EXAMPLE 80
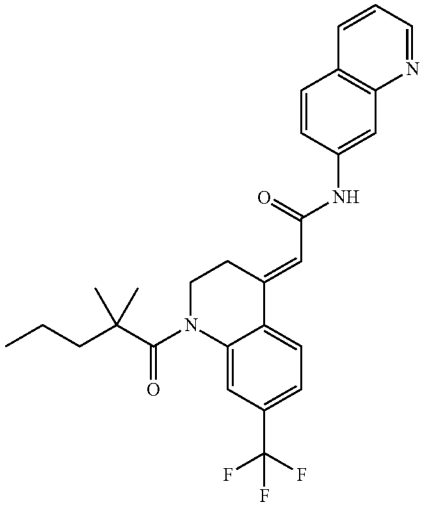
EXAMPLE 81
TABLE 2-continued
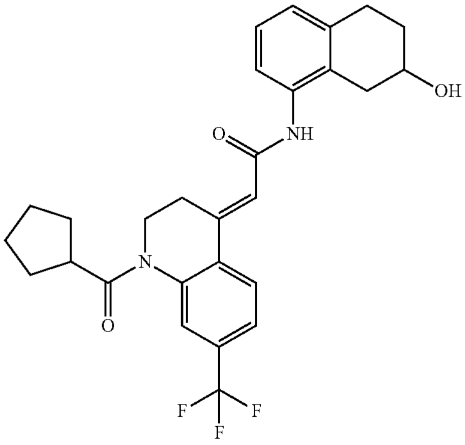
EXAMPLE 82
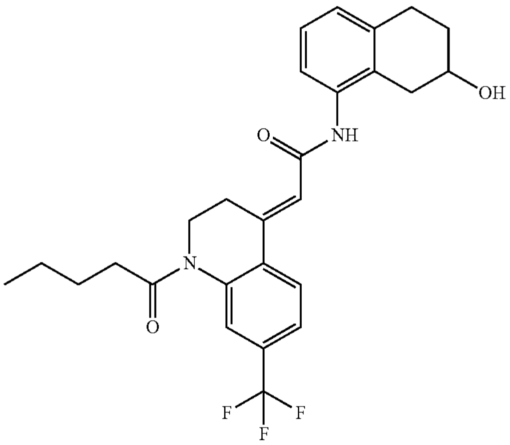
EXAMPLE 83
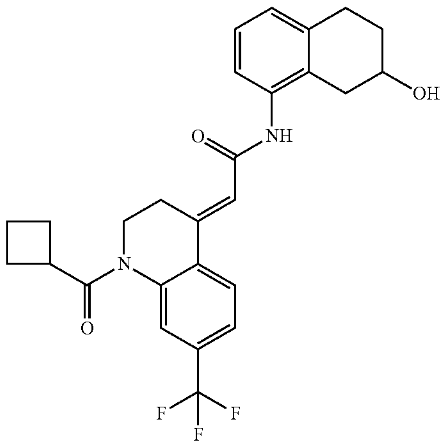
EXAMPLE 84

TABLE 2-continued
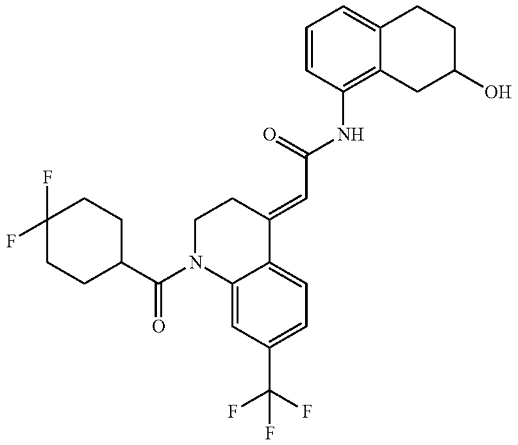
EXAMPLE 85
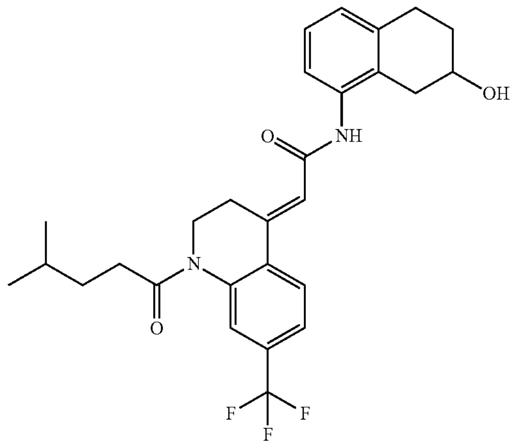
EXAMPLE 86
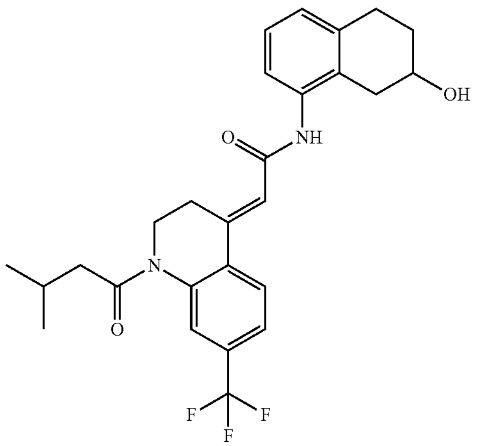
EXAMPLE 87
TABLE 2-continued
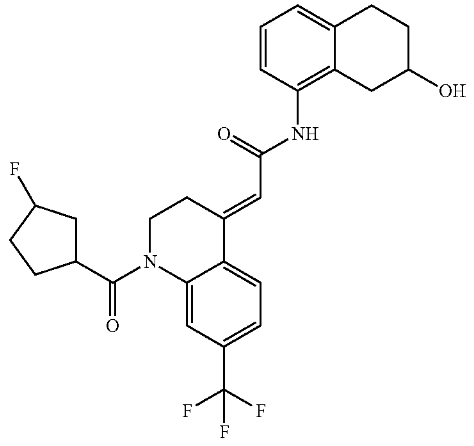
EXAMPLE 88
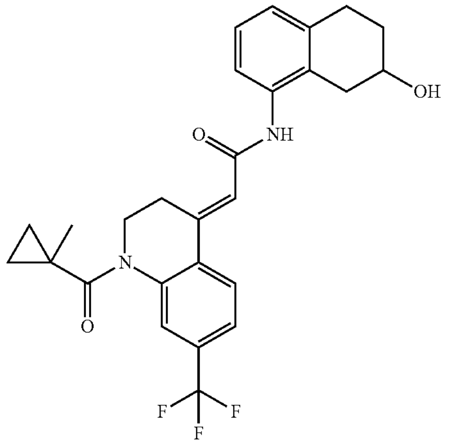
EXAMPLE 89
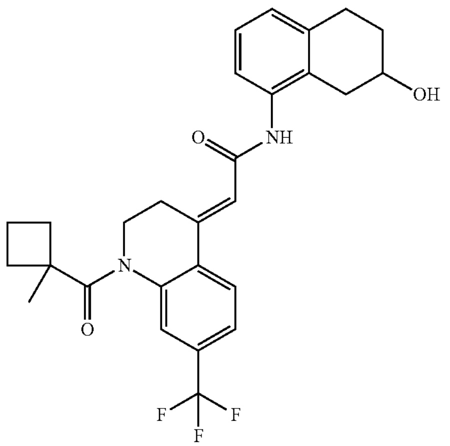
EXAMPLE 90

TABLE 2-continued
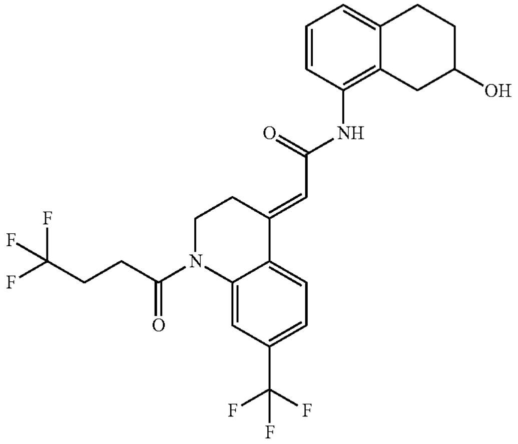
EXAMPLE 91
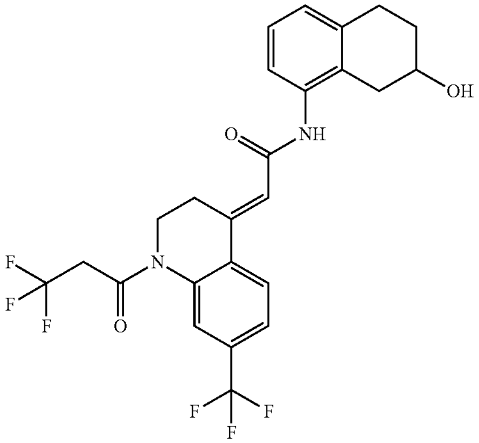
EXAMPLE 92
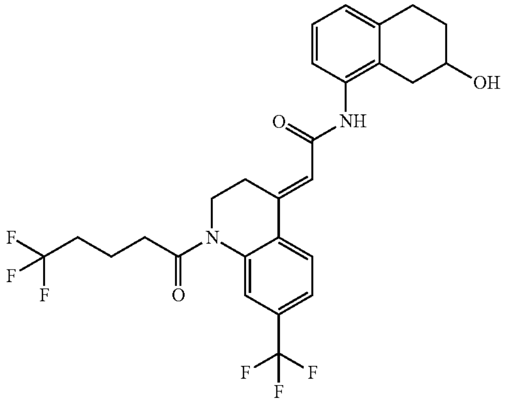
EXAMPLE 93
TABLE 2-continued
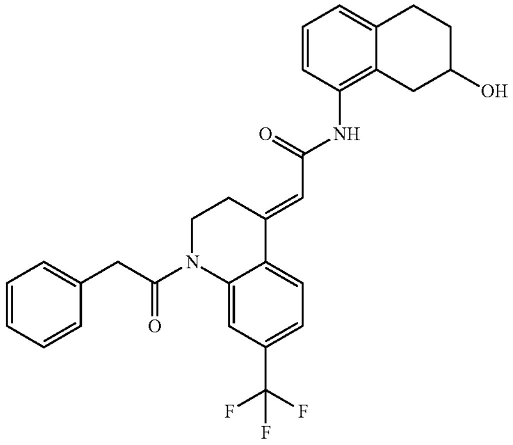
EXAMPLE 94
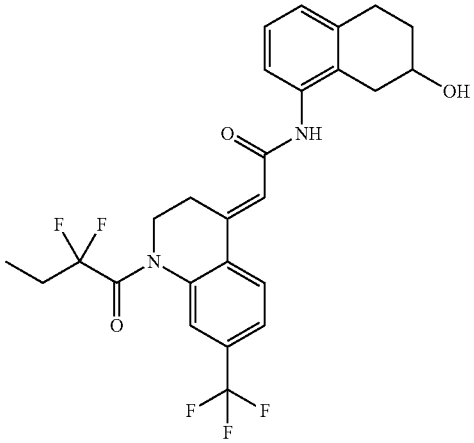
EXAMPLE 95
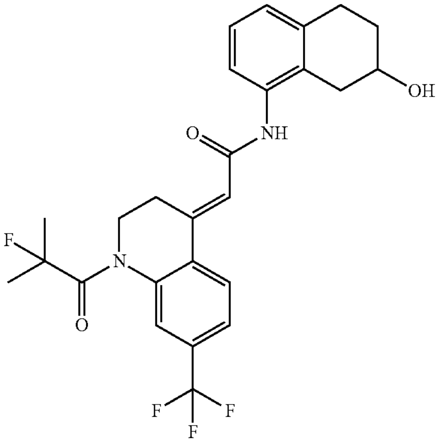
EXAMPLE 96

TABLE 2-continued
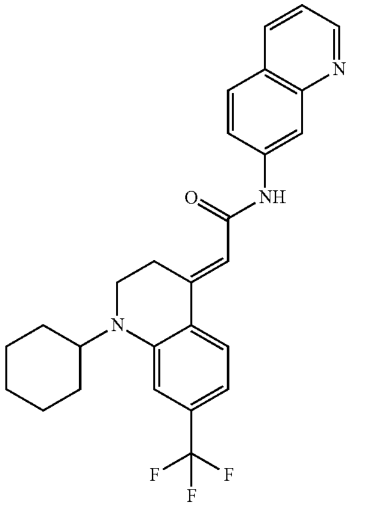
EXAMPLE 97
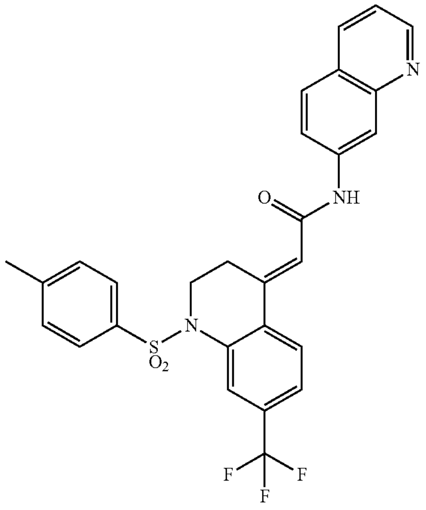
EXAMPLE 98
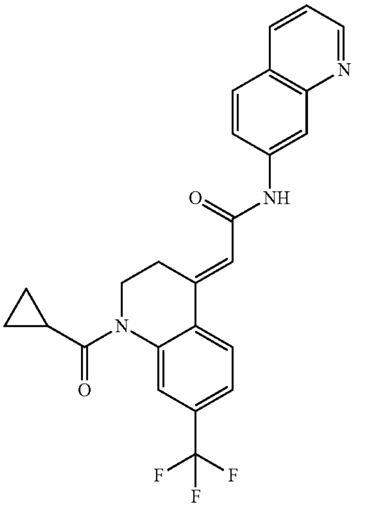
EXAMPLE 99
TABLE 2-continued
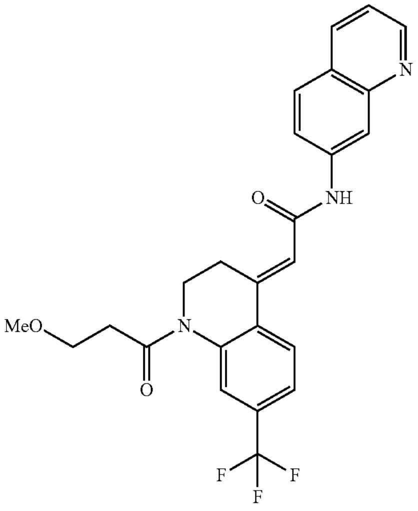
EXAMPLE 100
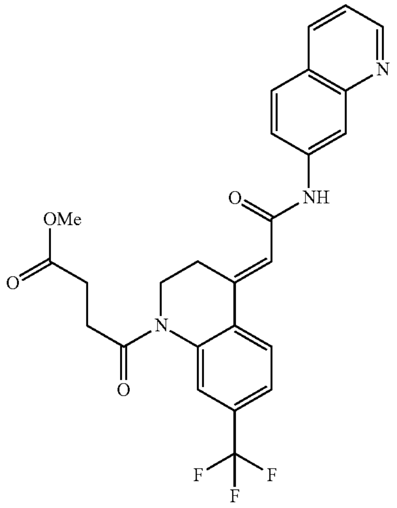
EXAMPLE 101
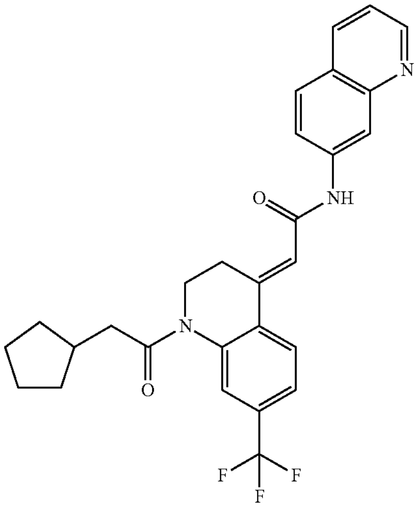
EXAMPLE 102

TABLE 2-continued
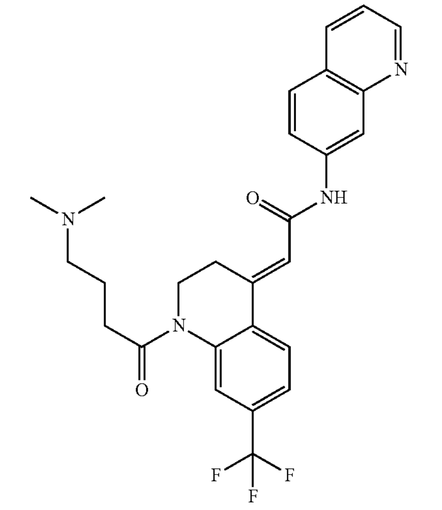
EXAMPLE 103
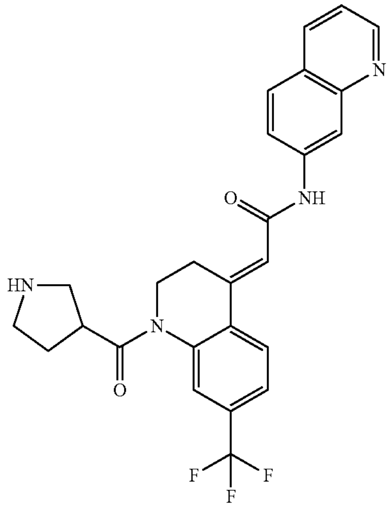
EXAMPLE 104
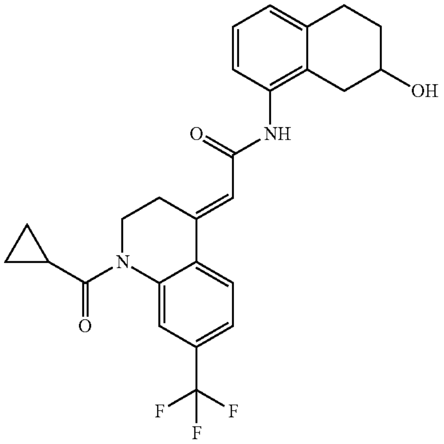
EXAMPLE 105
TABLE 2-continued
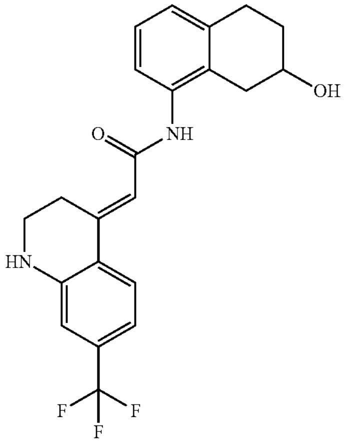
EXAMPLE 106
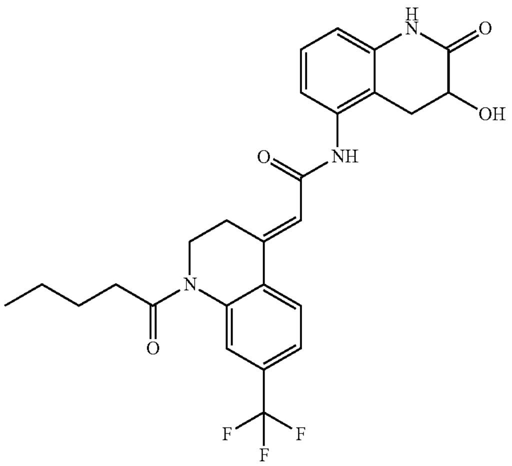
EXAMPLE 107
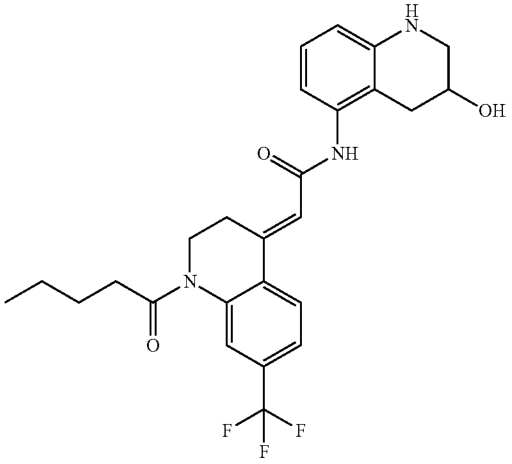
EXAMPLE 108

TABLE 2-continued
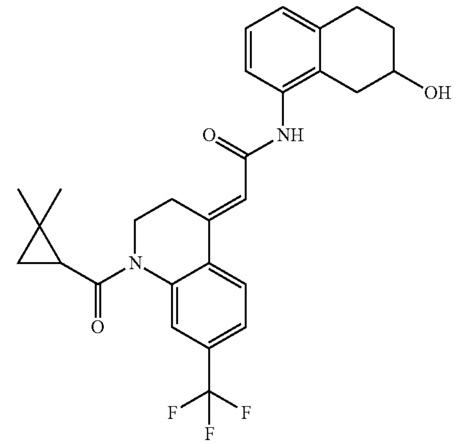
EXAMPLE 109
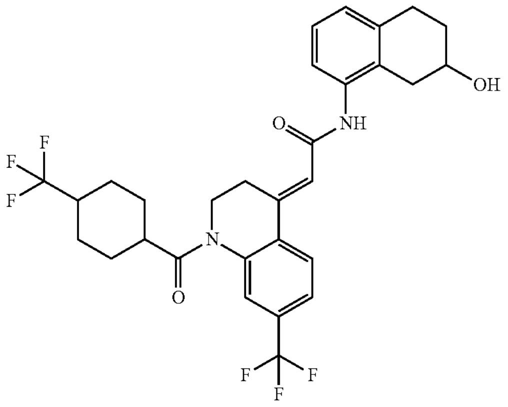
EXAMPLE 110
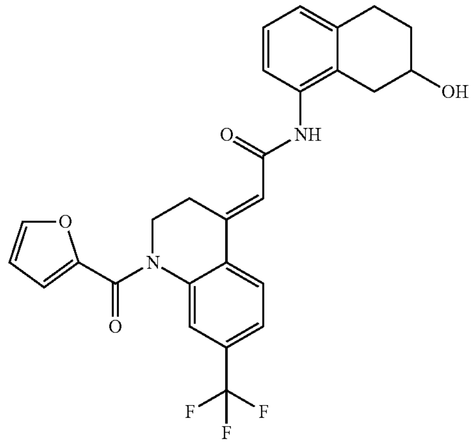
EXAMPLE 111
TABLE 2-continued
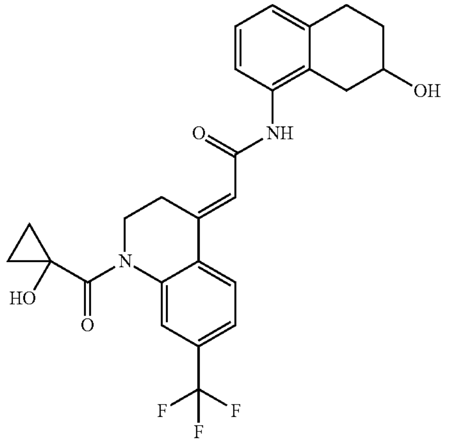
EXAMPLE 112
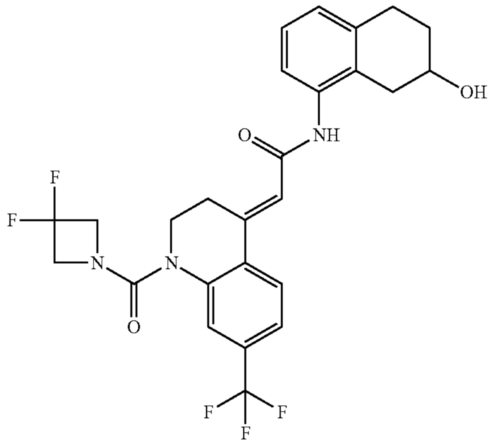
EXAMPLE 113
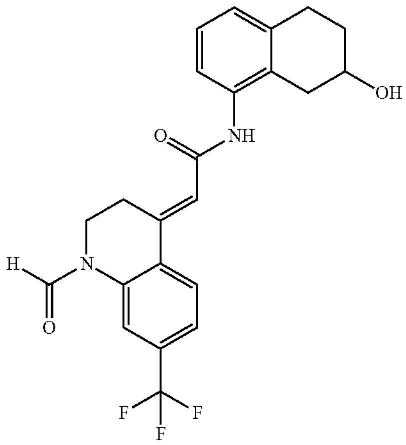
EXAMPLE 114

TABLE 2-continued
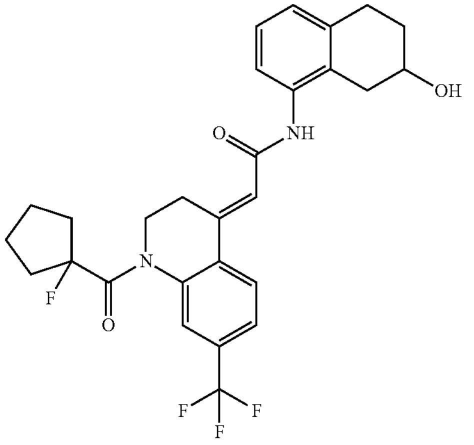
EXAMPLE 115
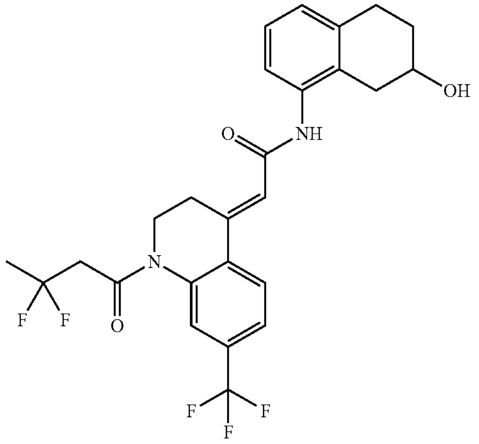
EXAMPLE 116
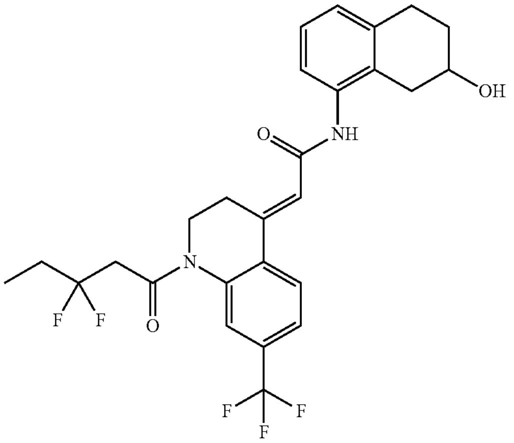
EXAMPLE 117
TABLE 2-continued
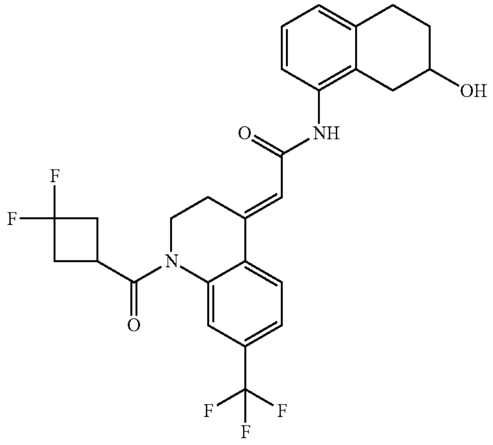
EXAMPLE 118
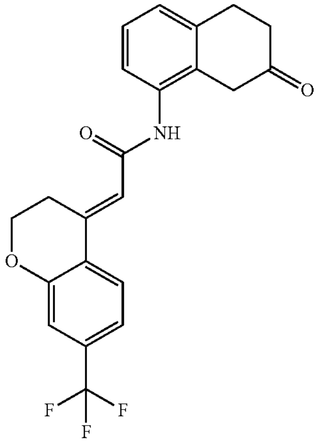
EXAMPLE 119
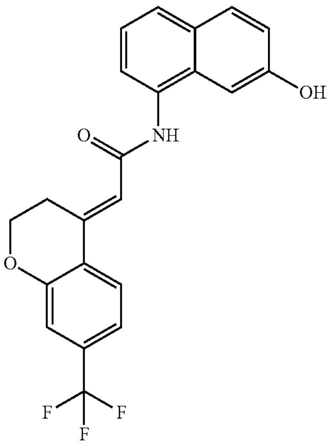
EXAMPLE 120

TABLE 2-continued
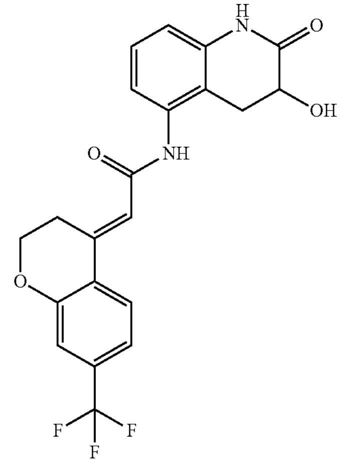
EXAMPLE 121
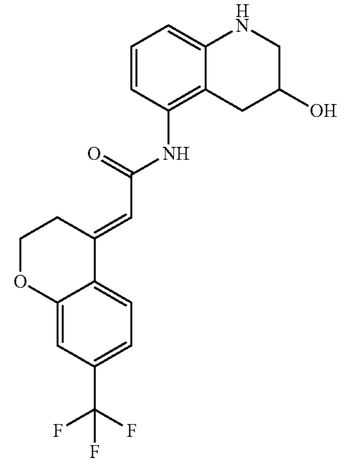
EXAMPLE 122
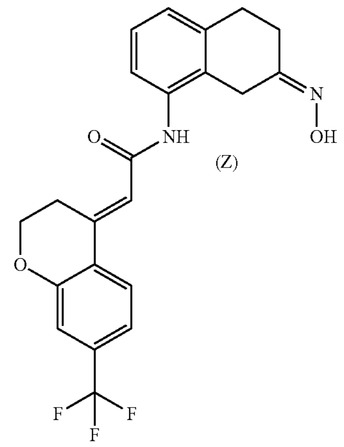
EXAMPLE 123
TABLE 2-continued
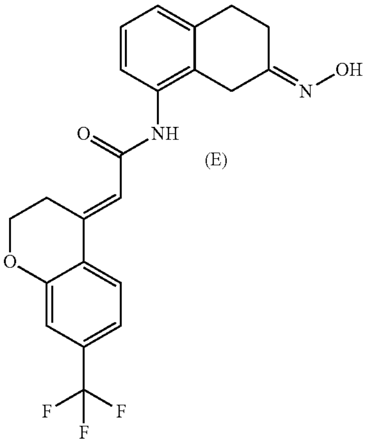
EXAMPLE 124
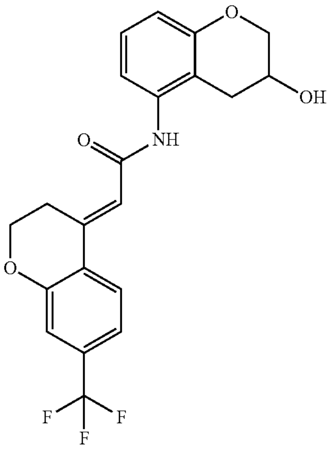
EXAMPLE 125
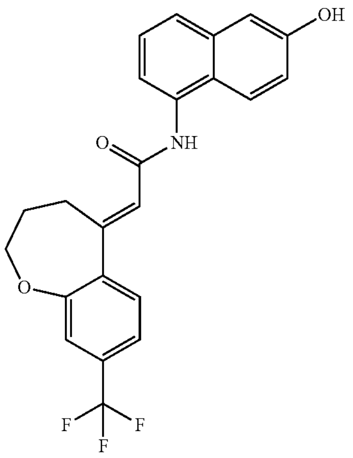
EXAMPLE 126

TABLE 2-continued
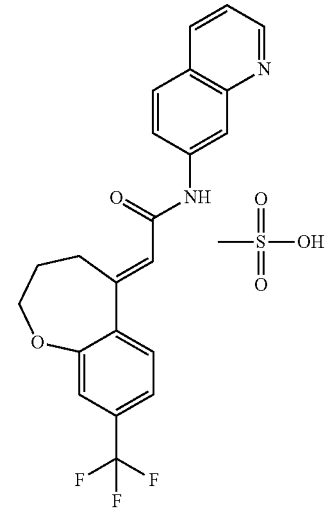
EXAMPLE 127
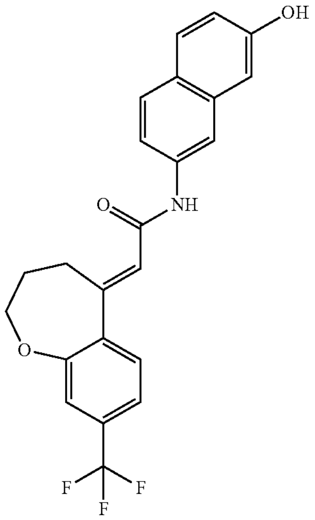
EXAMPLE 128
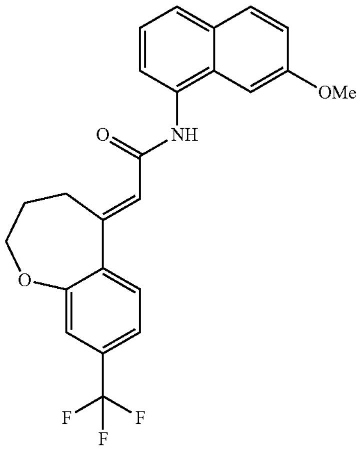
EXAMPLE 129
TABLE 2-continued
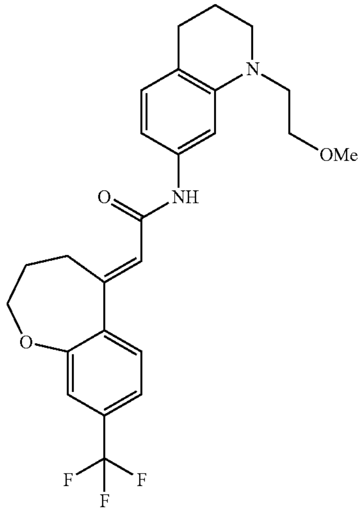
EXAMPLE 130
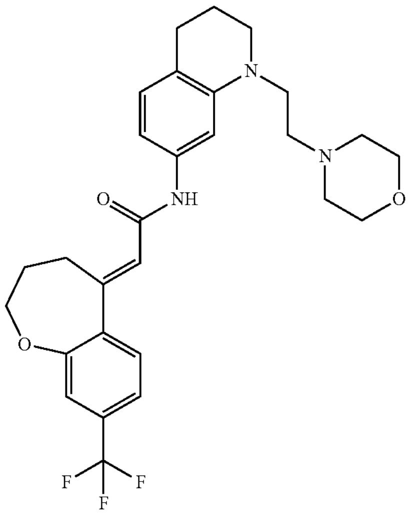
EXAMPLE 131
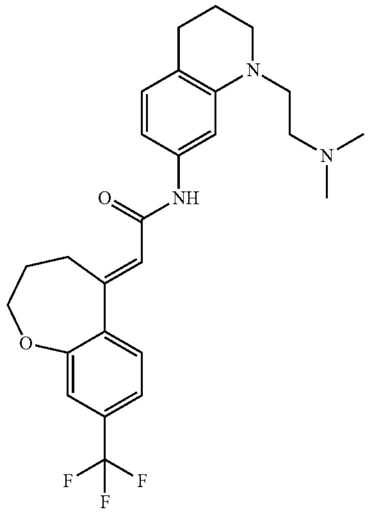
EXAMPLE 132

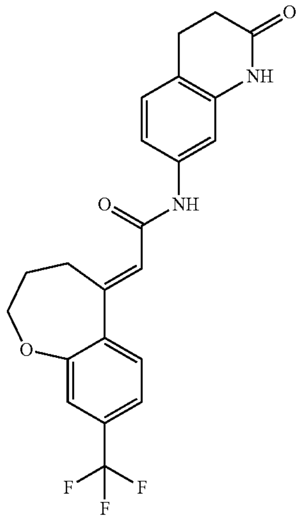
EXAMPLE 133
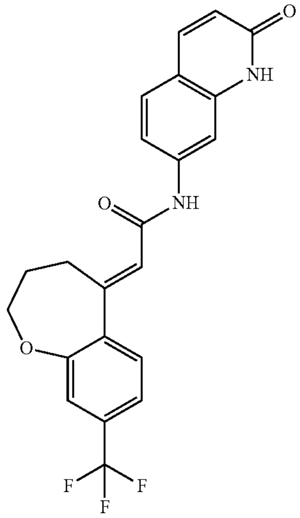
EXAMPLE 134
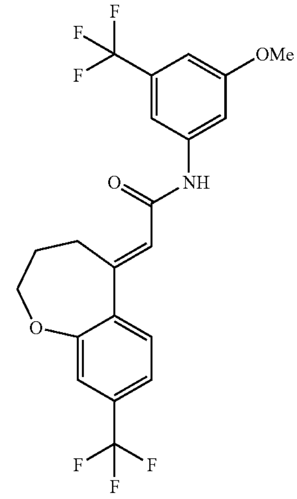
EXAMPLE 135
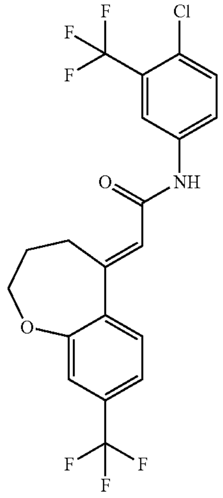
EXAMPLE 136
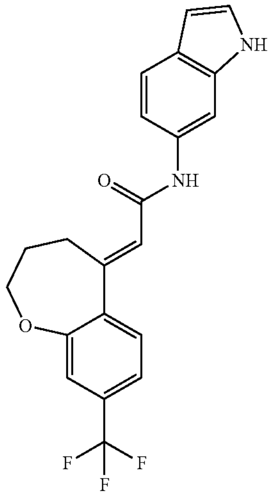
EXAMPLE 137

TABLE 2-continued
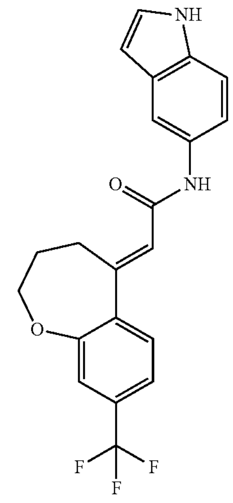
EXAMPLE 138
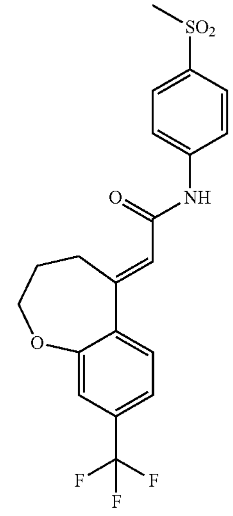
EXAMPLE 139
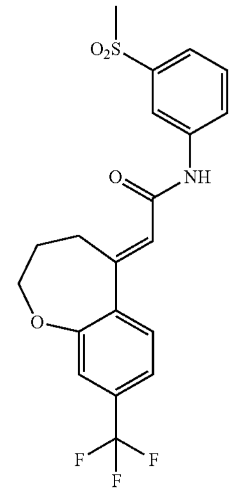
EXAMPLE 140
TABLE 2-continued
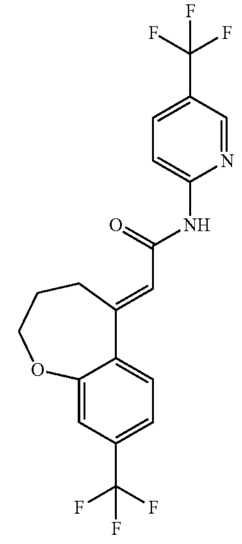
EXAMPLE 141
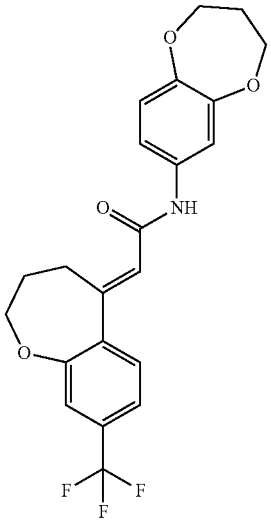
EXAMPLE 142

TABLE 2-continued
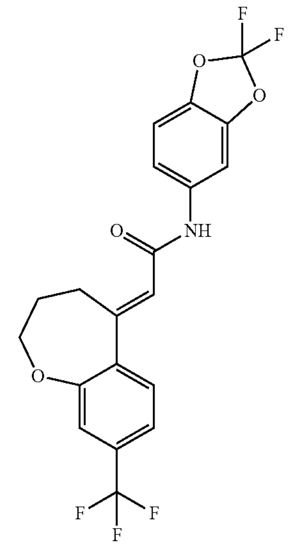
EXAMPLE 143
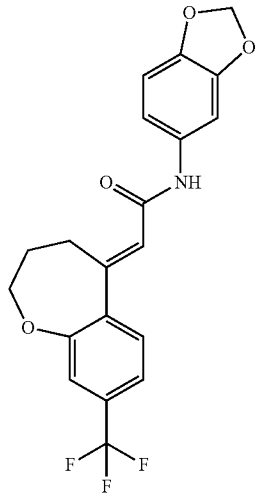
EXAMPLE 144
TABLE 2-continued
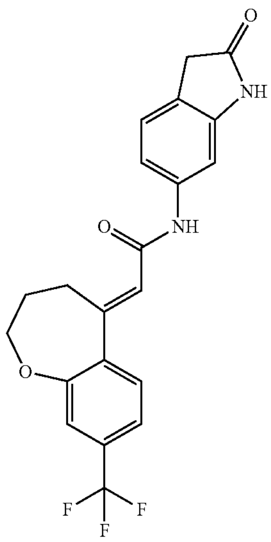
EXAMPLE 145
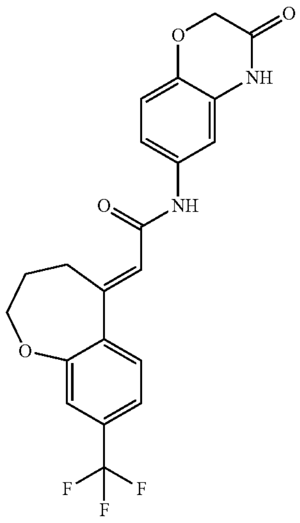
EXAMPLE 146

TABLE 2-continued
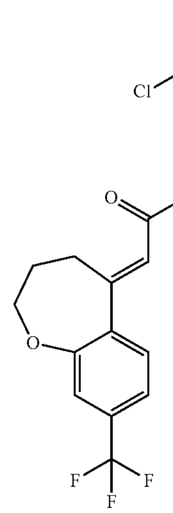
EXAMPLE 147
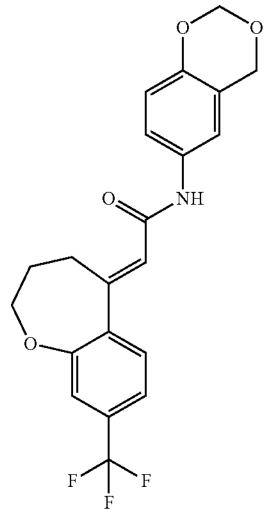
EXAMPLE 148
TABLE 2-continued
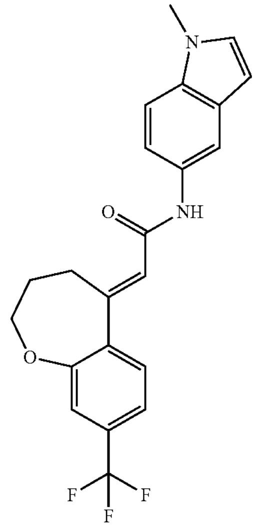
EXAMPLE 149
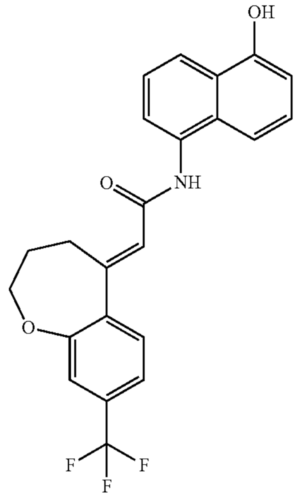
EXAMPLE 150
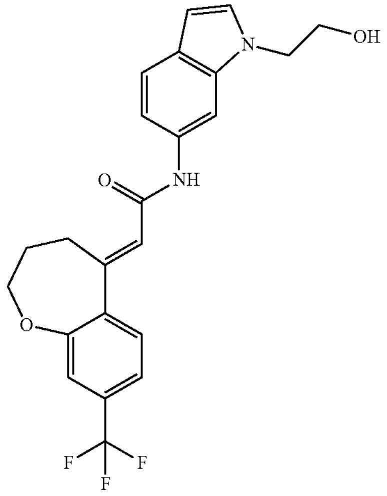
EXAMPLE 151

TABLE 2-continued
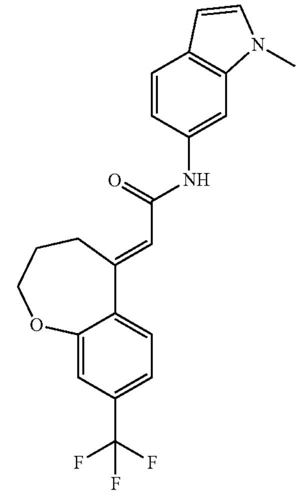
EXAMPLE 152
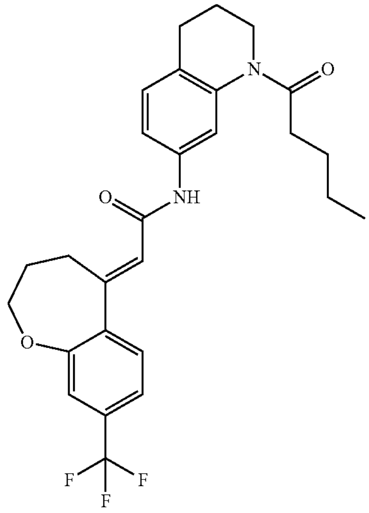
EXAMPLE 153
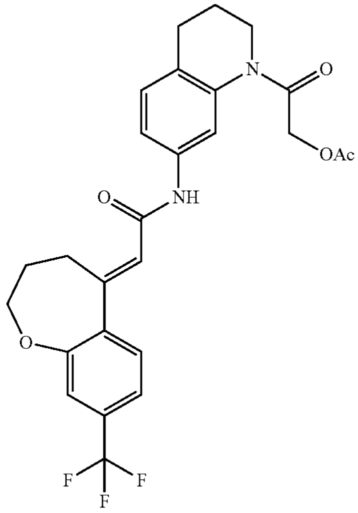
EXAMPLE 154
TABLE 2-continued
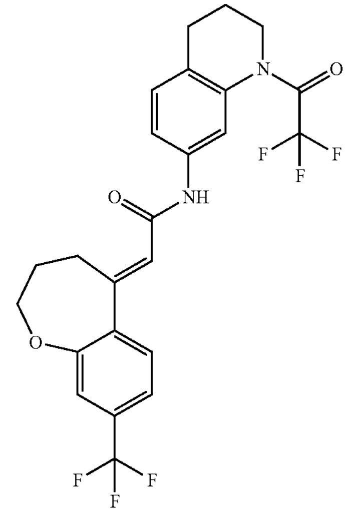
EXAMPLE 155
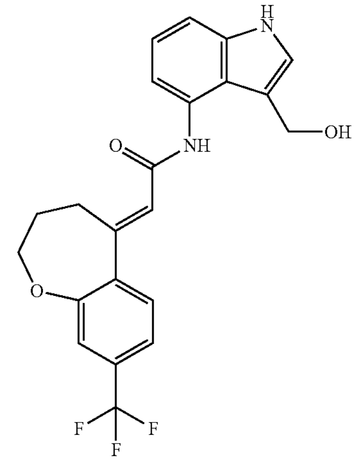
EXAMPLE 156
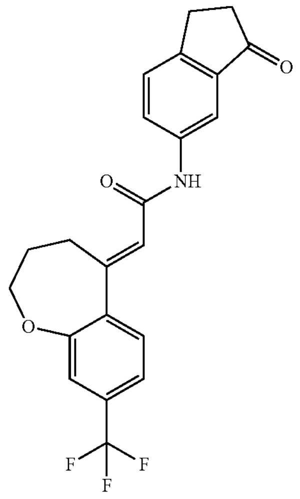
EXAMPLE 157

TABLE 2-continued
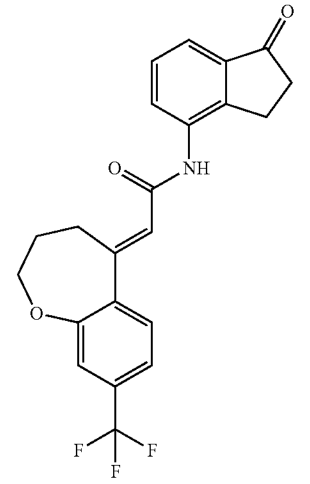
EXAMPLE 158
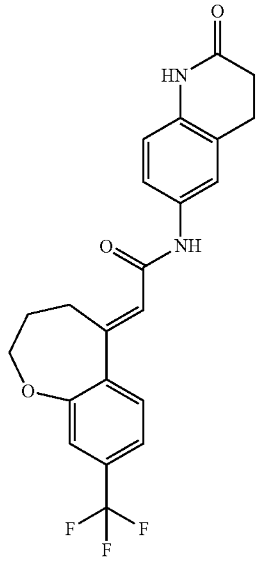
EXAMPLE 159
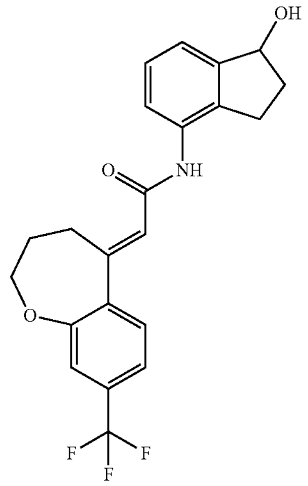
EXAMPLE 160
TABLE 2-continued
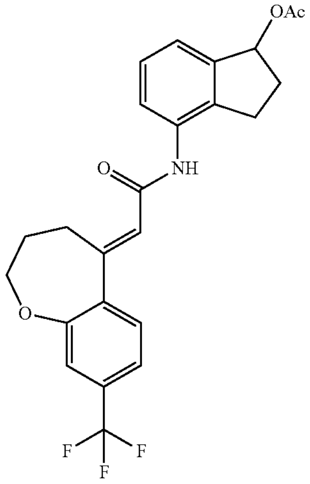
EXAMPLE 161
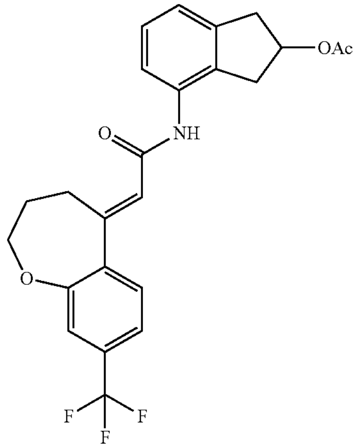
EXAMPLE 162
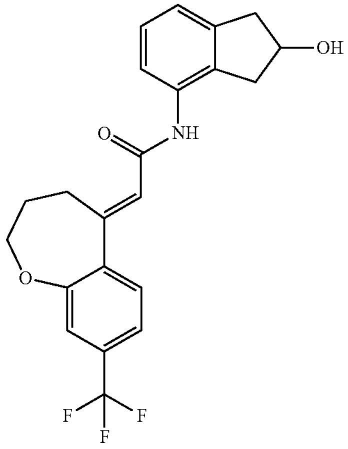
EXAMPLE 163

TABLE 2-continued
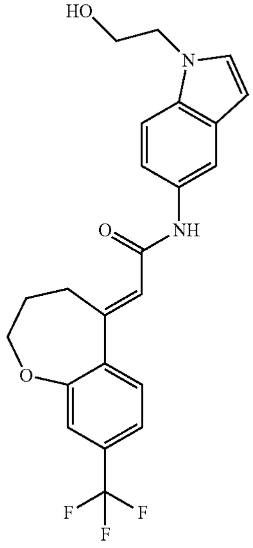
EXAMPLE 164
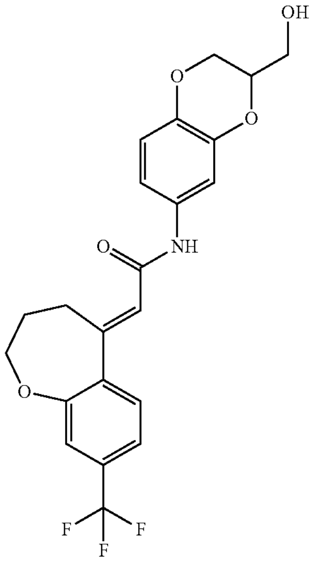
EXAMPLE 165
TABLE 2-continued
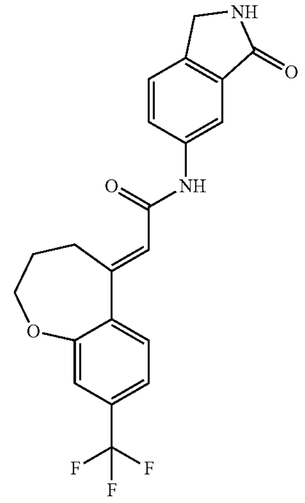
EXAMPLE 166
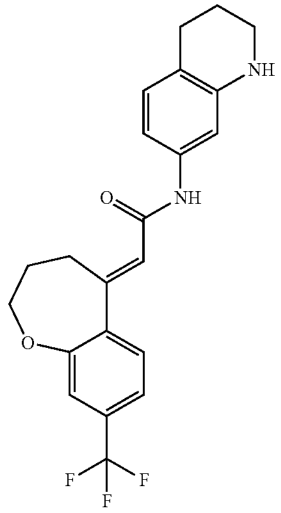
EXAMPLE 167
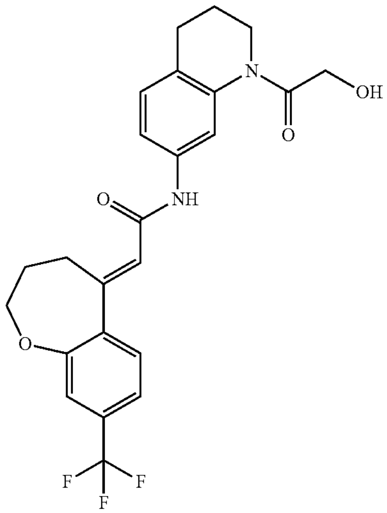
EXAMPLE 168

TABLE 2-continued
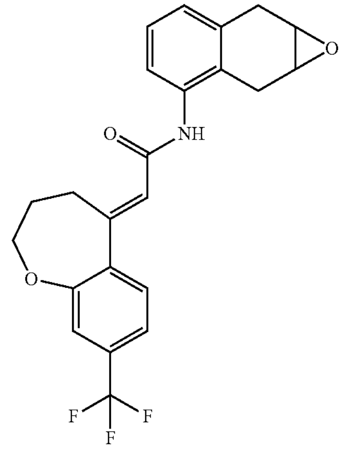
EXAMPLE 169
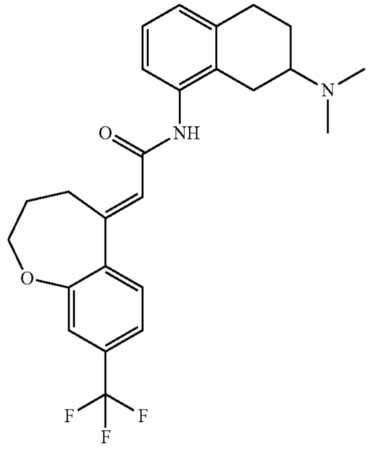
EXAMPLE 170
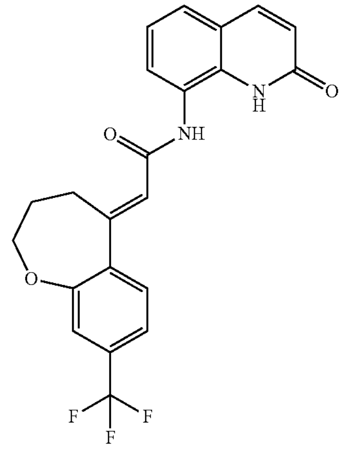
EXAMPLE 171
TABLE 2-continued
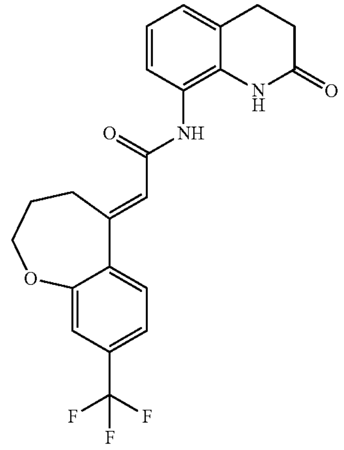
EXAMPLE 172
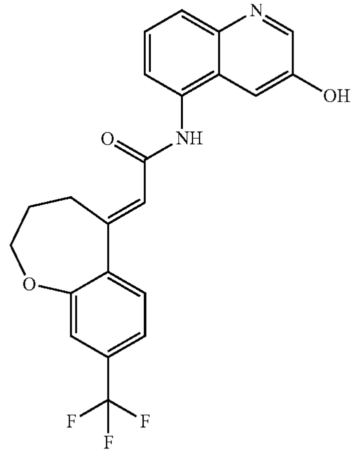
EXAMPLE 173
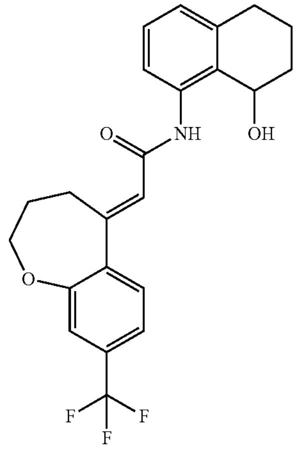
EXAMPLE 174

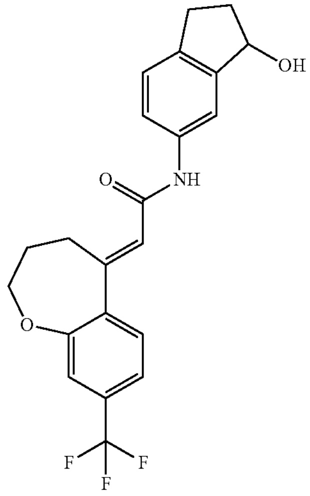
EXAMPLE 175
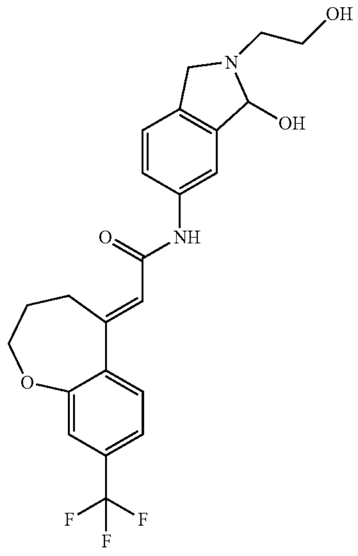
EXAMPLE 176
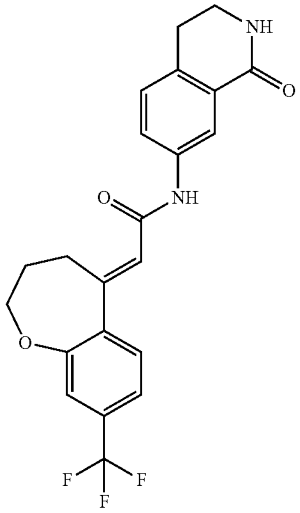
EXAMPLE 177
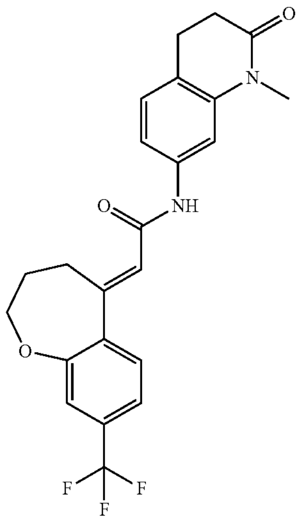
EXAMPLE 178
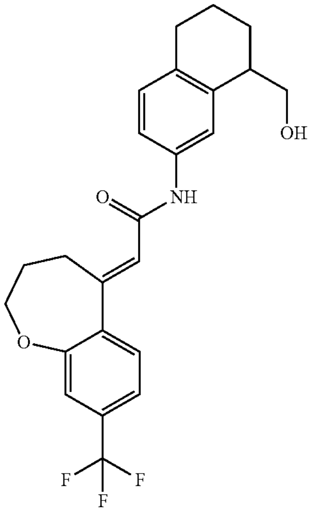
EXAMPLE 179

TABLE 2-continued
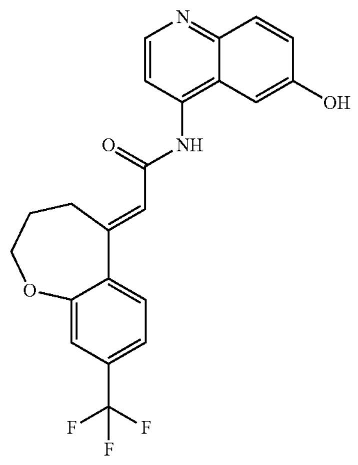
EXAMPLE 180
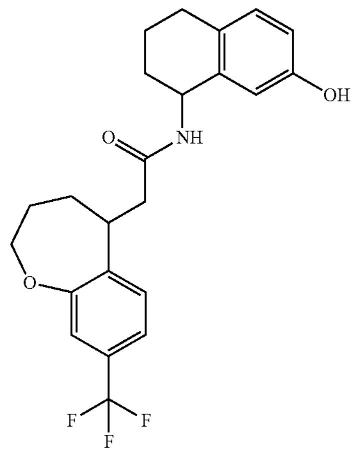
EXAMPLE 181
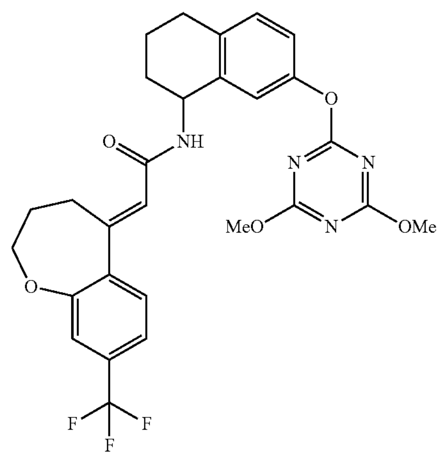
EXAMPLE 182
TABLE 2-continued
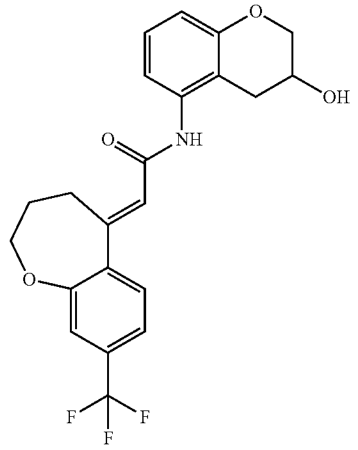
EXAMPLE 183
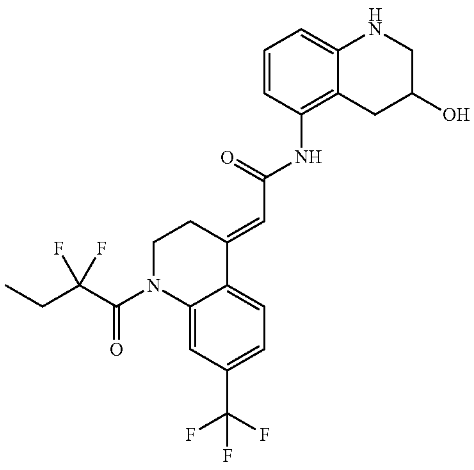
EXAMPLE 184
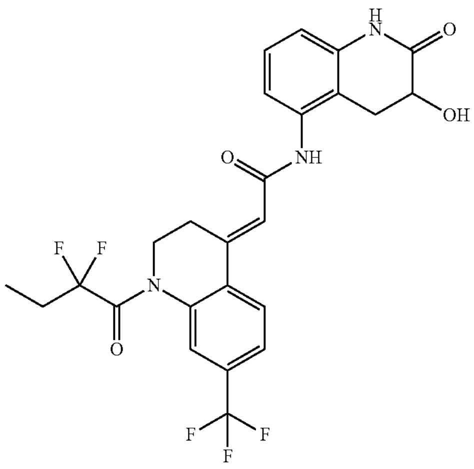
EXAMPLE 185

TABLE 2-continued
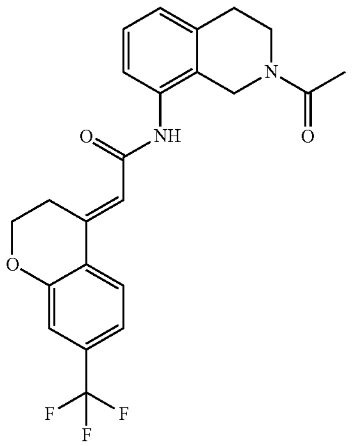
EXAMPLE 186
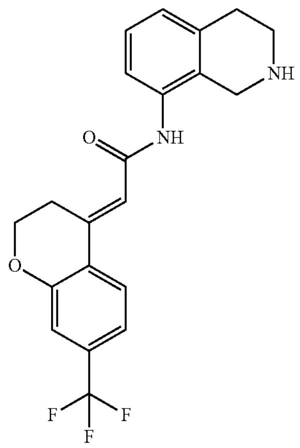
EXAMPLE 187
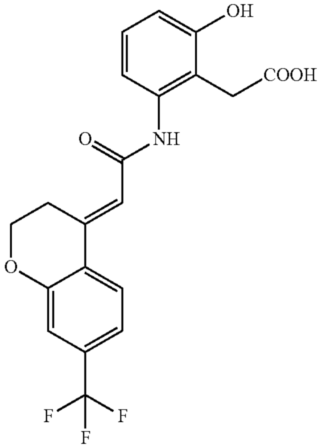
EXAMPLE 188
TABLE 2-continued
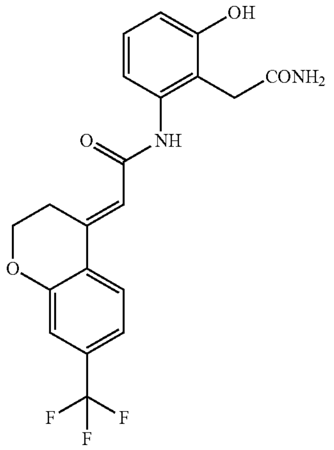
EXAMPLE 189
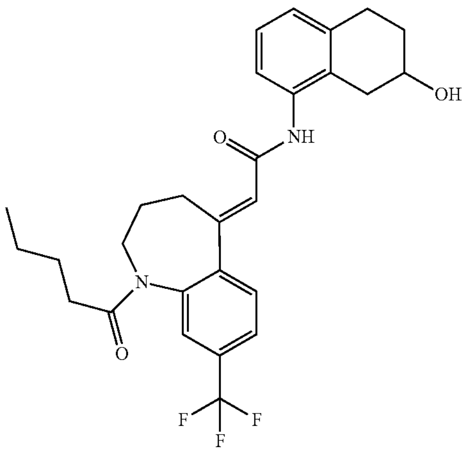
EXAMPLE 190
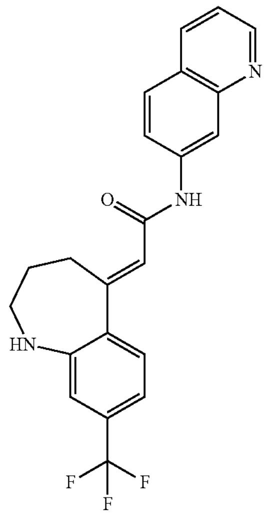
EXAMPLE 191

TABLE 2-continued
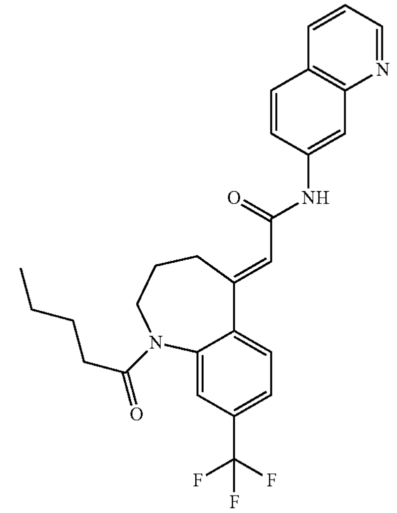
EXAMPLE 192
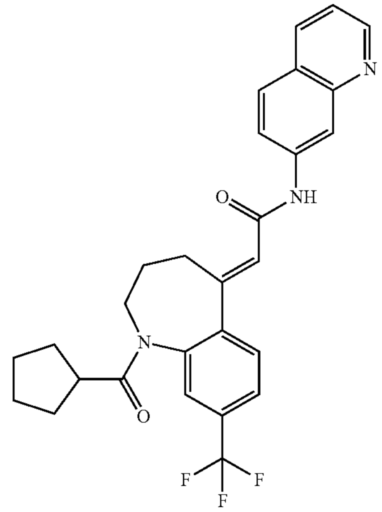
EXAMPLE 193
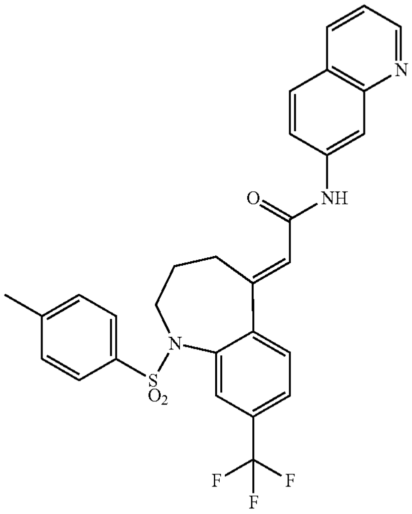
EXAMPLE 194
TABLE 2-continued
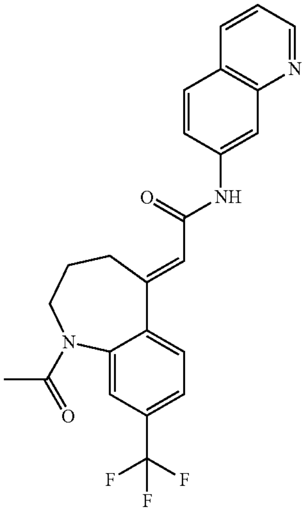
EXAMPLE 195
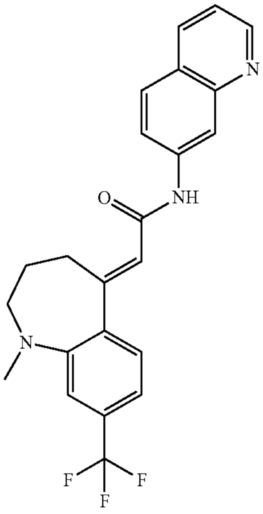
EXAMPLE 196

TABLE 2-continued
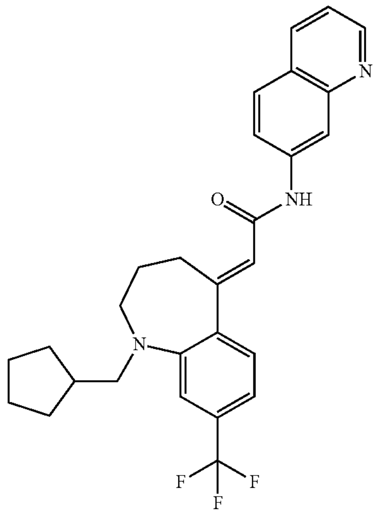
EXAMPLE 197
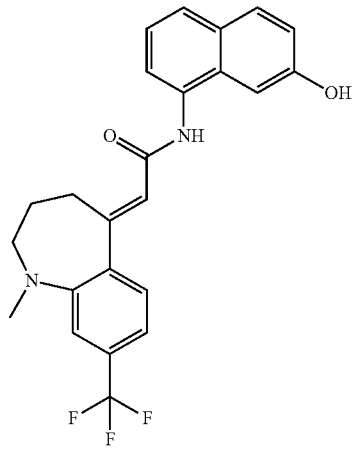
EXAMPLE 198
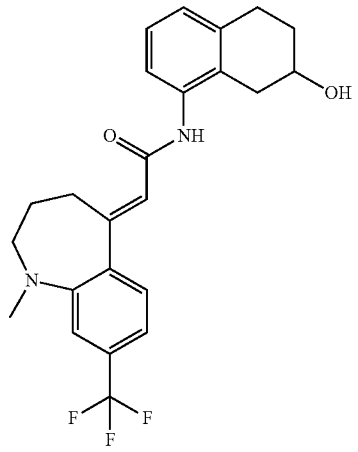
EXAMPLE 199
TABLE 2-continued
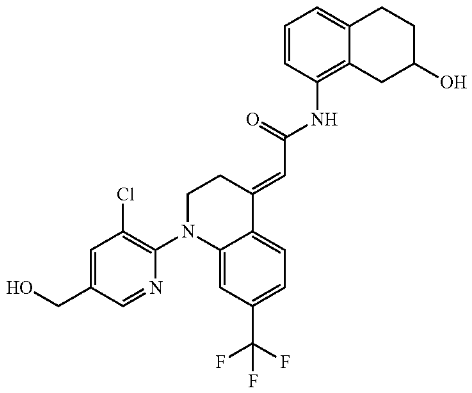
EXAMPLE 200
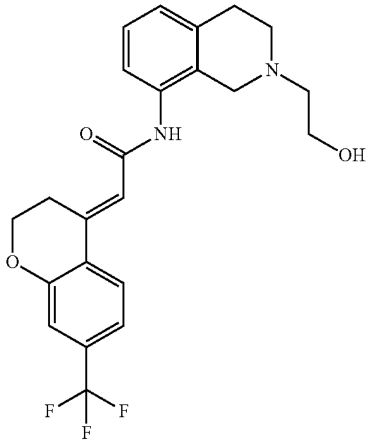
EXAMPLE 201
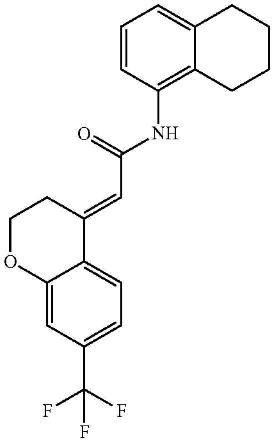
EXAMPLE 202

TABLE 2-continued
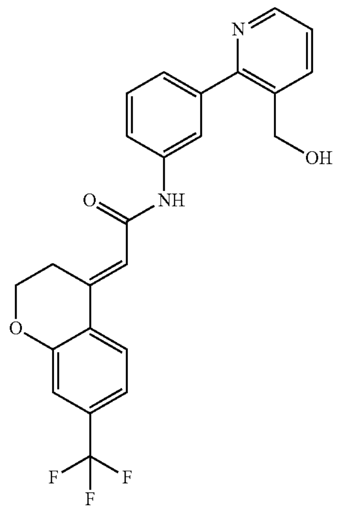
EXAMPLE 203
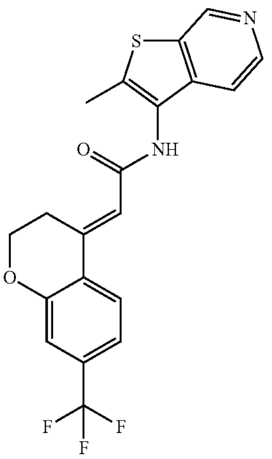
EXAMPLE 204
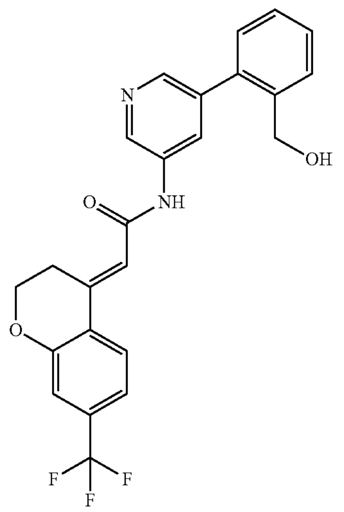
EXAMPLE 205
TABLE 2-continued
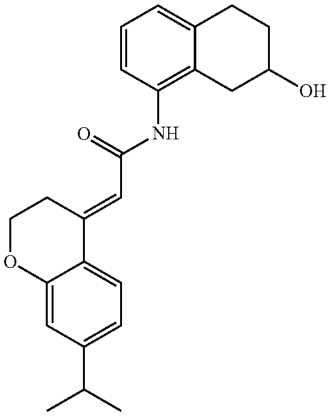
EXAMPLE 206
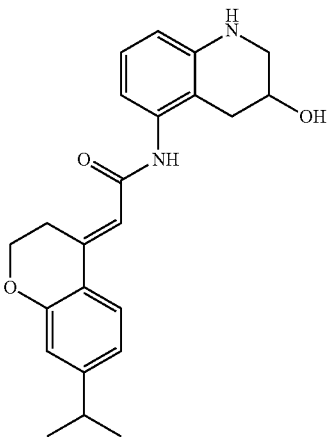
EXAMPLE 207
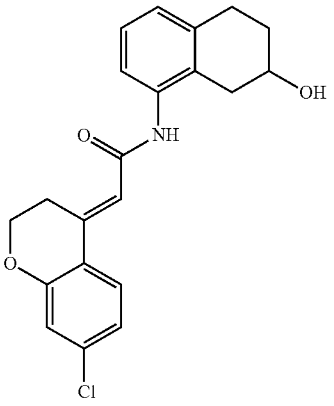
EXAMPLE 208

TABLE 2-continued
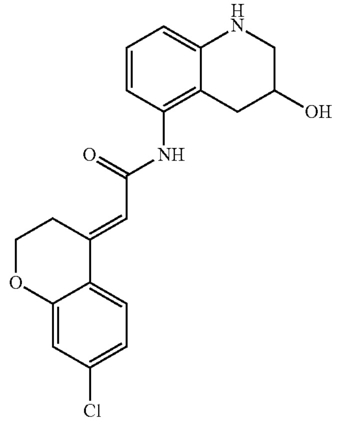
EXAMPLE 209
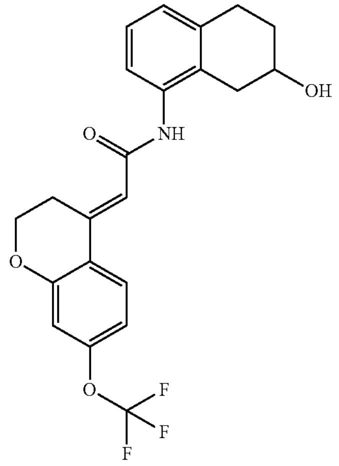
EXAMPLE 210
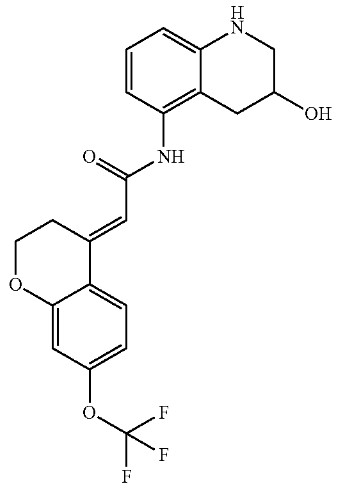
EXAMPLE 211
TABLE 2-continued
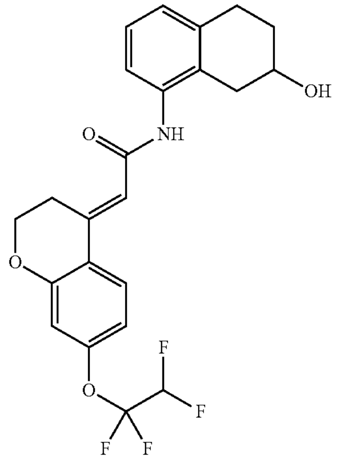
EXAMPLE 212
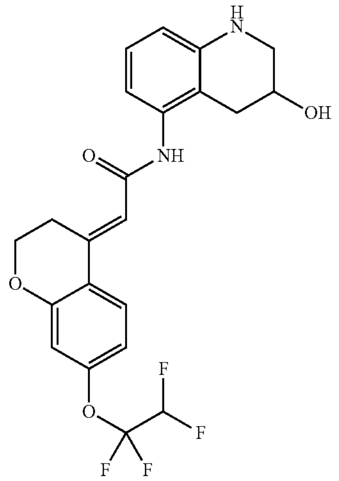
EXAMPLE 213
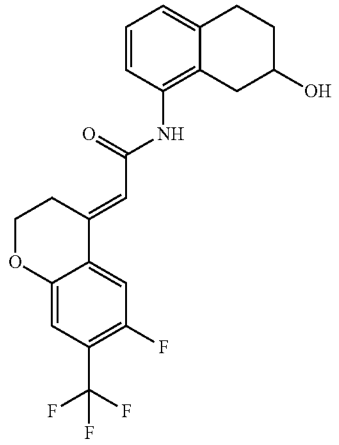
EXAMPLE 214

TABLE 2-continued
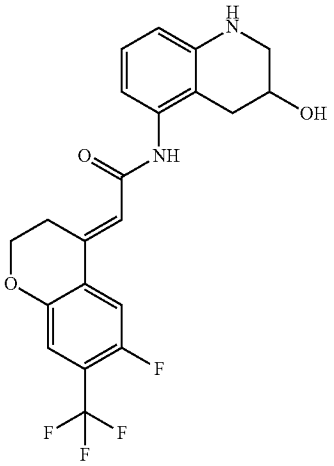
EXAMPLE 215
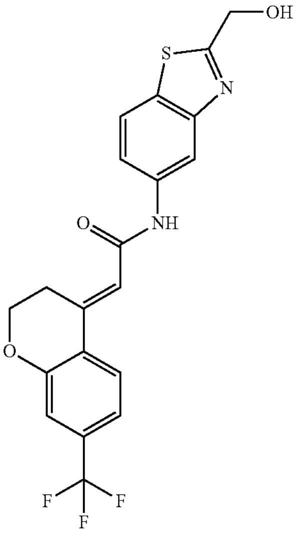
EXAMPLE 216
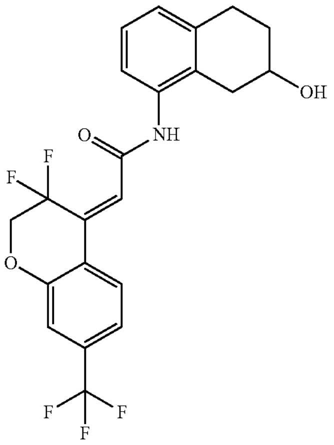
EXAMPLE 217
TABLE 2-continued
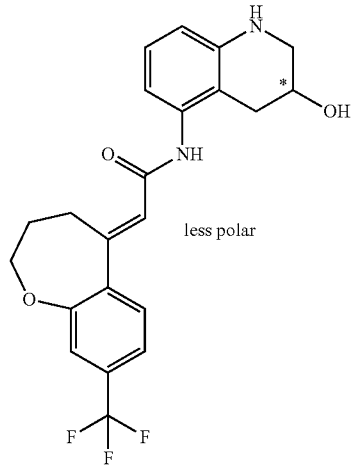
less polar
EXAMPLE 218
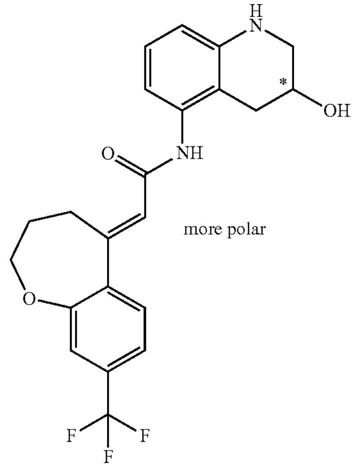
more polar
EXAMPLE 219
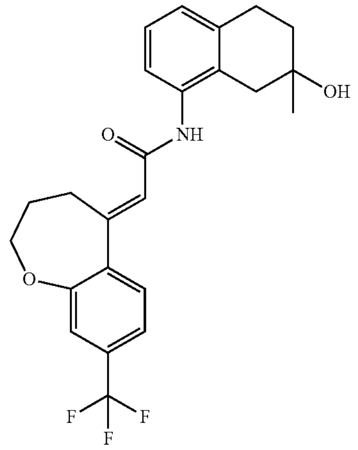
EXAMPLE 220

TABLE 2-continued
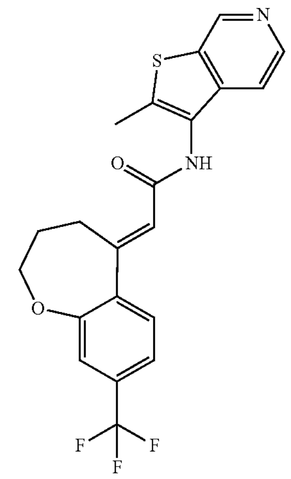
EXAMPLE 221
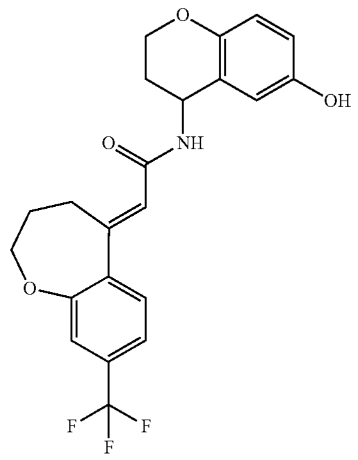
EXAMPLE 222
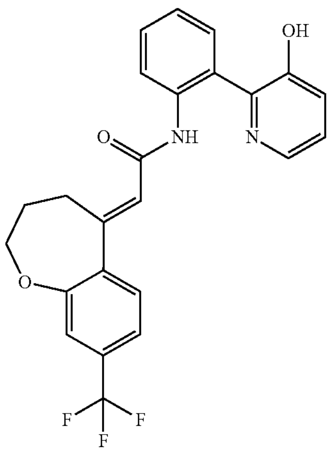
EXAMPLE 223
TABLE 2-continued
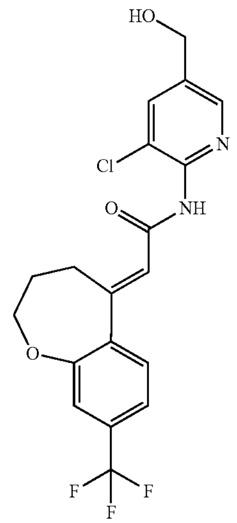
EXAMPLE 224
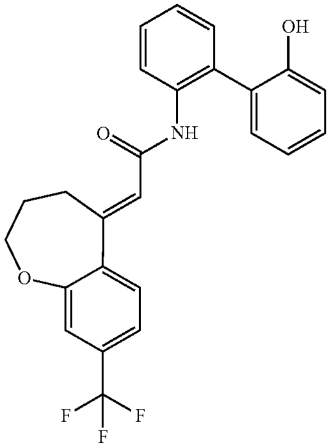
EXAMPLE 225
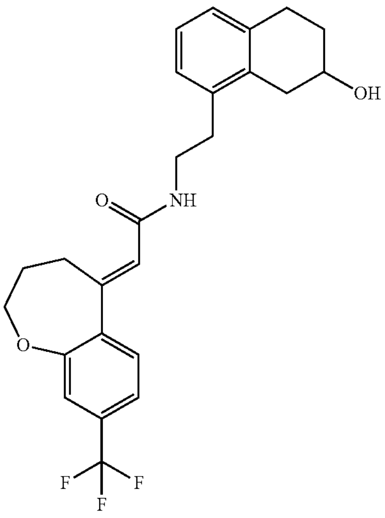
EXAMPLE 226

TABLE 2-continued
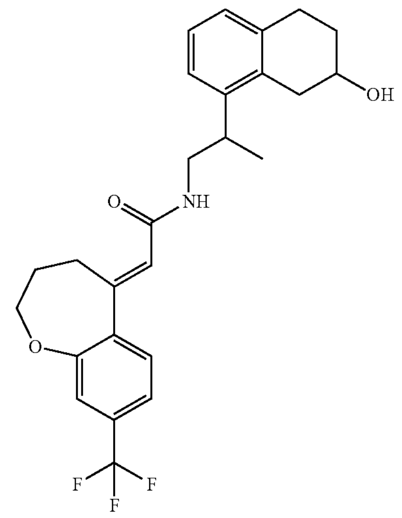
EXAMPLE 227
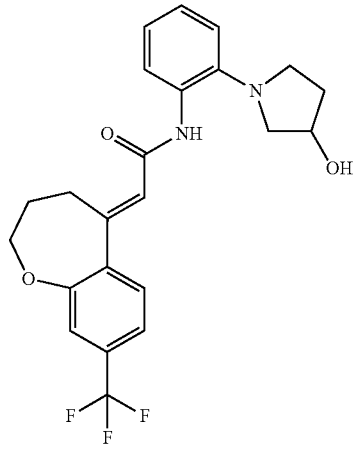
EXAMPLE 228
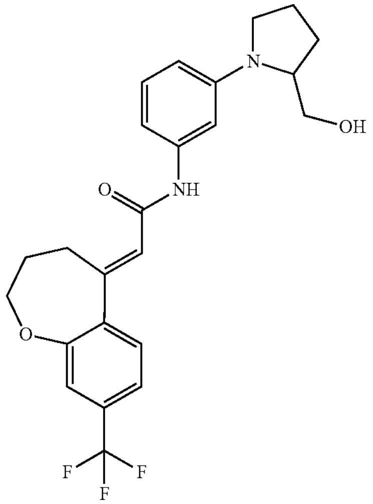
EXAMPLE 229
TABLE 2-continued
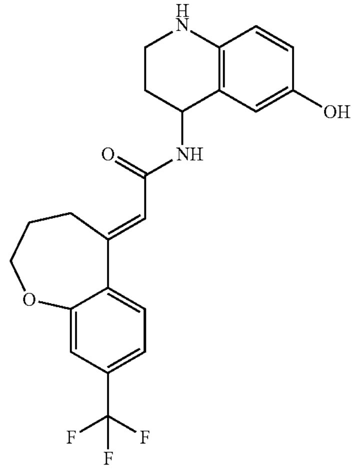
EXAMPLE 230
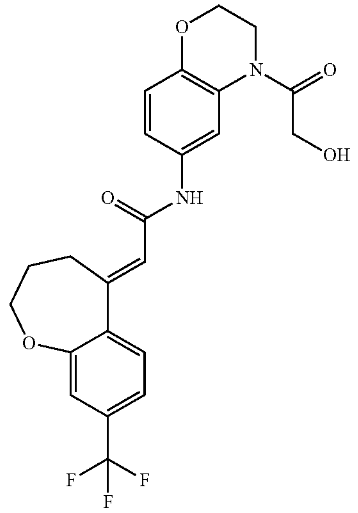
EXAMPLE 231
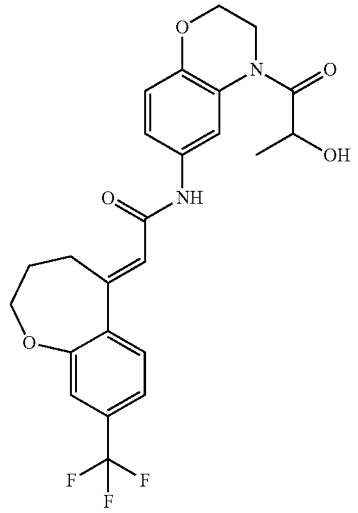
EXAMPLE 232

TABLE 2-continued
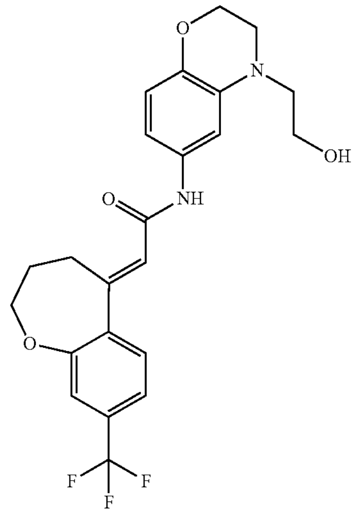
EXAMPLE 233
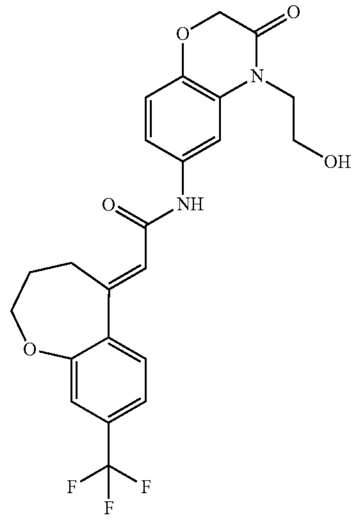
EXAMPLE 234
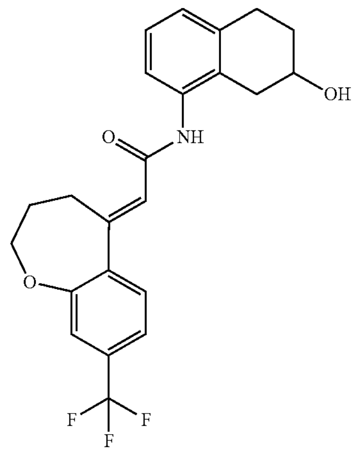
EXAMPLE 235
TABLE 2-continued
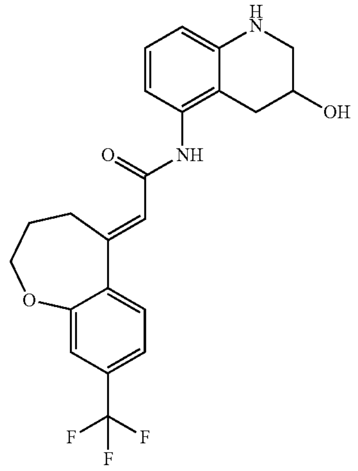
EXAMPLE 236
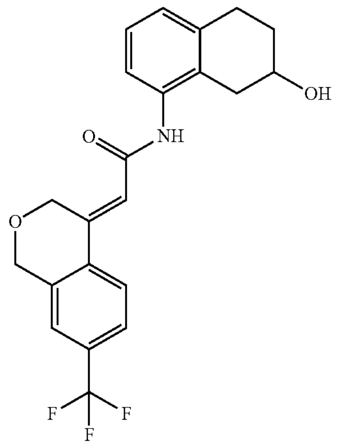
EXAMPLE 237
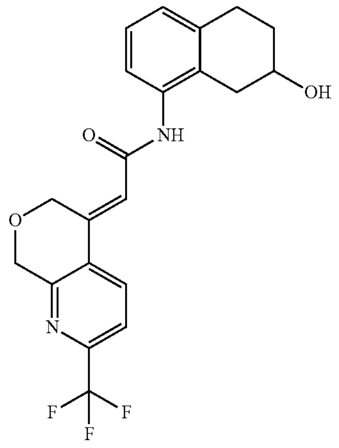
EXAMPLE 238

TABLE 2-continued
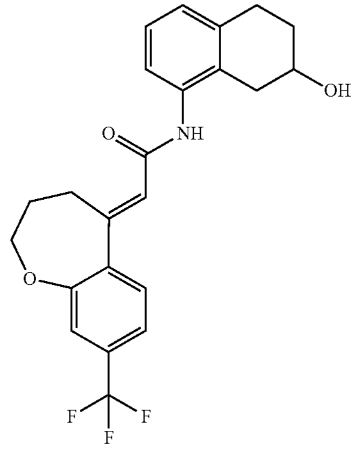
EXAMPLE 239
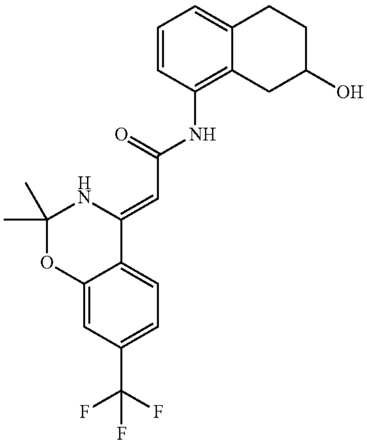
EXAMPLE 240
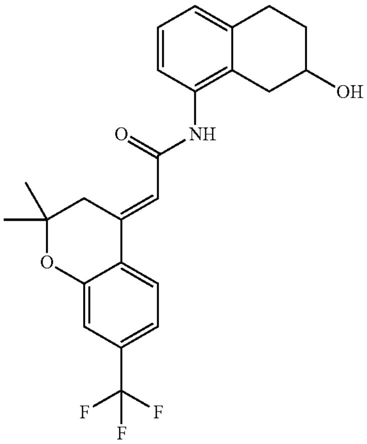
EXAMPLE 241
TABLE 2-continued
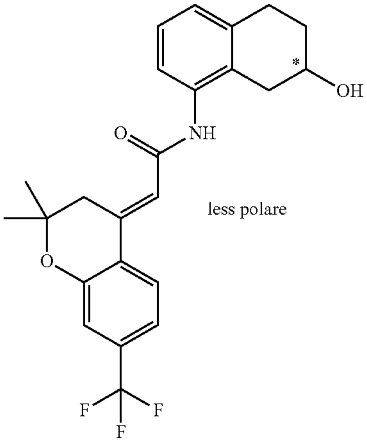
EXAMPLE 242
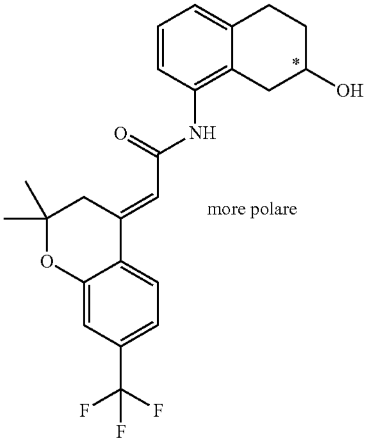
EXAMPLE 243
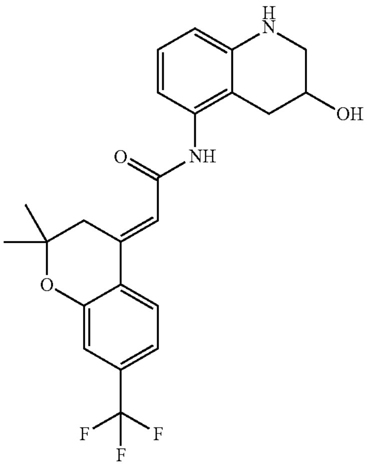
EXAMPLE 244

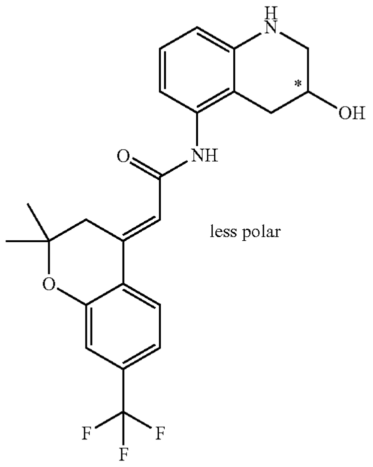
EXAMPLE 245
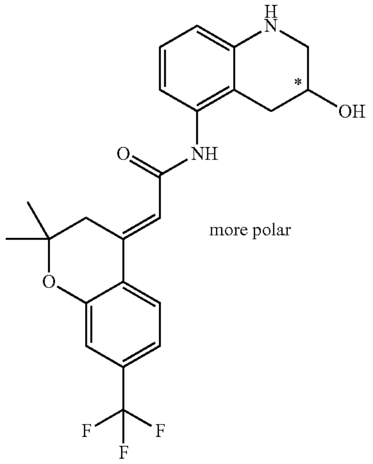
EXAMPLE 246
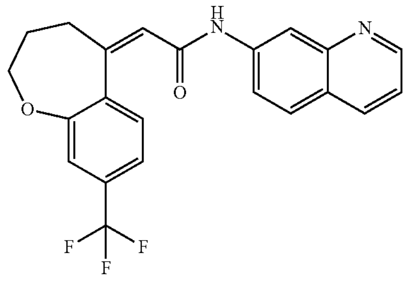
EXAMPLE 247
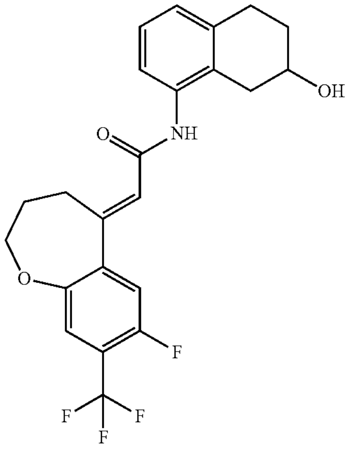
EXAMPLE 248
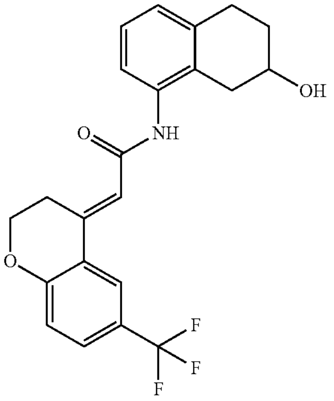
EXAMPLE 249
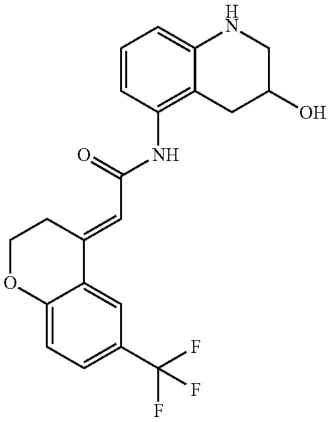
EXAMPLE 250

TABLE 2-continued
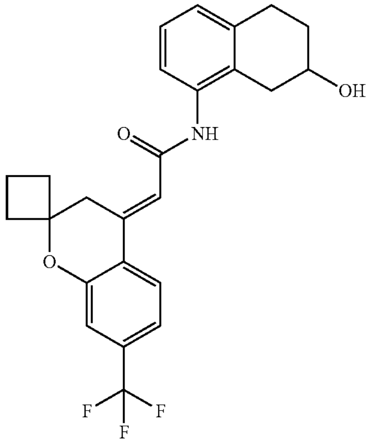
EXAMPLE 251
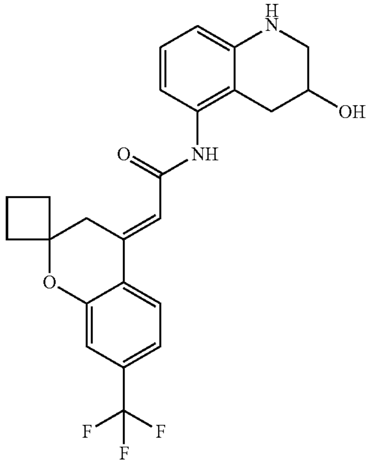
EXAMPLE 252
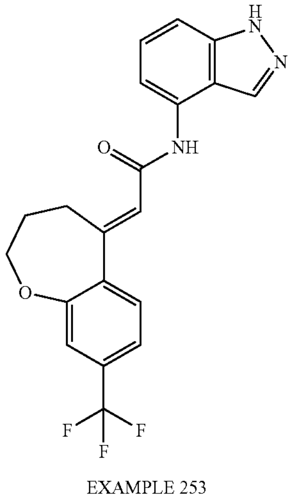 [SMILES: O=C(/C=C1\CCCOc2cc(C(F)(F)F)ccc21)Nc1cccc2[nH]ncc12]
EXAMPLE 253
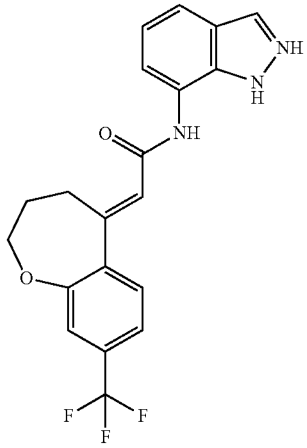
EXAMPLE 254
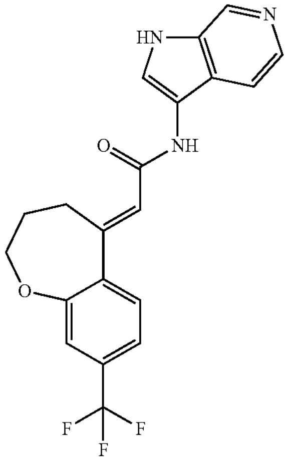
EXAMPLE 255
TABLE 3
| EXAMPLE | LC Mass ($M^+$) | RETENTION TIME (MIN) |
|---|---|---|
| $1^A$ | 324 | 7.52 |
| $2^A$ | 317 | 5.22 |
| $3^A$ | 377 | 5.42 |
| $4^A$ | 373 | 7.89 |
| $5^A$ | 373 | 7.49 |
| $6^A$ | 389 | 4.84 |
| $7^A$ | 385 | 7.21 |
| $8^A$ | 385 | 6.94 |
| $9^B$ | 406 | 5.51 |
| $10^A$ | 403 | 5.16 |
| $11^A$ | 399 | 7.68 |
| $12^B$ | 400 | 5.03 |
| $13^A$ | 399 | 7.38 |
| $14^B$ | 404 | 6.50 |
| $15^B$ | 416 | 6.26 |
| $16^B$ | 378 | 5.65 |
| $17^B$ | 417 | 6.05 |
| $18^B$ | 414 | 5.25 |
| $19^B$ | 419 | 5.45 |
| $20^A$ | 434 | 8.47 |
| $21^B$ | 430 | 5.59 |
| $22^B$ | 441 | 5.85 |
| $23^B$ | 416 | 5.63 |
| $24^B$ | 404 | 5.21 |

TABLE 3-continued

| EXAMPLE | LC Mass ($M^+$) | RETENTION TIME (MIN) |
|---|---|---|
| 25$^{B}$ | 461 | 4.86 |
| 26$^{A}$ | 497 | 9.00 |
| 27$^{B}$ | 509 | 5.69 |
| 28$^{A}$ | 476 | 9.88 |
| 29$^{A}$ | 439 | 7.50 |
| 30$^{B}$ | 377 | 4.60 |
| 31$^{B}$ | 439 | 5.53 |
| 32$^{B}$ | 420 | 5.27 |
| 33$^{B}$ | 434 | 5.43 |
| 34$^{B}$ | 420 | 5.57 |
| 35$^{B}$ | 404 | 5.37 |
| 36$^{B}$ | 447 | 5.43 |
| 37$^{B}$ | 446 | 5.35 |
| 38$^{B}$ | 428 | 5.25 |
| 39$^{B}$ | 493 | 6.16 |
| 40$^{B}$ | 403 | 4.18 |
| 41$^{B}$ | 403 | 5.13 |
| 42$^{B}$ | 388 | 5.09 |
| 43$^{B}$ | 416 | 5.63 |
| 44$^{B}$ | 390 | 4.77 |
| 45$^{B}$ | 419 | 5.47 |
| 46$^{B}$ | 352 (M-55) | 5.31 |
| 47$^{B}$ | 431 | 6.22 |
| 48$^{A}$ | 426 | 5.40 |
| 49$^{A}$ | 388 | 4.26 |
| 50$^{A}$ | 468 | 7.35 |
| 51$^{A}$ | 482 | 7.71 |
| 52$^{A}$ | 494 | 8.00 |
| 53$^{A}$ | 496 | 5.77 |
| 54$^{A}$ | 488 | 6.94 |
| 55$^{A}$ | 489 | 5.38 |
| 56$^{A}$ | 498 | 7.44 |
| 57$^{A}$ | 494 | 9.11 |
| 58$^{A}$ | 461 | 5.92 |
| 59$^{B}$ | 435 | 4.77 |
| 60$^{B}$ | 392 | 5.02 |
| 61$^{B}$ | 416 | 5.17 |
| 62$^{B}$ | 418 | 4.87 |
| 63$^{B}$ | 418 | 4.87 |
| 64$^{B}$ | 418 | 4.89 |
| 65$^{A}$ | 434 | 7.17 |
| 66$^{A}$ | 434 | 7.00 |
| 67$^{A}$ | 433 | 4.36 |
| 68$^{A}$ | 419 | 4.50 |
| 69$^{B}$ | 433 | 4.88 |
| 70$^{A}$ | 404 | 7.88 |
| 71 | 404 | 4.73 |
| 72 | 404 | 4.73 |
| 73$^{A}$ | 480 | 4.77 |
| 74$^{B}$ | 483 | 8.67 |
| 75$^{B}$ | 466 | 4.46 |
| 76$^{B}$ | 482 | 4.84 |
| 77$^{B}$ | 468 | 4.56 |
| 78$^{B}$ | 482 | 4.93 |
| 79$^{B}$ | 482 | 4.87 |
| 80$^{B}$ | 482 | 4.85 |
| 81$^{B}$ | 496 | 5.25 |
| 82$^{A}$ | 499 | 8.43 |
| 83$^{B}$ | 487 | 5.05 |
| 84 | 485 | 4.85 |
| 85 | 549 | 4.90 |
| 86 | 501 | 5.11 |
| 87 | 487 | 4.81 |
| 88 | 517 | 4.68 |
| 89 | 485 | 4.85 |
| 90 | 499 | 4.89 |
| 91 | 527 | 4.80 |
| 92 | 513 | 4.64 |
| 93 | 541 | 5.01 |
| 94 | 521 | 4.78 |
| 95 | 509 | 5.07 |
| 96 | 491 | 4.77 |
| 97 | 466 | 5.83 |
| 98 | 538 | 7.87 |
| 99 | 452 | 4.16 |
| 100 | 470 | 3.80 |

TABLE 3-continued

| EXAMPLE | LC Mass ($M^+$) | RETENTION TIME (MIN) |
|---|---|---|
| 101 | 498 | 3.96 |
| 102 | 494 | 5.04 |
| 103 | 497 | 4.78 |
| 104 | 481 | 3.17 |
| 105 | 471 | 4.48 |
| 106 | 403 | 4.34 |
| 107 | 502 | 4.38 |
| 108 | 488 | 4.44 |
| 109 | 499 | 4.99 |
| 110 | 581 | 5.23 |
| 111 | 497 | 4.38 |
| 112 | 487 | 4.08 |
| 113 | 552 | 4.42 |
| 114 | 431 | 4.38 |
| 115 | 517 | 5.27 |
| 116 | 509 | 4.58 |
| 117 | 523 | 4.77 |
| 118 | 521 | 4.74 |
| 119 | 402 | 4.91 |
| 120 | 400 | 4.97 |
| 121 | 419 | 4.12 |
| 122 | 405 | 4.26 |
| 123 | 417 | 4.72 |
| 124 | 417 | 4.70 |
| 125 | 406 | 4.50 |
| 126 | 414 | 5.21 |
| 127 | 399 | 7.40 |
| 128 | 414 | 5.25 |
| 129 | 428 | 5.97 |
| 130 | 461 | 5.95 |
| 131 | 516 | 3.41 |
| 132 | 474 | 3.05 |
| 133 | 417 | 4.68 |
| 134 | 415 | 4.50 |
| 135 | 446 | 6.28 |
| 136 | 450 | 6.49 |
| 137 | 387 | 5.27 |
| 138 | 387 | 5.15 |
| 139 | 426 | 5.18 |
| 140 | 426 | 5.20 |
| 141 | 417 | 6.17 |
| 142 | 420 | 5.65 |
| 143 | 428 | 6.25 |
| 144 | 392 | 5.41 |
| 145 | 403 | 4.56 |
| 146 | 419 | 4.72 |
| 147 | 410 | 5.77 |
| 148 | 406 | 5.31 |
| 149 | 401 | 5.57 |
| 150 | 414 | 5.33 |
| 151 | 431 | 4.94 |
| 152 | 401 | 5.47 |
| 153 | 487 | 5.95 |
| 154 | 503 | 5.25 |
| 155 | 499 | 5.93 |
| 156 | 415 ($M^-$) | 5.48 |
| 157 | 402 | 5.23 |
| 158 | 402 | 5.21 |
| 159 | 417 | 7.80 |
| 160 | 404 | 8.17 |
| 161 | 446 | 9.38 |
| 162 | 446 | 9.31 |
| 163 | 404 | 8.13 |
| 164 | 431 | 8.27 |
| 165 | 436 | 4.81 |
| 166 | 403 | 4.40 |
| 167 | 403 | 5.33 |
| 168 | 461 | 4.91 |
| 169 | 416 | 8.59 |
| 170 | 445 | 4.10 |
| 171 | 415 | 4.50 |
| 172 | 417 | 4.72 |
| 173 | 415 | 4.64 |
| 174 | 416 ($M^-$) | 5.46 |
| 175 | 404 | 4.91 |

TABLE 3-continued

| EXAMPLE | LC Mass ($M^+$) | RETENTION TIME (MIN) |
|---|---|---|
| 176 | 447 | 4.23 |
| 177 | 417 | 4.46 |
| 178 | 431 | 5.05 |
| 179 | 432 | 5.25 |
| 180 | 415 | 3.63 |
| 181 | 418 | 5.07 |
| 182 | 557 | 5.59 |
| 183 | 420 | 4.66 |
| 184 | 510 | 4.62 |
| 185 | 524 | 4.46 |
| 186 | 431 | 4.52 |
| 187 | 389 | 2.67 |
| 188 | 408 | 4.83 |
| 189 | 407 | 4.08 |
| 190 | 501 | 7.83 |
| 191 | 398 | 6.60 |
| 192 | 482 | 6.82 |
| 193 | 494 | 6.96 |
| 194 | 552 | 7.79 |
| 195 | 440 | 5.33 |
| 196 | 412 | 7.67 |
| 197 | 480 | 6.11 |
| 198 | 427 | 5.33 |
| 199 | 431 | 5.05 |
| 200 | 544 | 4.26 |
| 201 | 433 | 2.57 |
| 202 | 388 | 3.94 |
| 203 | 441 | 4.24 |
| 204 | 405 | 3.80 |
| 205 | 441 | 4.66 |
| 206 | 378 | 4.77 |
| 207 | 379 | 4.26 |
| 208 | 370 | 4.46 |
| 209 | 371 | 3.96 |
| 210 | 420 | 4.75 |
| 211 | 421 | 4.28 |
| 212 | 452 | 4.66 |
| 213 | 453 | 4.20 |
| 214 | 422 | 4.81 |
| 215 | 423 | 4.34 |
| 216 | 421 | 4.50 |
| 217 | 440 | 4.62 |

TABLE 3-continued

| EXAMPLE | LC Mass ($M^+$) | RETENTION TIME (MIN) |
|---|---|---|
| 218 | 419 | 4.32 |
| 219 | 419 | 4.30 |
| 220 | 432 | 4.99 |
| 221 | 419 | 4.27 |
| 222 | 420 ($M^-$) | 4.68 |
| 223 | 439 | 4.64 |
| 224 | 413 | 4.32 |
| 225 | 440 | 5.49 |
| 226 | 446 | 4.93 |
| 227 | 460 | 5.03 |
| 228 | 433 | 4.98 |
| 229 | 447 | 5.25 |
| 230 | 417 ($M^-$) | 3.71 |
| 231 | 463 | 4.70 |
| 232 | 477 | 4.83 |
| 233 | 449 | 4.75 |
| 234 | 463 | 4.58 |
| 235 | 418 | 4.39 |
| 236 | 419 | 4.00 |
| 237 | 404 | 4.40 |
| 238 | 405 | 3.94 |
| 239 | 419 | 4.06 |
| 240 | 433 | 5.09 |
| 241 | 432 | 5.15 |
| 242 | 432 | 5.13 |
| 243 | 432 | 5.13 |
| 244 | 433 | 4.68 |
| 245 | 433 | 4.60 |
| 246 | 433 | 4.58 |
| 247 | 399 | 3.98 |
| 248 | 436 | 4.99 |
| 249 | 404 | 4.66 |
| 250 | 405 | 4.16 |
| 251 | 444 | 5.39 |
| 252 | 445 | 4.95 |
| 253 | 388 | 4.85 |
| 254 | 388 | 5.05 |
| 255 | 388 | 2.79 |

TABLE 4

| EXAMPLE | NMR data (δ: ppm) |
|---|---|
| 1* | ($DMSO-d_6$) 9.98 (1H, s), 7.63 (1H, d, J = 7 Hz), 7.35-7.24 (2H, m), 7.05-6.94 (2H, m), 6.88 (1H, d, J = 8 Hz), 6.79 (1H, d, J = 9 Hz), 6.61 (1H, s), 4.28-4.13 (6H, m), 3.36 (2H, t, J = 6 Hz) |
| 3* | ($DMSO-d_6$) 8.35-8.30 (1H, m), 8.14 (1H, d, J = 7 Hz), 7.58-7.46 (2H, m), 7.15 (1H, dd, J = 5, 8 Hz), 6.99 (1H, dd, J = 2, 9 Hz), 6.82 (1H, d, J = 2 Hz), 6.47 (1H, s), 4.22-4.08 (3H, m), 3.36-3.25 (2H, m), 3.10 (1H, dd, J = 5, 17 Hz), 2.90-2.70 (3H, m), 2.05-1.93 (1H, m), 1.80-1.65 (1H, m), 1.25 (9H, s) |
| 6* | ($DMSO-d_6$) 8.32 (1H, d, J = 4 Hz), 8.20 (1H, bs), 7.77 (1H, d, J = 9 Hz), 7.50 (1H, d, J = 8 Hz), 7.28 (1H, d, J = 8 Hz), 7.19-7.11 (2H, m), 6.64 (1H, s), 4.25 (2H, t, J = 6 Hz), 4.25-4.10 (1H, m), 3.37 (2H, t, J = 6 Hz), 3.18-3.05 (1H, m), 2.90-2.70 (3H, m), 2.06-1.95 (1H, m), 1.82-1.66 (1H, m) |
| 9* | ($CDCl_3$) 7.38 (1H, d, J = 9 Hz), 7.28-7.12 (3H, m), 7.00-6.93 (1H, m), 6.83 (1H, d, J = 9 Hz), 6.12 (1H, s), 4.28-4.19 (6H, m), 3.28 (2H, t, J = 7 Hz), 2.30-2.18 (2H, m) |
| 10* | ($DMSO-d_6$) 8.32 (1H, d, J = 5 Hz) 8.26 (1H, d, J = 7 Hz), 7.56-7.44 (2H, m), 7.36 (1H, d, J = 8 Hz), 7.23 (1H, s), 7.18-7.11 (1H, m), 6.30 (1H, s), 4.28-4.08 (3H, m), 3.18-3.05 (3H, m), 2.90-2.64 (3H, m), 2.12-1.96 (3H, m), 1.84-1.67 (1H, m) |
| 11* | ($DMSO-d_6$) 10.26 (1H, s), 9.34 (1H, s), 8.57 (1H, d, J = 6 Hz), 8.23 (1H, d, J = 7 Hz), 8.05 (1H, d, J = 6 Hz), 7.96 (1H, d, J = 8 Hz), 7.75-7.62 (2H, m), 7.47 (1H, d, J = 8 Hz), 7.30 (1H, s), 6.79 (1H, s), 4.25 (2H, t, J = 6 Hz), 3.20 (2H, t, J = 7 Hz), 2.18-2.08 (2H, m) |
| 13* | ($DMSO-d_6$) 10.58 (1H, s), 8.85 (1H, dd, J = 2, 4 Hz), 8.54-8.50 (1H, m) 8.32-8.26 (1H, m), 7.94 (1H, d, J = 9 Hz), 7.76 (1H, dd, J = 2, 9 Hz), 7.61 (1H, d, J = 8 Hz), 7.49-7.40 (2H, m), 7.30 (1H, s), 6.54 (1H, s), 4.25 (2H, t, J = 6 Hz), 3.22 (2H, t, J = 7 Hz), 2.22-2.10 (2H, m) |

TABLE 4-continued

| EXAMPLE | NMR data (δ: ppm) |
|---|---|
| 18* | ($DMSO-d_6$) 9.99 (1H, s), 7.79 (1H, d, J = 9 Hz), 7.74-7.60 (3H, m), 7.50-7.36 (2H, m), 7.32-7.21 (2H, m), 7.12 (1H, dd, J = 2, 9 Hz), 6.77 (1H, s), 4.25 (2H, t, J = 6 Hz), 3.18 (2H, t, J = 6 Hz), 2.19-2.06 (2H, m) |
| 23* | ($DMSO-d_6$) 10.49 (1H, s), 7.83 (1H, d, J = 9 Hz), 7.75 (1H, s), 7.59-7.38 (3H, m), 7.27 (1H, s), 6.47 (1H, s), 4.21 (2H, t, J = 6 Hz), 3.20-3.12 (2H, m), 2.96-2.83 (2H, m), 2.55 (2H, t, J = 6 Hz), 2.18-1.97 (4H, m) |
| 48* | ($CDCl_3$) 8.90 (1H, dd, J = 2, 4 Hz), 8.15-8.00 (3H, m), 7.83 (1H, d, J = 9 Hz), 7.83-7.76 (2H, m), 7.70-7.65 (1H, m), 7.45 (1H, d, J = 9 Hz), 7.35 (1H, dd, J = 4, 8 Hz), 6.53-6.49 (1H, m), 3.87 (2H, t, J = 7 Hz), 3.57 (2H, dt, J = 2, 7 Hz), 2.31 (3H, s) |
| 52* | ($DMSO-d_6$) 10.60 (1H, s), 8.84 (1H, dd, J = 2, 4 Hz), 8.52 (1H, s), 8.26 (1H, d, J = 8 Hz), 8.00-7.85 (3H, m), 7.71 (1H, dd, J = 2, 9 Hz), 7.64 (1H, d, J = 9 Hz), 7.40 (1H, dd, J = 4, 8 Hz), 6.87 (1H, s), 3.83 (2H, t, J = 6 Hz), 3.48-3.33 (2H, m), 2.90-2.75 (1H, m), 1.80-1.10 (10H, m) |
| 56 | ($CDCl_3$) 8.44-8.38 (1H, m), 7.57 (1H, d, J = 8 Hz), 7.47-7.35 (3H, m), 7.18 (2H, d, J = 9 Hz), 7.10 (1H, dd, J = 5, 8 Hz), 6.91 (1H, dd, J = 1, 8 Hz), 6.81 (1H, s), 6.21 (1H, s), 5.67 (1H, d, J = 8 Hz), 4.54-4.42 (1H, m), 3.70-3.48 (4H, m), 3.33 (1H, dd, J = 5, 17 Hz), 3.02-2.80 (3H, m), 2.26-2.13 (1H, m), 1.94-1.79 (1H, m) |
| 59* | ($DMSO-d_6$) 10.4 (1H, s), 8.37 (1H, s), 7.99 (1H, d, J = 9 Hz), 7.63-7.54 (2H, m), 7.42 (1H, d, J = 9 Hz), 7.27 (1H, s), 6.48 (1H, s), 6.24 (1H, t, J = 5.9 Hz), 4.84 (2H, d, J = 6 Hz), 4.23 (2H, t, J = 6 Hz), 3.19 (2H, t, J = 7 Hz), 2.19-2.07 (2H, m) |
| 61 | ($CDCl_3$) 7.55-7.00 (6H, m), 6.20 (1H, s), 4.24 (2H, t, J = 6 Hz), 3.54 (2H, s), 3.26 (2H, t, J = 7 Hz), 3.12 (2H, t, J = 7 Hz), 2.60 (2H, t, J = 7 Hz), 2.23 (2H, m) |
| 62 | ($CDCl_3$) 7.75-7.58 (1H, m), 7.48-7.35 (1H, m), 7.30-6.88 (4H, m), 6.20 (1H, s), 4.30-4.10 (3H, m), 3.27 (2H, t, J = 7 Hz), 3.08-2.80 (3H, m), 2.68-2.50 (1H, m), 2.28-2.18 (2H, m), 1.90-1.65 (2H, m) |
| 65 | ($DMSO-d_6$) 7.61 (1H, d, J = 8 Hz), 7.42 (1H, d, J = 9 Hz), 7.38 (1H, d, J = 8 Hz), 7.27 (1H, s), 7.09 (1H, dd, J = 8, 8 Hz), 6.90 (1H, d, J = 8 Hz), 6.62 (1H, s), 4.96-4.83 (2H, m), 4.22 (2H, t, J = 6 Hz), 3.76-3.64 (2H, m), 3.15 (2H, t, J = 6 Hz), 3.07-2.90 (2H, m), 2.68-2.43 (2H, m), 2.16-2.02 (2H, m) |
| 66* | ($DMSO-d_6$) 7.60 (1H, d, J = 8 Hz), 7.42 (1H, d, J = 8 Hz), 7.37 (1H, d, J = 8 Hz), 7.27 (1H, s), 7.09 (1H, t, J = 7, 7 Hz), 6.90 (1H, d, J = 7 Hz), 6.62 (1H, s), 4.74-4.62 (2H, m), 4.22 (2H, t, J = 6 Hz), 3.94-3.82 (2H, m), 3.15 (2H, t, J = 7 Hz), 2.85 (1H, d, J = 6 Hz), 2.80-2.68 (2H, m), 2.18-2.03 (2H, m) |
| 67 | ($DMSO-d_6$) 10.18 (1H, s), 9.70 (1H, s), 7.59 (1H, d, J = 8 Hz), 7.40 (1H, d, J = 8 Hz), 7.25 (1H, s), 7.22-7.08 (3H, m), 6.69 (1H, d, J = 8 Hz), 6.58 (1H, s), 5.49 (1H, bs), 4.21 (2H, t, J = 6 Hz), 4.13-4.03 (2H, m), 3.18-3.08 (2H, m), 3.05 (1H, d, J = 6 Hz), 2.66 (1H, dd, J = 12, 16 Hz), 2.15-2.02 (2H, m) |
| 68 | ($DMSO-d_6$) 9.29 (1H, s), 7.58 (1H, d, J = 8 Hz), 7.40 (1H, d, J = 8 Hz), 7.25 (1H, s), 6.83 (1H, t, J = 8H), 6.67 (1H, d, J = 8 Hz), 6.55 (1H, s), 6.30 (1H, d, J = 8 Hz), 5.69 (1H, s), 4.92 (1H, bs), 4.20 (2H, t, J = 6 Hz), 4.06-3.97 (1H, m), 3.91-3.80 (1H, m), 3.24-3.07 (3H, m), 2.90-2.70 (2H, m), 2.41 (1H, dd, J = 8, 16 Hz), 2.13-2.02 (2H, m) |
| 69* | ($DMSO-d_6$) 9.35 (1H, s), 7.59 (1H, d, J = 8 Hz), 7.42 (1H, d, J = 8 Hz), 7.26 (1H, s), 6.99 (1H, dd, J = 8, 8 Hz), 6.78 (1H, d, J = 7 Hz), 6.57 (1H, s), 6.45 (1H, d, J = 8 Hz), 5.01 (1H, d, J = 4 Hz), 4.22 (2H, t, J = 6 Hz), 4.03-3.90 (1H, m), 3.28-3.20 (1H, m), 3.14 (2H, t, J = 6 Hz), 2.97-2.80 (2H, m), 2.84 (3H, s), 2.57-2.40 (1H, m), 2.10-2.03 (2H, m) |
| 70 | ($CDCl_3$) 7.80-7.58 (1H, m), 7.24-6.92 (5H, m), 6.45 (1H, s), 4.29 (2H, t, J = 6 Hz), 4.28-4.15 (1H, m), 3.51 (2H, t, J = 5 Hz), 3.10-2.78 (3H, m), 2.69-2.53 (1H, m), 2.14-2.00 (1H, m), 1.90-1.67 (2H, m) |
| 74 | ($DMSO-d_6$) 9.98 (1H, s), 9.85 (1H, br), 8.05-7.97 (2H, m), 7.80 (1H, d, J = 9 Hz), 7.72 (1H, d, J = 7 Hz), 7.68-7.60 (2H, m), 7.36 (1H, d, J = 2 Hz), 7.26 (1H, t, J = 8 Hz), 7.17-7.09 (2H, m), 3.81 (2H, t, J = 6 Hz), 3.45-3.25 (2H, m), 2.59 (2H, t, J = 7 Hz), 1.62-1.48 (2H, m), 1.38-1.22 (2H, m), 0.87 (3H, t, J = 7 Hz) |
| 83 | ($CDCl_3$) 7.90-7.73 (2H, m), 7.72-7.62 (1H, m), 7.49-7.39 (1H, m), 7.18 (1H, t, J = 7 Hz), 7.11-6.95 (2H, m), 6.45 (1H, s), 4.27-4.14 (1H, m), 3.84 (2H, t, J = 6 Hz), 3.58-3.45 (2H, m), 3.07-2.70 (3H, m), 2.61 (1H, dd, J = 7, 17 Hz), 2.53 (2H, t, J = 8 Hz), 2.13-2.01 (1H, m), 1.90-1.77 (1H, m), 1.77-1.63 (2H, m), 1.44-1.31 (2H, m), 0.92 (3H, t, J = 7 Hz) |
| 85* | ($CDCl_3$) 7.88-7.58 (3H, m), 7.52-7.40 (1H, m), 7.18 (1H, t, J = 8 Hz), 7.11-6.94 (2H, m), 6.45 (1H, s), 4.27-4.14 (1H, m), 3.84 (2H, t, J = 6 Hz), 3.58-3.42 (2H, m), 3.06-2.69 (4H, m), 2.59 (1H, dd, J = 7, 16 Hz), 2.31-1.46 (11H, m), |
| 86 | ($CDCl_3$) 7.98-7.60 (3H, m), 7.49-7.39 (1H, m), 7.22-7.10 (2H, m), 7.05-6.96 (1H, m), 6.46 (1H, s), 4.25-4.15 (1H, m), 3.84 (2H, t, J = 6 Hz), 3.57-3.45 (2H, m), 3.08-2.80 (3H, m), 2.65-2.46 (3H, m), 2.12-2.00 (1H, m), 1.90-1.49 (4H, m), 0.98-0.81 (6H, m) |
| 87 | ($CDCl_3$) 7.87-7.61 (3H, m), 7.48-7.40 (1H, m), 7.18 (1H, t, J = 8 Hz), 7.13-6.96 (2H, m), 6.45 (1H, s), 4.27-4.16 (1H, m), 3.84 (2H, t, J = 6 Hz), 3.56-3.46 (2H, m), 3.05-2.80 (3H, m), 2.59 (1H, dd, J = 8, 16 Hz), 2.41 (2H, d, J = 7 Hz), 2.28-2.16 (1H, m), 2.12-2.01 (1H, m), 1.89-1.74 (2H, m), 0.98 (6H, d, J = 7 Hz) |
| 91 | ($CDCl_3$) 7.87-7.41 (4H, m), 7.22-6.96 (3H, m), 6.46 (1H, s), 4.26-4.14 (1H, m), 3.88-3.77 (2H, m), 3.58-3.48 (2H, m), 3.16-2.72 (5H, m), 2.67-2.49 (3H, m), 2.12-2.01 (1H, m), 1.90-1.65 (2H, m) |
| 92 | ($CDCl_3$) 7.87-7.47 (3H, m), 7.19 (1H, t, J = 8 Hz), 7.12-6.97 (2H, m), 6.48 (1H, s), 4.26-4.15 (1H, m), 3.92-3.78 (2H, m), 3.60-3.33 (4H, m), 3.06-2.80 (3H, m), 2.59 (1H, dd, J = 7, 16 Hz), 2.12-2.00 (1H, m), 1.89-1.66 (2H, m) |
| 93* | ($DMSO-d_6$) 9.36 (1H, s), 8.06-7.94 (2H, m), 7.62 (1H, d, J = 8 Hz), 7.38 (1H, d, J = 8 Hz), 7.08 (1H, t, J = 8 Hz), 7.00 (1H, s), 6.92 (1H, d, J = 8 Hz), 4.83 (1H, d, J = 4 Hz), |

TABLE 4-continued

| EXAMPLE | NMR data (δ: ppm) |
|---|---|
| | 3.99-3.84 (1H, m), 3.78 (2H, t, J = 6 Hz), 3.43-3.29 (2H, m), 2.98-2.64 (6H, m), 2.40-2.20 (2H, m), 1.96-1.50 (4H, m) |
| 95 | ($CDCl_3$) 7.98 (1H, s), 7.88-7.63 (2H, m), 7.55-7.44 (1H, m), 7.18 (1H, t, J = 8 Hz), 7.12-6.93 (2H, m), 6.46 (1H, s), 4.26-4.14 (1H, m), 3.99 (2H, t, J = 6 Hz), 3.64-3.51 (2H, m), 3.09-2.79 (3H, m), 2.60 (1H, dd, J = 8, 16 Hz), 2.37-2.00 (3H, m), 1.90-1.64 (2H, m), 1.12 (3H, t, J = 8 Hz) |
| 96 | ($CDCl_3$) 7.91 (1H, s), 7.83-7.63 (2H, m), 7.49-7.41 (1H, m), 7.18 (1H, t, J = 8 Hz), 7.12-6.96 (2H, m), 6.44 (1H, s), 4.27-4.14 (1H, m), 4.02 (2H, t, J = 6 Hz), 3.60-3.49 (2H, m), 3.08-2.80 (3H, m), 2.60 (1H, dd, J = 7, 16 Hz), 2.13-2.00 (1H, m), 1.90-1.60 (7H, m) |
| 97 | (DMSO-$d_6$) 10.47 (1H, s), 8.84 (1H, dd, J = 2, 4 Hz), 8.53 (1H, d, J = 8 Hz), 8.27 (1H, dd, J = 1, 9 Hz), 7.92 (1H, d, J = 9 Hz), 7.74(1H, dd, J = 2, 9 Hz), 7.41 (1H, dd, J = 4, 8 Hz), 7.05 (1H, s), 6.92 (1H, d, J = 7 Hz), 6.62 (1H, s), 3.85-3.65 (1H, m), 3.65-3.20 (4H, m), 1.85-1.35 (9H, m), 1.35-1.10 (1H, m) |
| 98 | ($CDCl_3$) 8.93-8.88 (1H, m), 8.18-7.98 (4H, m), 7.83 (1H, d, J = 9 Hz), 7.67 (1H, d, J = 8 Hz), 7.56-7.49 (3H, m), 7.46 (1H, d, J = 8 Hz), 7.37 (1H, dd, J = 5, 8 Hz), 7.25-7.15 (2H, m), 6.18 (1H, s), 3.91 (2H, t, J = 7 Hz), 3.28-3.17 (2H, m), 2.30 (3H, s) |
| 99 | ($CDCl_3$) 8.90 (1H, dd, J = 2, 4 Hz), 8.17-8.03 (3H, m), 7.87-7.77 (3H, m), 7.66 (1H, s), 7.45 (1H, d, J = 8 Hz), 7.35 (1H, dd, J = 4, 8 Hz), 6.54 (1H, s), 3.98 (2H, t, J = 6 Hz), 3.56 (2H, dt, J = 2, 6 Hz), 1.96-1.86 (1H, m), 1.25-1.17 (2H, m), 0.95-0.85 (2H, m) |
| 100 | ($CDCl_3$) 8.90 (1H, dd, J = 2, 4 Hz), 8.16-8.02 (3H, m), 7.98-7.92 (1H, m), 7.86-7.77 (2H, m), 7.67 (1H, s), 7.46 (1H, d, J = 8 Hz), 7.35 (1H, dd, J = 4, 8 Hz), 6.51 (1H, s), 3.91 (2H, t, J = 6 Hz), 3.78 (2H, t, J = 6 Hz), 3.56 (2H, dt, J = 2, 6 Hz), 3.37 (3H, s), 2.79 (2H, t, J = 6 Hz) |
| 101 | ($CDCl_3$) 8.90 (1H, dd, J = 2, 4 Hz), 8.17-7.98 (3H, m), 7.95-7.70 (4H, m), 7.45 (1H, d, J = 8 Hz), 7.35(1H, dd, J = 4, 8 Hz), 6.51 (1H, s), 3.88 (2H, t, J = 6 Hz), 3.70 (3H, s), 3.62-3.53 (2H, m), 2.85 (2H, t, J = 7 Hz), 2.75 (2H, t, J = 7 Hz) |
| 102 | ($CDCl_3$) 8.90 (1H, dd, J = 2, 4 Hz), 8.17-8.00 (3H, m), 7.90-7.75 (3H, m), 7.68 (1H, s), 7.44 (1H, d, J = 8 Hz), 7.35 (1H, dd, J = 4, 8 Hz), 6.51 (1H, s), 3.86 (2H, t, J = 6 Hz), 3.56 (2H, dt, J = 2, 6 Hz), 2.57 (2H, d, J = 7 Hz), 2.40-2.26 (1H, m), 1.95-1.82 (2H, m), 1.68-1.48 (4H, m), 1.23-1.08 (2H, m) |
| 105 | ($CDCl_3$) 7.85-7.76 (2H, m), 7.71-7.62 (1H, m), 7.49-7.40 (1H, m), 7.24-7.14 (1H, m), 7.10-6.96 (2H, m), 6.47 (1H, s), 4.38-4.15 (1H, m), 3.95 (2H, t, J = 6 Hz), 3.51 (2H, dt, J = 2, 6 Hz), 3.08-2.80 (3H, m), 2.60 (1H, dd, J = 8, 16 Hz), 2.13-2.00 (1H, m), 1.95-1.76 (2H, m), 1.74-1.68 (1H, m), 1.30-1.15 (2H, m), 0.95-0.82 (2H, m) |
| 106 | (DMSO-$d_6$) 9.23 (1H, s), 7.64 (1H, d, J = 8 Hz), 7.36 (1H, d, J = 7 Hz), 7.10-7.03 (1H, m), 6.94-6.87 (2H, m), 6.83 (1H, d, J = 8 Hz), 6.78-6.69 (2H, m), 4.84 (1H, d, J = 4 Hz), 3.98-3.85 (1H, m), 3.25 (4H, s), 2.95-2.69 (3H, m), 2.55-2.40 (1H, m), 1.94-1.82 (1H, m), 1.69-1.52 (1H, m) |
| 107* | ($CDCl_3$) 10.20 (1H, s), 9.68 (1H, s), 8.02-7.94 (2H, m), 7.62 (1H, d, J = 8 Hz), 7.24 (1H, d, J = 7 Hz), 7.18-7.09 (1H, m), 6.98 (1H, s), 6.71 (1H, d, J = 7 Hz), 5.49 (1H, d, J = 5 Hz), 4.15-4.04 (1H, m), 3.79 (2H, t, J = 6 Hz), 3.40-3.28 (2H, m), 3.20-3.03 (1H, m), 2.78-2.65 (1H, m), 2.63-2.45 (2H, m), 1.54 (2H, quint, J = 7 Hz), 1.40-1.20 (2H, m), 0.86 (3H, t, J = 7 Hz) |
| 108* | (DMSO-$d_6$) 9.27 (1H, s), 8.04-7.92 (2H, m), 7.61 (1H, d, J = 8 Hz), 6.96 (1H, s), 6.88-6.78 (1H, m), 6.73 (1H, d, J = 8 Hz), 6.32 (1H, d, J = 8 Hz), 5.71 (1H, s), 4.92 (1H, d, J = 6 Hz), 3.95-3.78 (1H, m), 3.78 (2H, t, J = 6 Hz), 3.30-3.14 (2H, m), 2.93-2.72 (2H, m), 2.57 (2H, t, J = 7 Hz), 2.52-2.37 (2H, m), 1.54 (2H, quint, J = 7 Hz), 1.40-1.20 (2H, m), 0.86 (3H, t, J = 7 Hz) |
| 109 | ($CDCl_3$) 7.85-7.58 (2H, m), 7.48-7.39 (1H, m), 7.25-6.95 (4H, m), 6.47 (1H, s), 4.77-4.62 (1H, m), 4.28-4.15 (2H, m), 3.76-3.62 (2H, m), 3.08-2.82 (3H, m), 2.60 (1H, dd, J = 8, 16 Hz), 2.13-2.00 (1H, m), 1.91-1.75 (1H, m), 1.42-1.35 (1H, m), 1.25 (3H, s), 1.22 (3H, s), 0.94-0.83 (1H, m), 0.78 (2H, dd, J = 4, 8 Hz) |
| 110 | ($CDCl_3$) 7.84-7.62 (2H, m), 7.60-7.40 (1H, m), 7.24-6.95 (4H, m), 6.45 (1H, s), 4.28-4.13 (1H, m), 3.88-3.66 (2H, m), 3.56-3.47 (2H, m), 3.45-3.36 (1H, m), 3.08-2.82 (3H, m), 2.78-2.44 (2H, m), 2.38-2.23 (1H, m), 2.20-1.20 (10H, m) |
| 111 | ($CDCl_3$) 7.88-7.74 (1H, m), 7.72-7.58 (1H, m), 7.47-7.31 (3H, m), 7.21-6.93 (4H, m), 6.58-6.43 (2H, m), 4.27-4.12 (1H, m), 4.05 (2H, t, J = 6 Hz), 3.65-3.50 (2H, m), 3.10-2.80 (3H, m), 2.60 (1H, dd, J = 8, 16 Hz), 2.14-1.98 (1H, m), 1.90-1.72 (1H, m) |
| 112 | (DMSO-$d_6$) 9.42 (1H, s), 8.18-7.98 (2H, m), 7.85 (1H, s), 7.69 (1H, d, J = 7 Hz), 7.47 (1H, d, J = 7 Hz), 7.20-7.04 (2H, m), 6.99 (1H, d J = 7 Hz), 4.91 (1H, d, J = 3 Hz), 4.10-3.82 (3H, m), 3.52-3.24 (2H, m), 3.05-2.72 (3H, m), 2.68-2.40 (1H, m), 2.02-1.88 (1H, m), 1.78-1.56 (3H, m), 1.40-1.15 (2H, m) |
| 113* | (DMSO-$d_6$) 9.35 (1H, s), 7.97 (1H, d, J = 8 Hz), 7.89 (1H, s), 7.48 (1H, d, J = 8 Hz), 7.38 (1H, d, J = 7 Hz), 7.12-7.03 (1H, m), 6.98 (1H, s), 6.92 (1H, d, J = 7 Hz), 4.84 (1H, d, J = 4 Hz), 4.35 (4H, t, J = 13 Hz), 3.98-3.85 (1H, m), 3.65 (2H, t, J = 6 Hz), 3.40-3.27 (2H, m), 2.98-2.72 (3H, m), 2.56-2.38 (1H, m), 1.95-1.82 (1H, m), 1.68-1.53 (1H, m) |
| 114* | ($CDCl_3$) 8.84 (1H, s), 7.90-7.80 (1H, m), 7.73-7.58 (1H, m), 7.52-7.40 (2H, m), 7.23-7.14 (1H, m), 7.14-6.92 (2H, m), 6.51 (1H, s), 4.26-4.15 (1H, m), 3.94 (2H, t, J = 7 Hz), 3.52-3.42 (2H, m), 3.08-2.80 (3H, m), 2.60 (1H, dd, J = 7, 16 Hz), 2.13-1.95 (1H, m), 1.90-1.74 (1H, m), 1.72-1.65 (1H, m) |
| 115 | (DMSO-$d_6$) 9.37 (1H, s), 8.02 (1H, d, J = 8 Hz), 7.89 (1H, s), 7.66 (1H, d, J = 8 Hz), 7.40 (1H, d, J = 8 Hz), 7.15-7.03 (1H, m), 7.02 (1H, s), 6.92 (1H, d, J = 7 Hz), 4.89-4.79 (1H, m), 4.02-3.80 (3H, m), 3.50-3.24 (2H, m), 2.98-2.66 (3H, m), 2.62-2.24 (3H, m), 2.24-2.02 (2H, m), 1.94-1.52 (6H, m) |
| 116 | ($CDCl_3$) 7.88-7.74 (1H, m), 7.72-7.61 (1H, m), 7.54-7.43 (1H, m), 7.22-6.95 (3H, m), 6.46 (1H, s), 4.27-4.13 (1H, m), 3.94-3.80(2H, m), 3.58-3.45 (2H, m), 3.16 (2H, t, J = |

TABLE 4-continued

| EXAMPLE | NMR data (δ: ppm) |
|---|---|
| | 13 Hz), 3.06-2.80 (3H, m), 2.65-2.52 (1H, m), 2.03-2.00 (1H, m), 1.84 (3H, t, J = 19 Hz), 1.93-1.62 (2H, m) |
| 117 | ($CDCl_3$) 7.86-7.53 (1H, m), 7.73-7.62 (1H, m), 7.56-7.42 (1H, m), 7.22-6.95 (3H, m), 6.46 (1H, s), 4.28-4.14 (1H, m), 3.92-3.82(2H, m), 3.57-3.46 (2H, m), 3.15 (2H, t, J = 14 Hz), 3.07-2.78 (3H, m), 2.65-2.53 (1H, m), 2.23-2.00 (3H, m), 1.90-1.60 (2H, m), 1.06 (3H, t, J = 7 Hz) |
| 118 | ($CDCl_3$) 7.86-7.75 (1H, m), 7.72-7.59 (1H, m), 7.55-7.42 (1H, m), 7.22-6.94 (3H, m), 6.47 (1H, s), 4.28-4.09 (1H, m), 3.92-3.71(2H, m), 3.56-3.17 (4H, m), 3.10-2.53 (7H, m), 2.13-2.02 (1H, m), 1.89-1.68 (2H, m) |
| 119 | (CDCl3) 7.75-7.64 (1H, m), 7.52-7.42 (1H, m), 7.32-7.07 (5H, m), 6.46 (1H, s), 4.29 (2H, t, J = 6 Hz), 3.54 (2H, s), 3.49 (2H, t, J = 6 Hz), 3.13 (2H, t, J = 7 Hz), 2.60 (2H, t, J = 7 Hz) |
| 120 | (DMSO-$d_6$) 9.99 (1H, s), 9.85 (1H, s), 7.93 (1H, d, J = 8 Hz), 7.80 (1H, d, J = 9 Hz), 7.70(1H, d, J = 7 Hz), 7.65 (1H, d, J = 8 Hz), 7.43-7.34 (2H, m), 7.30-7.23 (2H, m), 7.16-7.08 (2H, m), 4.30 (2H, t, J = 6 Hz), 3.44 (2H, t, J = 6 Hz) |
| 121 | (DMSO-$d_6$) 10.20 (1H, s), 9.69 (1H, s), 7.89 (1H, d, J = 8 Hz), 7.35 (1H, d, J = 8 Hz), 7.27-7.19 (2H, m), 7.17-7.10 (1H, m), 6.96 (1H, s), 6.71 (1H, d, J = 8 Hz), 5.50 (1H, d, J = 4 Hz), 4.28 (2H, t, J = 6 Hz), 4.15-4.05 (1H, m), 3.39 (2H, t, J = 6 Hz), 3.11 (2H, dd, J = 6, 16 Hz), 2.68 (1H, dd, J = 12, 16 Hz) |
| 122* | (DMSO-$d_6$) 9.27 (1H, s), 7.88 (1H, d, J = 9 Hz), 7.34 (1H, d, J = 9 Hz), 7.23 (1H, s), 6.94 (1H, s), 6.84 (1H, t, J = 8 Hz), 6.71 (1H, d, J = 8 Hz), 6.31 (1H, d, J = 8 Hz), 5.71 (1H, s), 4.92 (1H, d, J = 6 Hz), 4.27 (2H, t, J = 6 Hz), 3.95-3.81 (1H, m), 3.43-3.13 (3H, m), 2.91-2.72 (2H, m), 2.55-2.37 (1H, m) |
| 125 | (DMSO-$d_6$) 9.42 (1H, s), 7.89 (1H, d, J = 8 Hz), 7.35 (1H, d, J = 8 Hz), 7.24 (1H, s), 7.18 (1H, d, J = 8 Hz), 7.10-7.03 (1H, m), 6.97 (1H, s), 6.61 (1H, d, J = 8 Hz), 5.12 (1H, d, J = 4 Hz), 4.28 (2H, t, J = 6 Hz), 4.10-3.96 (2H, m), 3.85-3.73 (1H, m), 3.39 (2H, t, J = 6 Hz), 2.94-2.81 (1H, m), 2.61-2.45 (1H, m) |
| 126 | (DMSO-$d_6$) 10.05 (1H, s), 7.99 (1H, d, J = 10 Hz), 7.69-7.61 (2H, m), 7.53-7.43 (2H, m), 7.37 (1H, t, J = 8 Hz), 7.29 (1H, s), 7.15-7.09 (2H, m), 6.76 (1H, s), 4.24 (2H, t, J = 6 Hz), 3.22-3.13 (2H, m), 2.17-2.07 (2H, m) |
| 127 | (DMSO-$d_6$) 11.11 (1H, s), 9.20 (1H, dd, J = 1, 5 Hz), 9.06 (1H, d, J = 8 Hz), 9.00 (1H, s), 8.33 (1H, d, J = 9 Hz), 7.97-7.85 (2H, m), 7.63 (1H, t, J = 8 Hz), 7.47 (1H, dd, J = 1, 8 Hz), 7.31 (1H, s), 6.58 (1H, s), 4.25 (2H, t, J = 6 Hz), 3.23 (2H, t, J = 6 Hz), 2.33 (3H, s), 2.24-2.12 (2H, m) |
| 128 | (DMSO-$d_6$) 10.30 (1H, s), 9.72 (1H, s), 8.21 (1H, d, J = 2 Hz), 7.72 (1H, d, J = 9 Hz), 7.67(1H, d, J = 9 Hz), 7.59 (1H, d, J = 8 Hz), 7.44 (1H, dd, J = 1, 8 Hz), 7.34 (1H, dd, J = 2, 9 Hz), 7.28 (1H, d, J = 1 Hz), 7.03 (1H, d, J = 2 Hz), 6.97 (1H, dd, J = 2, 9 Hz), 6.51 (1H, s), 4.24 (2H, t, J = 6 Hz), 3.21 (2H, t, J = 7 Hz), 2.19-2.09 (2H, m) |
| 129* | (DMSO-$d_6$) 10.07 (1H, s), 7.88 (1H, d, J = 9 Hz), 7.83 (1H, d, J = 8 Hz), 7.74-7.63 (2H, m), 7.49-7.42 (2H, m), 7.36 (1H, t, J = 8 Hz), 7.29 (1H, s), 7.23 (1H, dd, J = 2, 9 Hz), 6.76 (1H, s), 4.25 (2H, t, J = 6 Hz), 3.25-3.17 (2H, m), 2.18-2.07 (2H, m) |
| 130 | ($CDCl_3$) 7.39 (1H, d, J = 8 Hz), 7.25-7.14 (3H, m), 6.89 (1H, d, J = 8 Hz), 6.82 (1H, s), 6.77 (1H, d, J = 8 Hz), 6.14 (1H, s), 4.24 (2H, t, J = 6 Hz), 3.60 (2H, t, J = 6 Hz), 3.47 (2H, t, J = 6 Hz), 3.40-3.32 (5H, m), 3.27 (2H, t, J = 7 Hz), 2.71 (2H, t, J = 6 Hz), 2.29-2.18 (2H, m), 1.97-1.88 (2H, m) |
| 133 | (DMSO-$d_6$) 10.17 (1H, s), 10.12 (1H, s), 7.56 (1H, d, J = 9 Hz), 7.42 (1H, d, J = 8 Hz), 7.32 (1H, s), 7.26 (1H, s), 7.17 (1H, d J = 8 Hz), 7.09 (1H, d, J = 8 Hz), 6.45 (1H, s), 4.22 (2H, t, J = 6 Hz), 3.20-3.12 (2H, m), 2.85-2.77 (2H, m), 2.47-2.39 (2H, m), 2.15-2.05 (2H, m) |
| 134 | (DMSO-$d_6$) 11.69 (1H, s), 10.49 (1H, s), 7.91 (1H, s), 7.81 (1H, d, J = 10 Hz), 7.60-7.55 (2H, m), 7.48-7.27 (3H, m), 6.50 (1H, s), 6.36 (1H, dd, J = 2, 9 Hz), 4.25-4.20 (2H, m), 3.25-3.15 (2H, m), 2.24-2.10 (2H, m) |
| 135* | ($CDCl_3$) 7.50 (1H, s), 7.41-7.33 (3H, m), 7.23 (1H, s), 6.91 (1H, s), 6.14 (1H, s), 4.24 (2H, t, J = 6 Hz), 3.87 (3H, s), 3.29 (2H, t, J = 7 Hz), 2.31-2.20 (2H, m) |
| 136* | ($CDCl_3$) 7.95-7.89 (1H, m), 7.82-7.73 (1H, m), 7.48 (1H, d, J = 9 Hz), 7.42-7.33 (2H, m), 7.28-7.21 (2H, m), 6.14 (1H, s), 4.24 (2H, d, J = 6 Hz), 3.29 (2H, d, J = 6 Hz), 2.32-2.19 (2H, m) |
| 137 | (DMSO-$d_6$) 11.01 (1H, s), 10.12 (1H, s), 8.11 (1H, s), 7.59 (1H, d, J = 8 Hz), 7.48-7.40 (2H, m), 7.31-7.23 (2H, m), 7.06 (1H, dd, J = 2, 8 Hz), 6.49 (1H, s), 6.39-6.33 (1H, m), 4.24 (2H, t, J = 6 Hz), 3.21 (2H, t, J = 7 Hz), 2.20-2.07 (2H, m) |
| 138 | (DMSO-$d_6$) 11.02 (1H, s), 10.03 (1H, s), 8.03 (1H, d, J = 2 Hz), 7.58 (1H, d, J = 8 Hz), 7.46-7.41 (1H, m), 7.36-7.23 (4H, m), 6.48 (1H, s), 6.42-6.37 (1H, m), 4.23 (2H, t, J = 6 Hz), 3.21 (2H, t, J = 7 Hz), 2.18-2.07 (2H, m) |
| 142 | ($CDCl_3$) 7.43-7.36 (1H, m), 7.28-7.16 (4H, m), 7.14-7.05 (1H, m), 6.98-6.92 (1H, m), 6.13 (1H, s), 4.29-4.11 (6H, m), 3.33-3.23 (2H, m), 2.31-2.11 (2H, m) |
| 143 | ($CDCl_3$) 7.92 (1H, s), 7.40-7.23(4H, m), 7.01 (2H, s), 6.13 (1H, s), 4.27 (2H, t, J = 7 Hz), 3.28 (2H, t, J = 7 Hz), 2.30-2.20 (2H, m) |
| 144 | ($CDCl_3$) 7.38 (1H, d, J = 8 Hz), 7.33-7.15 (4H, m), 6.88-6.82 (1H, m), 6.77 (1H, d, J = 8 Hz), 6.12 (1H, s), 5.97 (2H, s), 4.24 (2H, t, J = 6 Hz), 3.28 (2H, t, J = 7 Hz), 2.33-2.18 (2H, m) |
| 149 | ($CDCl_3$) 8.13 (1H, s), 7.54 (1H, d, J = 8 Hz), 7.49-7.36 (2H, m), 7.33-7.20 (2H, m), 7.04 (1H, d, J = 3 Hz), 6.90-6.82 (1H, m), 6.45 (1H, d, J = 3 Hz), 6.20 (1H, s), 4.26 (2H, t, J = 6 Hz), 3.80 (3H, s), 3.33 (2H, t, J = 7 Hz), 2.35-2.22 (2H, m) |
| 150 | (DMSO-$d_6$) 10.03 (1H, s), 7.98 (1H, d, J = 9 Hz), 7.84 (1H, d, J = 7 Hz), 7.65 (1H, d, J = 8 Hz), 7.56 (1H, d, J = 8 Hz), 7.50-7.23 (5H, m), 6.89 (1H, d, J = 8 Hz), 6.76 (1H, s), 4.23 (2H, t, J = 6 Hz), 3.16 (2H, t, J = 7 Hz), 2.17-2.05 (2H, m) |

TABLE 4-continued

| EXAMPLE | NMR data (δ: ppm) |
|---|---|
| 151 | (DMSO-$d_6$) 10.18 (1H, s), 8.11 (1H, s), 7.58 (1H, d, J = 8 Hz), 7.50-7.40 (2H, m), 7.30 (1H, d, J = 3 Hz), 7.27 (1H, s), 7.07 (1H, dd, J = 2, 9 Hz), 6.50 (1H, s), 6.36 (1H, d, J = 3 Hz), 4.95 (1H, t, J = 5 Hz), 4.23 (2H, t, J = 6 Hz), 4.16 (2H, t, J = 5 Hz), 3.78-3.63 (2H, m), 3.21 (2H, t, J = 7 Hz), 2.22-2.06 (2H, m) |
| 152 | ($CDCl_3$) 7.93 (1H, s), 7.52-6.96 (7H, m), 6.46 (1H, d, J = 3 Hz), 6.20 (1H, s), 4.26 (2H, t, J = 6 Hz), 3.79 (3H, s), 3.32 (2H, t, J = 7 Hz), 2.35-2.20 (2H, m) |
| 157 | (DMSO-$d_6$) 10.44 (1H, s), 8.11 (1H, s), 7.78 (1H, d, J = 9 Hz), 7.60-7.52 (2H, m) 7.43 (1H, d, J = 7 Hz), 7.28 (1H, s), 6.45 (1H, s), 4.22 (2H, t, J = 6 Hz), 3.18 (2H, t, J = 6 Hz), 3.06 (2H, t, J = 6 Hz), 2.74-2.60 (2H, m), 2.21-2.06 (2H, m) |
| 160 | ($CDCl_3$) 8.04-7.94 (1H, m), 7.46-7.37 (1H, m), 7.35-7.19 (3H, m), 7.07 (1H, s), 6.19 (1H, s), 5.30 (1H, dt, J = 5, 12 Hz), 4.25 (2H, t, J = 6 Hz), 3.29 (2H, t, J = 6 Hz), 3.08-2.95 (1H, m), 2.83-2.70 (1H, m), 2.62-2.49 (1H, m), 2.32-2.19 (2H, m), 2.10-1.96 (1H, m), 1.77 (1H, d, J = 7 Hz) |
| 161 | ($CDCl_3$) 8.06-7.96 (1H, m), 7.47-7.12 (4H, m), 7.06 (1H, s), 6.22 (1H, dd, J = 4, 7 Hz), 6.19 (1H, s), 4.25 (2H, t, J = 6 Hz), 3.29 (2H, t, J = 6 Hz), 3.12-2.98 (1H, m), 2.88-2.77 (1H, m), 2.64-2.48 (1H, m), 2.30-2.09 (3H, m), 2.07 (3H, s) |
| 163 | (DMSO-$d_6$) 9.52 (1H, s), 7.66-7.57 (2H, m), 7.43 (1H, d, J = 9 Hz), 7.27 (1H, s), 7.16-7.08 (1H, m), 6.99 (1H, d, J = 7 Hz), 6.63 (1H, s), 4.87 (1H, d, J = 4 Hz), 4.56-4.47 (1H, m), 4.22 (2H, t, J = 6 Hz), 3.22-2.98 (4H, m), 2.76 (2H, dd, J = 3, 16 Hz), 2.18-2.05 (2H, m) |
| 164 | ($CDCl_3$) 7.93 (1H, s), 7.48-7.10 (6H, m), 6.56-6.47 (1H, m), 6.20 (1H, s), 4.37-4.18 (4H, m), 4.03-3.92 (2H, m), 3.39-3.26 (2H, m), 2.37-2.20 (2H, m) |
| 165* | (DMSO-$d_6$) 10.05 (1H, s), 7.55 (1H, d, J = 8 Hz), 7.41 (1H, d, J = 9 Hz), 7.34 (1H, d, J = 2 Hz), 7.26 (1H, d, J = 1 Hz), 7.04 (1H, dd, J = 2, 9 Hz), 6.81 (1H, d, J = 9 Hz), 6.39 (1H, s), 5.06 (1H, t, J = 6 Hz), 4.32 (1H, dd, J = 2, 11 Hz), 4.21 (2H, t, J = 6 Hz), 4.16-4.06 11H, m), 4.03-3.93 (1H, m), 3.70-3.53 (2H, m), 3.16 (2H, t J = 7 Hz), 2.16-2.03 (2H, m) |
| 166 | (DMSO-$d_6$) 10.42 (1H, s), 8.56 (1H, s), 8.12 (1H, s), 7.73 (1H, d, J = 8 Hz), 7.57 (1H, d, J = 8 Hz), 7.51 (1H, d, J = 8), 7.43 (1H, d, J = 8 Hz), 7.27 (1H, s), 6.46 (1H, s), 4.32 (2H, s), 4.22 (2H, t, J = 6 Hz), 3.23-3.13 (2H, m), 2.18-2.05 (2H, m) |
| 167* | (DMSO-$d_6$) 9.82 (1H, s), 7.55 (1H, d, J = 8 Hz), 7.41 (1H, d, J = 8 Hz), 7.25 (1H, s), 6.93 (1H, s), 6.74 (1H, d, J = 8 Hz), 6.63 (1H, d, J = 8 Hz), 6.43 (1H, s), 5.72 (1H, s), 4.21 (2H, t, J = 6 Hz), 3.21-3.08 (4H, m), 2.66-2.50 (2H, m), 2.17-2.03 (2H, m), 1.82-1.70 (2H, m) |
| 169* | (DMSO-$d_6$) 9.56 (1H, s), 7.60 (1H, d, J = 8 Hz), 7.43 (1H, d, J = 8 Hz), 7.35-7.23 (2H, m), 7.18-7.07 (1H, m), 6.92 (1H, d, J = 7 Hz), 6.56 (1H, s), 4..23 (2H, t, J = 6 Hz), 3.52-2.87 (8H, m), 2.18-2.02 (2H, m) |
| 174* | ($CDCl_3$) 8.83 (1H, s), 8.06-7.92 (1H, m), 7.48-6.73 (5H, m), 6.21 (1H, s), 4.97-4.81 (1H, m), 4.32-4.15 (2H, m), 3.42-3.18 (2H, m), 2.93-2.58 (2H, m), 2.38-2.12 (2H, m), 2.12-1.68 (5H, m) |
| 175 | (DMSO-$d_6$) 10.15 (1H, s), 7.75 (1H, s), 7.57 (1H, d, J = 8 Hz), 7.47-7.38 (2H, m), 7.27 (1H, s), 7.15 (1H, d, J = 8 Hz), 6.46 (1H, s), 5.27 (1H, d, J = 7 Hz), 5.06-4.97 (1H, m), 4.22 (2H, t, J = 6 Hz), 3.18 (2H, t, J = 6 Hz), 2.91-2.79 (1H, m), 2.75-2.59 (1H, m), 2.41-2.25 (1H, m), 2.18-2.06 (2H, m), 1.74-1.69 (1H, m) |
| 176 | (DMSO-$d_6$) 10.44 (1H, s), 8.15 (1H, d, J = 2 Hz), 7.73 (1H, dd, J = 2, 8 Hz), 7.61-7.51 (2H, m), 7.47-7.41 (1H, m), 7.28 (1H, s), 6.47 (1H, s), 4.85 (1H, t, J = 5 Hz), 4.50 (2H, s), 4.23 (2H, t, J = 6 Hz), 3.67-3.53 (4H, m), 3.20 (2H, t, J = 6 Hz), 2.20-2.08 (2H, m) |
| 178 | (DMSO-$d_6$) 10.25 (1H, s), 7.57 (1H, d, J = 8 Hz), 7.53-7.40 (2H, m) 7.31-7.22 (2H, m), 7.16 (1H, d, J = 8 Hz), 6.45 (1H, s), 4.22 (2H, t, J = 6 Hz), 3.24 (3H, s), 3.17 (2H, t, J = 7 Hz), 2.82 (2H, t, J = 7 Hz), 2.58-2.47 (2H, m) 2.17-2.06 (2H, m) |
| 179* | (DMSO-$d_6$) 10.05 (1H, s), 7.59-7.50 (2H, m), 7.45-7.32 (2H, m), 7.25 (1H, s), 6.98 (1H, d, J = 9 Hz), 6.43 (1H, s), 4.76 (1H, t, J = 5 Hz), 4.21 (1H, t, J = 6 Hz), 3.62-3.37 (2H, m), 3.16 (2H, t, J = 6 Hz), 2.90-2.55 (3H, m), 2.19-2.03 (2H, m), 1.95-1.57 (4H, m) |
| 183* | (DMSO-$d_6$) 9.43 (1H, s), 7.59 (1H, d, J = 8 Hz), 7.41 (1H, d, J = 8 Hz), 7.26 (1H, s), 7.14 (1H, d, J = 8 Hz), 7.05 (1H, t, J = 8 Hz), 6.65-6.55 (2H, m), 4.21 (2H, t, J = 6 Hz), 4.09-3.98 (2H, m), 3.78 (1H, dd, J = 7, 11 Hz), 3.14 (1H, t, J = 6 Hz), 2.94-2.78 (1H, m), 2.60-2.48 (1H, m), 2.16-2.01 (2H, m) |
| 184 | (DMSO-$d_6$) 10.20 (1H, s), 9.71 (1H, s), 8.04 (1H, d, J = 9 Hz), 7.93 (1H, s), 7.74 (1H, d, J = 8 Hz), 7.24 (1H, d, J = 8 Hz), 7.14 (1H, t, J = 8 Hz), 7.02 (1H, s), 6.70 (1H, d, J = 8 Hz), 5.76 (1H, s), 5.50 (1H, d, J = 4 Hz), 4.14-4.05 (1H, m), 3.93 (2H, t, J = 6 Hz), 3.45-3.30 (2H, m), 3.11 (1H, dd, J = 6, 16 Hz), 2.68 (1H, dd, J = 11, 16 Hz), 2.34-2.13 (2H, m), 1.03 (3H, t, J = 7 Hz) |
| 185 | ($CDCl_3$) 7.97 (1H, s), 7.86-7.75 (1H, m), 7.53-7.45 (1H, m), 7.21-7.02 (3H, m), 6.50-6.43 (2H, m), 4.35-4.26 (1H, m), 4.05-3.92 (2H, m), 3.62-3.54 (2H, m), 3.37-3.23 (2H, m), 2.89 (1H, dd, J = 4, 16 Hz), 2.77-2.65 (1H, m), 2.36-2.14 (2H, m), 1.12 (3H, t, J = 8 Hz) |
| 190* | ($CDCl_3$) 7.71-7.12 (4H, m), 7.06-6.88 (2H, m), 5.99 (1H, s), 4.75-4.58 (1H, m), 4.34-4.12 (1H, m), 3.55-3.35 (2H, m), 3.07-2.82 (4H, m), 2.55 (1H, dd, J = 8, 16 Hz), 2.16-1.11 (11H, m), 0.80 (3H, t, J = 7 Hz) |
| 191* | (DMSO-$d_6$) 10.45 (1H, s), 8.84 (1H, dd, J = 2, 4 Hz), 8.52-8.46 (1H, m), 8.30-8.22 (1H, m), 7.92 (1H, d, J = 9 Hz), 7.76 (1H, dd, J = 2, 9 Hz), 7.45-7.35 (2H, m), 7.05 (1H, s), 6.98-6.91 (1H, m), 6.67-6.58 (1H, m), 6.46 (1H, s), 3.24-3.12 (4H, m), 2.19-2.04 (2H, m) |
| 192* | (DMSO-$d_6$) 10.52 (1H, s), 8.88-8.83 (1H, m), 8.49 (1H, s), 8.28 (1H, d, J = 8 Hz), 7.98-7.65 (5H, m), 7.42 (1H, dd, J = 4, 8 Hz), 6.27 (1H, s), 4.62-4.42 (1H, m), 3.60-2.42 (3H, m), 2.20-0.80 (8H, m), 0.69 (3H, t, J = 7 Hz) |
| 193* | (DMSO-$d_6$) 10.52 (1H, s), 8.84 (1H, d, J = 4 Hz), 8.49 (1H, s), 8.27 (1H, d, J = 8 Hz), 7.92 (1H, d, J = 9 Hz), 7.87 (1H, d, J = 8 Hz), 7.82-7.63 (3H, m), 7.41 (1H, dd, J = 4, 8 Hz), 6.26 (1H, s), 4.60-4.30 (1H, m), 3.90-2.20 (5H, m), 2.00-1.20 (10H, m) |

TABLE 4-continued

| EXAMPLE | NMR data (δ: ppm) |
|---|---|
| 194* | (DMSO-$d_6$) 10.30 (1H, s), 8.84 (1H, dd, J = 4, 2 Hz), 8.47 (1H, s), 8.27 (1H, d, J = 8 Hz), 7.93 (1H, d, J = 9 Hz), 7.82 (1H, d, J = 8 Hz), 7.73, (1H, d, J = 9 Hz), 7.66 (1H, s), 7.50 (1H, d, J = 8 Hz), 7.45-7.34 (4H, m), 7.23 (2H, d, J = 8 Hz), 3.88-3.77 (2H, m), 2.88-2.79 (2H, m), 2.02 (3H, s), 1.78-1.63 (2H, m) |
| 195* | (DMSO-$d_6$) 10.53 (1H, s), 8.84 (1H, d, J = 4 Hz), 8.49 (1H, s), 8.26 (1H, d, J = 8 Hz), 7.95-7.60 (5H, m), 7.45-7.35 (1H, m), 6.28 (1H, s), 4.60-1.80 (6H, m), 1.70 (s, 3H) |
| 196* | (DMSO-$d_6$) 10.46 (1H, s), 8.84 (1H, dd, J = 2, 4 Hz), 8.50 (1H, s), 8.27 (1H, d, J = 8 Hz), 7.92 (1H, d, J = 9 Hz), 7.76 (1H, dd, J = 2, 9 Hz), 7.46 (1H, d, J = 8 Hz), 7.41 (1H, dd, J = 4, 8 Hz), 7.06 (1H, d, J = 8 Hz), 6.96 (1H, s), 6.46 (1H, s), 3.30 (2H, t, J = 6 Hz), 3.14 (2H, t, J = 6 Hz), 3.02 (3H, s), 2.22-2.10 (2H, m) |
| 197* | (DMSO-$d_6$) 9.86 (1H, s), 9.81 (1H, s), 7.78 (1H, d, J = 9 Hz), 7.67 (1H, d, J = 7 Hz), 7.62 (1H, d, J = 8 Hz), 7.49 (1H, d, J = 8 Hz), 7.34 (1H, s), 7.23 (1H, t, J = 8 Hz), 7.13-7.02 (2H, m), 6.95 (1H, s), 6.66 (1H, s), 3.36-3.24 (2H, m), 3.09 (2H, t, J = 6 Hz), 3.01 (3H, s), 2.07-2.03 (2H, m) |
| 198* | (DMSO-$d_6$) 9.25 (1H, s), 7.44 (1H, d, J = 8 Hz), 7.33 (1H, d, J = 8 Hz), 7.10-6.99 (2H, m), 6.95-6.85 (2H, m), 6.51 (1H, s), 4.81 (1H, d, J = 4 Hz), 3.96-3.83 (1H, m), 3.26 (2H, t, J = 6 Hz), 3.06 (2H, t, J = 6 Hz), 2.99 (3H, s), 2.96-2.65 (3H, m), 2.57-2.37 (1H, m), 2.15-2.00 (2H, m), 1.94-1.80 (1H, m), 1.68-1.50 (1H, m) |
| 199* | (DMSO-$d_6$) 10.45 (1H, s), 8.87-8.80 (1H, m), 8.50 (1H, s), 8.26 (1H, d, J = 8 Hz), 7.91 (1H, d, J = 9 Hz), 7.80-7.71 (1H, m), 7.46 (1H, d, J = 8 Hz), 7.40 (1H, dd, J = 4, 8 Hz), 7.06-6.97 (2H, m), 6.46 (1H, s), 3.21-3.09 (2H, m), 2.30-2.09 (2H, m), 1.81-1.17 (13H, m) |
| 200 | ($CDCl_3$) 8.40 (1H, d, J = 2 Hz), 7.88 (1H, d, J = 2 Hz), 7.80-7.57 (2H, m), 7.22-6.93 (4H, m), 6.58(1H, s), 6.45 (1H, s), 4.79 (2H, d, J = 5 Hz), 4.28-4.15 (1H, m), 3.80 (2H, t, J = 6 Hz), 3.60 (2H, t, J = 6 Hz), 3.08-2.80 (3H, m), 2.62 (1H, dd, J = 8, 16 Hz), 2.13-2.00 (1H, m), 1.97 (1H, t, J = 6 Hz), 1.90-1.75 (1H, m) |
| 202 | ($CDCl_3$) 7.80-7.64 (2H, m), 7.20-7.03 (4H, m), 7.00-6.92 (1H, m), 6.44 (1H, s), 4.29 (2H, t, J = 6 Hz), 3.51 (2H, t, J = 6 Hz), 2.80 (2H, t, J = 6 Hz), 2.65 (2H, t, J = 6 Hz), 1.92-1.73 (4H, m) |
| 204 | (DMSO-$d_6$) 10.06 (1H, s), 9.11 (1H, s), 8.44 (1H, d, J = 6 Hz), 7.92 (1H, d, J = 8 Hz), 7.50 (1H, d, J = 6 Hz), 7.37 (1H, d, J = 9 Hz), 7.25 (1H, s), 6.93 (1H, s), 4.30 (2H, t, J = 6 Hz), 3.38 (2H, t, J = 6 Hz), 2.49 (3H, s) |
| 206 | ($CDCl_3$) 7.76-7.62 (1H, m), 7.59-7.45 (1H, m), 7.21-7.12 (1H, m), 7.06-6.94 (2H, m), 6.86-6.72 (2H, m), 6.34 (1H, s), 4.24 (2H, t, J = 6 Hz), 4.26-4.12 (1H, m), 3.48 (2H, t, J = 6 Hz), 3.09-2.78 (4H, m), 2.60 (1H, dd, J = 16, 8 Hz), 2.13-2.00 (1H, m), 1.90-1.72 (2H, m), 1.24 (6H, d, J = 7 Hz) |
| 207 | ($CDCl_3$) 7.58-7.43 (1H, m), 7.23-6.94 (3H, m), 6.80 (1H, d, J = 8 Hz), 6.75 (1H, s), 6.44 (1H, d, J = 8 Hz), 6.34 (1H, s), 4.35-4.26 (1H, m), 4.23 (2H, t, J = 6 Hz), 4.01-3.84 (1H, m), 3.47 (2H, t, J = 6 Hz), 3.35-3.21 (2H, m), 2.95-2.79 (2H, m), 2.71 (1H, dd, J = 4, 15 Hz), 2.60-2.43 (1H, m), 1.24 (6H, d, J = 7 Hz) |
| 208 | (DMSO-$d_6$) 9.26 (1H, s), 7.70 (1H, d, J = 9 Hz), 7.38 (1H, d, J = 8 Hz), 7.14-7.04 (2H, m), 7.00 (1H, s), 6.91 (1H, d, J = 8 Hz), 6.86 (1H, s), 4.84 (1H, d, J = 4 Hz), 4.22 (2H, t., J = 6 Hz), 4.00-3.84 (1H, m), 3.48-3.29 (2H, m), 2.97-2.81 (2H, m), 2.81-2.65 (1H, m), 2.47-2.39 (1H, m), 1.95-1.82 (1H, m), 1.70-1.53 (1H, m) |
| 209 | (DMSO-$d_6$) 9.17 (1H, s), 7.69 (1H, d, J = 9 Hz), 7.07 (1H, d, J = 9 Hz), 7.00 (1H, s), 6.88-6.79 (2H, m), 6.71 (1H, d, J = 8 Hz), 6.31 (1H, d, J = 8 Hz), 5.70 (1H, s), 4.92 (1H, d, J = 4 Hz), 4.22 (2H, t, J = 6 Hz), 3.95-3.80 (1H, m), 3.45-3.31 (2H, m), 3.26-3.13 (1H, m), 2.93-2.71 (2H, m), 2.49-2.35 (1H, m) |
| 210 | ($CDCl_3$) 7.72-7.54 (2H, m), 7.23-7.13 (1H, m), 7.10-6.94 (2H, m), 6.85-6.71 (2H, m), 6.35 (1H, s), 4.27 (2H, t, J = 6 Hz), 4.25-4.13 (1H, m), 3.49 (2H, t, J = 6 Hz), 3.09-2.80 (3H, m), 2.60 (1H, dd, J = 8, 16 Hz), 2.13-2.01 (1H, m), 1.90-1.71 (2H, m) |
| 211 | (DMSO-$d_6$) 9.21 (1H, s), 7.78 (1H, d, J = 9 Hz), 7.01 (1H, d, J = 8 Hz), 6.90 (1H, s), 6.87-6.78 (2H, m), 6.71 (1H, d, J = 8 Hz), 6.31 (1H, d, J = 8 Hz), 5.70 (1H, s), 4.92 (1H, d, J = 4 Hz), 4.25 (2H, t, J = 6 Hz), 3.94-3.80 (1H, m), 3.44-3.30 (2H, m), 3.26-3.12 (1H, m), 2.92-2.71 (2H, m), 2.49-2.34 (1H, m) |
| 212 | (DMSO-$d_6$) 9.29 (1H, s), 7.78 (1H, d, J = 9 Hz), 7.38 (1H, d, J = 8 Hz), 7.13-7.03 (1H, m), 7.02-6.62 (5H, m), 4.85 (1H, s), 4.25 (2H, t, J = 6 Hz), 3.99-3.85 (1H, m), 3.50-3.33 (2H, m), 3.00-2.65 (3H, m), 2.51-2.40 (1H, m), 1.97-1.82 (1H, m), 1.71-1.53 (1H, m) |
| 213 | (DMSO-$d_6$) 9.20 (1H, s), 7.76 (1H, d, J = 9 Hz), 7.01-6.61 (6H, m), 6.31 (1H, d, J = 8 Hz), 5.70 (1H, s), 4.93 (1H, d, J = 4 Hz), 4.25 (2H, t, J = 6 Hz), 3.95-3.80 (1H, m), 3.46-3.32 (2H, m), 3.26-3.14 (1H, m), 2.92-2.70 (2H, m), 2.50-2.35 (1H, m) |
| 214 | (DMSO-$d_6$) 9.26 (1H, s), 7.77 (1H, d, J = 12 Hz), 7.43 (1H, d, J = 8 Hz), 7.29 (1H, d, J = 6 Hz), 7.15-7.05 (1H, m), 7.00 (1H, s), 6.92 (1H, d, J = 8 Hz), 4.86 (1H, d, J = 4 Hz), 4.26 (2H, t, J = 6 Hz), 3.99-3.86 (1H, m), 3.49-3.34 (2H, m), 2.98-2.66 (3H, m), 2.55-2.40 (1H, m), 1.96-1.82 (1H, m), 1.70-1.55 (1H, m) |
| 215 | (DMSO-$d_6$) 9.17 (1H, s), 7.76 (1H, d, J = 12 Hz), 7.29 (1H, d, J = 6 Hz), 6.97 (1H, s), 6.88-6.73 (2H, m), 6.32 (1H, d, J = 8 Hz), 5.72 (1H, s), 4.94 (1H, d, J = 4 Hz), 4.26 (2H, t, J = 6 Hz), 3.95-3.82 (1H, m), 3.42-3.33 (2H, m), 3.25-3.15 (1H, m), 2.94-2.74 (2H, m), 2.50-2.47 (1H, m) |
| 216 | DMSO-$d_6$) 10.46 (1H, s), 8.41 (1H, d, J = 2 Hz), 8.01 (1H, d, J = 9 Hz), 7.88 (1H, d, J = 8 Hz), 7.58 (1H, dd, J = 2, 9 Hz), 7.36 (1H, d, J = 8 Hz), 7.25 (1H, s), 6.83 (1H, s), 6.26 (1H, t, J = 6 Hz), 4.85 (2H, d J = 6 Hz), 4.30 (2H, t, J = 6 Hz), 3.43 (2H, t, J = 6 Hz) |
| 218 | (CDCl3) 7.46-7.36 (1H, m), 7.32-7.12 (3H, m), 7.10-6.94 (2H, m), 6.46 (1H, d, J = 8 Hz), 6.18 (1H, s,), 4.37-4.21 (1H, m), 4.24 (2H, t, J = 6 Hz), 4.00-3.86 (1H, m), 3.38-3.17 (4H, m), 2.88 (1H, dd, J = 4, 16 Hz), 2.71 (1H, d, J = 16 Hz), 2.53-2.40 (1H, m), 2.32-2.16 (2H, m) |
| 219 | (CDCl3) 7.46-7.36 (1H, m), 7.33-7.12 (3H, m), 7.10-6.94 (2H, m), 6.46 (1H, d, J = 8 Hz), 6.18 (1H, s), 4.37-4.22 (1H, m), 4.24 (2H, t, J = 6 Hz), 4.00-3.86 (1H, m), 3.39-3.20 |

TABLE 4-continued

| EXAMPLE | NMR data (δ: ppm) |
|---|---|
| | (4H, m), 2.89 (1H, dd, J = 4, 16 Hz), 2.71 (1H, d, J = 16 Hz), 2.52-2.40 (1H, m), 2.31-2.18 (2H, m) |
| 220* | (CDCl3) 7.72-7.60 (1H, m), 7.48-7.38 (1H, m), 7.29-7.13 (4H, m), 7.09-6.94 (2H, m), 6.20 (1H, s), 4.25 (2H, t, J = 6 Hz), 3.38-3.18 (2H, m), 3.12-2.98 (1H, m), 2.91-2.79 (1H, m), 2.71 (2H, s), 2.30-2.17 (2H, m), 1.98-1.72 (2H, m), 1.40 (3H, s) |
| 221 | (DMSO-d6) 10.05 (1H, s), 9.12 (1H, s), 8.45 (1H, d, J = 6 Hz), 7.63 (1H, d, J = 8 Hz), 7.51 (1H, d, J = 6 Hz), 7.45 (1H, d, J = 8 Hz), 7.30 (1H, s), 6.59 (1H, s), 4.24 (2H, t, J = 6 Hz), 3.16 (2H, t, J = 7 Hz), 2.49 (3H, s), 2.18-2.02 (2H, m) |
| 226 | (DMSO-$d_6$) 8.33-8.22 (1H, m), 7.47 (1H, d, J = 8 Hz), 7.38 (1H, d, J = 8 Hz), 7.23 (1H, s), 7.08-6.89 (3H, m), 6.22 (1H, s), 4.82 (1H, d, J = 4 Hz), 4.19 (2H, t, J = 6 Hz), 4.00-3.86 (1H, m), 3.46-3.25 (2H, m), 3.12 (2H, t, J = 7 Hz), 3.04-2.64 (6H, m), 2.12-1.98 (2H, m), 1.95-1.81 (1H, m), 1.67-1.52 (1H, m) |
| 227* | (DMSO-$d_6$) 8.24-8.12 (1H, m), 7.47 (1H, d, J = 8 Hz), 7.36 (1H, d, J = 9 Hz), 7.23 (1H, s), 7.12-7.02 (2H, m), 6.96-6.86 (1H, m), 6.24 (1H, s), 4.81 (1H, t, J = 4 Hz), 4.17 (2H, t, J = 6 Hz), 3.99-3.82 (1H, m), 3.46-2.65 (9H, m), 2.11-1.95 (2H, m), 1.94-1.81 (1H, m), 1.66-1.49 (1H, m), 1.15 (3H, d, J = 5 Hz) |
| 229 | (DMSO-d6) 9.62 (1H, s), 7.54 (1H, d, J = 8 Hz), 7.35 (1H, d, J = 8 Hz), 7.20 (1H, s), 7.05 (1H, t, J = 8 Hz), 6.97-6.85 (2H, m), 6.41 (1H, s), 6.35 (1H, dd, J = 9, 2 Hz), 4.32 (1H, t, J = 5 Hz), 4.21 (1H, t, J = 6 Hz), 3.78-3.60 (2H, m), 3.58-3.47 (1H, m), 3.38-3.23 (2H, m), 3.20-3.00 (3H, m), 2.16-1.83 (6H, m) |
| 231* | (DMSO-d6) 8.37-8.18 (1H, m), 7.56 (1H, d, J = 8 Hz), 7.46-7.36 (2H, m), 7.27 (1H, s), 6.85 (1H, d, J = 9 Hz), 6.44 (1H, s), 5.00 (1H, t, J = 6 Hz), 4.31 (2H, d, J = 6 Hz), 4.28-4.18 (4H, m), 3.79 (2H, t, J = 5 Hz), 3.17 (2H, t, J = 7 Hz), 2.16-2.05 (2H, m) |
| 233 | (DMSO-$d_6$) 9.89 (1H, s), 7.55 (1H, d, J = 8 Hz), 7.41 (1H, d, J = 8 Hz), 7.26 (1H, s), 7.04 (1H, d, J = 2 Hz), 6.82 (1H, dd, J = 2, 6 Hz), 6.59 (1H, d, J = 8 Hz), 6.40 (1H, s), 4.77 (1H, t, J = 5 Hz), 4.21 (2H, t, J = 6 Hz), 4.10 (2H, t, J = 4 Hz), 3.67-3.57 (2H, m), 3.39 (2H, t, J = 4 Hz), 3.30 (2H, t, J = 7 Hz), 3.16 (2H, t, J = 7 Hz), 2.16-2.02 (2H, m) |
| 234 | (DMSO-$d_6$) 10.23 (1H, s), 7.61 (1H, d, J = 2 Hz), 7.56 (1H, d, J = 8 Hz), 7.43 (1H, d, J = 8 Hz), 7.31 (1H, dd, J = 2, 9 Hz), 7.28 (1H, s), 6.96 (1H, d, J = 9 Hz), 6.43 (1H, s), 4.98 (1H, t, J = 6 Hz), 4.60 (2H, s), 4.22 (2H, t, J = 6 Hz), 3.92 (2H, t, J = 6 Hz), 3.62 (2H, dt, J = 6, 6 Hz), 3.18 (2H, t, J = 6 Hz), 2.19-2.06 (2H, m) |
| 235 | (DMSO-$d_6$) 9.43 (1H, s), 7.78-7.60 (3H, m), 7.33 (1H, d, J = 8 Hz), 7.13-7.04 (1H, m), 6.93 (1H, d, J = 7 Hz), 6.53 (1H, s), 4.84 (1H, d, J = 3 Hz), 4.82 (2H, s), 4.01-3.85 (3H, m), 3.41-3.25 (2H, m), 2.96-2.82 (2H, m), 2.81-2.67 (1H, m), 2.58-2.40 (1H, m), 1.98-1.82 (1H, m), 1.69-1.54 (1H, m) |
| 236 | (DMSO-$d_6$) 9.34 (1H, s), 7.77-7.58 (3H, m), 6.89-6.80 (1H, m), 6, .66 (1H, d, J = 7 Hz), 6.49 (1H, s), 6.32 (1H, d, J = 8 Hz), 5.71 (1H, s), 4.92 (1H, d, J = 4 Hz), 4.81 (2H, s), 3.94 (2H, t, J = 5 Hz), 3.95-3.81 (1H, m), 3.48-3.15 (3H, m), 2.92-2.70 (2H, m), 2.42 (1H, dd, J = 8, 16 Hz) |
| 237 | (DMSO-$d_6$) 9.45 (1H, s), 8.01 (1H, d, J = 8 Hz), 7.76 (1H, d, J = 8 Hz), 7.66 (1H, s), 7.38 (1H, d, J = 8 Hz), 7.13-7.01 (2H, m), 6.93 (1H, d, J = 8 Hz), 5.10 (2H, s), 4.85 (1H, d, J = 4 Hz), 4.76 (2H, s), 3.97-3.85 (1H, m), 2.96-2.81 (2H, m), 2.81-2.67 (1H, m), 2.50-2.39 (1H, m), 1.95-1.80 (1H, m), 1.70-1.55 (1H, m) |
| 238* | (DMSO-$d_6$) 9.40 (1H, s), 8.34 (1H, d, J = 8 Hz), 7.61 (1H, d, J = 8 Hz), 7.38 (1H, d, J = 8 Hz), 7.14-7.01 (2H, m), 6.93 (1H, d, J = 7 Hz), 4.84 (1H, d, J = 4 Hz), 4.42 (2H, t, J = 6 Hz), 3.98-3.83 (1H, m), 3.46-3.34 (2H, m), 2.97-2.65 (3H, m), 2.51-2.34 (1H, m), 1.95-1.80 (1H, m), 1.70-1.53 (1H, m) |
| 239* | (DMSO-$d_6$) 9.39 (1H, s), 8.06 (1H, d, J = 8 Hz), 7.64 (1H, d, J = 8 Hz), 7.35 (1H, d, J = 8 Hz), 7.13-7.01 (1H, m), 6.92 (1H, d, J = 8 Hz), 6.71 (1H, s), 4.83 (1H, d, J = 4 Hz), 4.34 (2H, t, J = 6 Hz), 3.98-3.81 (1H, m), 3.19-3.01 (2H, m), 2.95-2.63 (3H, m), 2.56-2.38 (1H, m), 2.21-2.06 (2H, m), 1.94-1.78 (1H, m), 1.68-1.50 (1H, m) |
| 240 | ($CDCl_3$) 9.67 (1H, s), 7.67-7.58 (1H, m), 7.57-7.47 (1H, m), 7.32-7.07 (3H, m), 6.97 (1H, d, J = 7 Hz), 6.62 (1H, s), 4.27-4.13 (1H, m), 3.09-2.80 (4H, m), 2.60 (1H, dd, J = 8, 16 Hz), 2.13-2.01 (1H, m), 1.91-1.64 (2H, m), 1.60 (6H, m) |
| 241 | (DMSO-$d_6$) 9.38 (1H, s), 7.87 (1H, d, J = 8 Hz), 7.39 (1H, d, J = 8 Hz), 7.31 (1H, d, J = 8 Hz), 7.17 (1H, s), 7.13-7.04 (1H, m), 7.03 (1H, s), 6.92 (1H, d, J = 8 Hz), 4.85 (1H, d, J = 4 Hz), 3.98-3.87 (1H, m), 3.48-3.30 (2H, m), 2.97-2.81 (2H, m), 2.81-2.67 (1H, m), 2.48-2.41 (1H, m), 1.94-1.83 (1H, m), 1.69-1.53 (1H, m), 1.33 (6H, s) |
| 242 | ($CDCl_3$) 7.80-7.55 (2H, m), 7.32-6.92 (5H, m), 6.50 (1H, s), 4.30-4.13 (1H, m), 3.38 (2H, s), 3.10-2.80 (3H, m), 2.61 (1H, dd, J = 7, 16 Hz), 2.14-2.01 (1H, m), 1.91-1.65 (2H, m), 1.38 (6H, s) |
| 243 | ($CDCl_3$) 7.80-7.55 (2H, m), 7.32-6.92 (5H, m), 6.49 (1H, s), 4.30-4.13 (1H, m), 3.38 (2H, s), 3.10-2.80 (3H, m), 2.61 (1H, dd, J = 8, 16 Hz), 2.14-2.01 (1H, m), 1.91-1.65 (2H, m), 1.38 (6H, s) |
| 244 | (DMSO-$d_6$) 9.29 (1H, s), 7.86 (1H, d, J = 8 Hz), 7.31 (1H, d, J = 8 Hz), 7.16 (1H, s), 6.99 (1H, s), 6.89-6.79 (1H, m), 6.73 (1H, d, J = 8 Hz), 6.32 (1H, d, J = 8 Hz), 5.71 (1H, s), 4.93 (1H, d, J = 4 Hz), 3.94-3.82 (1H, m), 3.57-3.13 (3H, m), 2.92-2.71 (2H, m), 2.47-2.36 (1H, m), 1.32 (6H, s) |
| 245 | ($CDCl_3$) 7.72-7.56 (1H, m), 7.33-6.98 (5H, m), 6.53-6.42 (2H, m), 4.37-4.26 (1H, m), 4.00-3.88 (1H, m), 3.48-3.22 (4H, m), 2.90 (1H, dd, J = 5, 16 Hz), 2.78-2.66 (1H, m), 2.52-2.37 (1H, m), 1.38 (3H, s), 1.37 (3H, s) |
| 246 | ($CDCl_3$) 7.74-7.54 (1H, m), 7.34-6.93 (5H, m), 6.56-6.40 (2H, m), 4.38-4.26 (1H, m), 4.02-3.85 (1H, m), 3.47-3.21 (4H, m), 2.90 (1H, dd, J = 4, 16 Hz), 2.78-2.66 (1H, m), 2.52-2.37 (1H, m), 1.38 (3H, s), 1.37 (3H, s) |
| 247* | ($CDCl_3$) 8.86 (1H, dd, J = 2, 4 Hz), 8.06 (1H, dd, J = 2, 8 Hz), 7.91 (1H, s), 7.70 (1H, d, J = 9 Hz), 7.60-7.53 (1H, m), 7.43 (1H, d, J = 8 Hz), 7.35-7.12 (4H, m), 6.19 (1H, s), 4.30-4.22 (2H, m), 2.67-2.59 (2H, m), 2.22-2.12 (2H, m) |

TABLE 4-continued

| EXAMPLE | NMR data (δ: ppm) |
|---|---|
| 248 | (DMSO-$d_6$) 9.32 (1H, s), 7.51 (1H, d, J = 12 Hz), 7.38 (1H, d, J = 8 Hz), 7.32 (1H, d, J = 6 Hz), 7.15-7.04 (1H, m), 6.92 (1H, d, J = 8 Hz), 6.62 (1H, s), 4.85 (1H, d, J = 4 Hz), 4.19 (2H, t, J = 6 Hz), 3.98-3.86 (1H, m), 3.12 (2H, t, J = 6 Hz), 2.99-2.67 (3H, m), 2.62-2.40 (1H, m), 2.15-2.00 (2H, m), 1.96-1.80 (1H, m), 1.73-1.52 (1H, m) |
| 251 | (DMSO-$d_6$) 9.41 (1H, s), 7.85 (1H, d, J = 8 Hz), 7.40 (1H, d, J = 8 Hz), 7.37-7.31 (1H, m), 7.22 (1H, s), 7.13-7.06 (1H, m), 7.04 (1H, s), 6.93 (1H, d, J = 8 Hz), 4.85 (1H, d, J = 4 Hz), 3.98-3.86 (1H, m), 3.47 (2H, s), 2.97-2.67 (3H, m), 2.57-2.42 (1H, m), 2.28-1.97 (4H, m), 1.95-1.76 (2H, m), 1.74-1.54 (2H, m) |
| 252 | (DMSO-$d_6$) 9.32 (1H, s), 7.83 (1H, d, J = 8 Hz), 7.38-7.29 (1H, m), 7.21 (1H, s), 7.00 (1H, s), 6.90-6.81 (1H, m), 6.74 (1H, d, J = 8 Hz), 6.33 (1H, d, J = 8 Hz), 5.72 (1H, s), 4.93 (1H, d, J = 4 Hz), 3.94-3.82 (1H, m), 3.46 (2H, s), 3.27-3.17 (1H, m), 2.92-2.75 (2H, m), 2.69-2.38 (1H, m), 2.30-1.98 (4H, m), 1.91-1.59 (2H, m) |
| 253 | (DMSO-$d_6$) 13.11 (1H, s), 10.19 (1H, s), 8.32 (1H, s), 7.83 (1H, d, J = 7 Hz), 7.65 (1H, d, J = 8 Hz), 7.46 (1H, d, J = 7 Hz), 7.33-7.22 (3H, m), 6.71 (1H, s), 4.24 (2H, t J = 6 Hz), 3.21 (2H, t, J = 7 Hz), 2.20-2.08 (2H, m) |
| 254 | (DMSO-$d_6$) 12.64 (1H, s), 10.20 (1H, s), 8.11 (1H, s), 7.67-7.53 (3H, m), 7.46 (1H, d, J = 8 Hz), 7.30 (1H, s), 7.15-7.06 (1H, m), 6.53 (1H, s), 4.25 (2H, t J = 6 Hz), 3.23 (2H, t, J = 6 Hz), 2.22-2.08 (2H, m) |

<*270 MHz>

TABLE 5-1

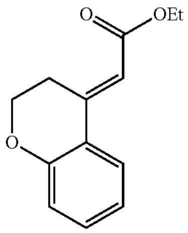

EXAMPLE 1-1

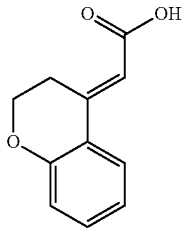

EXAMPLE 1-2

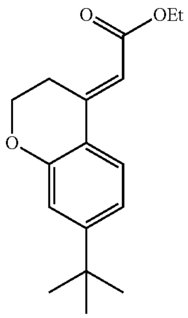

EXAMPLE 3-1

TABLE 5-1-continued

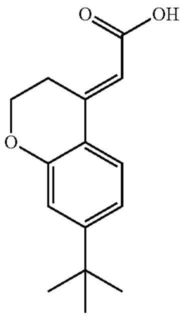

EXAMPLE 3-2

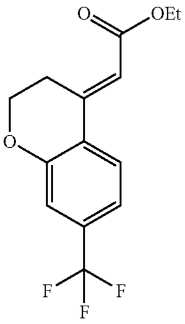

EXAMPLE 6-3

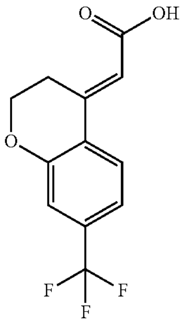

EXAMPLE 6-4

TABLE 5-1-continued
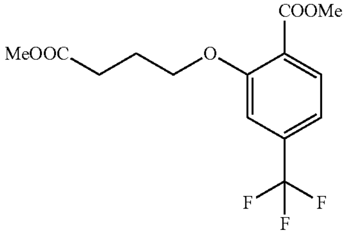
EXAMPLE 9-2
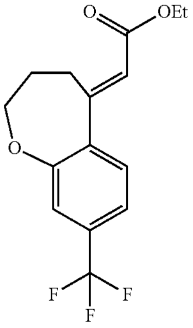
EXAMPLE 9-4a
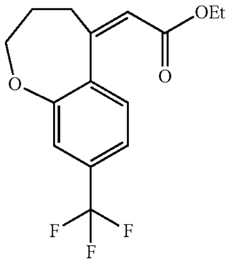
EXAMPLE 9-4b
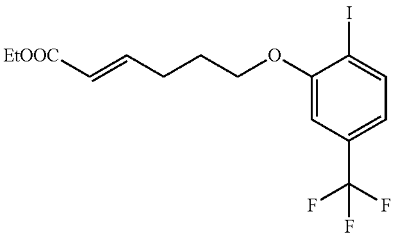
EXAMPLE 9B-2
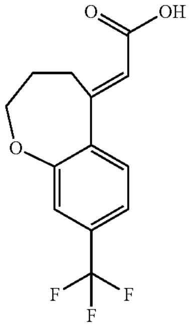
EXAMPLE 9-5
TABLE 5-1-continued
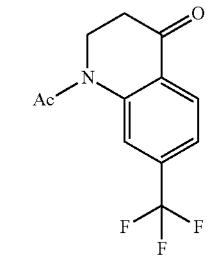
EXAMPLE 48-3
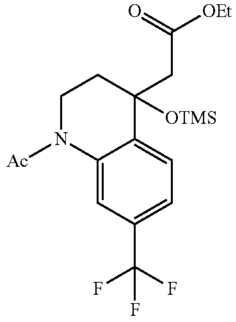
EXAMPLE 48-4
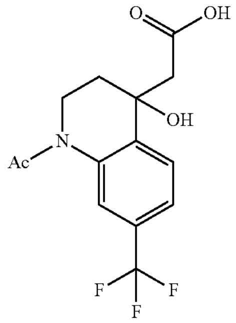
EXAMPLE 48-5
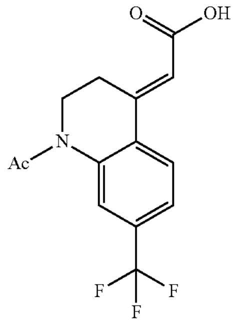
EXAMPLE 48-6

TABLE 5-1-continued
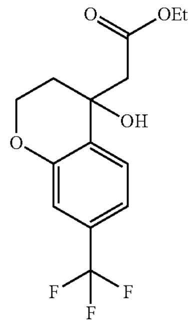
EXAMPLE 70A-2
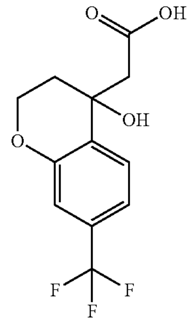
EXAMPLE 70A-3
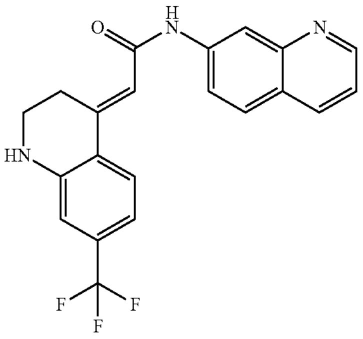
EXAMPLE 73-4
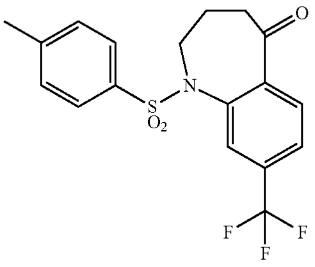
EXAMPLE 190-5
TABLE 5-1-continued
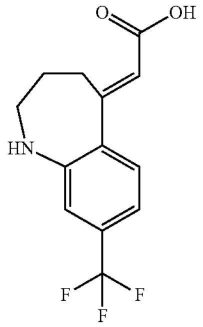
EXAMPLE 191-2
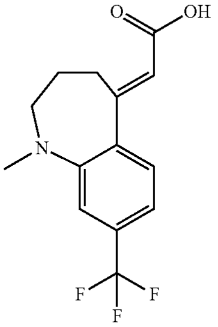
EXAMPLE 198-1
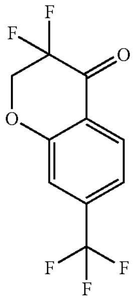
EXAMPLE 217-1
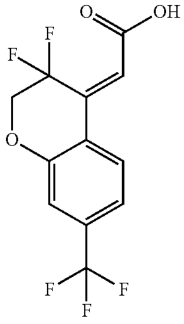
EXAMPLE 217-3

TABLE 5-1-continued
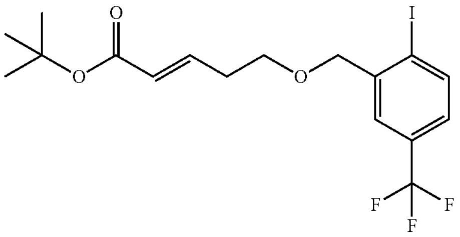
EXAMPLE 235-8
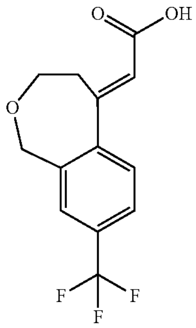
EXAMPLE 235-10
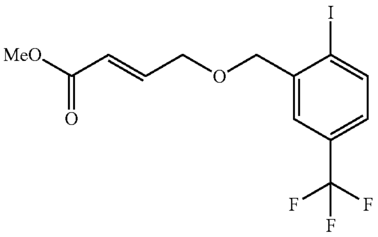
EXAMPLE 237-2
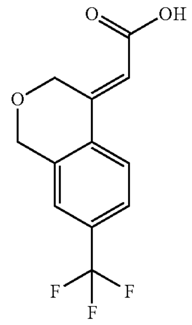
EXAMPLE 237-9
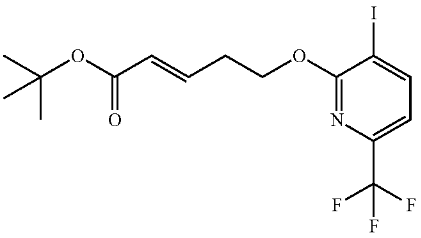
EXAMPLE 238-3
TABLE 5-1-continued
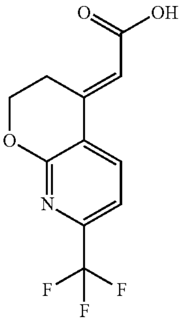
EXAMPLE 238-5
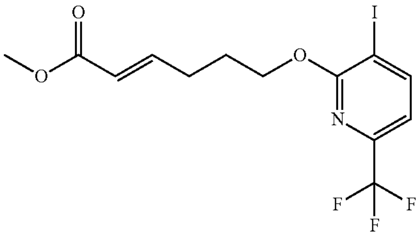
EXAMPLE 239-2
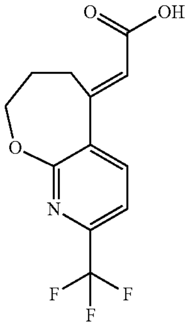
EXAMPLE 239-4
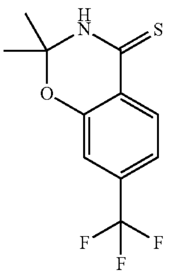
EXAMPLE 240-3

TABLE 5-1-continued

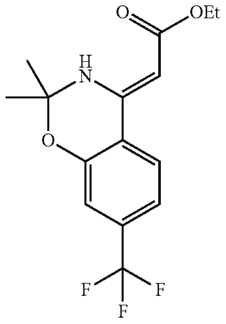

EXAMPLE 240-6

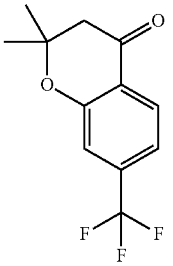

EXAMPLE 241-2

TABLE 5-1-continued

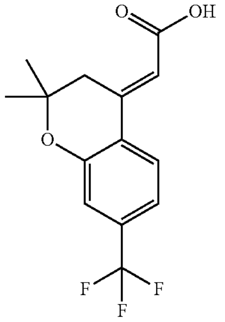

EXAMPLE 241-5

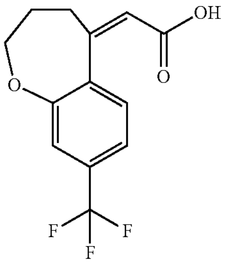

EXAMPLE 248-1

TABLE 6

| EXAMPLE | NMR data (δ: ppm) |
|---|---|
| 1-1* | ($CDCl_3$) 7.61 (1H, dd, J = 1, 8 Hz), 7.32-7.23 (1H, m), 6.98-6.84 (2H, m), 6.34 (1H, t, J = 2 Hz), 4.24 (2H, t, J = 6 Hz), 4.21 (2H, q, J = 7 Hz), 3.39 (2H, dt, J = 2, 6 Hz), 1.32 (3H, t, J = 7 Hz) |
| 1-2* | (DMSO-$d_6$) 7.76 (1H, dd, J = 2, 8 Hz), 7.35-7.26 (1H, m), 6.98-6.89 (1H, m), 6.87 (1H, dd, J = 1, 8 Hz), 6.38 (1H, s), 4.19 (2H, t, J = 6 Hz), 3.26 (2H, t, J = 6 Hz) |
| 3-1* | ($CDCl_3$) 7.55 (1H, d, J = 9 Hz), 6.96 (1H, dd, J = 2, 9 Hz), 6.89 (1H, d, J = 2 Hz), 6.31 (1H, t, J = 2 Hz), 4.23 (2H, t, J = 6 Hz), 4.20 (2H, q, J = 7 Hz), 3.38 (2H, dt, J = 2, 6 Hz), 1.32 (3H, t, J = 7 Hz), 1.30 (9H, s) |
| 3-2* | ($CDCl_3$) 7.57 (1H, d, J = 9 Hz), 6.99 (1H, dd, J = 2, 9 Hz), 6.90 (1H, d, J = 2 Hz), 6.35 (1H, s), 4.24 (2H, t, J = 6 Hz), 3.43-3.34 (2H, m), 1.30 (9H, s) |
| 6-3* | ($CDCl_3$) 7.69 (1H, d, J = 9 Hz), 7.18-7.08 (2H, m), 6.40 (1H, s), 4.28 (2H, t, J = 6 Hz), 4.22 (2H, q, J = 7 Hz), 3.41 (2H, t, J = 6 Hz), 1.33 (3H, t, J = 7 Hz) |
| 6-4* | (DMSO-$d_6$) 8.01 (1H, d, J = 8 Hz), 7.27-7.20 (2H, m), 6.52 (1H, s), 4.27 (2H, t, J = 6 Hz), 3.28 (2H, d, J = 6 Hz) |
| 9-2 | ($CDCl_3$) 7.86 (1H, d, J = 8 Hz), 7.23 (1H, d, J = 8 Hz), 7.17 (1H, s), 4.14 (2H, t, J = 6 Hz), 3.92 (3H, s), 3.70 (3H, s), 2.61 (3H, t, J = 7 Hz), 2.17 (2H, tt, J = 6, 7 Hz) |
| 9-4a* | ($CDCl_3$) 7.39 (1H, d, J = 8 Hz), 7.24-7.20 (2H, m), 6.15 (1H, s), 4.23 (2H, q, J = 7 Hz), 4.22 (2H, t, J = 6 Hz), 3.19 (2H, t, J = 7 Hz), 2.26-2.15 (2H, m), 1.33 (3H, t, J = 7 Hz) |
| 9-4b | ($CDCl_3$) 7.38-7.14 (3H, m), 5.98 (1H, s), 4.21 (2H, t, J = 6 Hz), 4.05 (2H, q, J = 7 Hz), 2.58 (2H, t, J = 6 Hz), 2.18-2.06 (2H, m), 1.26 (3H, t, J = 7 Hz) |
| 9B-2 | ($CDCl_3$) 7.89 (1H, d, J = 8 Hz), 7.13-6.84 (3H, m), 5.91 (1H, dt, J = 2, 16 Hz), 4.19 (2H, q, J = 7 Hz), 4.08 (2H, t, J = 6 Hz), 2.60-2.44 (2H, m), 2.12-1.97 (2H, m), 1.29 (3H, t, J = 7 Hz) |
| 9-5* | ($CDCl_3$) 7.42 (1H, d, J = 8 Hz), 7.28-7.18 (2H, m), 6.19 (1H, s), 4.23 (2H, t, J = 6 Hz), 3.22 (2H, t, J = 6 Hz), 2.30-2.16 (2H, m) |
| 48-3 | ($CDCl_3$) 8.14 (1H, d, J = 8 Hz), 7.89 (1H, s), 7.51 (1H, d, J = 8 Hz), 4.25 (2H, t, J = 6 Hz), 2.86 (2H, t, J = 6 Hz), 2.39 (3H, s) |
| 48-4 | ($CDCl_3$) 7.65 (1H, d, J = 8 Hz), 7.62 (1H, bs), 7.43 (1H, d, J = 8 Hz), 4.12-3.98 (3H, m), 3.75-3.60 (1H, m), 2.71 (2H, s), 2.60 (1H, ddd, J = 5, 6, 13 Hz), 2.27 (3H, s), 2.15-2.01 (1H, m), 1.19 (3H, t, J = 7 Hz), 0.09 (9H, s) |
| 48-5* | ($CDCl_3$) 7.73 (1H, d, J = 8 Hz), 7.66 (1H, bs), 7.48 (1H, d, J = 8 Hz), 4.15-3.98 (1H, m), 3.66-3.49 (1H, m), 2.85 (1H, d, J = 16 Hz), 2.71 (1H, d, J = 16 Hz), 2.42-2.24 (1H, m), 2.28 (3H, s), 2.15-2.01 (1H, m) |
| 48-6 | ($CDCl_3$) 7.81 (1H, d, J = 8 Hz), 7.74 (1H, bs), 7.47 (1H, d, J = 8 Hz), 6.46 (1H, t, J = 2 Hz), 3.87 (2H, t, J = 6 Hz), 3.41 (2H, dt, J = 2, 6 Hz), 2.30 (3H, s) |
| 70A-2* | ($CDCl_3$) 7.81 (1H, d, J = 8 Hz), 7.21-7.05 (2H, m), 4.41-4.14 (4H, m), 3.03 (1H, d, J = 16 Hz), 2.72 (1H, d, J = 16 Hz), 2.29-2.21 (2H, m), 1.29 (3H, t, J = 7 Hz) |

TABLE 6-continued

| EXAMPLE | NMR data (δ: ppm) |
|---|---|
| 70A-3* | ($CDCl_3$) 7.56 (1H, d, J = 8 Hz), 7.22-7.14 (1H, m), 7.10 (1H, d, J = 1 Hz), 4.40-4.18 (2H, m), 3.13 (1H, d, J = 16 Hz), 2.81 (1H, d, J = 16 Hz), 2.27 (2H, t, J = 6 Hz) |
| 73-4 | ($CDCl_3$) 8.89 (1H, dd, J = 2, 4 Hz), 8.18-8.00 (3H, m), 7.81 (1H, d, J = 9 Hz), 7.69-7.53 (2H, m), 7.34 (1H, dd, J = 4, 8 Hz), 6.92-6.83 (1H, m), 6.80 (1H, s), 6.40 (1H, s), 4.43-4.34 (1H, m), 3.54-3.33 (4H, m) |
| 190-5* | ($CDCl_3$) 7.82 (1H, d, J = 8 Hz), 7.72 (1H, s), 7.62 (2H, d, J = 8 Hz), 7.73-7.20 (3H, m), 3.88 (2H, t, J = 7 Hz), 2.53-2.47 (2H, m), 2.45 (3H, s), 2.07-1.97 (2H, m) |
| 191-2* | ($CDCl_3$) 7.33 (1H, d, J = 8 Hz), 6.95 (1H, d, J = 8 Hz), 6.83 (1H, s), 6.16 (1H, s), 3.28 (2H, t, J = 6 Hz), 3.19 (2H, t, J = 7 Hz), 2.25-2.12 (2H, m) |
| 198-1* | ($CDCl_3$) 7.34 (1H, d, J = 8 Hz), 6.97 (1H, d, J = 8 Hz), 6.92 (1H, s), 6.14 (1H, s), 3.27 (2H, t, J = 6 Hz), 3.14 (2H, t, J = 7 Hz), 3.05 (3H, s), 2.25-2.14 (2H, m) |
| 217-1 | ($CDCl_3$) 8.10 (1H, d, J = 8 Hz), 7.40 (1H, d, J = 8 Hz), 7.37 (1H, s), 4.64 (2H, t, J = 12 Hz) |
| 217-3 | ($CDCl_3$) 7.96 (1H, d, J = 9 Hz), 7.30-7.20 (2H, m), 6.48 (1H, s), 4.44 (2H, t, J = 11 Hz) |
| 235-8* | ($CDCl_3$) 7.94(1H, d, J = 8 Hz), 7.67 (1H, s), 7.23 (1H, d, J = 8 Hz), 6.90 (1H, dt, J = 7, 16 Hz), 5.86 (1H, d, J = 16 Hz), 4.50 (2H, s), 3.71 (2H, t, J = 6 Hz), 2.62-2.49 (2H, m), 1.48 (9H, s) |
| 235-10 | (DMSO-$d_6$) 12.6 (1H, bs), 7.72-7.62 (2H, m), 7.58 (1H, d, J = 9 Hz), 6.07 (1H, s), 4.79 (2H, s), 3.93 (2H, t, J = 6 Hz), 3.19 (2H, t, J = 6 Hz) |
| 237-2 | ($CDCl_3$) 7.96(1H, d, J = 8 Hz), 7.70 (1H, s), 7.31-7.21 (1H, m), 7.03 (1H, dt, J = 4, 16 Hz), 6.17 (1H, dt, J = 2, 16 Hz), 4.55 (2H, s), 4.32 (2H, dd, J = 2, 4 Hz), 3.77 (3H, s) |
| 237-9 | (DMSO-$d_6$) 12.6 (1H, bs), 8.14 (1H, d, J = 8 Hz), 7.69-7.60 (2H, m), 6.58 (1H, s), 5.00 (2H, s), 4.75 (2H, s) |
| 238-3* | ($CDCl_3$) 8.17 (1H, d, J = 8 Hz), 7.02-6.68 (2H, m), 5.90 (1H, dt, J = 2, 16 Hz), 4.49 (2H, t, J = 7 Hz), 2.74-2.60 (2H, m), 1.50 (9H, s) |
| 238-5* | (DMSO-$d_6$) 12.61 (1H, bs), 8.54 (1H, d, J = 9 Hz), 7.49 (1H, d, J = 9 Hz), 6.63 (1H, s), 4.40 (2H, t, J = 7 Hz), 3.33-3.27 (2H, m) |
| 239-2* | ($CDCl_3$) 8.17 (1H, d, J = 8 Hz), 7.10-6.95 (2H, m), 5.90 (1H, dt, J = 2, 16 Hz), 4.42 (2H, t, J = 7 Hz), 3.73 (3H, s), 2.52-2.36 (2H, m), 2.08-1.90 (2H, m) |
| 239-4* | ($CDCl_3$) 7.85 (1H, d, J = 8 Hz), 7.39 (1H, d, J = 8 Hz), 6.27 (1H, s), 4.39 (2H, t, J = 6 Hz), 3.23 (2H, t, J = 7 Hz), 2.39-2.26 (2H, m) |
| 240-3 | ($CDCl_3$) 8.43 (1H, d, J = 8 Hz), 8.28 (1H, bs), 7.30 (1H, dd, J = 1, 8 Hz), 7.18 (1H, d, J = 1 Hz), 1.68 (6H, s) |
| 240-6 | ($CDCl_3$) 8.92 (1H, bs), 7.67 (1H, d, J = 8 Hz), 7.23 (1H, d, J = 8 Hz), 7.18 (1H, s), 5.25 (1H, s), 4.17 (2H, q,, J = 7 Hz), 1.60 (6H, s), 1.31 (3H, t, J = 7 Hz) |
| 241-2 | ($CDCl_3$)7.96 (1H, d, J = 8 Hz), 7.28-7.12 (2H, m), 2.77 (2H, s), 1.48 (6H, s) |
| 241-5* | ($CDCl_3$)7.68 (1H, d, J = 9 Hz), 7.19-7.07 (2H, m), 6.47 (1H, s), 3.28 (2H, s), 1.39 (6H, s) |
| 248-1 | (DMSO-$d_6$) 12.26 (1H, bs), 7.40-7.23 (3H, m), 6.04 (1H, s), 4.15 (2H, t, J = 6 Hz), 2.53 (2H, t, J = 6 Hz), 2.10-1.94 (2H, m) |

<*270 MHz>

The invention claimed is:

1. A compound represented by formula (I'-D), or a salt thereof:

(I'-D)

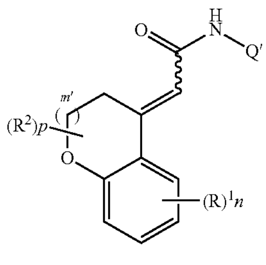

wherein m' represents an integer of 1 or 2;

wherein n and p each independently represent an integer of 0 to 2; with the proviso that when m' is 2, p is 0;

wherein $R^1$ represents a group selected from:

a halogen atom, a substituted or unsubstituted $C_{1-6}$ alkyl group, a substituted or unsubstituted $C_{2-6}$ alkenyl group, a substituted or unsubstituted $C_{2-6}$ alkynyl group, a substituted or unsubstituted $C_{3-9}$ cycloalkyl group, a substituted or unsubstituted $C_{3-6}$ cycloalkenyl group, a substituted or unsubstituted $C_{4-6}$ cycloalkanedienyl group, a substituted or unsubstituted $C_{6-14}$ aryl group, a substituted or unsubstituted heterocyclic group having five- to fourteen-membered rings, containing at least one heteroatom selected from the group consisting of N, O, and S in addition to the carbon atoms, a substituted or unsubstituted $C_{1-6}$ alkoxy group, a substituted or unsubstituted $C_{1-6}$ alkoxycarbonyl group, an amino group which is optionally mono- or di-substituted with a substituted or unsubstituted $C_{1-6}$ alkyl group, a protected or unprotected hydroxyl group, a protected or unprotected carboxyl group, a carbamoyl group which is optionally mono- or di-substituted with a substituted or unsubstituted $C_{1-6}$ alkyl group, a $C_{1-6}$ alkanoyl group, a $C_{1-6}$ alkylthio group, a $C_{1-6}$ alkylsulfinyl group, a $C_{1-6}$ alkylsulfonyl group, a sulfamoyl group which is optionally mono- or di-substituted with a substituted or unsubstituted $C_{1-6}$ alkyl group, a cyano group, and a nitro group;

wherein $R^2$ represents a group selected from:

a halogen atom, a substituted or unsubstituted $C_{1-6}$ alkyl group, and two geminal or vicinal $R^2$ groups may bind to each other to form a $C_{2-6}$ alkylene group, and form a cyclo ring group together with the carbon atom to which the two geminal or vicinal $R^2$ groups are bonded;

wherein Q' represents a group selected from:

a substituted or unsubstituted heteroaryl group having five- to fourteen-membered rings containing at least one heteroatom selected from the group consisting of N, O, and S in addition to carbon atoms, formula (B):

(B)

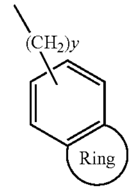

wherein in formula (B), the Ring moiety represents a monocyclic heterocycle that is optionally hydrogenated, the aromatic moiety and the Ring moiety are condensed, y is 0, 1, 2, or 3, and a substituted or unsubstituted heteroaryl—$C_{1-6}$ alkyl group; and wherein the wavy line in Formula (I'-D) represents an E-isomer or a Z-isomer.

2. The compound or a salt thereof according to claim 1, wherein:

$R^1$ is:

a halogen atom, a $C_{1-6}$ alkyl group which may be substituted with 1 to 5 halogen atoms or a $C_{1-6}$ alkoxy group which may be substituted with 1 to 5 halogen atoms, and n is 1 or 2.

3. The compound or a salt thereof according to claim 1, wherein:

$R^2$ is a $C_{1-6}$ alkyl group, and p is 0 or 2, or two geminal $R^2$ groups bind to each other to form a $C_{2-6}$ alkylene group, and form a cyclo ring group together with the carbon atom to which the two geminal $R^2$ groups are bonded.

4. The compound or a salt thereof according to claim 1, wherein m' is 1.

5. The compound or a salt thereof according to claim 1, wherein m' is 2.

6. The compound or a salt thereof according to claim 1, wherein Q' is unsubstituted or substituted with 1 to 5 substituents selected from groups (a-1)-(g-1):

(a-1): $C_{1-6}$ alkyl groups, $C_{2-6}$ alkenyl groups, $C_{2-6}$ alkynyl groups, $C_{6-14}$ aryl groups, $C_{3-7}$ cycloalkyl groups, and $C_{3-6}$ cycloalkenyl groups, each of which may be further substituted with a substituent RI, wherein RI is selected from the group consisting of a $C_{1-6}$ alkoxy group; a $C_{1-6}$ alkoxycarbonyl group; a carboxyl group; a carbamoyl group which is optionally mono- or di-substituted with a $C_{1-6}$ alkyl group; a halogen; a $C_{1-6}$ alkyl group; a halogenated $C_{1-6}$ alkyl group or an amino group which is optionally mono- or di-substituted with a $C_{1-6}$ alkyl group; a $C_{2-6}$ alkenoylamino group; a nitro group; a hydroxyl group; a pyridyl group; an oxo group; a cyano group; and an amidino group;

(b-1): any one of heterocyclic groups of (i) five- or six-membered, monocyclic aromatic heterocyclic groups, (ii) eight- to twelve-membered, fused aromatic heterocyclic groups, and (iii) three- to eight-membered, saturated or unsaturated, non-aromatic heterocyclic groups which contain 1 to 4 heteroatoms selected from the group consisting of an oxygen atom, a sulfur atom, and a nitrogen atom in addition to the carbon atoms, wherein the heterocyclic groups may be further substituted with a substituent RII, RII being a halogen atom, a $C_{1-6}$ alkyl group, a $C_{1-6}$ alkanoyl group, or a benzoyl group;

(c-1): an amino group which may be substituted with a substituent RIII, wherein RIII is selected from the group consisting of a $C_{1-6}$ alkyl group, a $C_{1-6}$ alkanoyl group, a $C_{2-6}$ alkenoyl group, a benzoyl group, a benzyl group, a phenyl group, a pyridyl group that is unsubstituted or substituted with a $C_{1-6}$ alkyl group, a halogen, a trifluoromethyl group, and a $C_{1-6}$ alkoxycarbonyl group that is unsubstituted or substituted with 1 to 5 halogen atoms, or a three- to eight-membered monocyclic amino group which may be substituted with a $C_{1-6}$ alkyl group, a $C_{7-10}$ aralkyl group, and a $C_{6-10}$ aryl group;

(d-1): an imidoyl group, an amidino group, a hydroxyl group, a thiol group, and an oxo group, and wherein the substituents in (d-1) may be substituted with the substituent RIII described above in (c-1);

(e-1): a halogen atom, a cyano group, or a nitro group;

(f-1): a carboxyl group, $C_{1-6}$ alkoxycarbonyl groups, $C_{7-12}$ aryloxycarbonyl groups, and $C_{6-10}$ aryl-$C_{1-4}$ alkoxycarbonyl groups, and the aryl groups in (f-1) may be further substituted with a substituent RIV', wherein RIV' is an amino group, which may be mono- or di-substituted with the substituent RIII; a $C_{1-6}$ alkyl group or a $C_{1-6}$ alkoxy group either of which may be substituted with 1 to 5 halogen atoms; a halogen atom; a hydroxyl group; a nitro group; and a cyano group;

(g-1): groups represented by —CONRgRg', —CSNRgRg', —CO-Rg, and —$SO_y$-Rg, wherein Rg represents a hydrogen atom or a substituent RV, RV being a $C_{1-6}$ alkyl group, a $C_{3-6}$ cycloalkyl group, a $C_{6-10}$ aryl group, a $C_{7-10}$ aralkyl group, or a heterocyclic group; the heterocyclic group is any one of (i) five-or six-membered monocyclic aromatic heterocyclic groups, (ii) eight-to twelve-membered fused aromatic heterocyclic groups, and (iii) three-to eight-membered saturated or unsaturated non-aromatic heterocyclic groups which contain 1 to 4 heteroatoms selected from the group consisting of an oxygen atom, a sulfur atom, and a nitrogen atom in addition to the carbon atoms; wherein the alkyl group, the cycloalkyl group, the aryl group, the aralkyl group, or the heterocyclic group of RV may be further substituted with 1 to 5 of the RIV substituents RIV;

wherein Rg' is a hydrogen atom or a group selected from a $C_{1-6}$ alkyl group, a $C_{3-6}$ cycloalkyl group, and a $C_{7-10}$ aralkyl group; and wherein y is 0, 1, or 2.

7. The compound or a salt thereof according to claim 1, wherein Q' is represented by formula (B):

(B)

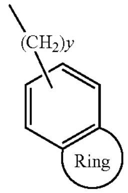

wherein in formula (B), the Ring moiety represents a monocyclic heterocycle that is optionally hydrogenated, the aromatic moiety and the Ring moiety are condensed, y is 0, 1, 2, or 3, and wherein formula (B) may be unsubstituted or substituted with 1 to 5 substituents optionally selected from the group consisting of $C_{1-6}$ alkyl, $C_{2-6}$ alkenyl, $C_{2-6}$ alkynyl, halogen atoms, halogenated $C_{1-6}$ alkyl, cyano, amino, hydroxyl, carbamoyl, $C_{1-6}$ alkoxy, $C_{2-6}$ alkenyloxy, $C_{2-6}$ alkynyloxy, $C_{1-6}$ alkylthio, $C_{1-6}$ alkylsulfinyl, $C_{1-6}$ alkylsulfonyl, mono/di $C_{1-6}$ alkylamino, $C_{1-6}$ alkoxycarbonyl, $C_{2-6}$ alkanoyl, $C_{2-6}$ alkanoylamino, hydroxy-$C_{1-6}$ alkyl, $C_{1-6}$ alkoxy-$C_{1-6}$ alkyl, carboxy-$C_{1-6}$ alkyl, $C_{1-6}$ alkoxycarbonyl-$C_{1-6}$ alkyl, carbamoyl-$C_{1-6}$ alkyl, N-$C_{1-6}$ alkylcarbamoyl-$C_{1-6}$ alkyl, N,N-di $C_{1-6}$ alkylcarbamoyl-$C_{1-6}$ alkyl, phenyl, phenoxy, phenylthio, phenylsulfinyl, phenylsulfonyl, benzyl, benzoyl, morpholino, oxo, morpholinylcarbonyl, morpholinylsulfonyl, 5-trifluoromethylpyridin-2-yloxy, quinoxalin-2-yl, (pyridin-4-yl)methyl, 1,2,3-thiadiazolo-4-yl, 1H-pyrazolo-1-yl, and 4-chlorophenyl; and any aromatic rings in these substituents may be further substituted with 1 to 3 substituents selected from halogen atoms, trifluoromethyl, cyano, hydroxyl, amino, nitro, carboxyl, carbamoyl, $C_{1-6}$ alkyl, $C_{1-6}$ alkoxy, mono/di $C_{1-6}$ alkylamino, di-$C_{1-6}$ alkylcarbamoyl, $C_{1-6}$ alkoxycarbonyl, N—$C_{1-6}$ alkylcarbamoyl, N,N-di $C_{1-6}$ alkylcarbamoyl, and $C_{2-6}$ alkenoylamino.

8. The compound or a salt thereof according to claim 7, wherein the Ring moiety of formula (B) is:

a monocyclic heterocycle, which is optionally hydrogenated, selected from the group of consisting of a five- or six-membered aromatic heterocyclic groups and a three- to eight-membered saturated and unsaturated non-aromatic heterocyclic groups.

9. A pharmaceutical composition comprising, as an active ingredient, at least one of the compound represented by formula (I'-D) according to claim 1, or a pharmaceutically acceptable salt thereof, and a pharmaceutically acceptable diluent or carrier.

10. A pharmaceutical composition comprising, as an active ingredient, at least one of the compound represented by formula (I'-D) according to claim 1, a pharmaceutically acceptable salt thereof; a pharmaceutically acceptable diluent or carrier, and at least one therapeutic ingredient.

11. The pharmaceutical composition according to claim 10, wherein the at least one therapeutic ingredient is selected from the group consisting of an opioid agonist, gabapentin, pregabalin, an antidepressant drug, an antiepileptic drug, an antiarrhythmic drug, a NSAID, an anti-inflammatory drug and a COX-2 inhibitor.

12. The pharmaceutical composition according to claim 10, wherein at least one therapeutic ingredient is a drug used in a field to treat a disease is selected from the group consisting of chronic rheumatic arthritis, COPD, allergic diseases, an overactive bladder and urinary incontinence.

13. A compound, optical isomers thereof or a salt thereof, which is:

(E)-2-(chroman-4-ylidene)-N-(2,3-dihydrobenzo[b][1,4]dioxin-6-yl)acetamide;

(E)-2-(chroman-4-ylidene)-N-(isoquinolin-5-yl)acetamide;

(E)-2-(7-tert-butyl-chroman-4-ylidene)-N-(5,6,7,8-tetrahydroquinolin-7-yl)acetamide;

(E)-2-(7-tert-butyl-chroman-4-ylidene)-N-(isoquinolin-5-yl)acetamide;

(E)-2-(7-tert-butyl-chroman-4-ylidene)-N-(quinolin-7-yl)acetamide;

(E)-2-(7-(trifluoromethyl)chroman-4-ylidene)-N-(5,6,7,8-tetrahydro-quinolin-7-yl)-acetamide;

(E)-2-(7-(trifluoromethyl)chroman-4-ylidene)-N-(isoquinolin-5-yl)-acetamide;

(E)-2-(7-(trifluoromethyl)chroman-4-ylidene)-N-(quinolin-7-yl)-acetamide;

(E)-2-(8-trifluoromethyl-3,4-dihydrobenzo[b]oxepin-5(2H)-ylidene)-N-(2,3-dihydrobenzo[b][1,4]dioxin-6-yl)acetamide;

(E)-2-(8-trifluoromethyl-3,4-dihydrobenzo[b]oxepin-5(2H)-ylidene)-N-(5,6,7,8-tetrahydroquinolin-7-yl)acetamide;

(E)-2-(8-trifluoromethyl-3,4-dihydrobenzo[b]oxepin-5(2H)-ylidene)-N-(isoquinolin-5-yl)acetamide;

(E)-2-(8-trifluoromethyl-3,4-dihydrobenzo[b]oxepin-5(2H)-ylidene)-N-(quinoxalin-6-yl)acetamide;

(E)-2-(8-trifluoromethyl-3,4-dihydrobenzo[b]oxepin-5(2H)-ylidene)-N-(quinolin-7-yl)acetamide;

(E)-2-(8-trifluoromethyl-3,4-dihydrobenzo[b]oxepin-5(2H)-ylidene)-N-(1,2,3,4-tetrahydro-1-methylquinolin-7-yl)acetamide;

(E)-2-(8-trifluoromethyl-3,4-dihydrobenzo[b]oxepin-5(2H)-ylidene)-N-(2-methyl-1,3-benzothiazolo-5-yl)acetamide;

(E)-2-(8-trifluoromethyl-3,4-dihydrobenzo[b]oxepin-5(2H)-ylidene)-N-(2-morpholinopyridin-3-yl)acetamide;

(E)-2-(8-trifluoromethyl-3,4-dihydrobenzo[b]oxepin-5(2H)-ylidene)-N-(4-methyl-2-oxo-2H-chromen-7-yl)acetamide;

(E)-2-(8-trifluoromethyl-3,4-dihydrobenzo[b]oxepin-5(2H)-ylidene)-N-(6-phenoxypyridin-3-yl)acetamide;

(E)-2-(8-trifluoromethyl-3,4-dihydrobenzo[b]oxepin-5(2H)-ylidene)-N-(1,3-dihydro-1-oxoisobenzofuran-6-yl)acetamide;

(E)-2-(8-trifluoromethyl-3,4-dihydrobenzo[b]oxepin-5(2H)-ylidene)-N-(1-(pyridin-2-yl)ethyl)acetamide;

(E)-2-(8-trifluoromethyl-3,4-dihydrobenzo[b]oxepin-5(2H)-ylidene)-N-(phenyl(pyridin-2-yl)methyl)acetamide;

(E)-2-(8-trifluoromethyl-3,4-dihydrobenzo[b]oxepin-5(2H)-ylidene)-N-((2,3-dihydrobenzo[b][1,4]dioxin-6-yl)methyl)acetamide;

(E)-2-(8-trifluoromethyl-3,4-dihydrobenzo[b]oxepin-5(2H)-ylidene)-N-(1-(2,3-dihydrobenzo[b][1,4]dioxin-6-yl)ethyl)acetamide;

(E)-2-(8-trifluoromethyl-3,4-dihydrobenzo[b]oxepin-5(2H)-ylidene)-N-((2,3-dihydrobenzo[b][1,4]dioxin-2-yl)methyl)acetamide;

(E)-2-(8-trifluoromethyl-3,4-dihydrobenzo[b]oxepin-5(2H)-ylidene)-N-((2,3-dihydrobenzofuran-5-yl)methyl)acetamide;

(E)-N-((2-(4-chlorophenyl)-4-methylthiazol-5-yl)methyl)-2-(8-trifluoromethyl-3,4-dihydrobenzo[b]oxepin-5(2H)-ylidene)acetamide;

(2E)-N-([1,2,4]triazolo[4,3-a]pyridin-3-yl)methyl)-2-(8-trifluoromethyl-3,4-dihydrobenzo[b]oxepin-5(2H)-ylidene)acetamide;

(E)-2-(8-trifluoromethyl-3,4-dihydrobenzo[b]oxepin-5(2H)-ylidene)-N-(1-methyl-1H-pyrazolo[3,4-b]pyridin-3-yl)acetamide;

(E)-2-(8-trifluoromethyl-3,4-dihydrobenzo[b]oxepin-5(2H)-ylidene)-N-(1H-indazol-3-yl)acetamide;

(E)-N-(1-ethyl-1H-benzo[d]imidazolo-2-yl)-2-(8-trifluoromethyl-3,4-dihydrobenzo[b]oxepin-5(2H)-ylidene)acetamide;

(2E)-N-([1,2,4]triazolo[1,5-a]pyrimidin-7-yl)-2-(8-trifluoromethyl-3,4-dihydrobenzo[b]oxepin-5(2H)-ylidene)acetamide;

(E)-2-(8-trifluoromethyl-3,4-dihydrobenzo[b]oxepin-5(2H)-ylidene)-N-(6,7,8,9-tetrahydro-5H-cyclohepta[b]pyridin-8-yl)acetamide;

(E)-N-(1-tert-butyl-3-methyl-1H-pyrazolo-5-yl)-2-(8-trifluoromethyl-3,4-dihydrobenzo[b]oxepin-5(2H)-ylidene)acetamide;

(E)-2-(8-trifluoromethyl-3,4-dihydrobenzo[b]oxepin-5(2H)-ylidene)-N-(4-phenylthiazolo-2-yl)acetamide;

(E)-2-(8-trifluoromethyl-3,4-dihydrobenzo[b]oxepin-5(2H)-ylidene)-N-(2-hydroxymethyl-1,3-benzothiazolo-5-yl)acetamide;

(E)-2-(8-trifluoromethyl-3,4-dihydrobenzo[b]oxepin-5(2H)-ylidene)-N-(3-hydroxy-2-oxo-1,2,3,4-tetrahydroquinolin-5-yl)acetamide;

(E)-2-(8-trifluoromethyl-3,4-dihydrobenzo[b]oxepin-5(2H)-ylidene)-N-(3-hydroxy-1,2,3,4-tetrahydroquinolin-5-yl)acetamide;

(E)-2-(8-trifluoromethyl-3,4-dihydrobenzo[b]oxepin-5(2H)-ylidene)-N-(1-methyl-3-hydroxy-1,2,3,4-tetrahydroquinolin-5-yl)acetamide;

(E)-N-(3-hydroxy-2-oxo-1,2,3,4-tetrahydroquinolin-5-yl)-2-(7-trifluoromethyl-chroman-4-ylidene)acetamide;

(E)-N-(3-hydroxy-1,2,3,4-tetrahydroquinolin-5-yl)-2-(7-trifluoromethyl-chroman-4-ylidene)acetamide;

(E)-N-(3-hydroxy-chroman-5-yl)-2-(7-trifluoromethyl-chroman-4-ylidene)acetamide;

(E)-2-(8-trifluoromethyl-3,4-dihydrobenzo[b]oxepin-5(2H)-ylidene)-N-(quinolin-7-yl)acetamide methanesulfonate;

(E)-2-(8-trifluoromethyl-3,4-dihydrobenzo[b]oxepin-5(2H)-ylidene)-N-(1-(2-methoxyethyl)-1,2,3,4-tetrahydroquinolin-7-yl)acetamide;

(E)-2-(8-trifluoromethyl-3,4-dihydrobenzo[b]oxepin-5(2H)-ylidene)-N-(3,4-dihydro-1H-quinolin-2-on-7-yl)acetamide;

(E)-2-(8-trifluoromethyl-3,4-dihydrobenzo[b]oxepin-5(2H)-ylidene)-N-(2-quinolon-7-yl)acetamide;

(E)-2-(8-trifluoromethyl-3,4-dihydrobenzo[b]oxepin-5(2H)-ylidene)-N-(indol-6-yl)acetamide;

(E)-2-(8-trifluoromethyl-3,4-dihydrobenzo[b]oxepin-5(2H)-ylidene)-N-(indol-5-yl)acetamide;

(E)-2-(8-trifluoromethyl-3,4-dihydrobenzo[b]oxepin-5(2H)-ylidene)-N-(3,4-dihydro-2H-benzo[b]dioxepin-7-yl)acetamide;

(E)-2-(8-trifluoromethyl-3,4-dihydrobenzo[b]oxepin-5(2H)-ylidene)-N-(2,2-difluoro-1,3-benzodioxol-5-yl)acetamide;

(E)-2-(8-trifluoromethyl-3,4-dihydrobenzo[b]oxepin-5(2H)-ylidene)-N-(1,3-benzodioxol-5-yl)acetamide;

(E)-2-(8-trifluoromethyl-3,4-dihydrobenzo[b]oxepin-5(2H)-ylidene)-N-(1-methylindol-5-yl)acetamide;

(E)-2-(8-trifluoromethyl-3,4-dihydrobenzo[b]oxepin-5(2H)-ylidene)-N-(1-(2-hydroxyethyl)indol-6-yl)acetamide;

(E)-2-(8-trifluoromethyl-3,4-dihydrobenzo[b]oxepin-5(2H)-ylidene)-N-(1-methylindol-6-yl)acetamide;

(E)-2-(8-trifluoromethyl-3,4-dihydrobenzo[b]oxepin-5(2H)-ylidene)-N-(1-(2-hydroxyethyl)indol-5-yl)acetamide;

(E)-2-(8-trifluoromethyl-3,4-dihydrobenzo[b]oxepin-5(2H)-ylidene)-N-(3-hydroxymethyl-2,3-dihydro-1,4-benzodioxin-6-yl)acetamide;

(E)-2-(8-trifluoromethyl-3,4-dihydrobenzo[b]oxepin-5(2H)-ylidene)-N-(2,3-dihydro-isoindol-1-on-6-yl)acetamide;

(E)-2-(8-trifluoromethyl-3,4-dihydrobenzo[b]oxepin-5(2H)-ylidene)-N-(1,2,3,4-tetrahydroquinolin-7-yl)acetamide;

(E)-2-(8-trifluoromethyl-3,4-dihydrobenzo[b]oxepin-5(2H)-ylidene)-N-(2-hydroxyethyl-2,3-dihydro-isoindol-1-on-6-yl)acetamide;

(E)-2-(8-trifluoromethyl-3,4-dihydrobenzo[b]oxepin-5(2H)-ylidene)-N-(1-methyl-2-oxo-1,2,3,4-tetrahydroquinolin-7-yl)acetamide;

(E)-2-(8-trifluoromethyl-3,4-dihydrobenzo[b]oxepin-5(2H)-ylidene)-N-(3-hydroxy-chroman-5-yl)acetamide;

(E)-2-(7-trifluoromethyl-chroman-4-ylidene)-N-(2-methylthieno[2,3-c]pyridin-3-yl)acetamide;

(E)-2-(7-isopropyl-chroman-4-ylidene)-N-(3-hydroxy-1,2,3,4-tetrahydroquinolin-5-yl)acetamide;

(E)-2-(7-chloro-chroman-4-ylidene)-N-(3-hydroxy-1,2,3,4-tetrahydroquinolin-5-yl)acetamide;

(E)-2-(7-trifluoromethoxy-chroman-4-ylidene)-N-(3-hydroxy-1,2,3,4-tetrahydroquinolin-5-yl)acetamide;

(E)-2-(7-(1,1,2,2-tetrafluoroethoxy)-chroman-4-ylidene)-N-(3-hydroxy-1,2,3,4-tetrahydroquinolin-5-yl)acetamide;

(E)-2-(6-fluoro-7-trifluoromethyl-chroman-4-ylidene)-N-(3-hydroxy-1,2,3,4-tetrahydroquinolin-5-yl)acetamide;

(E)-2-(7-trifluoromethyl-chroman-4-ylidene)-N-(2-hydroxymethyl-1,3-benzothiazolo-5-yl)acetamide;

(E)-2-(8-trifluoromethyl-3,4-dihydrobenzo[b]oxepin-5(2H)-ylidene)-N-(2-methylthieno[2,3-c]pyridin-3-yl)acetamide;

(E)-2-(8-trifluoromethyl-3,4-dihydrobenzo[b]oxepin-5(2H)-ylidene)-N-(3-chloro-5-hydroxymethyl-2-pyridyl)acetamide;

(E)-2-(8-trifluoromethyl-3,4-dihydrobenzo[b]oxepin-5(2H)-ylidene-N-(4-(2-hydroxyacetyl)-3,4-dihydro-2H-benzo[b][1,4]oxazin-6-yl)acetamide;

(E)-2-(8-trifluoromethyl-3,4-dihydrobenzo[b]oxepin-5(2H)-ylidene-N-(4-(2-hydroxyethyl)-3,4-dihydro-2H-benzo[b] [1,4]oxazin-6-yl)acetamide;

(E)-2-(8-trifluoromethyl-3,4-dihydrobenzo[b]oxepin-5(2H)-ylidene)-N-(4-(2-hydroxyethyl)-2H-1,4-benzoxazin-3(4H)-on-6-yl)acetamide;

(E)-2-(8-trifluoromethyl-3,4-dihydrobenzo[c]isooxepin-5(1H)-ylidene)-N-(3-hydroxy-1,2,3,4-tetrahydroquinolin-5-yl)acetamide;

(E)-2-(7-trifluoromethyl-2,2-dimethylchroman-4-ylidene)-N-(3-hydroxy-1,2,3,4-tetrahydroquinolin-5-yl)acetamide;

(Z)-2-(8-trifluoromethyl-3,4-dihydrobenzo[b]oxepin-5(2H)-ylidene)-N-(quinolin-7-yl)acetamide;

(E)-N-(3-hydroxy-1,2,3,4-tetrahydroquinolin-5-yl)-2-(7-trifluoromethyl-2,2-cyclobutylchroman-4-ylidene)acetamide;

(E)-2-(8-trifluoromethyl-3,4-dihydrobenzo[b]oxepin-5(2H)-ylidene)-N-(1H-indazol-4-yl)acetamide; and (E)-2-(8-trifluoromethyl-3,4-dihydrobenzo[b]oxepin-5(2H)-ylidene)-N-(1H-indazol-7-yl)acetamide.

* * * * *